United States Patent
Bizzarro et al.

(10) Patent No.: US 7,223,868 B2
(45) Date of Patent: *May 29, 2007

(54) HETEROAROMATIC GLUCOKINASE ACTIVATORS

(75) Inventors: Fred Thomas Bizzarro, Colonia, NJ (US); Wendy Lea Corbett, Randolph, NJ (US); Joseph Francis Grippo, Stirling, NJ (US); Nancy-Ellen Haynes, Cranford, NJ (US); George William Holland, Houston, TX (US); Robert Francis Kester, Verona, NJ (US); Paige Erin Mahaney, Montclair, NJ (US); Ramakanth Sarabu, Pine Brook, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/098,717

(22) Filed: Apr. 4, 2005

(65) Prior Publication Data

US 2005/0261503 A1 Nov. 24, 2005

Related U.S. Application Data

(60) Division of application No. 10/616,359, filed on Jul. 9, 2003, now Pat. No. 6,951,945, which is a division of application No. 09/675,781, filed on Sep. 28, 2000, now Pat. No. 6,610,846, which is a continuation-in-part of application No. 09/526,143, filed on Mar. 15, 2000, now Pat. No. 6,320,050.

(60) Provisional application No. 60/165,944, filed on Nov. 17, 1999, provisional application No. 60/126,707, filed on Mar. 29, 1999.

(51) Int. Cl.
*C07D 213/75* (2006.01)
*C07D 213/84* (2006.01)

(52) U.S. Cl. ............ 546/289; 546/297; 546/309; 546/310

(58) Field of Classification Search ............ None
See application file for complete search history.

(56) References Cited

U.S. PATENT DOCUMENTS

| 3,431,301 | A | | 3/1969 | Focella et al. |
| 3,776,917 | A | * | 12/1973 | Mann et al. ............ 546/307 |
| 5,538,939 | A | | 7/1996 | Munster et al. |
| 5,556,859 | A | | 9/1996 | Johnson |
| 5,972,843 | A | | 10/1999 | Heil et al. |
| 6,008,366 | A | | 12/1999 | Heil et al. |
| 6,114,365 | A | | 9/2000 | Pevarello et al. |
| 6,320,050 | B1 | * | 11/2001 | Bizzarro et al. ............ 544/332 |

FOREIGN PATENT DOCUMENTS

| CA | 2299013 | 9/2004 |
| DE | 19542372 | 11/1995 |
| EP | 566 138 | 10/1993 |
| WO | WO 00/26202 | 5/2000 |
| WO | WO 01/85706 A1 | 11/2001 |
| WO | WO 01/85707 A1 | 11/2001 |

OTHER PUBLICATIONS

Mann et al., STN International (2005), HCAPLUS Database, Columbus, OH, Accession No. 80:82694, Registry No. 51505-04-5.*

* cited by examiner

*Primary Examiner*—Joseph K. McKane
*Assistant Examiner*—Andrew B. Freistein
(74) *Attorney, Agent, or Firm*—George W. Johnston; Dennis P. Tramaloni; Samuel H. Megerditchian

(57) ABSTRACT

2,3-Di-substituted N-heteroaromatic propionamides with said substitution at the 3-position being a substituted phenyl group and at the 2-position being a methyl cycloalkyl ring, said propionamides being glucokinase activators which increase insulin secretion in the treatment of type II diabetes.

3 Claims, No Drawings

HETEROAROMATIC GLUCOKINASE ACTIVATORS

CROSS-REFERENCE TO RELATED APPLICATIONS

This application is a divisional of application Ser. No. 10/616,359, filed Jul. 9, 2003, now U.S. Pat. No. 6,951,945 which is a divisional of application Ser. No. 09/675,781, filed on Sep. 28, 2000, now U.S. Pat. No. 6,610,846, which is a CIP of U.S. Ser. No. 09/526,143 filed on Mar. 15, 2000, now U.S. Pat. No. 6,320,050, which claims benefit of U.S. Provisional Application No. 60/126,707 filed Mar. 29, 1999, and claims benefit of U.S. Provisional Application No. 60/165,944 filed Nov. 17, 1999.

BACKGROUND OF THE INVENTION

Glucokinase (GK) is one of four hexokinases that are found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

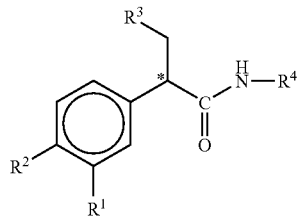

I wherein $R^1$ and $R^2$ are independently hydrogen, halo, amino, hydroxyamino, cyano, nitro, lower alkyl, —$OR^5$, —C(O)$OR^6$, perfluoro-lower alkyl, lower alkyl thio, perfluoro-lower alkyl thio, lower alkyl sulfonyl, lower alkoxy lower alkyl sulfonyl, perfluoro-lower alkyl sulfonyl, lower alkyl sulfinyl, or sulfonamido; $R^3$ is cycloalkyl having from 3 to 7 carbon atoms or lower alkyl having from 2 to 4 carbon atoms;

$R^4$ is an unsubstituted or mono-substituted five- or six-membered heteroaromatic ring connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being monosubstituted at a position on a ring carbon atom other than adjacent to said connecting carbon atom with a substituent selected from the group consisting of lower alkyl, halo, nitro, cyano, perfluoro-lower alkyl; oxo, —$(CH_2)_n$—$OR^7$, —$(CH_2)_n$—C(O)—$OR^7$, —$(CH_2)_n$—C(O)—NH—$R^7$, —C(O)C(O)—$OR^7$, or —$(CH_2)_n$—$NHR^7$; n is 0, 1, 2, 3 or 4; $R^5$ is hydrogen, lower alkyl, or perfluoro-lower alkyl; $R^6$ is lower alkyl; and $R^7$ is hydrogen or lower alkyl; or a pharmaceutically acceptable salt thereof.

The compounds of formula I have been found to activate glucokinase in vitro. Glucokinase activators are useful for increasing insulin secretion in the treatment of type II diabetes.

DETAILED DESCRIPTION OF THE INVENTION

This invention provides a compound, comprising an amide of the formula:

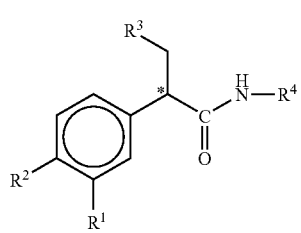

I wherein $R^1$ and $R^2$ are independently hydrogen, halo, amino, hydroxyamino, cyano, nitro, lower alkyl, —$OR^5$, —C(O) $OR^6$, perfluoro-lower alkyl, lower alkyl thio, perfluoro-lower alkyl thio, lower alkyl sulfinyl, lower alkyl sulfonyl ring, lower alkoxy lower alkyl sulfonyl, perfluoro-lower alkyl sulfonyl, or sulfonamido; $R^3$ is preferably cycloalkyl having from 3 to 7 carbon atoms atoms but also includes lower alkyl having from 2 to 4 carbon atoms, $R^4$ is an unsubstituted or mono-substituted five or six-membered heteroaromatic connected by a ring carbon atom to the amine group shown, which five- or six-membered heteroaromatic ring contains from 1 to 3 heteroatoms selected from sulfur, oxygen or nitrogen, with one heteroatom being nitrogen which is adjacent to the connecting ring carbon atom; said mono-substituted heteroaromatic ring being monosubstituted at a position on a ring carbon atom other than adjacent to said connecting carbon atom with a substituent selected from the group consisting of lower alkyl, halo, nitro, cyano, perfluoro-lower alkyl; oxo, —$(CH_2)_n$—$OR^7$, —$(CH_2)_n$—C(O)—$OR^7$, —$(CH_2)_n$—C(O)—NH—$R^7$, —C(O)C(O)—$OR^7$, or —$(CH_2)_n$—$NHR^7$; n is 0, 1, 2, 3 or 4; $R^5$ is hydrogen, lower alkyl, or perfluoro-lower alkyl; $R^6$ is lower alkyl; and $R^7$ is hydrogen or lower alkyl; or a pharmaceutically acceptable salt thereof.

In the compound of formula I, the "*" illustrates the asymmetric carbon atom in this compound. The compound of formula I may be present either as a racemate or in the "R" configuration at the asymmetric carbon shown. The "R" enantiomers are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, the term "halogen" is used interchangeably with the word "halo", and, unless otherwise stated, designates all four halogens, i.e. fluorine, chlorine, bromine, and iodine. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, the term "lower alkoxy" signifies a lower alkyl group as defined above linked via an oxygen to the remainder of the molecule and includes both straight chain and branched chain alkoxy groups having from 1 to 7 carbon atoms, such as methoxy, ethoxy, propoxy, isopropoxy, preferably methoxy and ethoxy. "Lower alkoxy lower alkyl" signifies a lower alkoxy linked via an oxygen to a lower alkyl group, which is linked to the remainder of the molecule.

As used herein the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydroxide group of the COOH moiety removed. Among the preferred aroyl groups is benzoyl.

As used herein, —C(O)$OR^6$ represents

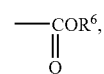

and so forth.

The heteroaromatic ring defined by $R^4$ can be an unsubstituted or mono-substituted five- or six-membered heteroaromatic ring having from 1 to 3 heteroatoms selected from the group consisting of oxygen, nitrogen, or sulfur and connected by a ring carbon to the amine of the amide group shown. The heteroaromatic ring contains a first nitrogen heteroatom adjacent to the connecting ring carbon atom and if present, the other heteroatoms can be sulfur, oxygen or nitrogen. Such heteroaromatic rings include, for example, pyrazinyl, pyridazinyl, isoxazolyl, isothiazolyl, and pyrazolyl. Among the preferred heteroaromatic rings are included pyridinyl, pyrimidinyl, pyrazinyl, thiazolyl, oxazolyl, and imidazolyl. These heteroaromatic rings which constitute $R^4$ are connected via a ring carbon atom to the amide group to form the amides of formula I. The ring carbon atom of the heteroaromatic ring which is connected via the amide linkage to form the compound of formula I cannot contain any substituent.

When $R^4$ is an unsubstituted or mono-substituted five-membered heteroaromatic ring, the preferred rings are those which contain a nitrogen heteroatom adjacent to the connecting ring carbon and a second heteroatom adjacent to the connecting ring carbon.

The preferred five-membered heteroaromatic rings contain 2 or 3 heteroatom with thiazolyl, imidazolyl, oxazolyl and thiadiazolyl being especially present. When the heteroaromatic ring is a six-membered heteroaromatic ring, the ring is connected by a ring carbon to the amine group shown, with one nitrogen heteroatom being adjacent to the connecting ring carbon atom. The preferred six-membered heteroaromatic rings include, for example, pyridinyl, pyrimidinyl, pyrazinyl, pyridazinyl, and triazinyl.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

During the course of the reactions provided below in the Reaction Scheme and discussion, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxyl or hydroxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Examples of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

Similarly, the term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2 to 3. Particularly preferred amino protecting groups are t-butyl carbamate (BOC), benzyl carbamate (CBZ), and 9-fluorenylmethyl carbamate (FMOC).

In accordance with one embodiment of this invention, $R^3$ is cyclopentyl (the compound I-D). The embodiments of the compound I-D are those compounds where $R^4$ is an unsubstituted thiazole (Compound I-D1). Among the various embodiments of the compound of I-D1 are included those compounds where:
(a) one of $R^1$ and $R^2$ is hydrogen, halo, perfluoro-lower alkyl and the other of said $R^1$ and $R^2$ is halo, nitro, or perfluoro-lower alkyl;
(b) one of $R^1$ and $R^2$ is amino, halo, nitro or hydrogen and the other of said $R^1$ and $R^2$ is amino, cyano or nitro;
(c) one of $R^1$ and $R^2$ is lower alkylthio, perfluoro-lower alkyl thio, halo or hydrogen and the other of said $R^1$ and $R^2$ is perfluoro-lower alkylthio, lower alkylsulfinyl or lower alkylthio;
(d) one of $R^1$ and $R^2$ is lower alkyl sulfonyl, hydrogen, nitro, cyano, amino, hydroxyamino, sulfonamido or halo, and the other of said $R^1$ and $R^2$ is lower alkyl sulfonyl;
(e) one of $R^1$ and $R^2$ is lower alkyl sulfonyl, and the other of said $R^1$ and $R^2$ is halo or perfluoro-lower alkyl;
one of $R^1$ and $R^2$ is perfluoro-lower alkyl sulfonyl or hydrogen and the other of said $R^1$ and $R^2$ is perfluoro-lower alkyl sulfonyl;
(g) one of $R^1$ and $R^2$ is —$OR^5$, or —C(O)—$OR^6$ and the other of said $R^1$ and $R^2$ is hydrogen or —$OR^5$; and $R^5$ and $R^6$ are as above
(h) one of $R^1$ and $R^2$ is —$OR^5$ and the other is halo, and
(i) one of $R^1$ and $R^2$ is hydrogen (preferably $R^1$) and the other of said $R^1$ and $R^2$ is lower alkoxy lower alkyl sulfonyl (preferably $R^2$).

In accordance with another embodiment of this invention where $R^3$ is cyclopentyl, the embodiments are those compounds where $R^4$ is a mono-substituted thiazole (compounds I-D2). Among the embodiments of compounds I-D2, are those compounds where the mono-substitution is —$(CH_2)_n$—$OR^7$ and n and $R^7$ are as above (compounds I-D2(a)).

Among the embodiments of compounds I-D2 (a) are those compounds where:
a) one of $R^1$ and $R^2$ is halo and the other of said $R^1$ and $R^2$ is hydrogen or halo;
b) one of $R^1$ and $R^2$ is lower alkyl sulfonyl, and the other of said $R^1$ and $R^2$ is lower alkyl sulfonyl or hydrogen; and
c) one of $R^1$ and $R^2$ is hydrogen and the other of said $R^1$ and $R^2$ is lower alkyl or perfluoro-lower alkyl.

In accordance with another embodiment of the invention where $R^3$ is cyclopentyl and $R^4$ is a mono-substituted thiazole (Compounds I-D2), are those compounds where the mono-substitution is lower alkyl. Among the embodiments of these compounds are compounds where:
a) one of $R^1$ and $R^2$ is hydrogen or halo and the other of $R^1$ and $R^2$ is halo;
b) one of $R^1$ and $R^2$ is lower alkyl sulfonyl and the other of $R^1$ and $R^2$ is hydrogen or halo.

Among another embodiment of the compounds I-D are those compounds where the mono-substituted thiazole is substituted with —$(CH_2)_n$—C(O)—$OR^7$ wherein n is 0 or 1 and $R^7$ is hydrogen, or lower alkyl (Compounds I-D2(c)). Among the embodiments of compounds of formula I-D2(c) are those compounds where:
a) one of $R^1$ and $R^2$ is hydrogen and the other of said $R^1$ and $R^2$ is halo;
b) $R^1$ and $R^2$ are each independently halo;
c) one of $R^1$ and $R^2$ is halo and the other of said $R^1$ and $R^2$ is perfluoro-lower alkyl;
d) one of $R^1$ or $R^2$ is nitro, amino or hydrogen and the other of said $R^1$ and $R^2$ is nitro or amino; and
e) one of $R^1$ and $R^2$ is lower alkyl sulfonyl, perfluoro-lower alkyl, halo or hydrogen and the other of said $R^1$ and $R^2$ is lower alkyl sulfonyl;
f) one of of $R^1$ and $R^2$ is hydrogen, halo or perfluoro-lower alkyl and the other of said $R^1$ and $R^2$ is perfluoro-lower alkyl sulfonyl.

In accordance with another embodiment of this invention, where $R^3$ and cyclopentyl and $R^4$ is a mono-substituted thiazole (Compounds I-D2) are those compounds where the mono-substituted thiazole is substituted with —C(O)—C(O)—$OR^7$ wherein $R^7$ is as above (Compounds I-D2(d)).

Among the embodiments of compound I-D2(d) are those compounds where:
a) one of $R^1$ and $R^2$ are hydrogen and the other of said $R^1$ and $R^2$ is nitro or amino;
b) one of $R^1$ and $R^2$ is halo or perfluoro-lower alkyl and the other of said $R^1$ and $R^2$ is perfluoro-lower alkyl, halo or hydrogen; and
c) one of $R^1$ and $R^2$ is hydrogen or halo and the other of said $R^1$ and $R^2$ is lower alkyl sulfonyl.

In accordance with another embodiment of this invention, where $R^3$ is cyclopentyl and $R^4$ is a mono-substituted thiazole, compounds I-D2, are those compounds where the mono-substitution on the thiazole ring is a nitro group and one of $R^1$ and $R^2$ are hydrogen and halo and the other of $R^1$ and $R^2$ is halo or lower alkyl sulfonyl, or $R^1$ and $R^2$ are each independently halo (compound of formula I-D2(e)).

In accordance with another embodiment of this invention, where $R^3$ is cyclopentyl and $R^4$ is a mono-substituted thiazole, compounds I-D2, are those compounds where the mono-substitution on the thiazole ring is —$(CH_2)_n$—C(O)—NH—$R^7$ where n and $R^7$ are as in formula I, preferably where one of $R^1$ and $R^2$ is lower alkyl sulfonyl or halo and the other of $R^1$ and $R^2$ is halo or hydrogen.

In accordance with another embodiment of this invention, where $R^3$ is cyclopentyl and $R^4$ is a mono-substituted thiazole, compounds I-D2, are those compounds where the mono-substitution on the thiazole ring is halo, preferably where one of $R^1$ and $R^2$ is hydrogen or halo and the other of $R^1$ and $R^2$ is lower alkyl sulfonyl.

In accordance with another embodiment of this invention, where $R^3$ is cyclopentyl (Compound I-D) and $R^4$ is an unsubstituted pyridine (Compounds I-D3). Among the embodiments of compound I-D3 are those compounds where:
a) one of $R^1$ and $R^2$ is halo and the other of $R^1$ and $R^2$ is lower alkyl sulfonyl;
b) one of $R^1$ and $R^2$ are halo, perfluoro-lower alkyl or hydrogen and the other of said $R^1$ and $R^2$ is halo, perfluoro-lower alkyl, amino, cyano or nitro;
c) one of $R^1$ and $R^2$ is lower alkyl thio, perfluoro-lower alkyl thio or cyano, and the other is hydrogen;
d) one of $R^1$ and $R^2$ is lower alkyl sulfonyl, halo, cyano, nitro or hydrogen and the other of said $R^1$ and $R^2$ is lower alkyl sulfonyl, and
e) one of $R^1$ and $R^2$ is perfluoro-lower alkyl sulfonyl, lower alkyl sulfonyl or hydrogen and the other of said $R^1$ and $R^2$ is perfluoro-lower alkyl sulfonyl, or perfluoro-lower alkyl.

In accordance with another embodiment of the invention, where $R^3$ is cyclopentyl (Compounds I-D) are those compounds where $R^4$ is a mono-substituted pyridine ring. Among the embodiments of the mono-substituted pyridine (Compounds I-D4) are those compounds where the mono-substitution is cyano. Among the embodiments of such compounds are those compounds where one of $R^1$ and $R^2$ is perfluoro-lower alkyl or halo and the other of $R^1$ and $R^2$ is lower alkyl thio or halo, especially where $R^1$ and $R^2$ are each independently halo.

In accordance with another embodiment of the invention, where $R^3$ is cyclopentyl (Compounds I-D) are those compounds where $R^4$ is a mono-substituted pyridine ring. Among the embodiments of the mono-substituted pyridine (Compounds I-D4) are those compounds where the mono-substitution is —$(CH_2)_n$—$C(O)$—$OR^7$ wherein n and $R^7$ are as above (compound I-D4(a)). Among the embodiments of compounds I-D4(a) are those compounds where:
a) $R^1$ and $R^2$ are each independently halo;
b) one of $R^1$ and $R^2$ is halo or hydrogen and the other of said $R^1$ and $R^2$ is halo, amino, cyano, nitro or perfluoro-lower alkyl; and
c) one of $R^1$ and $R^2$ is perfluoro-lower alkyl sulfonyl, lower alkyl sulfonyl or hydrogen and the other of said $R^1$ and $R^2$ is perfluoro-lower alkyl sulfonyl or lower alkyl sulfonyl.

Other embodiments of the compounds of formula I-D4 are those compounds where the pyridine ring is mono-substituted with —$(CH_2)_n$—$OR^7$ wherein n and $R^7$ are as above (Compounds I-D4(b)). Among the embodiments of the compound I-D4(b) are those compounds where:
a) one of $R^1$ and $R^2$ is halo and the other of said $R^1$ and $R^2$ is hydrogen or halo; and
b) one of $R^1$ and $R^2$ is lower alkyl sulfonyl or hydrogen and the other of said $R^1$ and $R^2$ is lower alkyl sulfonyl.

Another embodiment of compounds where $R^3$ is cyclopentyl and $R^4$ is a mono-substituted pyridine ring are those compounds where the pyridine ring is mono-substituted with a halo or perfluoro lower alkyl substituent, the compound of formula I-D4(c). Among the embodiments of the compound of formula I-D4(c) are those compounds where:
a) one of $R^1$ and $R^2$ is halo or perfluoro-lower alkyl and the other of said $R^1$ and $R^2$ is halo, nitro, lower alkyl sulfonyl, or lower alkyl thio;
b) one of $R^1$ and $R^2$ is halo or hydrogen and the other of said $R^1$ and $R^2$ is halo; and
c) one of $R^1$ and $R^2$ is halo, nitro or hydrogen and the other of said $R_1$ and $R^2$ is perfluoro-lower alkyl sulfonyl or lower alkyl sulfonyl.

In accordance with another embodiment of this invention are compounds of where $R^3$ is cyclopentyl and $R^4$ is a mono-substituted pyridine are those compounds where the pyridine is mono-substituted with a nitro substituent, (Compound I-D4(d)). The embodiments of the compound I-D4(d) include compounds where one of $R^1$ and $R^2$ is halo and the other of said $R^1$ or $R^2$ is hydrogen, halo, or lower alkyl sulfonyl and compounds where one of $R^1$ and $R^2$ is halo or perfluoro-lower alkyl and the other of said $R^1$ or $R^2$ is halo or lower alkyl thio.

In accordance with another embodiment of this invention are compounds of formula I where $R^3$ is cyclopentyl and $R^4$ is mono-substituted pyridine and the mono-substitution is a lower alkyl group (Compounds I-D4(e)). Among the embodiments of compounds I-D4(e) are those compounds where one of $R^1$ and $R^2$ is halo or hydrogen and the other of said $R^1$ and $R^2$ is halo, perfluoro-lower alkyl, perfluoro-lower alkyl sulfonyl, or lower alkyl sulfonyl, and compounds where one of $R^1$ and $R^2$ is halo and other of said $R^1$ or $R^2$ is lower alkyl sulfonyl.

In accordance with another embodiment of this invention where $R^3$ is cyclopentyl and $R^4$ is a mono-substituted pyridine are those compounds where the mono-substituent is —$(CH_2)_n$—$C(O)$—$NH$—$R^7$ wherein n and $R^7$ are as above (Compound I-D4(f)). Among the embodiments of compound I-D4(f) are those compounds wherein one of $R^1$ and $R^2$ are independently selected from the group consisting of halo or hydrogen and the other of said $R^1$ and $R^2$ is halo, or lower alkyl sulfonyl, and those compounds where one of $R^1$ and $R^2$ is halo and other of said $R^1$ or $R^2$ is perfluoro-lower alkyl.

Another embodiment of this invention where $R^3$ is cyclopentyl are those compounds where $R^4$ is an unsubstituted imidazolyl (Compound I-D5). Among the embodiments of compounds I-D5 are those compounds wherein one of $R^1$ and $R^2$ is selected from the group consisting of halo and hydrogen and the other of said $R^1$ and $R^2$ is halo, or lower alkyl sulfonyl and those compounds where one of $R^1$ and $R^2$ is lower alkyl sulfonyl and other of said $R^1$ or $R^2$ is nitro or perfluoro-lower alkyl.

Another embodiment of the compounds of this invention are those compounds where $R^3$ is cyclopentyl and $R^4$ is an isoxazolyl ring (the compound I-D6). The embodiments of compound I-D6 are those compounds where the isoxazolyl ring is unsubstituted or substituted, preferably mono-substituted. Among the mono-substituted substituents, the preferred substituents substituted on the isoxazolyl ring is lower alkyl. An embodiment of the compound I-D6, either where the isoxazolyl ring is unsubstituted or substituted with a lower alkyl substituent are those compounds where one of $R^1$ and $R^2$ is halo, nitro, perfluoro-lower alkyl, or lower alkyl sulfonyl and the other of $R^1$ and $R^2$ is hydrogen or halo.

Another embodiment of this invention where $R^3$ is cyclopentyl are those compounds where $R^4$ is either an unsubstituted oxazolyl, or an oxazolyl mono-substituted with a lower alkyl group. Another embodiment with respect to either of those compounds are those compounds where one of $R^1$ or $R^2$ is halo, nitro or perfluoro-lower alkyl, or lower alkyl sulfonyl and the other is of $R^1$ or $R^2$ is hydrogen or halo.

Another embodiment of this invention where $R^3$ is cyclopentyl are those compounds where $R^4$ is pyridazinyl which is either unsubstituted or substituted with a lower alkyl group (Compound I-D7). Embodiments of the compound I-D7 are encompassed by this invention include those compounds where one of $R^1$ or $R^2$ is halo, nitro or perfluoro-lower alkyl, or lower alkyl sulfonyl and the other of said $R^1$ or $R^2$ is hydrogen or halo.

Another embodiment of this invention where $R^3$ is cyclopentyl include compounds where $R^4$ is unsubstituted pyrimidinyl. The embodiments of those compounds where $R^3$ is cyclopentyl and $R^4$ is unsubstituted pyrimidinyl include those compounds where one of $R^1$ or $R^2$ is halo, nitro, perfluoro-lower alkyl, or lower alkyl sulfonyl and the other is hydrogen or halo and those compounds where one of $R^1$ and $R^2$ is lower alkyl sulfonyl and other of said $R^1$ or $R^2$ is cyano, nitro, or perfluoro-lower alkyl.

In accordance with another embodiment of the invention, where $R^3$ is cyclopentyl (Compounds I-D) are those compounds where $R^4$ is a mono-substituted pyrimidine ring. Among the embodiments of the mono-substituted pyrimidine are those compounds where the mono-substitution is lower alkyl. Among the embodiments of such compounds are those compounds where:

a) one of $R^1$ and $R^2$ is perfluoro-lower alkyl and the other of said $R^1$ and $R^2$ is hydrogen;
b) one of $R^1$ and $R^2$ is lower alkyl sulfonyl and the other of said $R^1$ and $R^2$ is cyano or nitro; and
c) one of $R^1$ and $R^2$ is lower alkyl sulfonyl and the other of said $R^1$ and $R^2$ is perfluoro-lower alkyl,
d) one of $R^1$ and $R^2$ is lower alkyl sulfonyl and the other of said $R^1$ and $R^2$ is halo.

In accordance with yet another embodiment of the invention, where $R^3$ is cyclopentyl (Compounds I-D) are those compounds where $R^4$ is a mono-substituted dihydro pyrimidine ring. Among the embodiments of the mono-substituted pyrimidine are those compounds where the mono-substitution is oxo. Among the embodiments of such compounds are those compounds where one of $R^1$ and $R^2$ is lower alkyl sulfonyl and the other of said $R^1$ and $R^2$ is halo, nitro, or perfluoro-lower alkyl.

Another embodiment of this invention includes compounds where $R^3$ is cyclopentyl where $R^4$ is an unsubstituted thiadiazolyl ring. Among the embodiments included within those compounds where $R^3$ is cyclopentyl and $R^4$ is an unsubstituted thiadiazolyl ring are those compounds wherein one of $R^1$ or $R^2$ is halo, nitro or perfluoro-lower alkyl, or lower alkyl sulfonyl and the other of said $R^1$ and $R^2$ is hydrogen or halo.

In accordance with other embodiments of this invention, $R^3$ in the compound of formula I can be cycloheptyl or cyclohexyl. The embodiments of the compound of formula I where $R^3$ is cycloheptyl or cyclohexyl include those compounds where $R^4$ is thiazolyl which can be mono-substituted or unsubstituted. Embodiments included within such compounds where $R^3$ is cycloheptyl or cyclohexyl and $R^4$ is an unsubstituted thiazolyl include those compounds wherein one of $R^1$ and $R^2$ is halo, lower alkyl sulfonyl, perfluoro-lower alkyl sulfonyl, perfluoro-lower alkyl, and the other is of said $R^1$ and $R^2$ is halo, perfluoro-lower alkyl or hydrogen.

In accordance with another embodiment of this invention, $R^3$ is cyclopentyl (Compound I-D) and $R^4$ is an unsubstituted pyrazinyl. Among the embodiments of such compounds are those compounds where:

a) one of $R^1$ and $R^2$ is lower alkyl sulfonyl, halo, or perfluoro-lower alkyl and the other of $R^1$ and $R^2$ is hydrogen, halo, cyano, nitro, or perfluoro-lower alkyl;
b) one of $R^1$ and $R^2$ is perfluoro-lower alkyl or lower alkyl sulfonyl and the other of said $R^1$ and $R^2$ is hydrogen, cyano or nitro;
c) one of $R^1$ and $R^2$ is lower alkyl sulfonyl and the other is perfluoro-lower alkyl or halo.

In accordance with yet another embodiment of the invention, where $R^3$ is cyclopentyl (Compounds I-D) are those compounds where $R^4$ is unsubstituted triazinyl. Among the embodiments of such compounds are those compounds where $R^1$ and $R^2$ are each independently halo.

The compound of formula I can be prepared starting from the compound of formula V by the following Reaction Scheme:

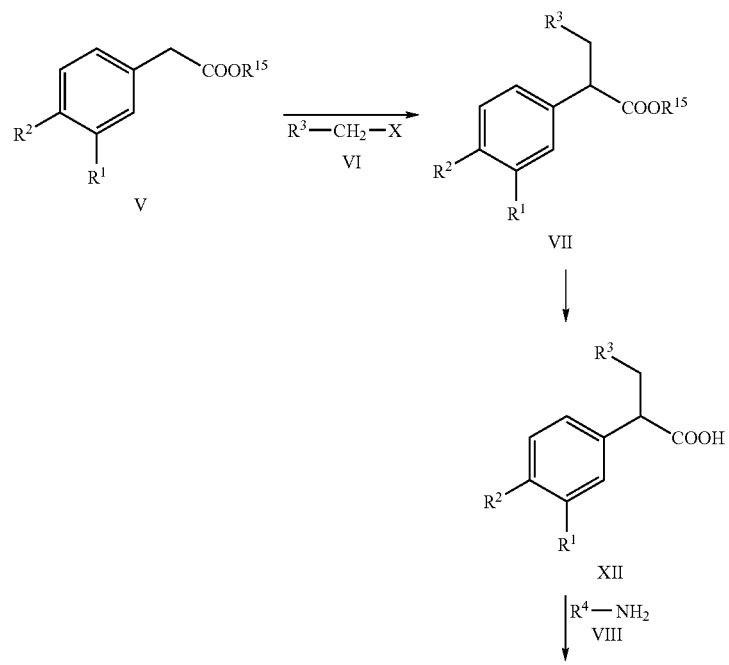

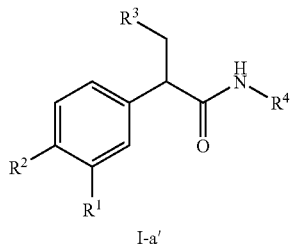

I-a' wherein $R^1$, $R^2$, $R^3$ and $R^4$ are as above and $R^{15}$ is hydrogen or lower alkyl.

The carboxylic acids or their lower alkyl esters of formula V wherein one of $R^1$ and $R^2$ is nitro, cyano, thiol, thiomethyl, methylsulfonyl, amino, chloro, bromo, or iodo and the other is hydrogen are commercially available. In cases where only the carboxylic acids are available, they can be converted to the corresponding esters of lower alkyl alcohols using any conventional esterification methods. All the reactions hereto forward are to be carried out on lower alkyl esters of the carboxylic acids of formula V, or may be carried out on the carboxylic acids themselves. The amino substituted compounds of formula V can be converted to other substituents either before or after conversion to the compounds of formula 1-a'. In this respect, the amino groups can be diazotized to yield the corresponding diazonium compound, which in situ can be reacted with the desired lower alkyl thiol, perfluoro-lower alkyl thiol (see for example, Baleja, J. D. Synth. Comm. 1984, 14, 215; Giam, C. S.; Kikukawa, K., J. Chem. Soc, Chem. Comm. 1980, 756; Kau, D.; Krushniski, J. H.; Robertson, D. W, J. Labelled Compd Rad. 1985, 22, 1045; Oade, S.; Shinhama, K.; Kim, Y. H., Bull Chem Soc. Jpn. 1980, 53, 2023; Baker, B. R.; et al, J. Org. Chem. 1952, 17, 164) to yield corresponding compounds of formula V where one of the substituents is lower alkyl thio, perfluoro-lower alkyl thio and the other is hydrogen. If desired, the lower alkyl thio or perfluoro-lower alkyl thio compounds can then be converted to the corresponding lower alkyl sulfonyl or perfluoro-lower alkyl sulfonyl substituted compounds of formula V by oxidation. Any conventional method of oxidizing alkyl thio substituents to sulfones can be utilized to effect this conversion. If it is desired to produce compounds of lower alkyl or perfluoro-lower alkyl groups of compounds of formula V, the corresponding halo substituted compounds of formula V can be used as starting materials. Any conventional method of converting an aromatic halo group to the corresponding alkyl group (see for example, Katayama, T.; Umeno, M., Chem. Lett. 1991, 2073; Reddy, G. S.; Tam., Organometallics, 1984, 3, 630; Novak, J.; Salemink, C. A., Synthesis, 1983, 7, 597; Eapen, K. C.; Dua, S. S.; Tamboroski, C., J. Org. Chem. 1984, 49, 478; Chen, Q,-Y.; Duan, J.-X. J. Chem. Soc. Chem. Comm. 1993, 1389; Clark, J. H.; McClinton, M. A.; Jone, C. W.; Landon, P.; Bisohp, D.; Blade, R. J., Tetrahedron Lett. 1989, 2133; Powell, R. L.; Heaton, C. A, U.S. Pat. No. 5,113,013) can be utilized to effect this conversion. On the other hand, the thio substituent can be oxidized to a —$SO_3H$ group which then can be converted to —$SO_2Cl$ which is reacted with ammonia to form the sulfonamide substituent —$S(O)_2$—$NH_2$.

For compounds of formula V where one of $R^1$ and $R^2$ is hydrogen and the other is lower alkoxy lower alkyl sulfonyl, the corresponding thiol compound may be used as a starting material. The compound of formula V where one of $R^1$ and $R^2$ is hydrogen and the other is thiol may be alkoxylated by conventional methods (for example with alkoxy alkyl halide) to the corresponding lower alkoxy lower alkyl sulfanyl of formula V, which is then hydrolyzed by conventional methods (for example with lithium hydroxide, water, and tetrahydrofuran or sodium hydroxide and methanol) to the corresponding carboxylic acid. The latter is alkylated by conventional methods to add the desired methyl-cycloalkyl $R^3$ substituent. The resulting compound is oxidized by conventional methods at the sulfanyl to provide lower alkoxy lower alkyl sulfonyl compound of formula XII. Conversion of the compound of formula XII to a compound of formula I-a' is described below.

For compounds of formula V wherein one or both of $R^1$ and $R^2$ is hydroxyamino, the corresponding nitro compounds can be used as starting material and can be converted to the corresponding compounds where $R^1$ and/or $R^2$ are hydroxyamino. Any conventional method of converting a nitro group to the corresponding aromatic hydroxyamino compound can be used to affect this conversion.

The carboxylic acids or esters of formula V wherein both of $R^1$ and $R^2$ are chloro, or fluoro are commercially available. In cases, where only the carboxylic acids are available, they can converted to the corresponding esters of lower alkyl alcohols using any conventional esterification method. To produce the compound of formula V where both $R^1$ and $R^2$ are nitro, 3,4-dinitrotoluene can be used as starting material. This compound can be converted to the corresponding 3,4-dinitrophenyl acetic acid. This conversion can take place either before or after the compound of formula V is converted to the compound of formula 1-a'. Any conventional method of converting an aryl methyl group to the corresponding aryl acetic acid can be utilized to effect this conversion (see for example, Clark, R. D.; Muchowski, J. M.; Fisher, L. E.; Flippin, L. A.; Repke, D. B.; Souchet, M, Synthesis, 1991, 871). The compounds of formula V where both $R^1$ and $R^2$ substituents are amino can be obtained from the corresponding dinitro compound of formula V, described above. Any conventional method of reducing a nitro group to an amine can be utilized to effect this conversion. The compound of formula V where both $R^1$ and $R^2$ are amine groups can be used to prepare the corresponding compound of formula V where both $R^1$ and $R^2$ are iodine or bromine via a diazotization reaction. Any conventional method of converting amino group to an iodo or bromo group (see for example, Lucas, H. J.; Kennedy, E. R. Org. Synth. Coll. Vol, II 1943, 351) can be utilized to effect this conversion. If it is desired to produce compounds of formula V where both $R^1$ and $R^2$ are lower alkyl thio or perfluoro-lower alkyl thio groups, the compound of formula V where $R^1$ and $R^2$ are amino can be used as starting material. Any conventional method of converting aryl amino group to aryl thioalkyl group can be utilized to effect this conversion. If it is desired to produce compound of formula V where $R^1$ and $R^2$ are lower alkyl sulfonyl or lower perfluoro alkyl sulfonyl, the corresponding compounds of formula V where $R^1$ and $R^2$ are lower alkyl thio or perfluoro-lower alkyl thio can be used as starting material. Any conventional method of oxidizing alkyl thio substituents to sulfones can be utilized to effect this conversion. If it is desired to produce compounds of formula V where both $R^1$ and $R^2$ are substituted with lower alkyl or perfluoro-lower alkyl groups, the corresponding halo substituted compounds of formula V can be used as starting materials. Any conventional method of converting an aromatic halo group to the corresponding alkyl or perfluoro-lower alkyl group can be utilized to effect this conversion.

The carboxylic acids corresponding to the compounds of formula V where one of $R^1$ and $R^2$ is nitro and the other is halo are known from the literature (see for 4-chloro-3-nitrophenyl acetic acid, Tadayuki, S.; Hiroki, M.; Shinji, U.; Mitsuhiro, S. Japanese patent, JP 71–99504, *Chemical Abstracts* 80: 59716; see for 4-nitro-3-chlorophenyl acetic acid, Zhu, J.; Beugelmans, R.; Bourdet, S.; Chastanet, J.; Roussi, G. *J. Org. Chem.* 1995, 60, 6389; Beugelmans, R.; Bourdet, S.; Zhu, J. *Tetrahedron Lett.* 1995, 36, 1279). These carboxylic acids can be converted to the corresponding lower alkyl esters using any conventional esterification methods. Thus, if it is desired to produce the compound of formula V where one of $R^1$ and $R^2$ is nitro and the other is lower alkyl thio or perfluoro-lower alkyl thio, the corresponding compound where one of $R^1$ and $R^2$ is nitro and the other is chloro can be used as starting material. In this reaction, any conventional method of nucleophilic displacement of aromatic chlorine group with a lower alkyl thiol can be used (see for example, Singh, P.; Batra, M. S.; Singh, H, *J. Chem. Res.-S* 1985 (6), S204; Ono, M.; Nakamura, Y.; Sata, S.; Itoh, I, *Chem. Lett,* 1988, 1393; Wohrle, D.; Eskes, M.; Shigehara, K.; Yamada, A, Synthesis, 1993, 194; Sutter, M.; Kunz, W, U.S. Pat. No. 5,169,951). Once the compounds of formula V where one of $R^1$ and $R^2$ is nitro and the other is lower alkyl thio or perfluoro-lower alkyl thio are available, they can be converted to the corresponding compounds of formula V where one of $R^1$ and $R^2$ is nitro and the other is lower alkyl sulfonyl or perfluoro-lower alkyl sulfonyl using conventional oxidation procedures. If it is desired to produce compounds of formula V where one of $R^1$ and $R^2$ is amino and the other is lower alkyl thio or perfluoro-lower alkyl thio, the corresponding compound where one of $R^1$ and $R^2$ is nitro and the other is lower alkyl thio or perfluoro-lower alkyl thio can be used as starting materials. Any conventional method of reducing an aromatic nitro group to an amine can be utilized to effect this conversion. If it is desired to produce compounds of formula V where one of $R^1$ and $R^2$ is lower alkyl thio and the other is perfluoro-lower alkyl thio, the corresponding compound where one of $R^1$ and $R^2$ is amino and the other is lower alkyl thio or perfluoro-lower alkyl thio can be used as starting materials. Any conventional method of diazotizing aromatic amino group and reacting it in situ with the desired lower alkyl thiol can be utilized to effect this conversion. If it is desired to produce compounds of formula V where one of $R^1$ and $R^2$ is lower alkyl sulfonyl and the other is perfluoro-lower alkyl sulfonyl, the corresponding compounds where one of $R^1$ and $R^2$ is lower alkyl thio and the other is perfluoro-lower alkyl thio can be used as starting materials. Any conventional method of oxidizing an aromatic thio ether group to the corresponding sulfone group can be utilized to effect this conversion. If it is desired to produce compounds of formula V where one of $R^1$ and $R^2$ is halo and the other is lower alkyl thio or perfluoro-lower alkyl thio, the corresponding compounds where one of $R^1$ and $R^2$ is amino and the other is lower alkyl thio or perfluoro-lower alkyl thio can be used as starting materials. Any conventional method of diazotizing an aromatic amino group and conversion of it in situ to an aromatic halide can be utilized to effect this conversion. If it is desired to produce compounds of formula V where one of $R^1$ and $R^2$ is halo and the other is lower alkyl sulfonyl or perfluoro-lower alkyl sulfonyl, the corresponding compounds where one of $R^1$ and $R^2$ is halo and the other is lower alkyl thio or perfluoro-lower alkyl thio can be used as starting materials. Any conventional method of oxidizing an aromatic thio ether to the corresponding sulfone can be utilized to effect this conversion. If it is desired to produce compounds of various combinations of lower alkyl and perfluoro-lower alkyl groups of compounds of formula V, the corresponding halo substituted compounds of formula V can be used as starting materials. Any conventional method of converting an aromatic halo group to the corresponding alkyl group can be utilized to effect this conversion. If one wishes to prepare the compound formula V where one of $R^1$ and $R^2$ is nitro and the other is amino, the compound of formula V where one of $R^1$ and $R^2$ is nitro and other is chloro can be used as a starting material. The chloro substituent on the phenyl ring can be converted to an iodo substituent (see for example, Bunnett, J. F.; Conner, R. M.; *Org. Synth. Coll Vol V,* 1973, 478; Clark, J. H.; Jones, C. W. *J. Chem. Soc. Chem. Commun.* 1987, 1409), which in turn can be reacted with an azide transferring agent to form the corresponding azide (see for example, Suzuki, H.; Miyoshi, K.; Shinoda, M. *Bull. Chem. Soc. Jpn,* 1980, 53, 1765). This azide can then be reduced in a conventional manner to form the amine substituent by reducing it with commonly used reducing agent for converting azides to amines (see for example, Soai, K.; Yokoyama, S.; Ookawa, A. *Synthesis,* 1987, 48).

If it is desired to produce the compound of formula V where both $R^1$ and $R^2$ are cyano, this compound can be prepared as described hereinbefore from compounds where $R^1$ and $R^2$ are amino via diazotization to produce the diazonium salt followed by reaction with cyano group transferring agent. If it is desired to convert the commercially available compound to the compound of formula V where one of $R^1$ and $R^2$ is cyano and the other is not cyano, the compound of formula V where one of $R^1$ and $R^2$ is nitro and the other is chloro is used as a starting material. Using this starting material, the nitro is converted to the cyano and the halo is converted to any other desired $R^1$ and $R^2$ substituent as described hereinbefore.

If it is desired to produce the compound of formula V where both $R^1$ and $R^2$ are lower alkoxy lower alkyl sulfonyl, the compound of formula V where both $R^1$ and $R^2$ are amino can be used as starting material. Any conventional method of converting an aryl amino group to an aryl thio group may be utilized to effect this conversion. The thio groups can then be converted to lower alkoxy lower alkyl sulfonyl groups as described above.

If it is desired to produce the compound of formula V wherein one of $R^1$ or $R^2$ is a —C(O)—$OR^6$, this compound can be formed from the corresponding compound where $R^1$ and $R^2$ is an amino group by converting the amino group to a diazonium salt, reacting the diazonium salt with a hydrohalic acid to form the corresponding halide, and then reacting this halide with a Grignard reagent to produce the corresponding acid which can be esterified. On the other hand, if one wants to produce the compound of formula V where both $R^1$ and $R^2$ are carboxylic acid groups, this compound can be produced as described above from the corresponding compound of formula V where both $R^1$ and $R^2$ are amino groups. In the same manner, the amino groups in the compound of formula V can be converted to the corresponding compound where $R^1$ or R or both of $R^1$ and $R^2$ is $OR^5$ by simply reacting the amino group with sodium nitrate in sulfuric acid to convert the amino group to a hydroxy group and thereafter etherifying, if desired, the hydroxy group.

The substituents which form $R^1$ and $R^2$ can be added to the ring after condensation after the compound of formula XII with the compound of formula VIII to form the compound of formula I-a'. Hence, all of the reactions described to produce various substituents of $R^1$ and $R^2$ in the compound of formula I can be carried out on the compound of formula I-a' after its formation by the reaction of compound of formula XII and VIII to form the compound of formula I-a'.

In the first step of this Reaction Scheme, the alkyl halide of formula VI is reacted with the compound of formula V, to produce the compound of formula VII. In this reaction, if in the compounds of formula V, $R^1$ or $R^2$ is an amino group, such amino group(s) have to be protected before carrying out the alkylation reaction with the alkyl halide of formula VI. The amino group can be protected with any conventional acid removable group (see for example, for t-butyloxycarbonyl group see, Bodanszky, M. *Principles of Peptide Chemistry*, Springer-Verlag, N.Y., 1984, p 99). The protecting group has to be removed from the amino groups after preparing the corresponding amine protected compounds of formula I-a' to obtain the corresponding amines. The compound of formula V is an organic acid derivative or the organic acid having an alpha carbon atom and the compound of formula VI is an alkyl halide so that alkylation occurs at the alpha carbon atom of this carboxylic acid. This reaction is carried out by any conventional means of alkylation of the alpha carbon atom of a carboxylic acid or a lower alkyl ester of a carboxylic acid. Generally, in these alkylation reactions any alkyl halide is reacted with the anion generated from any acetic acid ester or the dianion of the acid. The anion can be generated by using a strong organic base such as lithium diisopropylamide, n-butyl lithium as well as other organic lithium bases. In carrying out this reaction, low boiling ether solvents are utilized such as tetrahydrofuran at low temperatures from −80° C. to about −10° C. being preferred. However any temperature from −80° C. to room temperature can be used.

The compound of formula VII can be converted to the compound of formula XII by any conventional procedure to convert a carboxylic acid ester to an acid. The compound of formula XII is condensed with the compound of formula VIII via conventional peptide coupling to produce the compound of formula I-a'. In carrying out this reaction, any conventional method of condensing a primary amine with a carboxylic acid can be utilized to effect this conversion. The required amino heteroaromatic compounds of formula VIII are commercially available or can be prepared from the reported literature. The heteroaromatics of formula VIII, wherein one of the substitutions is —$(CH_2)_n COOR^6$, where n=0, 1, 2, 3, or 4 can be prepared from the corresponding carboxylic acid. Any conventional carbon homologation methods to convert a lower carboxylic acid to its higher homologs, (see for example, Skeean, R. W.; Goel, O. P. *Synthesis*, 1990, 628) which then can be converted to the corresponding lower alkyl esters using any conventional esterification methods. The heteroaromatics of formula VIII, wherein one of the claimed substitutions is —$(CH_2)_n OR^7$, where n=0, 1, 2, 3, or 4 can be prepared from the corresponding carboxylic acid. Any conventional carbon homologation methods to convert a lower carboxylic acid to its higher homologs, which then can be converted to the corresponding alcohols using any conventional ester reduction methods. The heteroaromatics of formula VIII, wherein one of the substituents is —$C(O)C(O)OR^7$, or —$C(O)$—$OR^6$, can be prepared from the corresponding halogen. Any conventional acylation method to convert an aromatic or heteroaromatic halogen to its oxoacetic acid lower ester or ester derivative (see for example, Hayakawa, K.; Yasukouchi, T.; Kanematsu, K. *Tetrahedron Lett*, 1987, 28, 5895) can be utilized.

The compound of formula VII has an asymmetric carbon atom through which the group —$CH_2R^3$ and the acid amide substituents are connected. In accordance with this invention, the preferred stereoconfiguration of this group is R.

If it is desired to produce the R or the S isomer of the compound of formula I, this compound can be separated into these isomers by any conventional chemical means. Among the preferred chemical means is to react the compound of formula XII with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula XII is reacted with the optically active base in an inert organic solvent medium to produce salts of the optically active amine with both the R and S isomers of the compound of formula XII. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula XII in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula XII which is produced by this method of resolution is carried out throughout the entire reaction scheme to produce the desired R or S isomer of formula I. The separation of R and S isomers can also be achieved using an enzymatic ester hydrolysis of any lower alkyl esters corresponding to the compound of the formula XII (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula XII is via the formation of corresponding diastereomeric esters or amides. These diastereomeric esters or amides can be prepared by coupling the carboxylic acids of the formula XII with a chiral alcohol or a chiral amine. This reaction can be carried out using any conventional method of coupling a carboxylic acid with an alcohol or an amine. The corresponding diastereomers of compounds of the formula XII can then be separated using any conventional separation methods. The resulting pure diastereomeric esters or amides can then be hydrolyzed to yield the corresponding pure R or S isomers.

The hydrolysis reaction can be carried out using conventional known methods to hydrolyze an ester or an amide without racemization.

All of the compounds of formula I which include the compounds set forth in the Examples activated glucokinase in vitro by the procedure of Example A. In this manner, they increase the flux of glucose metabolism which causes increased insulin secretion. Therefore, the compounds of formula I are glucokinase activators useful for increasing insulin secretion.

The following compounds were tested and found to have excellent glucokinase activator in vivo activity when administered orally in accordance with the assay described in Example B:

3-Cyclopentyl-2-(4-methanesulfonyl-phenyl)-N-thiazol-2-yl-propionamide

3-Cyclopentyl-N-thiazol-2-yl-2-(4-trifluoromethoxy-phenyl)-propionamide

3-Cyclopentyl-N-thiazol-2-yl-2-(4-trifluoromethanesulfonyl-phenyl)-propionamide

3-Cyclopentyl-2(R)-(3,4-dichloro-phenyl)-N-pyridin-2-yl-propionamide

6-[3-Cyclopentyl-2(R)-(3,4-dichloro-phenyl)-propionylamino]-nicotinic acid methyl ester N-(5-Chloro-pyridin-2-yl)-3-cyclopentyl-2(R)-(3,4-dichloro-phenyl)-propionamide 3-Cyclopentyl-N-pyridin-2-yl-2-(4-trifluoromethanesulfonyl-phenyl)-propionamide 3-Cyclopentyl-N-(5-methyl-pyridin-2-yl)-2-(4-trifluoromethanesulfonyl-phenyl)-propionamide 3-Cyclopentyl-2(R)-(3,4-dichloro-phenyl)-N-(5-hydroxymethyl-pyridin-2-yl) propionamide 6-[3-Cyclopentyl-2-(4-trifluoromethanesulfonyl-phenyl)-propionylamino]-nicotinic acid methyl ester 3-Cyclopentyl-2-(3-fluoro-4-trifluoromethyl-phenyl)-N-pyridin-2-yl-propionamide 3-Cyclopentyl-2-(4-methanesulfonyl-3-nitrophenyl)-N-pyridin-2-yl-propionamide 2-(3-Bromo-4-methanesulfonyl-phenyl)-3-cyclopentyl-N-pyridin-2-yl-propionamide 2-(3-Cyano-4-methanesulfonyl-phenyl)-3-cyclopentyl-N-pyridin-2-yl-propionamide 2-(4-Chloro-3-nitro-phenyl)-3-cyclopentyl-N-pyridin-2-yl-propionamide 2-(3-Chloro-4-methanesulfonyl-phenyl)-3-cyclopentyl-N-pyridin-2-yl-propionamide 1. N-(5-Bromo-pyridin-2-yl)-2-(3-chloro-4-methanesulfonyl-phenyl)-3-cyclopentyl-propionamide 2-[3-Chloro-4-methanesulfonyl-phenyl]-3-cyclopentyl-N-thiazol-2-yl-propionamide (2R)-3-Cyclopentyl-2-(4-methanesulfonylphenyl)-N-thiazol-2-yl-propionamide 2-(3-Bromo-4-methanesulfonyl-phenyl)-3-cyclopentyl-N-thiazol-2-yl-propionamide 2-(3-Cyano-4-methanesulfonyl-phenyl)-3-cyclopentyl-N-thiazol-2-yl-propionamide 3-Cyclopentyl-2-(4-ethanesulfonyl-phenyl)-N-thiazol-2-yl-propionamide 3-Cyclopentyl-2-(4-methanesulfonyl-3-trifluoromethyl-phenyl)-N-thiazol-2-yl-propionamide N-(5-Bromo-pyridin-2-yl)-2(R)-(3-chloro-4-methanesulfonyl-phenyl)-3-cyclopentyl-propionamide 3-Cyclopentyl-2-(4-methoxymethanesulfonyl-phenyl)-N-thiazol-2-yl-propionamide 3-Cyclopentyl-2(R)-(4-methanesulfonyl-phenyl)-N-(4-methyl-thiazol-2-yl)-propionamide 3-Cyclopentyl-2 (R)-(4-methanesulfonyl-phenyl)-N-(5-methyl-thiazol-2-yl)-propionamide N-(5-Chloro-thiazol-2-yl)-3-cyclopentyl-2-(4-methanesulfonyl-phenyl)-propionamide N-(5-Chloro-thiazol-2-yl)-3-cyclopentyl-2(R)-(4-methanesulfonyl-phenyl)-propionamide N-(5-Bromo-thiazol-2-yl)-3-cyclopentyl-2(R)-(4-methanesulfonyl-phenyl)-propionamide 2(R)-(3-Chloro-4-methanesulfonyl-phenyl)-3-cyclopentyl-N-(4-methyl-thiazol-2-yl)-propionamide 2(R)-(3-Chloro-4-methanesulfonyl-phenyl)-3-cyclopentyl-N-(5-methyl-pyridin-2-yl)-propionamide 2-(3-Chloro-4-methanesulfonyl-phenyl)-3-cyclopentyl-N-pyrimidin-4-yl-propionamide 2(R)-(3-Chloro-4-methanesulfonyl-phenyl)-3-cyclopentyl-N-pyrimidin-4-yl-propionamide 2-(3-Chloro-4-methanesulfonyl-phenyl)-3-cyclopentyl-N-(2-methyl-pyrimidin-4-yl)-propionamide 2(R)-(3-Chloro-4-methanesulfonyl-phenyl)-3-cyclopentyl-N-(2-methyl-pyrimidin-4-yl)-propionamide 2-(3-Chloro-4-methanesulfonyl-phenyl)-3-cyclopentyl-N-pyrazin-2-yl-propionamide 2(R)-(3-Chloro-4-methanesulfonyl-phenyl)-3-cyclopentyl-N-pyrazin-2-yl-propionamide 2-(3-Bromo-4-methanesulfonyl-phenyl)-3-cyclopentyl-N-pyrimidin-4-yl-propionamide 2-(3-Bromo-4-methanesulfonyl-phenyl)-3-cyclopentyl-N-(2-methyl-pyrimidin-4-yl)-propionamide 2-(3-Bromo-4-methanesulfonyl-phenyl)-3-cyclopentyl-N-pyrazin-2-yl-propionamide 3-Cyclopentyl-2-(4-methanesulfonyl-3-trifluoromethyl-phenyl)-N-pyrimidin-4-yl-propionamide 3-Cyclopentyl-2-(4-methanesulfonyl-3-trifluoromethyl-phenyl)-N-pyrazin-2-yl-propionamide 3-Cyclopentyl-2-(4-methanesulfonyl-3-trifluoromethyl-phenyl)-N-(2-methyl-pyrimidin-4-yl)-propionamide 3-Cyclopentyl-2(R)-(4-methanesulfonyl-3-trifluoromethyl-phenyl)-N-pyrimidin-4-yl-propionamide 3-Cyclopentyl-2(R)-(4-methanesulfonyl-3-trifluoromethyl-phenyl)-N-pyrazin-2-yl-propionamide 3-Cyclopentyl-2(R)-(4-methanesulfonyl-3-trifluoromethyl-phenyl)-N-(2-methyl-pyrimidin-4-yl)-propionamide This invention will be better understood from the following examples, which are for purposes of illustration and are not intended to limit the invention defined in the claims which follow thereafter.

EXAMPLE 1

3-Cyclopentyl-2-(3,4-dichlorophenyl)-N-thiazol-2-yl-propionamide

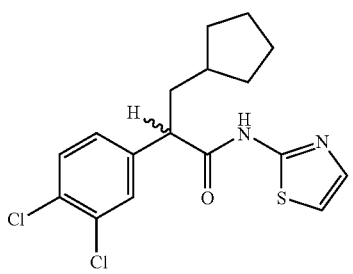

A solution of 3-cyclopentyl-2-(3,4-dichlorophenyl)-propionic acid (prepared as in Example 38A, 2.0 g, 6.96 mmol), benzotriazol-1-yloxy-tris(dimethylamino)phosphonium hexafluorophosphate (4.62 g, 10.44 mmol), and 2-aminothiazole (1.05 g, 10.44 mmol) in methylene chloride (50 mL) at 25° C. was treated with triethylamine (2.9 mL, 20.88 mmol). The reaction mixture was stirred for 14 h. The reaction mixture was then diluted with water (10 mL) and extracted with methylene chloride (3×10 mL). The combined organic layers were sequentially washed with water (1×10 mL), a 1N aqueous sodium hydroxide solution (1×10 mL), a 1N aqueous hydrochloric acid solution (1×10 mL), and a saturated aqueous sodium chloride solution (1×10 mL). The organic layer was dried over sodium sulfate, filtered, and concentrated in vacuo. Flash chromatography (Merck Silica gel 60, 230–400 mesh, 80/20 hexanes/ethyl acetate) afforded 3-cyclopentyl-2-(3,4-dichlorophenyl)-N-thiazol-2-yl-propionamide (2.48 g, 96%) as a white solid: mp 143.5–145.5° C.; EI-HRMS m/e calcd for $C_{17}H_{18}Cl_2N_2OS$ (M+) 368.0516, found 368.0516.

In an analogous manner, there were obtained:
a) From 3-cyclopentyl-2-(3,4-dichlorophenyl)-propionic acid and 2-(amino-thiazol-4-yl)-oxo-acetic acid ethyl ester: {2-[3-Cyclopentyl-2-(3,4-dichloro-phenyl)-propionylamino]-thiazol-4-yl}-oxo-acetic acid ethyl ester as a white solid: mp 134–136° C.; FAB-HRMS m/e calcd for $C_{21}H_{22}Cl_2N_2O_4S$ (M+H)+ 469.0755, found 469.0746.
b) From 3-cyclopentyl-2-(3,4-dichlorophenyl)-propionic acid and 2-(amino-thiazol-5-yl)-oxo-acetic acid ethyl ester: {2-[3-Cyclopentyl-2-(3,4-dichlorophenyl)-propionylamino]-thiazol-5-yl}-oxo-acetic acid ethyl ester as a white solid: mp 129–131° C.; FAB-HRMS m/e calcd for $C_{21}H_{22}Cl_2N_2O_4S$ (M+H)+469.0755, found 469.0765.
c) From 3-cyclopentyl-2-(3,4-dichlorophenyl)-propionic acid and (2-amino-thiazol-4-yl)-acetic acid ethyl ester: {2-[3-Cyclopentyl-2-(3,4-dichlorophenyl)-propionylamino]-thiazol-4-yl}-acetic acid ethyl ester as a yellow solid: mp 138–139° C.; FAB-HRMS m/e calcd for $C_{21}H_{24}Cl_2N_2O_3S$ (M+H)+ 455.0963, found 455.0960.
d) From 3-cyclopentyl-2-(3,4-dichlorophenyl)-propionic acid and 2-amino-5-methylthiazole: 3-Cyclopentyl-2-(3,4-dichlorophenyl)-N-(5-methyl-thiazol-2-yl)-propionamide as a white solid: mp 142–143° C.; EI-HRMS m/e calcd for $C_{18}H_{20}Cl_2N_2OS$ (M+) 382.0673, found 382.0679.
e) From 3-cyclopentyl-2-(3,4-dichlorophenyl)-propionic acid and 2-amino-4-methylthiazole: 3-Cyclopentyl-2-(3,4-dichlorophenyl)-N-(4-methyl-thiazol-2-yl)-propionamide as a white foam: mp 151–152° C.; FAB-HRMS m/e calcd for $C_{18}H_{20}Cl_2N_2OS$ (M+H)+ 383.0751, found 383.0758.
f) From 3-cyclopentyl-2-(3,4-dichlorophenyl)-propionic acid and 2-amino thiazole-4-carboxylic acid ethyl ester: 2-[3-Cyclopentyl-2-(3,4-dichlorophenyl)-propionylamino]-thiazole-4-carboxylic acid ethyl ester as a white solid: mp 104–107° C.; FAB-HRMS m/e calcd for $C_{20}H_{22}Cl_2N_2O_3S$ (M+H)+ 441.0807, found 441.0808.
g) From 3-cyclopentyl-2-(3,4-dichlorophenyl)-propionic acid and 2-amino-thiazole-5-carboxylic acid ethyl ester: 2-[3-Cyclopentyl-2-(3,4-dichlorophenyl)-propionylamino]-thiazole-5-carboxylic acid ethyl ester as a light yellow solid: mp 136–137° C.; FAB-HRMS m/e calcd for $C_{20}H_{22}Cl_2N_2O_3S$ (M+H)+ 441.0807, found 441.0803.
h) From 3-cyclopentyl-2-(3,4-dichlorophenyl)-propionic acid and 2-amino-5-nitrothiazole: 3-Cyclopentyl-2-(3,4-dichlorophenyl)-N-(5-nitro-thiazol-2-yl)-propionamide as an orange solid: mp 67–71° C.; FAB-HRMS m/e calcd for $C_{17}H_{17}Cl_2N_3O_3S$ (M+H)+ 414.0446, found 414.0442.
i) From 3-cyclopentyl-2-(3,4-dichlorophenyl)-propionic acid and 2-amino-thiazole-4-carboxylic acid amide: 2-[3-Cyclopentyl-2-(3,4-dichlorophenyl)-propionylamino]-thiazole-4-carboxylic acid amide as a light orange solid: mp 120–122° C.; EI-HRMS m/e calcd for $C_{18}H_{19}Cl_2N_3O_2S$ (M+) 411.0575, found 411.0572.

EXAMPLE 2

2-(4-Bromo-phenyl)-3-cyclopentyl-N-thiazol-2-yl-propionamide

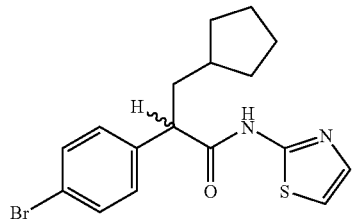

A solution of diisopropylamine (7.7 mL, 54.88 mmol) in dry tetrahydrofuran (23 mL) and 1,3-dimethyl-3,4,5,6-tetrahydro-2(1H)-pyrimidinone (10 mL) was cooled to −78° C. under nitrogen and then treated with a 2.5M solution of n-butyllithium in hexanes (22.0 mL, 54.88 mmol). The resulting reaction mixture was stirred at −78° C. for 30 min and then treated dropwise with a solution of 4-bromophenylacetic acid (5.62 g, 26.13 mmol) in dry tetrahydrofuran (23 mL) and 1,3-dimethyl-3,4,5,6-tetrahydro-2(1H)-pyrimidinone (10 mL). The reaction mixture turned dark in color and was allowed to stir at −78° C. for 1 h, at which time, a solution of iodomethylcyclopentane (5.76 g, 27.44 mmol) in a small amount of dry tetrahydrofuran was added dropwise. The reaction mixture was allowed to warm to 25° C. where it was stirred for 24 h. The reaction mixture was quenched with water and then concentrated in vacuo to remove tetrahydrofuran. The aqueous residue was acidified using a 10% aqueous hydrochloric acid solution. The resulting aqueous layer was extracted with ethyl acetate (2×100 mL). The combined organic extracts were dried over sodium sulfate, filtered, and concentrated in vacuo. Flash chromatography (Merck Silica gel 60, 230–400 mesh, 3/1 hexanes/ethyl acetate) afforded 2-(4-bromo-phenyl)-3-cyclopentyl-propionic acid (3.88 g, 50%) as a light yellow solid: mp 91–93° C.; EI-HRMS m/e calcd for $C_{14}H_{17}BrO_2$ (M+) 296.0412, found 296.0417.

A solution of 2-(4-bromo-phenyl)-3-cyclopentyl-propionic acid (1.01 g, 3.39 mmol) in methylene chloride (8.5 mL) was treated with 2 drops of dry N,N-dimethylformamide. The reaction mixture was cooled to 0° C. and then treated with oxalyl chloride (3 mL, 33.98 mmol). The reaction mixture was stirred at 0° C. for 10 min and then stirred at 25° C. for 15 h. The reaction mixture was concentrated in vacuo. The resulting yellow oil was dissolved in a small amount of methylene chloride and slowly added to a cooled solution (0° C.) of 2-aminothiazole (680.6 mg, 6.79 mmol) and N,N-diisopropylethylamine (1.2 mL, 6.79 mmol) in methylene chloride (17 mL). The resulting reaction mixture was stirred at 0° C. for 10 min and then at 25° C. for 15 h. The reaction mixture was concentrated in vacuo to remove methylene chloride. The resulting residue was diluted with ethyl acetate (200 mL). The organic phase was washed with a 10% aqueous hydrochloric acid solution (2×100 mL), washed with a saturated aqueous sodium bicarbonate solution (2×100 mL), and washed with a saturated aqueous sodium chloride solution (1×100 mL). The organic layer was then dried over sodium sulfate, filtered, and concentrated in vacuo to afford 2-(4-bromo-phenyl)-3-cyclopentyl-N-thiazol-2-yl-propionamide (1.23 g, 95%) as an orange solid which was used in subsequent reactions without further purification. An analytical sample was recrystallized from ethyl acetate to provide a cream solid: mp 201–202° C.; EI-HRMS m/e calcd for $C_{17}H_{19}BrN_2OS$ ($M^+$) 378.0401, found 378.0405.

EXAMPLE 3

3-Cyclopentyl-2-(4-methanesulfonyl-phenyl)-N-thiazol-2-yl-propionamide

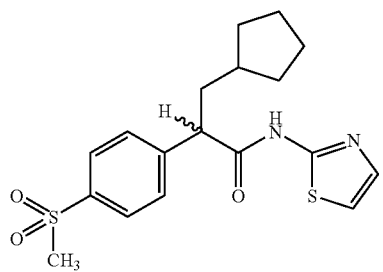

A solution of diisopropylamine (3.3 mL, 23.5 mmol) in dry tetrahydrofuran (50 mL) and 1,3-dimethyl-3,4,5,6-tetrahydro-2(1H)-pyrimidinone (10 mL) was cooled to −78° C. under nitrogen and then treated with a 10M solution of n-butyllithium in hexanes (2.35 mL, 23.5 mmol). The yellow reaction mixture was stirred at −78° C. for 30 min and then treated dropwise with a solution of 4-methylsulfonylphenylacetic acid (2.40 g, 11.2 mmol) in a small amount of dry tetrahydrofuran. After approximately one-half of the 4-methylsulfonylphenylacetic acid in dry tetrahydrofuran was added, a precipitate formed. Upon further addition of the remaining 4-methylsulfonylphenylacetic acid in dry tetrahydrofuran, the reaction mixture became thick in nature. After complete addition of the 4-methylsulfonylphenylacetic acid in dry tetrahydrofuran, the reaction mixture was very thick and became difficult to stir. An additional amount of dry tetrahydrofuran (20 mL) was added to the thick reaction mixture, and the reaction mixture was then stirred at −78° C. for 45 min, at which time, a solution of iodomethylcyclopentane (2.35 g, 11.2 mmol) in a small amount of dry tetrahydrofuran was added dropwise. The reaction mixture was allowed to warm to 25° C. where it was stirred for 15 h. The reaction mixture was quenched with water (100 mL), and the resulting yellow reaction mixture was concentrated in vacuo to remove tetrahydrofuran. The aqueous residue was acidified to pH=2 using concentrated hydrochloric acid. The aqueous layer was extracted with ethyl acetate. The organic phase was dried over magnesium sulfate, filtered, and concentrated in vacuo. Flash chromatography (Merck Silica gel 60, 230–400 mesh, 1/3 hexanes/ethyl acetate) afforded 3-cyclopentyl-2-(4-methanesulfonyl-phenyl)propionic acid (1.80 g, 52%) as a white solid: mp 152–154° C.; EI-HRMS m/e calcd for $C_{15}H_{20}O_4S$ ($M^+$) 296.1082, found 296.1080.

A solution of 3-cyclopentyl-2-(4-methanesulfonyl-phenyl)propionic acid (4.91 g, 16.56 mmol) and triphenylphosphine (6.52 g, 24.85 mmol) in methylene chloride (41 mL) was cooled to 0° C. and then treated with N-bromosuccinimide (5.01 g, 28.16 mmol) in small portions. The reaction mixture color changed from light yellow to a darker yellow then to brown. After the complete addition of N-bromosuccinimide, the reaction mixture was allowed to warm to 25° C. over 30 min. The brown reaction mixture was then treated with 2-aminothiazole (4.98 g, 49.69 mmol). The resulting reaction mixture was stirred at 25° C. for 19 h. The reaction mixture was then concentrated in vacuo to remove methylene chloride. The remaining black residue was diluted with a 10% aqueous hydrochloric acid solution (400 mL) and then extracted with ethyl acetate (3×200 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate then 1/1 hexanes/ethyl acetate) afforded 3-cyclopentyl-2-(4-methanesulfonyl-phenyl)-N-thiazol-2-yl-propionamide (4.49 g, 72%) as a white solid: mp 216–217° C.; EI-HRMS m/e calcd for $C_{18}H_{22}N_2O_3S_2$ ($M^+$) 378.1072, found 378.1071.

In an analogous manner, there were obtained:

a) From 3-cyclopentyl-2-(4-methanesulfonyl-phenyl)propionic acid and 2-aminothiazole-4-carboxylic acid methyl ester: 2-[3-Cyclopentyl-2-(4-methanesulfonyl-phenyl)-propionylamino]-thiazole-4-carboxylic acid methyl ester as a tan solid: mp 126–128° C.; EI-HRMS m/e calcd for $C_{20}H_{24}N_2O_5S_2$ ($M^+$) 436.1127, found 436.1119.

b) From 3-cyclopentyl-2-(4-methanesulfonyl-phenyl)propionic acid and 2-aminothiazole-4-carboxylic acid ethyl ester: 2-[3-Cyclopentyl-2-(4-methanesulfonyl-phenyl)-propionylamino]-thiazole-4-carboxylic acid ethyl ester as a light yellow solid: mp 101–103° C.; EI-HRMS m/e calcd for $C_{21}H_{26}N_2O_5S_2$ ($M^+$) 450.1283, found 450.1284.

c) From 3-cyclopentyl-2-(4-methanesulfonyl-phenyl)propionic acid and methyl 2-amino-4-thiazoleacetate: {2-[3-Cyclopentyl-2-(4-methanesulfonyl-phenyl)-propionylamino]-thiazol-4-yl}-acetic acid methyl ester as a yellow solid: mp 63–65° C.; EI-HRMS m/e calcd for $C_{21}H_{26}N_2O_5S_2$ ($M^+$) 450.1283, found 450.1294.

d) From 3-cyclopentyl-2-(4-methanesulfonyl-phenyl)propionic acid and ethyl 2-amino-4-thiazoleacetate: {2-[3-Cyclopentyl-2-(4-methanesulfonyl-phenyl)-propionylamino]-thiazol-4-yl}-acetic acid ethyl ester as a light yellow solid: mp 61–63° C.; EI-HRMS m/e calcd for $C_{22}H_{28}N_2O_5S_2$ ($M^+$) 464.1440, found 464.1431.

EXAMPLE 4

2-(4-Amino-phenyl)-3-cyclopentyl-N-thiazol-2-yl-propionamide

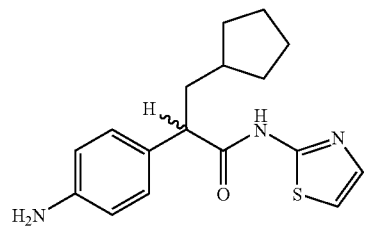

A solution of 3-cyclopentyl-2-(4-nitro-phenyl)-N-thiazol-2-yl-propionamide (prepared as in Example 22, 345 mg, 1.0 mmol) in ethyl acetate (100 mL) was treated with 10% palladium on activated carbon (34.5 mg). The reaction mixture was stirred under hydrogen gas at 60 psi at 25° C. for 6 h. The catalyst was then filtered off through a pad of celite, which was washed well with ethyl acetate. The resulting filtrate was concentrated in vacuo to give 2-(4-amino-phenyl)-3-cyclopentyl-N-thiazol-2-yl-propionamide (288.3 mg, 91.4%) as a yellow solid: mp 102–107° C.; EI-HRMS m/e calcd for $C_{17}H_{21}N_3OS$ (M$^+$) 315.1405, found 315.1401.

EXAMPLE 5

2-(3-Amino-phenyl)-3-cyclopentyl-N-thiazol-2-yl-propionamide

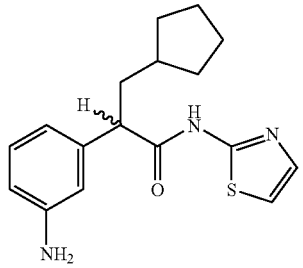

A solution of (3-nitro-phenyl)-acetic acid (5.0 g, 27.6 mmol) in methanol (50 mL) was treated with a catalytic amount of sulfuric acid. The reaction mixture was heated under reflux for 48 h. The reaction was then concentrated in vacuo. The residue was dissolved in methylene chloride (50 mL) and washed with a saturated aqueous sodium bicarbonate solution (2×25 mL), water (1×50 mL), and a saturated aqueous sodium chloride solution (1×50 mL). The combined organic layers were dried over sodium sulfate, filtered, and concentrated in vacuo to give (4-nitro-phenyl)-acetic acid methyl ester (5.27 g, 97.9%) as a pale yellow solid: mp 29–30° C.; EI-HRMS m/e calcd for $C_9H_9NO_4$ (M$^+$) 195.0531, found 195.0532.

A solution of freshly prepared lithium diisopropylamide (43.3 mL of a 0.3M stock solution, 12.99 mmol) cooled to −78° C. was treated with (3-nitro-phenyl)-acetic acid methyl ester (2.45 g, 12.56 mmol) in tetrahydrofuran/1,3-dimethyl-3,4,5,6-tetrahydro-2(1H)-pyrimidinone (32 mL, 3:1). The resulting solution was stirred at −78° C. for 45 min. Iodomethylcyclopentane (2.78 g, 13.23 mmol) was then added in 1,3-dimethyl-3,4,5,6-tetrahydro-2(1H)-pyrimidinone (2.78 mL), and the mixture was stirred at −78° C. for 3 h. The reaction was warmed to 25° C. and was stirred at 25° C. for 16 h. The reaction mixture was then quenched by the dropwise addition of a saturated aqueous ammonium chloride solution (25 mL) and was concentrated in vacuo. The residue was diluted with water (50 mL) and extracted with ethyl acetate (3×50 mL). The combined organic layers were washed with a saturated aqueous lithium chloride solution (2×25 mL), dried over sodium sulfate, filtered, and concentrated in vacuo. Flash chromatography (Merck Silica gel 60, 230–400 mesh 80/20 hexanes/ethyl acetate) afforded 3-cyclopentyl-2-(3-nitro-phenyl)-propionic acid methyl ester (1.63 g, 46.8%) as pale yellow oil: EI-HRMS m/e calcd for $C_{15}H_{19}NO_4$ (M$^+$) 277.1314, found 277.1317.

A solution of 3-cyclopentyl-2-(3-nitro-phenyl)-propionic acid methyl ester (0.55 g, 2.0 mmol) in tetrahydrofuran/water (10 mL, 3:1) was treated with lithium hydroxide (185 mg, 4.40 mmol). The reaction was stirred at 25° C. for 48 h. The tetrahydrofuran was then removed in vacuo. The residue was diluted with water (25 mL) and extracted with ether (1×20 mL). The aqueous layer was acidified to pH=2 with a 3N aqueous hydrochloric acid solution. The product was extracted into methylene chloride (3×25 mL). The combined organic layers were washed with a saturated aqueous sodium chloride solution (2×25 mL), dried over sodium sulfate, filtered, and concentrated in vacuo to give 3-cyclopentyl-2-(3-nitro-phenyl)-propionic acid (0.48 g, 91.9%) as a tan solid: mp 95–99° C.; EI-HRMS m/e calcd for $C_{14}H_{17}NO_4$ (M$^+$) 263.1157, found 263.1156.

A solution of 3-cyclopentyl-2-(3-nitro-phenyl)-propionic acid (432 mg, 1.64 mmol) in methylene chloride (16 mL) was cooled to 0° C. and then treated with a 2.0M solution of oxalyl chloride in methylene chloride (0.90 mL, 1.80 mmol) and a few drops of N,N-dimethylformamide. The reaction mixture was stirred at 0° C. for 15 min and at 25° C. for 1.2 h. The reaction mixture was then treated with a solution of 2-aminothiazole (361.4 mg, 3.61 mmol) in tetrahydrofuran (16 mL) and N,N-diisopropylethylamine (0.70 mL, 3.93 mmol). The reaction mixture was stirred at 25° C. for 6 h. At this time, the reaction was concentrated in vacuo. Flash chromatography (Merck Silica gel 60, 230–400 mesh 70/30 hexanes/ethyl acetate) afforded 3-cyclopentyl-2-(nitrophenyl)-N-thiazol-2-yl-propionamide (409.3 mg, 72.2%) as a tan solid: mp 171–174° C.; EI-HRMS m/e calcd for $C_{17}H_{19}N_3O_3S$ (M$^+$) 345.1147, found 345.1153.

A solution of 3-cyclopentyl-2-(nitrophenyl)-N-thiazol-2-yl-propionamide (327.8 mg, 0.95 mmol) in ethyl acetate (25 mL) was treated with 10% palladium on activated carbon. The reaction mixture was stirred under hydrogen gas at 60 psi at 25° C. for 3 h. The catalyst was then filtered off through a pad of celite, which was washed well with ethyl acetate. The resulting filtrate was concentrated in vacuo to give 2-(3-amino-phenyl)-3-cyclopentyl-N-thiazol-2-yl-propionamide (310 mg, 100%) as a white solid: mp 158–160° C.; EI-HRMS m/e calcd for $C_{17}H_{21}N_3OS$ (M$^+$) 315.1405, found 315.1405.

EXAMPLE 6

2-(3-Chloro-phenyl)-3-cyclopentyl-N-thiazol-2-yl-propionamide

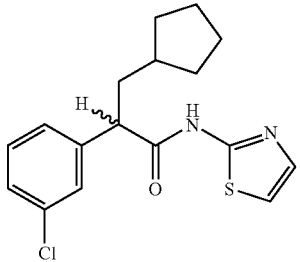

(3-Chloro-phenyl)-acetic acid (6.03 g, 0.03 mol) was dissolved in ethanol (37.7 mL) and treated with a catalytic amount of sulfuric acid. The reaction mixture was heated under reflux for 12 h. The reaction was concentrated in vacuo. Flash chromatography (Merck Silica gel 60, 230–400 mesh, 50/50 hexanes/ethyl acetate) afforded (3-chloro-phenyl)-acetic acid ethyl ester (6.10 g, 86.8%) as a clear oil: EI-HRMS m/e calcd for $C_{10}H_{11}ClO_2$(M$^+$) 198.0448, found 198.0442.

A solution of freshly prepared lithium diisopropylamide (23 mL of 0.31M stock solution, 7.13 mmol) cooled to −78° C. was treated with (3-chloro-phenyl)-acetic acid ethyl ester (1.28 g, 6.48 mmol) in tetrahydrofuran/hexamethylphosphoramide (16.1 mL, 3:1). The resulting solution was stirred at −78° C. for 45 min. At this time, the reaction was treated with a solution of iodomethylcyclopentane (1.50 g, 7.13 mmol) in hexamethylphosphoramide (1 mL). The reaction mixture was stirred at −78° C. for 4 h. The reaction was warmed to 25° C. and stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The combined organic layers were dried over sodium sulfate, filtered, and concentrated in vacuo. Flash chromatography (Merck Silica gel 60, 230–400 mesh, 75/25 hexanes/ethyl acetate) afforded 2-(3-chloro-phenyl)-3-cyclopentyl-propionic acid ethyl ester (1.70 g, 93%) as a yellow oil: EI-HRMS m/e calcd for $C_{16}H_{21}ClO_2$ ($M^+$) 280.1230, found 280.1238.

A mixture of 2-(3-chloro-phenyl)-3-cyclopentyl-propionic acid ethyl ester (1.70 g, 6.05 mmol) and methyl urea (673 mg, 9.08 mmol) in a solution of magnesium methoxide in methanol (7.4 wt %, 17.3 mL, 12.1 mmol) was heated under reflux at 100° C. for 6 h. The reaction mixture was then concentrated in vacuo. Flash chromatography (Merck Silica gel 60, 230–400 mesh, 75/25 hexanes/ethyl acetate) afforded 1-[2-(3-chloro-phenyl)-3-cyclopentyl-propionyl]-3-methyl-urea (149.1 mg, 8%) as a white solid: mp 52–55° C.; EI-HRMS m/e calcd for $C_{16}H_{21}ClN_2O_2$ ($M^+$) 308.1292, found 308.1287. The methyl ester of the starting material was recovered from the reaction mixture due to transesterification.

A mixture of 2-(3-chloro-phenyl)-3-cyclopentyl-propionic acid methyl ester (113 mg, 0.42 mmol) and 2-aminothiazole (84 mg, 0.84 mmol) in a solution of magnesium methoxide in methanol (7.4 wt %, 2.4 mL, 1.69 mmol) was heated under reflux at 100° C. for 20 h. The reaction mixture was then concentrated in vacuo. Flash chromatography (Merck Silica gel 60, 230–400 mesh, 80/20 hexanes/ethyl acetate) afforded 2-(3-chloro-phenyl)-3-cyclopentyl-N-thiazol-2-yl-propionamide (87 mg, 53%) as a white solid: mp 138.8–141.2° C.; EI-HRMS m/e calcd for $C_{17}H_{19}ClN_2OS$ ($M^+$) 334.0906, found 334.0907.

EXAMPLE 7

2-(4-Chloro-phenyl)-3-cyclopentyl-N-thiazol-2-yl-propionamide

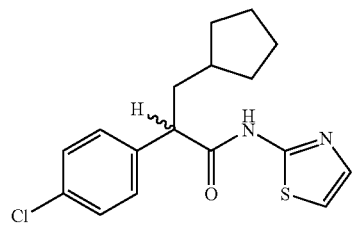

A solution of (4-chloro-phenyl)-acetic acid (6.29 g, 0.03 mol) in ethanol (38.4 mL) was treated with a catalytic amount of sulfuric acid. The reaction mixture was heated under reflux for 12 h. The reaction was then concentrated in vacuo. Flash chromatography (Merck Silica gel 60, 230–400 mesh, 50/50 hexanes/ethyl acetate) afforded (4-chloro-phenyl)-acetic acid ethyl ester (6.45 g, 88%) as a pale yellow solid: mp 39–41° C.; EI-HRMS m/e calcd for $C_{10}H_{11}ClO_2$ ($M^+$) 198.0448, found 198.0452.

A solution of freshly prepared lithium diisopropylamide (23.0 mL of 0.31M stock solution, 7.13 mmol) cooled to −78° C. was treated with (4-chloro-phenyl)-acetic acid ethyl ester (1.28 g, 6.48 mmol) in tetrahydrofuran/hexamethylphosphoramide (16.1 mL, 3:1). The resulting solution was stirred at −78° C. for 45 min. At this time, the reaction was treated with a solution of iodomethylcyclopentane (1.50 mg, 7.13 mmol) in hexamethylphosphoramide (1 mL). The reaction mixture was stirred at −78° C. for 4 h. The reaction was warmed to 25° C. and stirred at 25° C. for 16 h. The reaction mixture was then quenched by the dropwise addition of a saturated aqueous ammonium chloride solution (20 mL). This mixture was poured into water (100 mL) and extracted with ethyl acetate (3×50 mL). The combined organic layers were dried over sodium sulfate, filtered, and concentrated in vacuo. Flash chromatography (Merck Silica gel 60, 230–400 mesh, 75/25 hexanes/ethyl acetate) afforded 2-(4-chloro-phenyl)-3-cyclopentyl-propionic acid ethyl ester (1.65 g, 90.9%) as a yellow oil: EI-HRMS m/e calcd for $C_{16}H_{21}Cl_2O_2(M^+)$ 280.1230, found 280.1227.

A mixture of 2-(4-chloro-phenyl)-3-cyclopentyl-propionic acid ethyl ester (1.65 g, 5.89 mmol) and methyl urea (654 mg, 8.83 mmol) in a solution of magnesium methoxide in methanol (7.4 wt %, 16.9 mL, 11.78 mmol) was heated under reflux at 100° C. for 6 h. The reaction mixture was then concentrated in vacuo. Flash chromatography (Merck Silica gel 60, 230–400 mesh, 75/25 hexanes/ethyl acetate) afforded 1-[2-(4-chloro-phenyl)-3-cyclopentyl-propionyl]-3-methyl-urea (105.3 mg, 5.8%) as a white solid: mp 145–147° C.; EI-HRMS m/e calcd for $C_{16}H_{21}ClN_2O_2$ ($M^+$) 308.1292, found 308.1291. The methyl ester of the starting material was recovered from the reaction mixture due to transesterification.

A mixture of 2-(4-chloro-phenyl)-3-cyclopentyl-propionic acid methyl ester (648 mg, 2.43 mmol) and 2-aminothiazole (487 mg, 4.86 mmol) in a solution of magnesium methoxide in methanol (7.4 wt %, 14.0 mL, 9.72 mmol) was heated under reflux at 100° C. for 20 h. The reaction mixture was then concentrated in vacuo. Flash chromatography (Merck Silica gel 60, 230–400 mesh, 80/20 hexanes/ethyl acetate) afforded 2-(4-chloro-phenyl)-3-cyclopentyl-N-thiazol-2-yl-propionamide (286 mg, 35%) as a white solid: mp 156.6–159.8° C.; EI-HRMS m/e calcd for $C_{17}H_{19}ClN_2OS$ ($M^+$) 334.0906, found 334.0910.

EXAMPLE 8

3-Cyclopentyl-N-thiazol-2-yl-2-(4-trifluoromethyl-phenyl)-propionamide

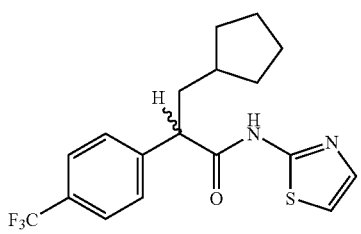

A solution of freshly prepared lithium diisopropylamide (23 mL of a 0.31M stock solution, 7.13 mmol) cooled to −78° C. was treated with (4-trifluoromethyl-phenyl)-acetic acid (693 mg, 3.4 mmol) in tetrahydrofuran/hexamethylphosphoramide (8.5 mL, 3:1). The resulting solution was stirred at −78° C. for 30 min. Iodomethylcyclopentane (784 mg, 3.7 mmol) was then added in hexamethylphosphoramide (1 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (10 mL). The excess solvent was removed in vacuo. The residue was acidified to pH=1 with a 1N aqueous hydrochloric acid solution. The mixture was then poured into water (150 mL) and extracted with ethyl acetate (3×100 mL). The combined organic layers were dried over sodium sulfate, filtered, and concentrated in vacuo. Flash chromatography (Merck Silica gel 60, 230–400 mesh, 75/25 hexanes/ethyl acetate) afforded 3-cyclopentyl-2-(4-trifluoromethyl-phenyl)-propionic acid (634.9 mg, 65%) as a white solid: mp 94–95° C.; EI-HRMS m/e calcd for $C_{15}H_{17}F_3O_2$ (M+) 309.1079, found 309.1072.

A solution of 3-cyclopentyl-2-(4-trifluoromethyl-phenyl)-propionic acid (185 mg, 0.64 mmol) in methylene chloride (6.5 mL) was cooled to 0° C. and was treated with a 2.0M solution of oxalyl chloride in methylene chloride (0.35 mL, 0.71 mmol) and a few drops of N,N-dimethylformamide. The reaction mixture was stirred at 0° C. for 10 min and at 25° C. for 30 min. The reaction mixture was then treated with a solution of 2-aminothiazole (142 mg, 1.42 mmol) in tetrahydrofuran (3.23 mL) and N,N-diisopropylethylamine (0.27 mL, 1.55 mmol). The solution was stirred at 25° C. for 5 h. At this time, the reaction was concentrated in vacuo. Flash chromatography (Merck Silica gel 60, 230–400 mesh, 80/20 hexanes/ethyl acetate) afforded 3-cyclopentyl-N-thiazol-2-yl-2-(4-trifluoromethyl-phenyl)-propionamide (127 mg, 53.3%) as a white solid: mp 210–212° C.; EI-HRMS m/e calcd for $C_{18}H_{19}F_3N_2OS$ (M+) 368.1175, found 368.1170.

EXAMPLE 9

3-Cyclopentyl-2-(4-methylsulfanyl-phenyl)-N-thiazol-2-yl-propionamide

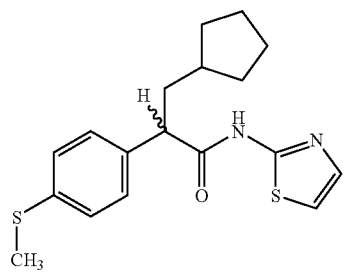

A solution of diisopropylamine (3.2 mL, 23.16 mmol) in dry tetrahydrofuran (10.3 mL) and 1,3-dimethyl-3,4,5,6-tetrahydro-2(1H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio)phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1 h, at which time, a solution of iodomethylcyclopentane (2.55 g, 12.13 mmol) in a small amount of dry tetrahydrofuran was added dropwise. The reaction mixture was then stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ (M+) 264.1184, found 264.1177.

A solution of 3-cyclopentyl-2-(4-methylsulfanyl-phenyl) propionic acid (200 mg, 0.76 mmol) and triphenylphosphine (198 mg, 0.76 mmol) in methylene chloride (2 mL) was cooled to 0° C. and then treated with N-bromosuccinimide (150 mg, 0.84 mmol) in small portions. After the complete addition of N-bromosuccinimide, the reaction mixture was allowed to warm to 25° C. over 30 min. The reaction mixture was then treated with 2-aminothiazole (160 mg, 1.60 mmol), and the resulting reaction mixture was stirred at 25° C. for 15 h. The reaction mixture was then concentrated in vacuo to remove methylene chloride. The remaining residue was diluted with water and ethyl acetate. The organic layer was further washed with a 1N aqueous hydrochloric acid solution and a saturated aqueous sodium bicarbonate solution, dried over magnesium sulfate, filtered, and concentrated in vacuo. Flash chromatography (Merck Silica gel 60, 230–400 mesh, 2/1 hexanes/ethyl acetate) afforded crude 3-cyclopentyl-2-(4-methylsulfanyl-phenyl)-N-thiazol-2-yl-propionamide as a yellow solid. Recrystallization from 2/1 hexanes/ethyl acetate afforded pure 3-cyclopentyl-2-(4-methylsulfanyl-phenyl)-N-thiazol-2-yl-propionamide (114 mg, 44%) as a white solid: mp 195–196° C.; EI-HRMS m/e calcd for $C_{18}H_{22}N_2OS_2$ (M+) 346.1174, found 346.1171.

EXAMPLE 10

3-Cyclo pentyl-N-thiazol-2-yl-2-(4-trifluoromethylsulfanyl-phenyl)-propionamide

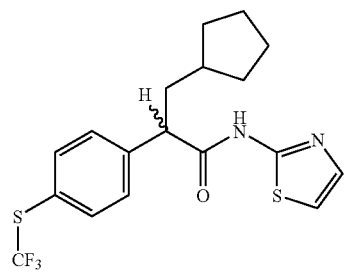

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (60 mg, 0.19 mmol) and triphenylphosphine (49.4 mg, 0.19 mmol) in methylene chloride (471 μL) was cooled to 0° C. and then treated with N-bromosuccinimide (36.9 mg, 0.21 mmol) in small portions. After the complete addition of N-bromosuccinimide, the reaction mixture was allowed to warm to 25° C. over 30 min. The bright orange reaction mixture was then treated with 2-aminothiazole (39.6 mg, 0.40 mmol). The resulting reaction mixture was stirred at 25° C. for 18 h. The reaction mixture was then concentrated in vacuo to remove methylene chloride. The remaining residue was diluted with ethyl acetate (50 mL). The organic layer was washed sequentially with a 10% aqueous hydrochloric acid solution (1×50 mL), a saturated aqueous sodium bicarbonate solution (1×50 mL) and water (1×50 mL), dried over sodium sulfate, filtered, and concentrated in vacuo. Flash chromatography (Merck Silica gel 60, 70–230 mesh, 9/1 hexanes/ethyl acetate) afforded 3-cyclopentyl-N-thiazol-2-yl-2-(4-trifluoromethylsulfanyl-phenyl)-propionamide (49.9 mg, 66%) as a white foam: mp 58–60° C.; EI-HRMS m/e calcd for $C_{18}H_{19}F_3N_2OS_2$ ($M^+$) 400.0890, found 400.0895.

EXAMPLE 11

3-Cyclopentyl-N-thiazol-2-yl-2-(4-trifluoromethanesulfonyl-phenyl)-propionamide

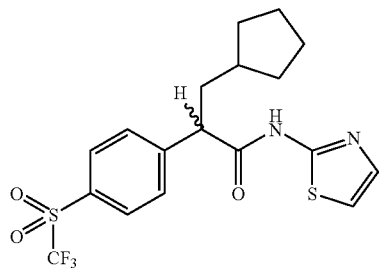

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL), washed with a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ ($M^+$) 332.1058, found 332.1052.

A solution of 3-cyclopentyl-2-(4-trifluoromethylsulfanyl-phenyl)propionic acid methyl ester (1.14 g, 3.43 mmol) in methylene chloride (8.6 mL) was treated with 3-chloroperoxybenzoic acid (80–85% grade, 2.00 g based on 80%, 9.26 mmol). The reaction mixture was stirred at 25° C. for 17 h, at which time, thin layer chromatography showed the presence of two new lower $R_f$ products. An additional 2.00 g of 3-chloroperoxybenzoic acid was added to the reaction mixture to drive the conversion of the sulfoxide to the sulfone, and the resulting reaction mixture was stirred at 25° C. for 3 d. The reaction mixture was concentrated in vacuo to remove methylene chloride. The resulting residue was diluted with ethyl acetate (300 mL). The organic phase was washed with a saturated aqueous sodium bicarbonate solution (3×100 mL), washed with a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-trifluoromethanesulfonyl-phenyl)propionic acid methyl ester (1.19 g, 95%) as a light yellow oil: EI-HRMS m/e calcd for $C_{16}H_{19}F_3O_4S$ ($M^+$) 364.0956, found 364.0965.

A solution of 3-cyclopentyl-2-(4-trifluoromethanesulfonyl-phenyl)propionic acid methyl ester (708.2 mg, 1.94 mmol) in tetrahydrofuran (2.4 mL) was treated with a 0.8M aqueous lithium hydroxide solution (3.6 mL, 2.92 mmol). The reaction mixture was stirred at 25° C. for 23 h and then concentrated in vacuo to remove tetrahydrofuran. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford a cream solid. This solid was purified by triturating with diethyl ether/petroleum ether to provide pure 3-cyclopentyl-2-(4-trifluoromethanesulfonyl-phenyl)propionic acid (527.0 mg, 77%) as a white solid: mp 143–145° C.; EI-HRMS m/e calcd for $C_{15}H_{17}F_3O_4S$ ($M^+$) 350.0800, found 350.0816.

A solution of 3-cyclopentyl-2-(4-trifluoromethanesulfonyl-phenyl)propionic acid (164.0 mg, 0.47 mmol) and triphenylphosphine (184.2 mg, 0.70 mmol) in methylene chloride (1.2 mL) was cooled to 0° C. and then treated with N-bromosuccinimide (141.6 mg, 0.80 mmol) in small portions. After the complete addition of N-bromosuccinimide, the reaction mixture was allowed to warm to 25° C. where it was stirred for 1 h. The reaction mixture was then treated with 2-aminothiazole (140.6 mg, 1.40 mmol). The resulting reaction mixture was stirred at 25° C. for 22 h. The reaction mixture was then concentrated in vacuo. Flash chromatography (Merck Silica gel 60, 230–400 mesh, 3/1 hexanes/ethyl acetate) afforded 3-cyclopentyl-N-thiazol-2-yl-2-(4-trifluoromethanesulfonyl-phenyl)-propionamide (47.9 mg, 24%) as a cream solid: mp 189–191° C.; EI-HRMS m/e calcd for $C_{18}H_{19}F_3N_2O_3S_2$ ($M^+$) 432.0789, found 432.0791.

In an analogous manner, there were obtained:
a) From 3-cyclopentyl-2-(4-trifluoromethanesulfonyl-phenyl)propionic acid and 2-aminothiazole-4-carboxylic acid methyl ester: 2-[3-Cyclopentyl-2-(4-trifluoromethanesulfonyl-phenyl)-propionylamino]-thiazole-4-carboxylic acid methyl ester as a gray solid: mp 122–125° C.; EI-HRMS m/e calcd for $C_{20}H_{21}F_3N_2O_5S_2$ ($M^+$) 490.0844, found 490.0844.
b) From 3-cyclopentyl-2-(4-trifluoromethanesulfonyl-phenyl)propionic acid and 2-aminothiazole-4-carboxylic acid ethyl ester: 2-[3-Cyclopentyl-2-(4-trifluoromethanesulfonyl-phenyl)-propionylamino]-thiazole-4-carboxylic acid ethyl ester as a white solid: mp 132–134° C.; EI-HRMS m/e calcd for $C_{21}H_{23}F_3N_2O_5S_2$ ($M^+$) 504.1000, found 504.0988.
c) From 3-cyclopentyl-2-(4-trifluoromethanesulfonyl-phenyl)propionic acid and methyl 2-amino-4-thiazoleacetate: {2-[3-Cyclopentyl-2-(4-trifluoromethanesulfonyl-phenyl)-propionylamino]-thiazol-4-yl}-acetic acid methyl ester as a yellow foam: mp 48–52° C.; EI-HRMS m/e calcd for $C_{21}H_{23}F_3N_2O_5S_2$ ($M^+$) 504.1000, found 504.0998.

EXAMPLE 12

2-[3-Chloro-4-methanesulfonyl-phenyl]-3-cyclopentyl-N-thiazol-2-yl-propionamide

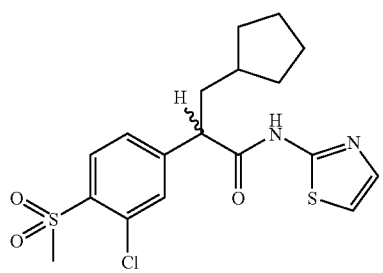

A solution of anhydrous aluminum chloride (5.00 g, 37.50 mmol) in chloroform (15 mL) was cooled to 0° C. and stirred for 30 min under a nitrogen atmosphere. A solution of ethyl oxalyl chloride (3.91 g, 28.64 mmol) in chloroform (5 mL) was then added, and the resulting reaction mixture was stirred at 0° C. for an additional 30 min. A solution of 2-chlorothioanisole (4.08 g, 25.58 mmol) in chloroform (20 mL) was then slowly added to the cooled reaction mixture. The solution became red in color and slowly became gum-like over a period of 30 min. The resulting reaction mixture was then stirred for an additional 3.5 h, and during this period, the reaction mixture was allowed to warm to 25° C. The reaction mixture was then quenched by the addition of water (25 mL). The aqueous layer was extracted with chloroform (3×25 mL). The combined organic layers were concentrated in vacuo. Flash chromatography (Merck Silica gel 60, 230–400 mesh, 4/1 hexanes/ethyl acetate) afforded (3-chloro-4-methylsulfanyl-phenyl)-oxo-acetic acid ethyl ester (4.32 g, 65.3%) as a yellow oil.

A solution of (3-chloro-4-methylsulfanyl-phenyl)-oxo-acetic acid ethyl ester (3.93 g, 15.19 mmol) in methanol (30 mL) was cooled to 0° C. and then treated with sodium borohydride (530.9 mg, 14.03 mmol). The reaction mixture changed from yellow to colorless. The mixture was stirred for 15 min and then quenched with a 1N aqueous hydrochloric acid solution (10 mL). The resulting reaction mixture was then extracted with methylene chloride (2×30 mL). The combined organic layers were washed with a saturated aqueous sodium chloride solution (1×30 mL), dried over sodium sulfate, filtered, and concentrated in vacuo. Flash chromatography (Merck Silica gel 60, 230–400 mesh, 9/1 then 4/1 hexanes/ethyl acetate) afforded (3-chloro-4-methylsulfanyl-phenyl)-hydroxy-acetic acid ethyl ester (1.43 g, 38%) as a white solid: mp 56–57° C.; EI-HRMS m/e calcd for $C_{11}H_{13}ClO_3S$ ($M^+$) 260.0273, found 260.0276.

A solution of (3-chloro-4-methylsulfanyl-phenyl)-hydroxy-acetic acid ethyl ester (1.43 g, 5.49 mmol) in pyridine (2 mL) was treated with acetic anhydride (2 mL) and 4-dimethylaminopyridine (50 mg, 0.41 mmol). The reaction mixture was stirred at 25° C. for 16 h. The reaction mixture was then diluted with methylene chloride (100 mL). The organic layer was washed with a 1N aqueous hydrochloric acid solution (2×30 mL), washed with a saturated aqueous sodium chloride solution (1×30 mL), dried over sodium sulfate, filtered, and concentrated in vacuo. Flash chromatography (Merck Silica gel 60, 230–400 mesh, 4/1 hexanes/ethyl acetate) afforded acetoxy-(3-chloro-4-methylsulfanyl-phenyl)-acetic acid ethyl ester (1.51 g, 91%) as a light yellow oil: EI-HRMS m/e calcd for $C_{13}H_{15}ClO_4S$ ($M^+$) 302.0379, found 302.0387.

A solution of acetoxy-(3-chloro-4-methylsulfanyl-phenyl)-acetic acid ethyl ester (1.47 g, 4.87 mmol) in hexamethylphosphoramide (7.2 mL) and methanol (20 μL) was treated with a 0.1M solution of samarium iodide in tetrahydrofuran (146 mL, 14.6 mmol). The reaction mixture was stirred at 25° C. under nitrogen for 6 min. During this time period, the reaction mixture changed from purple to white. The reaction mixture was diluted with water (150 mL) and then extracted with methylene chloride (3×100 mL). The combined organic layers were dried over sodium sulfate, filtered, and concentrated in vacuo. Flash chromatography (Merck Silica gel 60, 230–400 mesh, 4/1 hexanes/ethyl acetate) afforded (3-chloro-4-methylsulfanyl-phenyl)-acetic acid ethyl ester (0.71 g, 60%) as a light yellow oil: EI-HRMS m/e calcd for $C_{11}H_{13}ClO_2S$ ($M^+$) 244.0324, found 244.0332.

A solution of diisopropylamine (457 μL, 3.26 mmol) in tetrahydrofuran (5 mL) was cooled to −78° C. under a nitrogen atmosphere and then treated with a 2.5M solution of n-butyllithium in hexanes (1.3 mL, 3.26 mmol). The mixture was stirred at −78° C. for 30 min, at which time, a solution of (3-chloro-4-methylsulfanyl-phenyl)-acetic acid ethyl ester (0.67 g, 2.75 mmol) in tetrahydrofuran (8 mL) was slowly added to the reaction mixture. The reaction mixture turned deep yellow in color. The reaction mixture was then further stirred at −78° C. for 30 min, at which time, a solution of iodomethylcyclopentane (0.65 g, 3.09 mmol) in 1,3-dimethyl-3,4,5,6-tetrahydro-2(1H)-pyrimidone (1 mL) was added via syringe. The reaction mixture was then allowed to warm to 25° C. where it was stirred for 16 h. The reaction mixture turned red in color during this time period. The reaction mixture was quenched with a 6N aqueous hydrochloric acid solution (5 mL) and further diluted with water (20 mL). The reaction mixture was then extracted with methylene chloride (3×20 mL). The combined organic layers were washed with a saturated aqueous sodium chloride solution (1×25 mL), dried over sodium sulfate, filtered, and concentrated in vacuo. Flash chromatography (Merck Silica gel 60, 230–400 mesh, 4/1 hexanes/ethyl acetate) afforded 2-(3-chloro-4-methylsulfanyl-phenyl)-3-cyclopentyl-propionic acid ethyl ester (0.50 g, 56%) as a light yellow oil.

A solution of 2-(3-chloro-4-methylsulfanyl-phenyl)-3-cyclopentyl-propionic acid ethyl ester (0.45 g, 1.39 mmol) in ethanol (3 mL) was treated with a 10% aqueous potassium hydroxide solution (2 mL). The reaction mixture was stirred under nitrogen at 25° C. for 16 h. The reaction mixture was then acidified with a 1N aqueous hydrochloric acid solution (5 mL). The reaction mixture was then extracted with methylene chloride (3×15 mL). The combined organic layers were dried over sodium sulfate, filtered, and concentrated in vacuo to afford 2-(3-chloro-4-methylsulfanyl-phenyl)-3-cyclopentyl-propionic acid (0.29 g, 70%) as a white solid: EI-HRMS m/e calcd for $C_{15}H_{19}ClO_2S$ ($M^+$) 298.0794, found 298.0798.

A solution of benzotriazol-1-yloxytris(dimethylamino) phosphonium hexafluorophosphate (0.62 g, 1.41 mmol) and 2-(3-chloro-4-methylsulfanyl-phenyl)-3-cyclopentyl-propionic acid (0.29 g, 0.95 mmol) in methylene chloride (10 mL) was treated with N,N-diisopropylethylamine (500 μL, 2.87 mmol) and 2-aminothiazole (140 mg, 1.27 mmol). The mixture was stirred under nitrogen at 25° C. for 14 h. The reaction mixture was then washed with a 6N aqueous hydrochloric acid solution (1×15 mL) and washed with a saturated aqueous sodium chloride solution (1×25 mL). The organic layer was dried over sodium sulfate, filtered, and concentrated in vacuo. Flash chromatography (Merck Silica gel 60, 230–400 mesh, 4/1 hexanes/ethyl acetate) afforded 2-(3-chloro-4-methylsulfanyl-phenyl)-3-cyclopentyl-N-thiazol-2-yl-propionamide (0.26 g, 71%) as a white solid: EI-HRMS m/e calcd for $C_{18}H_{21}ClN_2OS_2$ ($M^+$) 380.0783, found 380.0792.

A solution of 2-(3-chloro-4-methylsulfanyl-phenyl)-3-cyclopentyl-N-thiazol-2-yl-propionamide (187 mg, 0.49 mmol) in methylene chloride (10 mL) was cooled to 0° C. under nitrogen and then treated with 3-chloroperoxybenzoic acid (456.8 mg based on 50% purity). The reaction mixture was stirred for 3 h, and during this period, the temperature was allowed to warm to 25° C. The reaction mixture was then diluted with methylene chloride (50 mL). The organic layer was washed with a saturated aqueous sodium carbonate solution (1×20 mL), washed with a saturated aqueous sodium chloride solution (1×20 mL), dried over sodium sulfate, filtered, and concentrated in vacuo. Flash chromatography (Merck Silica gel 60, 230–400 mesh, 4/1 hexanes/ethyl acetate) afforded 2-(3-chloro-4-methanesulfonyl-phenyl)-3-cyclopentyl-N-thiazol-2-yl-propionamide (102 mg, 50%) as a white solid: EI-HRMS m/e calcd for $C_{18}H_{21}ClN_2O_3S_2$ ($M^+$) 412.0682, found 412.0674.

EXAMPLE 13

(2R)-3-Cyclopentyl-2-(4-methanesulfonylphenyl)-N-thiazol-2-yl-propionamide

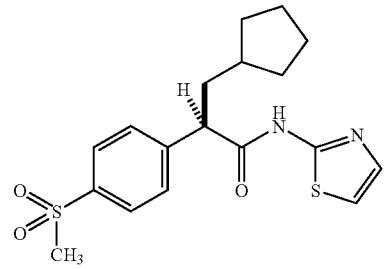

A solution of 4-(methanesulfonyl)phenyl acetic acid (43.63 g, 0.204 mol) in methanol (509 mL) was treated slowly with concentrated sulfuric acid (2 mL). The resulting reaction mixture was heated under reflux for 19 h. The reaction mixture was allowed to cool to 25° C. and then concentrated in vacuo to remove methanol. The residue was diluted with ethyl acetate (800 mL). The organic phase was washed with a saturated aqueous sodium bicarbonate solution (1×200 mL), washed with a saturated aqueous sodium chloride solution (1×200 mL), dried over sodium sulfate, filtered, and concentrated in vacuo. Flash chromatography (Merck Silica gel 60, 70–230 mesh, 1/1 hexanes/ethyl acetate) afforded 4-(methanesulfonyl)phenyl acetic acid methyl ester (45.42 g, 98%) as a yellow oil which solidified to a cream colored solid upon sitting over time at 25° C.: mp 78–80° C.; EI-HRMS m/e calcd for $C_{10}H_{12}O_4S$ ($M^+$) 228.0456, found 228.0451.

A mechanical stirrer was used for this reaction. A solution of diisopropylamine (29.2 mL, 0.21 mol) in dry tetrahydrofuran (186 mL) and 1,3-dimethyl-3,4,5,6-tetrahydro-2(1H)-pyrimidinone (62 mL) was cooled to −78° C. and then treated with a 2.5M solution of n-butyllithium in hexanes (83.4 mL, 0.21 mol). The yellow-orange reaction mixture was stirred at −78° C. for 35 min and then slowly treated with a solution of 4-(methanesulfonyl)phenyl acetic acid methyl ester (45.35 g, 0.20 mol) in dry tetrahydrofuran (186 mL) and 1,3-dimethyl-3,4,5,6-tetrahydro-2(1H)-pyrimidinone (62 mL). The reaction mixture turned dark in color. The reaction mixture was then stirred at −78° C. for 50 min, at which time, a solution of iodomethylcyclopentane (50.08 g, 0.24 mol) in a small amount of dry tetrahydrofuran was added slowly. The reaction mixture was then stirred at −78° C. for 50 min, and then allowed to warm to 25° C. where it was stirred for 36 h. The reaction mixture was quenched with water (100 mL), and the resulting reaction mixture was concentrated in vacuo to remove tetrahydrofuran. The remaining residue was diluted with ethyl acetate (1.5 L). The organic phase was washed with a saturated aqueous sodium chloride solution (1×500 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methanesulfonylphenyl)propionic acid methyl ester (41.79 g, 68%) as a yellow viscous oil: EI-HRMS m/e calcd for $C_{16}H_{22}O_4S$ ($M^+$) 310.1239, found 310.1230.

A solution of 3-cyclopentyl-2-(4-methanesulfonylphenyl) propionic acid methyl ester (50.96 g, 0.16 mol) in methanol (410 mL) was treated with a 1N aqueous sodium hydroxide solution (345 mL, 0.35 mol). The reaction mixture was stirred at 25° C. for 24 h. The reaction mixture was concentrated in vacuo to remove methanol. The resulting aqueous residue was acidified to pH=2 with concentrated hydrochloric acid and then extracted with ethyl acetate (5×200 mL). The combined organic layers were dried over sodium sulfate, filtered, and concentrated in vacuo to afford pure 3-cyclopentyl-2-(4-methanesulfonylphenyl)propionic acid (43.61 g, 90%) as a white solid which was used without further purification: mp 152–154° C.; EI-HRMS m/e calcd for $C_{15}H_{20}O_4S$ ($M^+$) 296.1082, found 296.1080.

Two separate reactions were setup in parallel: (1) A solution of (R)-(+)-4-benzyl-2-oxazolidinone (3.67 g, 20.73 mmol) in dry tetrahydrofuran (35 mL) was cooled to −78° C. and then treated with a 2.5M solution of n-butyllithium in hexanes (7.9 mL, 19.86 mmol). The resulting reaction mixture was stirred at −78° C. for 30 min and then allowed to warm to 25° C. where it was stirred for 1.5 h. (2) A solution of racemic 3-cyclopentyl-2-(4-methanesulfonylphenyl)propionic acid (5.12 g, 17.27 mmol) in dry tetrahydrofuran (35 mL) was cooled to 0° C. and then treated with triethylamine (2.8 mL, 19.86 mmol). The reaction mixture was stirred at 0° C. for 10 min and then treated dropwise with trimethylacetyl chloride (2.6 mL, 20.73 mmol). The resulting reaction mixture was stirred at 0° C. for 2 h and then cooled to −78° C. for the addition of the freshly prepared chiral oxazolidinone. The reaction mixture containing the oxazolidinone was then added to the cooled (−78° C.) mixed anhydride solution. The resulting reaction mixture was stirred as −78° C. for 1 h and allowed to gradually warm to 25° C. The reaction mixture was then stirred at 25° C. for 3 d. The resulting reaction mixture was quenched with water (100 mL) and then concentrated in vacuo to remove tetrahydrofuran. The resulting aqueous residue was diluted with ethyl acetate (600 mL). The organic layer was washed with a saturated aqueous sodium chloride solution (1×300 mL), dried over sodium sulfate, filtered, and concentrated in vacuo. Thin layer chromatography using 13/7 hexanes/ethyl acetate as the developing solvent indicated the presence of two products. The higher moving product had a $R_f$=0.32 and the lower moving product had a $R_f$=0.19. Flash chromatography (Merck Silica gel 60, 230–400 mesh, 9/1 then 13/7 hexanes/ethyl acetate) afforded two products: (1) The higher $R_f$ product (4R,2'S)-4-benzyl-3-[3-cyclopentyl-2-(4-methanesulfonylphenyl)propionyl]-oxazolidin-2-one (2.12 g, 54%) as a white foam: mp 62–64° C.; $[\alpha]^{23}_{589}$=+6.3° (c=0.24, chloroform); EI-HRMS m/e calcd for $C_{25}H_{29}NO_5S$ ($M^+$) 455.1766, found 455.1757. (2) The lower $R_f$ product (4R,2'R)-4-benzyl-3-[3-cyclopentyl-2-(4-methanesulfonylphenyl)propionyl]-oxazolidin-2-one (3.88 g, 99%) as a white foam: mp 59–61° C.; $[\alpha]^{23}_{589}$=−98.3° (c=0.35, chloroform); EI-HRMS m/e calcd for $C_{25}H_{29}NO_5S$ ($M^+$) 455.1766, found 455.1753. The combined mass recovery from the two products was 6.00 g, providing a 76% conversion yield for the reaction.

An aqueous solution of lithium hydroperoxide was freshly prepared from mixing a solution of anhydrous lithium hydroxide powder (707.3 mg, 16.86 mmol) in 5.27 mL of water with a 30% aqueous hydrogen peroxide solution (3.44 mL, 33.71 mmol). This freshly prepared aqueous lithium hydroperoxide solution was cooled to 0° C. and then slowly added to a cooled (0° C.) solution of (4R,2'R)-4-benzyl-3-[3-cyclopentyl-2-(4-methanesulfonylphenyl)propionyl]-oxazolidin-2-one (3.84 g, 8.43 mmol) in tetrahydrofuran (33 mL) and water (11 mL). The reaction mixture was stirred 0° C. for 1.5 h. The reaction mixture was then quenched with a 1.5N aqueous sodium sulfite solution (25 mL). The reaction mixture was further diluted with water (300 mL). The resulting aqueous layer was continuously extracted with diethyl ether until thin layer chromatography indicated the absence of the recovered chiral oxazolidinone in the aqueous layer. The aqueous layer was then acidified to pH=2 with a 10% aqueous hydrochloric acid solution and extracted with ethyl acetate (1×300 mL). The organic extract was dried over sodium sulfate, filtered, and concentrated in vacuo to afford (2R)-3-cyclopentyl-2-(4-methanesulfonylphenyl)propionic acid as a white solid (2.23 g, 89%) which was used without further purification. Flash chromatography (Merck Silica gel 60, 70–230 mesh, 30/1 methylene chloride/methanol then 10/1 methylene chloride/methanol) was used to obtain a purified sample for analytical data and afforded pure (2R)-3-cyclopentyl-2-(4-methanesulfonylphenyl)propionic acid as a white foam: mp 62–64° C. (foam to gel); $[\alpha]^{23}_{589}$=−50.0° (c=0.02, chloroform); EI-HRMS m/e calcd for $C_{15}H_{20}O_4S$ ($M^+$) 296.1082, found 296.1080.

A solution of triphenylphosphine (3.35 g, 12.79 mmol) in methylene chloride (19 mL) was cooled to 0° C. and then slowly treated with N-bromosuccinimide (2.28 g, 12.79 mmol) in small portions. The reaction mixture was stirred at 0° C. for 30 min, and during this time period, the color of the reaction mixture changed from light yellow to a darker yellow then to a purple color. The cooled purple reaction mixture was then treated with the (2R)-3-cyclopentyl-2-(4-methanesulfonylphenyl)propionic acid (2.23 g, 7.52 mmol). The resulting reaction mixture was then allowed to warm to 25° C. over 45 min, at which time, the reaction mixture was then treated with 2-aminothiazole (1.88 g, 18.81 mmol). The resulting reaction mixture was stirred at 25° C. for 12 h. The reaction mixture was then concentrated in vacuo to remove methylene chloride. The remaining black residue was diluted with ethyl acetate (300 mL) and then washed well with a 10% aqueous hydrochloric acid solution (2×100 mL), a 5% aqueous sodium bicarbonate solution (3×100 mL), and a saturated aqueous sodium chloride solution (1×200 mL). The organic layer was then dried over sodium sulfate, filtered, and concentrated in vacuo. Flash chromatography (Merck Silica gel 60, 70–230 mesh, 9/1, 3/1, and then 11/9 hexanes/ethyl acetate) afforded (2R)-3-cyclopentyl-2-(4-methanesulfonylphenyl)-N-thiazol-2-yl-propionamide (2.10 g, 74%) as a white foam: mp 78–80° C. (foam to gel); $[\alpha]^{23}_{589}$=−70.4° (c=0.027, chloroform); EI-HRMS m/e calcd for $C_{18}H_{22}N_2O_3S_2$ ($M^+$) 378.1072, found 378.1081.

EXAMPLE 14

3-Cyclopentyl-2-(4-methanesulfonyl-3-nitrophenyl)-N-thiazol-2-yl-propionamide

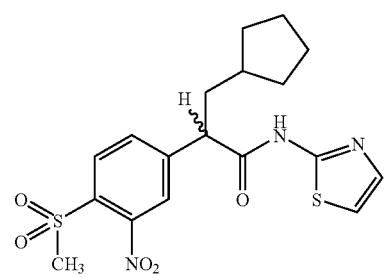

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_9H_8ClNO_4$ ($M^+$) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C. where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_4$ ($M^+$) 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3 mL) was heated at 130° C. for 5 h. The black reaction mixture was then poured over ice (20 g), resulting in the formation of a brown sticky substance. The resulting mixture was then treated with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_6S$ $(M+H)^+$ 356.1169, found 356.1175.

A solution of 3-cyclopentyl-2-(4-methanesulfonyl-3-nitrophenyl)-propionic acid methyl ester (1.17 g, 3.29 mmol) in tetrahydrofuran (6 mL) was treated with a 0.8M aqueous lithium hydroxide solution (6.17 mL, 4.94 mmol). The reaction mixture was stirred at 25° C. for 3 h. The reaction mixture was then diluted with water (50 mL), a 1N aqueous hydrochloric acid solution (10 mL), and ethyl acetate (50 mL). The layers were separated, and the aqueous layer was back-extracted with ethyl acetate (2×50 mL). The combined organic layers were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid (993 mg, 88%) as a yellow foam which contained a small impurity. A small amount of the yellow foam (50 mg) was re-purified using Biotage chromatography (FLASH 40S, Silica, 3/1 then 1/1 hexanes/ethyl acetate) to afford 3-cyclopentyl-2-(4-methanesulfonyl-3-nitrophenyl)-propionic acid as a white foam: mp 114–118° C. (foam to gel); FAB-HRMS m/e calcd for $C_{15}H_{19}NO_6S$ $(M+H)^+$ 342.1011, found 342.1014.

A solution of triphenylphosphine (138 mg, 0.53 mmol) in methylene chloride (2 mL) was cooled to 0° C. and then slowly treated with N-bromosuccinimide (94 mg, 0.53 mmol) in small portions. The reaction mixture was stirred at 0° C. for 10 min and then treated with 3-cyclopentyl-2-(4-methanesulfonyl-3-nitrophenyl)-propionic acid (150 mg, 0.44 mmol). The resulting reaction mixture was stirred at 0° C. for 5 min and then allowed to warm to 25° C. where it was stirred for 25 min. The reaction mixture was then treated with 2-aminothiazole (97 mg, 0.97 mmol). The resulting reaction mixture was stirred at 25° C. for 15 h. The crude reaction mixture was directly purified by flash chromatography, (Merck Silica gel 60, 230–400 mesh, 1/1 hexanes/ethyl acetate), to afford 3-cyclopentyl-2-(4-methanesulfonyl-3-nitrophenyl)-N-thiazol-2-yl-propionamide (96 mg, 52%) as a pale yellow solid: mp 121–124° C.; FAB-HRMS m/e calcd for $C_{18}H_{21}N_3O_5S_2$ $(M+H)^+$ 424.1001, found 424.1000.

EXAMPLE 15

3-Cyclopentyl-2-(3,4-dichlorophenyl)-N-(5-hydroxymethyl-thiazol-2-yl)-propionamide

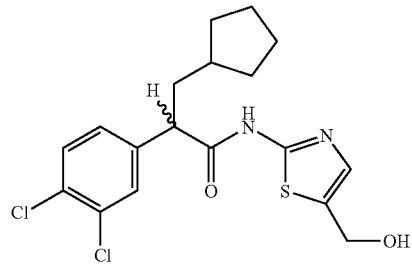

A solution of 2-[3-cyclopentyl-2-(3,4-dichlorophenyl)-propionylamino]-thiazole-5-carboxylic acid ethyl ester (prepared as in Example 1(B)(g), 110 mg, 0.25 mmol) in diethyl ether (2 mL) at 0° C. was slowly treated with lithium aluminum hydride (12 mg, 0.31 mmol). The resulting reaction mixture continued to stir at 0° C. and was allowed to gradually warm to 25° C. The reaction mixture was then stirred at 25° C. over a period of 14 h. The reaction mixture was slowly quenched by the dropwise addition of water (5 mL). The resulting reaction mixture was partitioned between water and ethyl acetate. A saturated aqueous sodium chloride solution was added to break up the emulsions. The organic layer was dried over magnesium sulfate, filtered, and concentrated in vacuo. Flash chromatography (Merck Silica gel 60, 230–400 mesh, 1/3 hexanes/ethyl acetate) afforded 3-cyclopentyl-2-(3,4-dichlorophenyl)-N-(5-hydroxymethyl-thiazol-2-yl)-propionamide (52.9 mg, 53%) as a light yellow solid: mp 128–130° C.; EI-HRMS m/e calcd for $C_{18}H_{20}Cl_2N_2O_2S$ ($M^+$) 398.0623, found 398.0623.

EXAMPLE 16

3-Cyclopentyl-2-(3,4-dichlorophenyl)-N-[4-(2-hydroxyethyl)-thiazol-2-yl]-propionamide

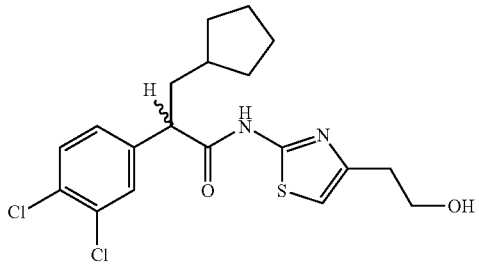

A solution of {2-[3-cyclopentyl-2-(3,4-dichlorophenyl)-propionylamino]-thiazol-4-yl}-acetic acid ethyl ester (prepared as in Example 1(B)(c), 129 mg, 0.28 mmol) in tetrahydrofuran (1.4 mL) at 25° C. was slowly treated with sodium borohydride (22.5 mg, 0.59 mmol). The resulting reaction mixture was stirred at 25° C. for 10 h. After 10 h at 25° C., a substantial amount of starting material still remained. An additional amount of sodium borohydride (21.4 mg, 0.57 mmol) was added to the reaction mixture, and the reaction mixture was heated under reflux for 14 h. The reaction mixture was allowed to cool to 25° C. and then slowly quenched by the dropwise addition of water. The resulting reaction mixture was concentrated in vacuo to remove tetrahydrofuran. The resulting residue was diluted with ethyl acetate (100 mL) and washed with a saturated aqueous sodium chloride solution (1×50 mL). The organic layer was dried over sodium sulfate, filtered, and concentrated in vacuo. Flash chromatography (Merck Silica gel 60, 230–400 mesh, 3/1 then 1/1 hexanes/ethyl acetate) afforded 3-cyclopentyl-2-(3,4-dichlorophenyl)-N-[4-(2-hydroxyethyl)-thiazol-2-yl]-propionamide (68.1 mg, 58%) as a white foam: mp 85–86° C.; FAB-HRMS m/e calcd for $C_{19}H_{22}Cl_2N_2O_2S$ (M+H)$^+$ 413.0858, found 413.0838.

EXAMPLE 17

3-Cyclopentyl-2-(3,4-dichlorophenyl)-N-(4-hydroxymethyl-thiazol-2-yl)-propionamide

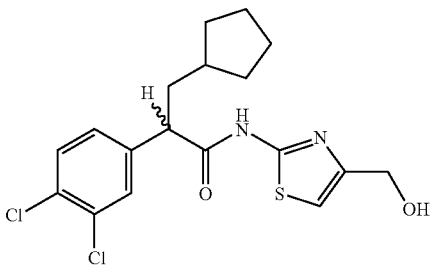

A solution of 2-[3-cyclopentyl-2-(3,4-dichlorophenyl)-propionylamino]-thiazole-4-carboxylic acid ethyl ester (prepared as in Example 1(B)(f), 200 mg, 0.45 mmol) in tetrahydrofuran (3 mL) at 25° C. was slowly treated with sodium borohydride (26.0 mg, 0.68 mmol). The reaction mixture was heated under reflux for 48 h. The reaction mixture was allowed to cool to 25° C. and then slowly quenched by the dropwise addition of water. The resulting reaction mixture was partitioned between water and ethyl acetate. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(3,4-dichlorophenyl)-N-(4-hydroxymethyl-thiazol-2-yl)-propionamide (44.9 mg, 25%) as a white solid: mp 88–90° C.; EI-HRMS m/e calcd for $C_{18}H_{20}Cl_2N_2O_2S$ (M$^+$) 398.0623, found 398.0631.

EXAMPLE 18

{2-[3-Cyclopentyl-2-(3,4-dichlorophenyl)-propionylamino]-thiazol-4-yl}-acetic Acid

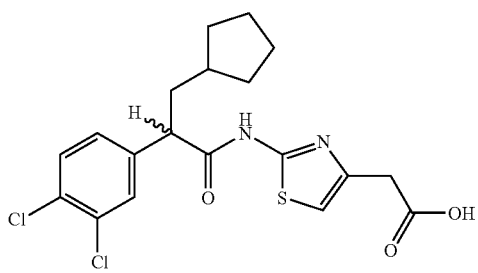

A solution of {2-[3-cyclopentyl-2-(3,4-dichlorophenyl)-propionylamino]-thiazol-4-yl}-acetic acid ethyl ester (prepared as in Example 1(B)(c), 198.1 mg, 0.44 mmol) in absolute ethanol (2.2 mL) was treated with a 1N aqueous sodium hydroxide solution (910 µL, 0.91 mmol). The reaction mixture was heated under reflux for 2 h. The reaction mixture was allowed to cool to 25° C. and then concentrated in vacuo to remove absolute ethanol. The resulting residue was acidified to pH=2 with a 10% aqueous hydrochloric acid solution and extracted with ethyl acetate (1×150 mL). The organic layer was washed with a saturated aqueous sodium chloride solution (1×100 mL), dried over sodium sulfate, filtered, and concentrated in vacuo. The resulting white residue was washed well with cold water and dried to afford {2-[3-cyclopentyl-2-(3,4-dichlorophenyl)-propionylamino]-thiazol-4-yl}-acetic acid (150 mg, 81%) as a white solid: mp 100–102° C.; FAB-HRMS m/e calcd for $C_{19}H_{20}Cl_2N_2O_3S$ (M+H)$^+$ 427.0650, found 427.0633.

EXAMPLE 19

2-[3-Cyclopentyl-2-(3,4-dichlorophenyl)-propionylamino]-thiazole-5-carboxylic Acid

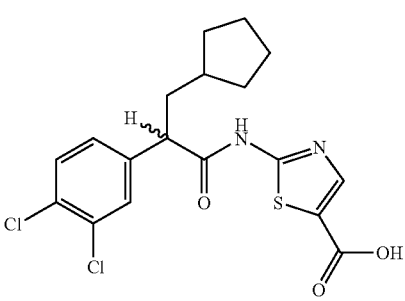

A solution of 2-[3-cyclopentyl-2-(3,4-dichlorophenyl)-propionylamino]-thiazole-5-carboxylic acid ethyl ester (prepared as in Example 1(B)(g), 1.0 g, 2.27 mmol) in absolute ethanol (10 mL) was treated with a 1N aqueous sodium hydroxide solution (4.77 mL, 4.77 mmol). The reaction mixture was heated under reflux for 15 h. The reaction mixture was allowed to cool to 25° C. and then concentrated in vacuo to remove absolute ethanol. The resulting yellow residue was acidified to pH=2 with concentrated hydrochloric acid and extracted with ethyl acetate (2×75 mL). The combined organic layers were dried over magnesium sulfate, filtered, and concentrated in vacuo. Recrystallization from ethyl acetate afforded 2-[3-cyclopentyl-2-(3,4-dichlorophenyl)-propionylamino]-thiazole-5-carboxylic acid (210 mg, 22%) as a white solid: mp 269–270° C.; FAB-HRMS m/e calcd for $C_{18}H_{18}Cl_2N_2O_3S$ (M+H)$^+$ 413.0493, found 413.0483.

EXAMPLE 20

2-[3-Cyclopentyl-2-(3,4-dichlorophenyl)-propionylamino]-thiazole-4-carboxylic Acid

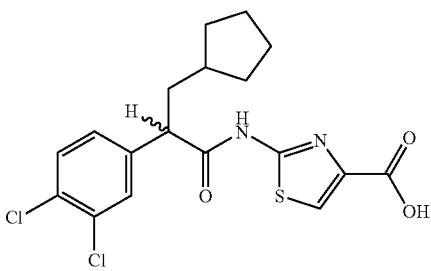

A solution of 2-[3-cyclopentyl-2-(3,4-dichlorophenyl)-propionylamino]-thiazole-4-carboxylic acid ethyl ester (prepared as in Example 1(B)(f), 600 mg, 1.36 mmol) in absolute ethanol (6 mL) was treated with a 1N aqueous sodium hydroxide solution (2.85 mL, 2.85 mmol). The reaction mixture was heated under reflux for 15 h. The reaction mixture was allowed to cool to 25° C. and then concentrated in vacuo to remove absolute ethanol. The resulting yellow residue was acidified to pH=2 with concentrated hydrochloric acid and extracted with ethyl acetate (2×100 mL). The combined organic layers were dried over magnesium sulfate, filtered, and concentrated in vacuo. Precipitation from 1/1 hexanes/ethyl acetate afforded 2-[3-cyclopentyl-2-(3,4-dichlorophenyl)-propionylamino]-thiazole-4-carboxylic acid (399 mg, 71%) as a white solid: mp 285–287° C.; FAB-HRMS m/e calcd for $C_{18}H_{18}Cl_2N_2O_3S$ (M+H)$^+$ 413.0493, found 413.0481.

EXAMPLE 21

{2-[3-Cyclopentyl-2-(3,4-dichlorophenyl)-propionylamino]-thiazol-4-yl}-acetic Acid Methyl Ester

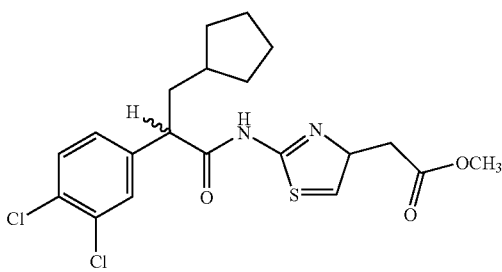

A solution of {2-[3-cyclopentyl-2-(3,4-dichlorophenyl)-propionylamino]-thiazol-4-yl}-acetic acid (prepared as in Example 18, 95.4 mg, 0.223 mmol) in methanol (1.1 mL) was treated with 1 drop of concentrated sulfuric acid. The reaction mixture was heated under reflux for 15 h. The reaction mixture was allowed to cool to 25° C. and then concentrated in vacuo to remove methanol. The resulting residue was diluted with ethyl acetate (100 mL). The organic phase was washed with a saturated aqueous sodium chloride solution (1×100 mL), dried over sodium sulfate, filtered, and concentrated in vacuo. Flash chromatography (Merck Silica gel 60, 230–400 mesh, 3/1 hexanes/ethyl acetate) afforded {2-[3-cyclopentyl-2-(3,4-dichlorophenyl)-propionylamino]-thiazol-4-yl}-acetic acid methyl ester (77.2 mg, 78%) as a yellow viscous oil: FAB-HRMS m/e calcd for $C_{20}H_{22}Cl_2N_2O_3S$ (M+H)$^+$ 441.0807, found 441.0804.

In an analogous manner, there were obtained:

a) From 2-[3-cyclopentyl-2-(3,4-dichlorophenyl)-propionylamino]-thiazole-4-carboxylic acid (prepared as in Example 20): 2-[3-Cyclopentyl-2-(3,4-dichlorophenyl)-propionylamino]-thiazole-4-carboxylic acid methyl ester as a white solid: mp 153–155° C.; FAB-HRMS m/e calcd for $C_{19}H_{20}Cl_2N_2O_3S$ (M+H)$^+$ 427.0650, found 427.0659.

b) From 2-[3-cyclopentyl-2-(3,4-dichlorophenyl)-propionylamino]-thiazole-5-carboxylic acid (prepared as in Example 19): 2-[3-Cyclopentyl-2-(3,4-dichlorophenyl)-propionylamino]-thiazole-5-carboxylic acid methyl ester as a white solid: mp 150–151° C.; FAB-HRMS m/e calcd for $C_{19}H_{20}Cl_2N_2O_3S$ (M+H)$^+$ 427.0650, found 427.0650.

EXAMPLE 22

3-Cyclopentyl-2-(4-nitro-phenyl)-N-thiazol-2-yl-propionamide

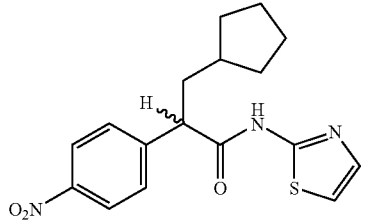

A solution of freshly prepared lithium diisopropylamide (430.55 mL of a 0.3M stock solution, 129.16 mmol) cooled to −78° C. was treated with (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. Iodomethylcyclopentane (27.75 g, 132.1 mmol) was then added in hexamethylphosphoramide (27.75 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (250 mL). This mixture was concentrated, diluted with water (250 mL), and extracted with ethyl acetate (3×300 mL). The combined organic layers were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ (M$^+$) 291.1470, found 291.1470.

A solution of 3-cyclopentyl-2-(4-nitro-phenyl)-propionic acid ethyl ester (14.1 g, 48.06 mmol) in tetrahydrofuran/water (300 mL, 3:1) was treated with lithium hydroxide (4.35 g, 103.67 mmol). The reaction was stirred at 25° C. for 21 h. The tetrahydrofuran was then removed in vacuo. The residue was diluted with water (75 mL) and extracted with ether (3×75 mL). The aqueous layer was acidified to pH=1 with a 3N aqueous hydrochloric acid solution. The product was extracted into methylene chloride (3×75 mL). The combined organic layers were washed with a saturated aqueous sodium chloride solution (2×100 mL), dried over magnesium sulfate, filtered, and concentrated in vacuo to give 3-cyclopentyl-2-(4-nitro-phenyl)-propionic acid (11.97 g, 93.6%) as a yellow solid: mp 119–125° C.; EI-HRMS m/e calcd for $C_{14}H_{17}NO_4$ (M+) 263.1157, found 263.1162.

A solution of 3-cyclopentyl-2-(4-nitro-phenyl)-propionic acid (131 mg, 0.5 mmol) in methylene chloride (5.0 mL) was cooled to 0° C. and then treated with a 2.0M solution of oxalyl chloride in methylene chloride (1.0 mL, 2.0 mmol) and a few drops of N,N-dimethylformamide. The reaction mixture was stirred at 0° C. for 15 min and at 25° C. for 30 min. The reaction mixture was then treated with a solution of 2-aminothiazole (110 mg, 1.0 mmol) in tetrahydrofuran (5 mL) and N,N-diisopropylethylamine (0.28 mL, 0.55 mmol). The solution was stirred at 25° C. for 24 h. At this time, the reaction was concentrated in vacuo. Flash chromatography (Merck Silica gel 60, 230–400 mesh, 50/50 hexanes/ethyl acetate) afforded 3-cyclopentyl-2-(4-nitro-phenyl)-N-thiazol-2-yl-propionamide (38 mg, 22.4%) as a yellow solid: mp 186–187° C.; EI-HRMS m/e calcd for $C_{17}H_{19}N_3O_3S$ (M+) 345.1147, found 345.1148.

In an analogous manner, there was obtained:
a) From ethyl 2-amino-4-thiazole glyoxylate and 3-cyclopentyl-2-(4-nitro-phenyl)-propionic acid: {2-[3-Cyclopentyl-2-(4-nitro-phenyl)-propionylamino]-thiazol-4-yl}-oxo-acetic acid ethyl ester (57.5%) as a white solid: mp 134–136° C.; FAB-HRMS m/e calcd for $C_{21}H_{23}N_3O_6S$ (M+H)+ 446.1400, found 446.1386.

EXAMPLE 23

{2-[3-Cyclopentyl-2-(4-nitro-phenyl)-propionylamino]-thiazol-4-yl}-acetic Acid Ethyl Ester

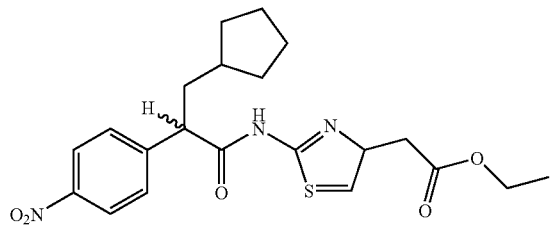

A solution of 3-cyclopentyl-2-(4-nitro-phenyl)-propionic acid (prepared as in Example 22A, 263.0 mg, 1.0 mmol) in N,N-dimethylformamide (10 mL) was treated with O-benzotriazol-1-yl-N,N,N',N'-tetramethyluronium hexafluorophosphate (379 mg, 1.0 mmol), (2-amino-thiazol-4-yl)-acetic acid ethyl ester (279 mg, 1.5 mmol) and N,N-diisopropylethylamine (0.34 mL, 2.0 mmol). The reaction mixture was stirred at 25° C. for 5 h. The reaction mixture was then poured into a 2N aqueous hydrochloric acid solution (25 mL) and extracted with ethyl acetate (3×25 mL). The combined organic layers were washed with water (1×75 mL), a saturated aqueous sodium bicarbonate solution (1×75 mL), and a saturated aqueous sodium chloride solution (3×75 mL), dried over sodium sulfate, filtered and concentrated in vacuo. Flash chromatography (Merck Silica gel 60, 230–400 mesh, 70/30 hexanes/ethyl acetate) afforded {2-[3-cyclopentyl-2-(4-nitro-phenyl)-propionylamino]-thiazol-4-yl}-acetic acid ethyl ester (70.0 mg, 39.4%) as a pale yellow oil: FAB-HRMS m/e calcd for $C_{21}H_{25}N_3O_5S$ (M+H)+ 432.1593, found 432.1595.

EXAMPLE 24

{2-[3-Cyclopentyl-2-(4-nitro-phenyl)-propionylamino]-thiazol-4-yl}-acetic Acid Methyl Ester

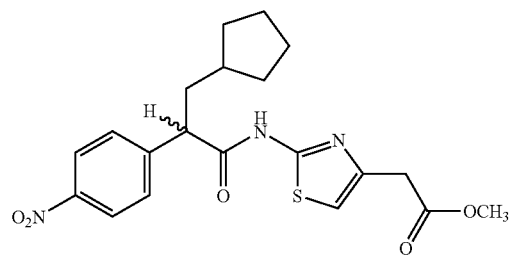

A solution of {2-[3-cyclopentyl-2-(4-nitro-phenyl)-propionylamino]-thiazol-4-yl}-acetic acid ethyl ester (prepared as in Example 23, 160 mg, 0.37 mmol) in methanol (10 mL) was treated with a catalytic amount of sulfuric acid. The reaction mixture was heated under reflux for 68 h. The reaction was concentrated in vacuo. Flash chromatography (Merck Silica gel 60, 230–400 mesh, 75/25 hexanes/ethyl acetate) afforded {2-[3-cyclopentyl-2-(4-nitro-phenyl)-propionylamino]-thiazol-4-yl}-acetic acid methyl ester (82.3 mg, 53.3%) as a pale yellow oil: FAB-HRMS m/e calcd for $C_{20}H_{23}N_3O_5S$ (M+H)+ 418.1436, found 418.1424.

EXAMPLE 25

{2-[2-(4-Amino-phenyl)-3-cyclopentyl-propionylamino]-thiazol-4-yl}-acetic Acid Methyl Ester

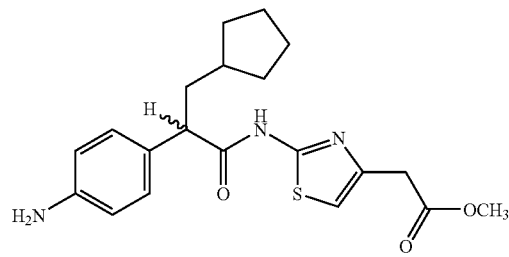

A solution of {2-[3-cyclopentyl-2-(4-nitro-phenyl)-propionylamino]-thiazol-4-yl}-acetic acid methyl ester (prepared as in Example 24, 75.3 mg, 0.18 mmol) in ethyl acetate (25 mL) was treated with 10% palladium on activated carbon. The reaction mixture was stirred under hydrogen gas at 60 psi at 25° C. for 4 h. The catalyst was then filtered off through a pad of celite, which was washed well with ethyl acetate. The resulting filtrate was concentrated in vacuo to give {2-[2-(4-amino-phenyl)-3-cyclopentyl-propionylamino]-thiazol-4-yl}-acetic acid methyl ester (64.5 mg, 93.3%) as a tan oil: EI-HRMS m/e calcd for $C_{20}H_{25}N_3O_3S$ (M+) 387.1616, found 387.1612.

EXAMPLE 26

2-[3-Cyclopentyl-2-(4-nitro-phenyl)-propionylamino]-thiazole-4-carboxylic Acid Methyl Ester

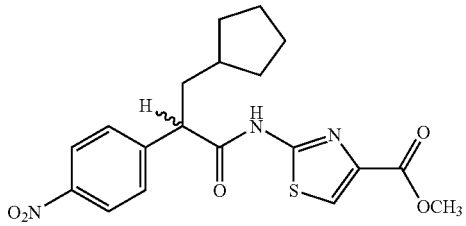

A solution of 2-[3-cyclopentyl-2-(4-nitro-phenyl)-propionylamino]-thiazole-4-carboxylic acid ethyl ester (prepared as in Example 39(B)(b), 135 mg, 0.32 mmol) in methanol (10 mL) was treated with a catalytic amount of sulfuric acid. The reaction mixture was heated under reflux for 68 h. The reaction was concentrated in vacuo. Flash chromatography (Merck Silica gel 60, 230–400 mesh, 50/50 hexanes/ethyl acetate) afforded 2-[3-cyclopentyl-2-(4-nitro-phenyl)-propionylamino]-thiazole-4-carboxylic acid methyl ester (71.4 mg, 54.8%) as a pale yellow solid: EI-HRMS m/e calcd for $C_{19}H_{21}N_3O_5S$ (M+) 403.1201, found 403.1188.

EXAMPLE 27

2-[2-(4-Amino-phenyl)-3-cyclopentyl-propionylamino]-thiazole-4-carboxylic Acid Methyl Ester

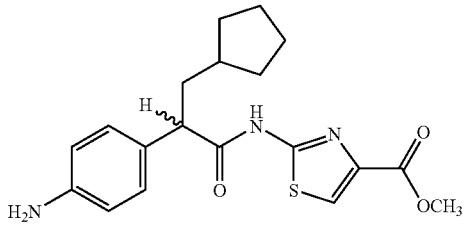

A solution of 2-[3-cyclopentyl-2-(4-nitro-phenyl)-propionylamino]-thiazole-4-carboxylic acid methyl ester (prepared as in Example 26, 60.0 mg, 0.14 mmol) in ethyl acetate (25 mL) was treated with 10% palladium on activated carbon. The reaction mixture was stirred under hydrogen gas at 60 psi at 25° C. for 4.5 h. The catalyst was then filtered off through a pad of celite, which was washed well with ethyl acetate. The resulting filtrate was concentrated in vacuo to give 2-[2-(4-amino-phenyl)-3-cyclopentyl-propionylamino]-thiazole-4-carboxylic acid methyl ester (61.3 mg, 100%) as a pale yellow oil: EI-HRMS m/e calcd for $C_{19}H_{23}N_3O_3S$ (M+) 373.1460, found 373.1454.

EXAMPLE 28

{2-[2-(3-Chloro-phenyl)-3-cyclopentyl-propionylamino]-thiazol-4-yl}-acetic Acid Ethyl Ester

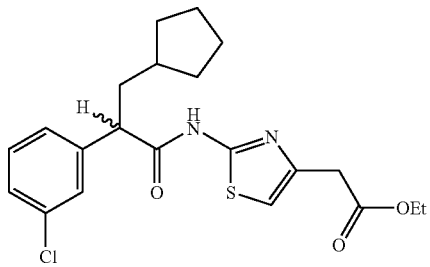

A solution of freshly prepared lithium diisopropylamide (141.3 mL of a 0.32M stock solution, 45.0 mmol) cooled to −78° C. was treated with (3-chloro-phenyl)-acetic acid (3.41 g, 20.0 mmol) in tetrahydrofuran/1,3-dimethyl-3,4,5,6-tetrahydro-2(1H)-pyrimidinone (49.7 mL, 3:1). The resulting reaction solution was stirred at −78° C. for 1 h. Iodomethylcyclopentane (4.64 g, 22.08 mmol) was then added in 1,3-dimethyl-3,4,5,6-tetrahydro-2(1H)-pyrimidinone (4.64 mL). The reaction mixture was stirred at −78° C. for 4 h. The reaction was then warmed to 25° C. and was stirred at 25° C. for 48 h. The solution was then quenched by the slow addition of the reaction mixture to a 2N aqueous hydrochloric acid solution (50 mL). The product was extracted into ethyl acetate (1×150 mL). The organic layer was dried over sodium sulfate, filtered, and concentrated in vacuo. Flash chromatography (Merck Silica gel 60, 230–400 mesh, 85/15 hexanes/ethyl acetate) afforded 2-(3-chloro-phenyl)-3-cyclopentyl-propionic acid (3.68 g, 72.9%) as a yellow solid: mp 70–72° C.; EI-HRMS m/e calcd for $C_{14}H_{17}ClO_2$ (M+) 252.0917, found 252.0915.

A solution of 2-(3-chloro-phenyl)-3-cyclopentyl-propionic acid (252 mg, 1.0 mmol) in methylene chloride (10 mL) was cooled to 0° C. and then treated with a 2.0M solution oxalyl chloride in methylene chloride (0.6 mL, 1.2 mmol) and a few drops of N,N-dimethylformamide. The reaction mixture was stirred at 0° C. for 15 min and at 25° C. for 2 h. The reaction mixture was then treated with (2-aminothiazol-4-yl)-acetic acid ethyl ester (409 mg, 2.2 mmol) and N,N-diisopropylethylamine (0.5 mL, 2.4 mmol). This solution was stirred at 25° C. for 48 h. At this time, the reaction was concentrated in vacuo. Flash chromatography (Merck Silica gel 60, 230–400 mesh, 80/20 hexanes/ethyl acetate) afforded {2-[2-(3-chloro-phenyl)-3-cyclopentyl-propionylamino]-thiazol-4-yl}-acetic acid ethyl ester (254 mg, 60.3%) as a white solid: mp 121–125° C.; EI-HRMS m/e calcd for $C_{21}H_{25}ClN_2O_3S$ (M+) 420.1274, found 420.1268.

In an analogous manner, there were obtained:
a) From 2-amino-thiazole-4-carboxylic acid ethyl ester and 2-(3-chloro-phenyl)-3-cyclopentyl-propionic acid: 2-[2-(3-Chloro-phenyl)-3-cyclopentyl-propionylamino]-thiazole-4-carboxylic acid ethyl ester as a white solid: mp 167–168° C.; EI-HRMS m/e calcd for $C_{20}H_{23}ClN_2O_3S$ (M+) 406.1117, found 406.1103.
b) From 2-amino-pyridine and 2-(3-chloro-phenyl)-3-cyclopentyl-propionic acid: 2-(3-Chloro-phenyl)-3-cyclopentyl-N-pyridin-2-yl-propionamide as a clear oil: EI-HRMS m/e calcd for $C_{19}H_{21}ClN_2O$ (M+) 328.1342, found 328.1333.
c) From 6-amino-nicotinic acid methyl ester and 2-(3-chloro-phenyl)-3-cyclopentyl-propionic acid: 6-[2-(3-Chloro-phenyl)-3-cyclopentyl-propionylamino]-nicotinic acid methyl ester as a colorless oil: EI-HRMS m/e calcd for $C_{21}H_{23}ClN_2O_3$ (M+) 386.1397, found 386.1398.

EXAMPLE 29

{2-[2-(3-Chloro-phenyl)-3-cyclopentyl-propionylamino]-thiazol-4-yl}-acetic Acid Methyl Ester

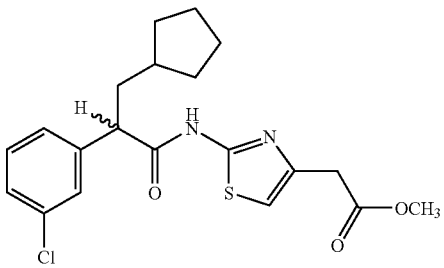

A solution of {2-[2-(3-chloro-phenyl)-3-cyclopentyl-propionylamino]-thiazol-4-yl}-acetic acid ethyl ester (prepared as in Example 28A, 177.2 mg, 0.42 mmol) in methanol (15 mL) was treated with a catalytic amount of sulfuric acid. The reaction mixture was heated under reflux for 40 h. The reaction was then concentrated in vacuo. Flash chromatography (Merck Silica gel 60, 230–400 mesh, 70/30 hexanes/ethyl acetate) afforded {2-[2-(3-chloro-phenyl)-3-cyclopentyl-propionylamino]-thiazol-4-yl}-acetic acid methyl ester (104.4 mg, 60.9%) as a clear oil: EI-HRMS m/e calcd for $C_{20}H_{23}ClN_2O_3S$ (M$^+$) 406.1117, found 406.1118.

EXAMPLE 30

2-[2-(3-Chloro-phenyl)-3-cyclopentyl-propionylamino]-thiazole-4-carboxylic Acid Methyl Ester

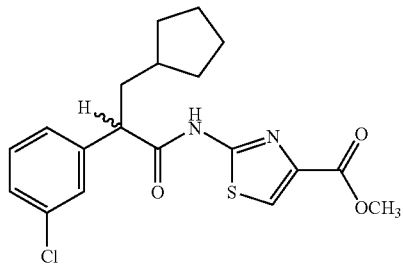

A solution of 2-[2-(3-chloro-phenyl)-3-cyclopentyl-propionylamino]-thiazole-4-carboxylic acid ethyl ester (prepared as in Example 28(B)(a), 94.5 mg, 0.23 mmol) in methanol (15 mL) was treated with a catalytic amount of sulfuric acid. The reaction mixture was heated under reflux for 40 h. The reaction was then concentrated in vacuo. Flash chromatography (Merck Silica gel 60, 230–400 mesh, 75/25 hexanes/ethyl acetate) afforded 2-[2-(3-chloro-phenyl)-3-cyclopentyl-propionylamino]-thiazole-4-carboxylic acid methyl ester (36.8 mg, 40.3%) as a white solid: mp 95–98° C.; EI-HRMS m/e calcd for $C_{19}H_{21}ClN_2O_3S$ (M$^+$) 392.0961, found 392.0989.

EXAMPLE 31

{2-[2-(4-Chloro-phenyl)-3-cyclopentyl-propionylamino]-thiazol-4-yl}-acetic Acid Ethyl Ester

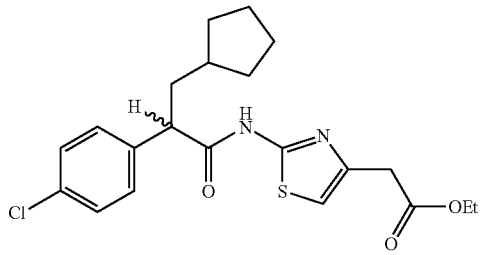

A solution of freshly prepared lithium diisopropylamide (78.0 mL of a 0.91M stock solution, 70.98 mmol) cooled to −78° C. was treated with (4-chloro-phenyl)-acetic acid (5.76 g, 33.8 mmol) in tetrahydrofuran/1,3-dimethyl-3,4,5,6-tetrahydro-2(1H)-pyrimidinone (84 mL, 3:1). The resulting solution was stirred at −78° C. for 1 h. Iodomethylcyclopentane (7.45 g, 35.49 mmol) was then added in 1,3-dimethyl-3,4,5,6-tetrahydro-2(1H)-pyrimidinone (2 mL). This solution was stirred at −78° C. for 4 h. The reaction was then warmed to 25° C. and was stirred at 25° C. for 16 h. The reaction mixture was then quenched by the dropwise addition of a saturated aqueous ammonium chloride solution (20 mL). The excess solvent was removed in vacuo. The residue was acidified to pH=1 with a 1N aqueous hydrochloric acid solution. The mixture was then poured into water (150 mL) and extracted with ethyl acetate (3×50 mL). The combined organic layers were dried over sodium sulfate, filtered, and concentrated in vacuo. Flash chromatography (Merck Silica gel 60, 230–400 mesh, 80/20 hexanes/ethyl acetate) afforded 2-(4-chloro-phenyl)-3-cyclopentyl-propionic acid (6.76 g, 79.1%) as a yellow solid: mp 82–84° C.: EI-HRMS m/e calcd for $C_{14}H_{17}ClO_2$ (M$^+$) 252.0917, found 252.0906.

A solution of 2-(4-chloro-phenyl)-3-cyclopentyl-propionic acid (252 mg, 1.0 mmol) in methylene chloride (10 mL) was cooled to 0° C. and then treated with a 2.0M solution of oxalyl chloride in methylene chloride (0.55 mL, 1.1 mmol), and a few drops of N,N-dimethylformamide. The reaction mixture was stirred at 0° C. for 15 min and then at 25° C. for 1.5 h. The reaction mixture was then treated with (2-amino-thiazol-4-yl)-acetic acid ethyl ester (409 mg, 2.2 mmol) and N,N-diisopropylethylamine (0.5 mL, 2.4 mmol). This solution was stirred at 25° C. for 24 h. At this time, the reaction was concentrated in vacuo. Flash chromatography (Merck Silica gel 60, 230–400 mesh, 85/15 hexanes/ethyl acetate) afforded {2-[2-(4-chloro-phenyl)-3-cyclopentyl-propionylamino]-thiazol-4-yl}-acetic acid ethyl ester (183.3 mg, 43.5%) as a pale yellow oil: EI-HRMS m/e calcd for $C_{21}H_{25}ClN_2O_3S$ (M$^+$) 420.1274, found 420.1272.

In an analogous manner, there were obtained:
a) From 2-amino-thiazole-4-carboxylic acid ethyl ester and 2-(4-chloro-phenyl)-3-cyclopentyl-propionic acid: 2-[2-(4-Chloro-phenyl)-3-cyclopentyl-propionylamino]-thiazole-4-carboxylic acid ethyl ester as a white solid: mp 114–116° C.; EI-HRMS m/e calcd for $C_{20}H_{23}ClN_2O_3S$ (M$^+$) 406.1117, found 406.1119.
b) From 2-amino-pyridine and 2-(4-chloro-phenyl)-3-cyclopentyl-propionic acid: 2-(4-Chloro-phenyl)-3-cyclopentyl-N-pyridin-2-yl-propionamide as a clear oil: EI-HRMS m/e calcd for $C_{19}H_{21}ClN_2O$ (M$^+$) 328.1342, found 328.1355.
c) From 6-amino-nicotinic acid methyl ester and 2-(4-chloro-phenyl)-3-cyclopentyl-propionic acid: 6-[2-(4-Chloro-phenyl)-3-cyclopentyl-propionylamino]-nicotinic acid methyl ester as a white foam: EI-HRMS m/e calcd for $C_{21}H_{23}ClN_2O_3$ (M$^+$) 386.1397, found 386.1384.

EXAMPLE 32

2-[2-(4-Chloro-phenyl)-3-cyclopentyl-propionylamino]-thiazole-4-carboxylic Acid Methyl Ester

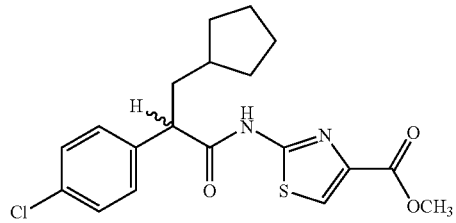

A solution of 2-[2-(4-chloro-phenyl)-3-cyclopentyl-propionylamino]-thiazole-4-carboxylic acid ethyl ester (prepared as in Example 31(B)(a), 105 mg, 0.25 mmol) in methanol (10 mL) was treated with a catalytic amount of sulfuric acid. The reaction mixture was heated under reflux for 68 h. The reaction was concentrated in vacuo. High pressure liquid chromatography (Chromegasphere SI-60, 10 μm, 60 Å, 25 cm×23 cm ID, 75/25 heptane/ethyl acetate) afforded 2-[2-(4-chloro-phenyl)-3-cyclopentyl-propionylamino]-thiazole-4-carboxylic acid methyl ester (41.3 mg,

EXAMPLE 33

{2-[2-(4-Chloro-phenyl)-3-cyclopentyl-propionylamino]-thiazol-4-yl}-acetic Acid Methyl Ester

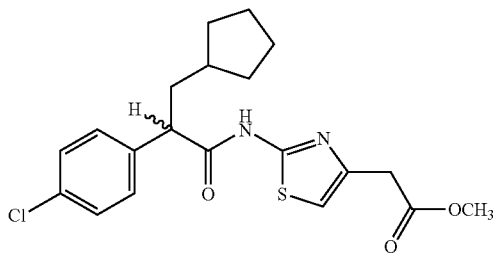

A solution of {2-[2-(4-chloro-phenyl)-3-cyclopentyl-propionylamino]-thiazol-4-yl}-acetic acid ethyl ester (prepared as in Example 31A, 76.1 mg, 0.18 mmol) in methanol (5 mL) was treated with a catalytic amount of sulfuric acid. The reaction mixture was heated under reflux for 72 h. The reaction was concentrated in vacuo. High pressure liquid chromatography (Chromegasphere SI-60, 10 μM, 60 Å, 25 cm×23 cm ID, 75/25 heptane/ethyl acetate) afforded {2-[3-cyclopentyl-2-(4-nitro-phenyl)-propionylamino]-thiazol-4-yl}-acetic acid methyl ester (21.5 mg, 29.2%) as a colorless oil: EI-HRMS m/e calcd for $C_{20}H_{23}ClN_2O_3S$ (M+) 406.1117, found 406.1114.

EXAMPLE 34

2-(4-Chloro-phenyl)-3-cyclopentyl-N-(5-hydroxymethyl-thiazol-2-yl)-propionamide

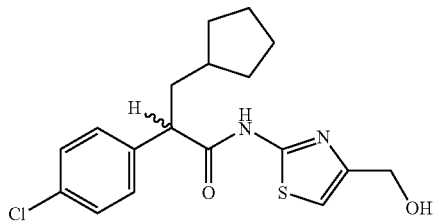

A solution of 2-[2-(4-chloro-phenyl)-3-cyclopentyl-propionylamino]-thiazole-4-carboxylic acid methyl ester (prepared as in Example 32, 127.7 mg, 0.31 mmol) in tetrahydrofuran (0.4 mL) was added to a slurry of lithium aluminum hydride (15.0 mg, 0.39 mmol) in tetrahydrofuran (2.24 mL) at 0° C. The reaction mixture was stirred at 0° C. for 2 h. The reaction was then quenched by the dropwise addition of water. The reaction was then diluted with more water (25 mL) and extracted with ethyl acetate (3×25 mL). The combined organic layers were dried over sodium sulfate, filtered and concentrated in vacuo. Flash chromatography (Merck Silica gel 60, 230–400 mesh, 75/25 hexanes/ethyl acetate) afforded 2-(4-chloro-phenyl)-3-cyclopentyl-N-(5-hydroxymethyl-thiazol-2-yl)-propionamide (63.4 mg, 55.4%) as a white solid: mp 115–117° C.; EI-HRMS m/e calcd for $C_{18}H_{21}ClN_2O_2S$ (M+) 364.1012, found 364.1004.

EXAMPLE 35

3-Cyclopentyl-N-(4-hydroxymethyl-thiazol-2-yl)-2-(4-methanesulfonyl-phenyl)-propionamide

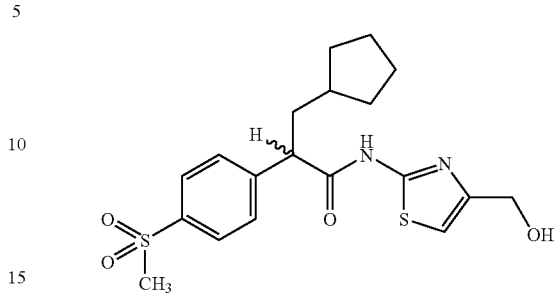

A solution of 2-[3-cyclopentyl-2-(4-methanesulfonyl-phenyl)-propionylamino]-thiazole-4-carboxylic acid ethyl ester (prepared as in Example 3(B)(b), 130 mg, 0.29 mmol) in diethyl ether (2 mL) was cooled to 0° C. and then slowly treated with lithium aluminum hydride (17 mg, 0.44 mmol). The reaction mixture was allowed to warm to 25° C. where it was stirred for 4 h. After 4 h at 25° C., thin layer chromatography indicated the presence of starting material. An additional amount of lithium aluminum hydride (11 mg, 0.29 mmol) was added to the reaction mixture. The resulting reaction mixture was allowed to stir at 25° C. for 15 h. The reaction was then slowly quenched by the dropwise addition of water. The resulting mixture was then partitioned between water and ethyl acetate. The organic layer was then dried over magnesium sulfate, filtered, and concentrated in vacuo. Flash chromatography (Merck Silica gel 60, 230–400 mesh, ethyl acetate) afforded 3-cyclopentyl-N-(4-hydroxymethyl-thiazol-2-yl)-2-(4-methanesulfonyl-phenyl)-propionamide (55 mg, 46%) as a white solid: mp 124–126° C.; EI-HRMS m/e calcd for $C_{19}H_{24}N_2O_4S_2$ (M+) 408.11–78, found 408.1164.

EXAMPLE 36

3-Cyclopentyl-N-[4-(2-hydroxyethyl)-thiazol-2-yl]-2-(4-methanesulfonyl-phenyl)-propionamide

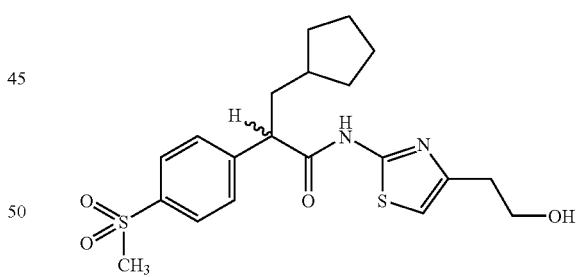

A solution of {2-[3-cyclopentyl-2-(4-methanesulfonyl-phenyl)-propionylamino]-thiazol-4-yl}-acetic acid ethyl ester (prepared as in Example 3(B)(d), 120 mg, 0.26 mmol) in diethyl ether (500 μL) was cooled to 0° C. and then slowly treated with lithium aluminum hydride (15 mg, 0.39 mmol). The reaction mixture was allowed to warm to 25° C. where it was stirred for 1 h. After 1 h at 25° C., thin layer chromatography still indicated the presence of the starting material. An additional amount of lithium aluminum hydride (10 mg, 0.26 mmol) was added to the reaction mixture, and the reaction mixture was allowed to stir at 25° C. for 1 h. The reaction mixture was then slowly quenched by the dropwise addition of water (10 mL). The resulting mixture was partitioned between water and ethyl acetate. The organic layer was dried over magnesium sulfate, filtered, and concentrated in vacuo. Flash chromatography (Merck Silica gel 60, 230–400 mesh, 1/3 hexanes/ethyl acetate) afforded 3-cyclopentyl-N-[4-(2-hydroxyethyl)-thiazol-2-yl]-2-(4-methanesulfonyl-phenyl)-propionamide (20 mg, 18%) as a yellow foam: mp 84–87° C.; EI-HRMS m/e calcd for $C_{20}H_{26}N_2O_4S_2$ ($M^+$) 422.1334, found 422.1335.

EXAMPLE 37

(2R)-2-[3-Cyclopentyl-2-(3,4-dichloro-phenyl)-propionylamino]-thiazole-4-carboxylic Acid Methyl Ester

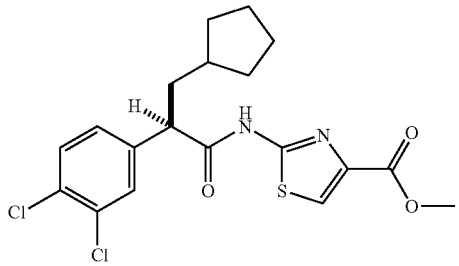

A solution triphenylphosphine (164 mg, 0.63 mmol) in methylene chloride (3 mL) was cooled to 0° C. and then treated with N-bromosuccinimide (112 mg, 0.63 mmol) in small portions. The resulting orange reaction mixture was stirred at 0° C. for 20 min and then treated with 3-cyclopentyl-2(R)-(3,4-dichloro-phenyl)-propionic acid (prepared as in Example 54A, 150 mg, 0.52 mmol). The reaction mixture was stirred at 0° C. for an additional 15 min and then allowed to warm to 25° C. The reaction mixture was then treated with 2-aminothiazole-4-carboxylic acid methyl ester (181 mg, 1.15 mmol). The resulting reaction mixture was stirred at 25° C. for 15 h. The crude reaction mixture was directly purified by flash chromatography (Merck Silica gel 60, 230–400 mesh, 3/1 hexanes/ethyl acetate) to afford impure (2R)-2-[3-cyclopentyl-2-(3,4-dichloro-phenyl)-propionylamino]-thiazole-4-carboxylic acid methyl ester. The impure product was diluted with ethyl acetate and then washed with a saturated aqueous sodium bicarbonate solution. The organic layer was dried over magnesium sulfate, filtered, and concentrated in vacuo to provide pure (2R)-2-[3-cyclopentyl-2-(3,4-dichloro-phenyl)-propionylamino]-thiazole-4-carboxylic acid methyl ester (92 mg, 41%) as a white solid: mp 143–144° C.; $[\alpha]^{23}_{589}$=–10.2° (c=0.98, chloroform); EI-HRMS m/e calcd for $C_{19}H_{20}Cl_2N_2O_3S$ ($M^+$) 426.0572, found 426.0562.

EXAMPLE 38

3-Cyclopentyl-2-(3,4-dichloro-phenyl)-N-pyridin-2-yl-propionamide

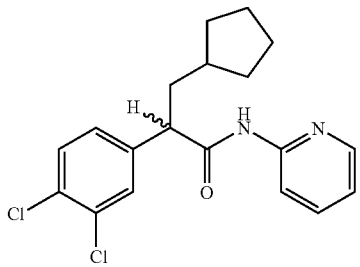

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.0 g, 99.8 mmol) in methylene chloride (10 mL). The resulting reaction mixture was allowed to warm to 25° C. where it was stirred for 4 h. The reaction mixture was then diluted with water (50 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I_1$ ($M^+$) 209.9906, found 209.9911.

A solution of diisopropylamine (13.36 mL, 101.89 mmol) in tetrahydrofuran (250 mL) was cooled to –78° C. under a nitrogen atmosphere and then treated with a 2.0M solution of n-butyllithium in hexanes (51 mL, 101.89 mmol). The reaction mixture was stirred at –78° C. for 15 min, at which time, a solution of 3,4-dichlorophenyl acetic acid (9.08 g, 44.3 mmol) in tetrahydrofuran (60 mL) and hexamethylphosphoramide (20 mL) was slowly added via a cannula. The bright yellow solution was allowed to stir at –78° C. for 1 h, at which time, a solution of iodomethylcyclopentane (11.17 g, 53.2 mmol) in hexamethylphosphoramide (10 mL) was added via a cannula. The reaction mixture was stirred at –78° C. for 1 h. The reaction mixture was then allowed to warm to 25° C. where it was stirred for 14 h. The reaction mixture was then acidified to pH=2 by the dropwise addition of a 1N aqueous hydrochloric acid solution and extracted with ethyl acetate (3×50 mL). The combined organic layers were dried over sodium sulfate, filtered, and concentrated in vacuo. Flash chromatography (Merck Silica gel 60, 230–400 mesh, chloroform then 99/1 chloroform/methanol) afforded 3-cyclopentyl-2-(3,4-dichlorophenyl)-propionic acid (10.28 g, 81%) as a white solid: mp 74.5–76.9° C.; EI-HRMS m/e calcd for $C_{14}H_{16}Cl_2O_2$ ($M^+$) 286.0527, found 286.0534.

A solution of 3-cyclopentyl-2-(3,4-dichlorophenyl)-propionic acid (114 mg, 0.39 mmol) in methylene chloride (10 mL) was treated with 1 drop of N,N-dimethylformamide and then cooled to 0° C. The reaction mixture was then treated with a 2.0M solution of oxalyl chloride in methylene chloride (0.22 mL, 0.44 mmol). The reaction mixture was stirred at 0° C. for 30 min and then treated with a solution of 2-aminopyridine (78 mg, 0.83 mmol) and N,N-diisopropylethylamine (0.16 mL, 0.95 mmol) in tetrahydrofuran (2 mL). The resulting reaction mixture was stirred at 25° C. for 14 h. The reaction mixture was then diluted with water (10 mL) and extracted with methylene chloride (2×15 mL). The combined organic layers were dried over sodium sulfate, filtered, and concentrated in vacuo. Flash chromatography (Merck Silica gel 60, 230–400 mesh, hexanes then 19/1 to 4/1 hexanes/ethyl acetate) afforded 3-cyclopentyl-2-(3,4-dichloro-phenyl)-N-pyridin-2-yl-propionamide (58 mg, 50%) as a white foam: EI-HRMS m/e calcd for $C_{19}H_{20}Cl_2N_2O$ ($M^+$) 362.0953, found 362.0955.

In an analogous manner, there were obtained:
a) From 2-amino-5-nitropyridine and 3-cyclopentyl-2-(3,4-dichlorophenyl)-propionic acid: 3-Cyclopentyl-2-(3,4-dichloro-phenyl)-N-(5-nitropyridin)-2-yl-propionamide as a yellow-orange foam: EI-HRMS m/e calcd for $C_{19}H_{19}Cl_2N_3O_3$ ($M^+$) 407.0803, found 407.0799.
b) From 6-aminonicotinic acid methyl ester and 3-cyclopentyl-2-(3,4-dichlorophenyl)-propionic acid: 3-Cyclopentyl-2-(3,4-dichloro-phenyl)-N-(5-carboxymethylpyridin)-2-yl-propionamide as a white foam: EI-HRMS m/e calcd for $C_{21}H_{22}Cl_2N_2O_3$ ($M^+$) 420.1007, found 420.0994.

c) From 4-aminopyrimidine and 3-cyclopentyl-2-(3,4-dichlorophenyl)-propionic acid: 3-Cyclopentyl-2-(3,4-dichloro-phenyl)-N-pyrimidine-4-yl-propionamide as a white foam: EI-HRMS m/e calcd for $C_{18}H_{19}Cl_2N_3O$ ($M^+$) 363.0905, found 363.0910.

d) From 2-amino-5-methylpyridine and 3-cyclopentyl-2-(3,4-dichlorophenyl)-propionic acid: 3-Cyclopentyl-2-(3,4-dichloro-phenyl)-N-(5-methylpyridin)-2-yl-propionamide as a white solid: EI-HRMS m/e calcd for $C_{20}H_{22}Cl_2N_2O$ ($M^+$) 376.1109, found 376.1119.

e) From 2-amino-4-methylpyridine and 3-cyclopentyl-2-(3,4-dichlorophenyl)-propionic acid: 3-Cyclopentyl-2-(3,4-dichloro-phenyl)-N-(4-methylpyridin)-2-yl-propionamide as a white solid: EI-HRMS m/e calcd for $C_{20}H_{22}Cl_2N_2O$ ($M^+$) 376.1109, found 376.1106.

f) From 2-amino-6-methylpyridine and 3-cyclopentyl-2-(3,4-dichlorophenyl)-propionic acid: 3-Cyclopentyl-2-(3,4-dichloro-phenyl)-N-(6-methylpyridin)-2-yl-propionamide as a light yellow solid: EI-HRMS m/e calcd for $C_{20}H_{22}Cl_2N_2O$ ($M^+$) 376.1109, found 376.1107.

g) From 2-amino-5-chloropyridine and 3-cyclopentyl-2-(3,4-dichlorophenyl)-propionic acid: 3-Cyclopentyl-2-(3,4-dichloro-phenyl)-N-(5-chloropyridin)-2-yl-propionamide as a white foam: EI-HRMS m/e calcd for $C_{19}H_{19}Cl_3N_2O$ ($M^+$) 396.0563, found 396.0564.

h) From 2-amino-5-bromopyridine and 3-cyclopentyl-2-(3,4-dichlorophenyl)-propionic acid: 3-Cyclopentyl-2-(3,4-dichloro-phenyl)-N-(5-bromopyridin)-2-yl-propionamide as a white solid: EI-HRMS m/e calcd for $C_{19}H_{19}BrCl_2N_2O$ ($M^+$) 440.0058, found 440.0066.

EXAMPLE 39

3-Cyclopentyl-2-(4-nitro-phenyl)-N-pyridin-2-yl-propionamide

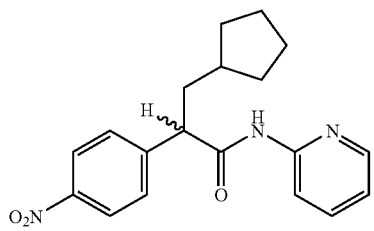

A solution of 3-cyclopentyl-2-(4-nitro-phenyl)-propionic acid (prepared as in Example 22, 263 mg, 1.0 mmol) in methylene chloride (5 mL) was cooled to 0° C. and then treated with a 2.0M solution of oxalyl chloride in methylene chloride (0.6 mL, 1.2 mmol) and a few drops of N,N-dimethylformamide. The reaction mixture was stirred at 0° C. for 15 min and then at 25° C. for 1 h. The reaction mixture was then treated with a solution of 2-aminopyridine (207 mg, 2.2 mmol) in tetrahydrofuran (5 mL) and N,N-diisopropylethylamine (0.42 mL, 2.5 mmol). The reaction mixture was stirred at 25° C. for 24 h. At this time, the reaction was concentrated in vacuo. Flash chromatography (Merck Silica gel 60, 230–400 mesh, 80/20 hexanes/ethyl acetate) afforded 3-cyclopentyl-2-(4-nitro-phenyl)-N-pyridin-2-yl-propionamide (110.2 mg, 32.5%) as a white solid: mp 152–154° C.; EI-HRMS m/e calcd for $C_{19}H_{21}N_3O_3$ ($M^+$) 339.1582, found 339.1581.

In an analogous manner, there were obtained:

a) From 4-aminopyrimidine and 3-cyclopentyl-2-(4-nitro-phenyl)-propionic acid: 3-Cyclopentyl-2-(4-nitro-phenyl)-N-pyrimidin-4-yl-propionamide as a white solid: mp 152–153° C.; EI-HRMS m/e calcd for $C_{18}H_{20}N_4O_3$ ($M^+$) 340.1535, found 340.1533.

b) From 2-amino-thiazole-4-carboxylic acid ethyl ester and 3-cyclopentyl-2-(4-nitro-phenyl)-propionic acid: 2-[3-Cyclopentyl-2-(4-nitro-phenyl)-propionylamino]-thiazole-4-carboxylic acid ethyl ester as a pale yellow solid: mp 110–115° C.; EI-HRMS m/e calcd for $C_{20}H_{23}N_3O_5S$ ($M^+$) 417.1358, found 417.1346.

EXAMPLE 40

3-Cyclopentyl-2-(4-methylsulfanyl-phenyl)-N-pyridin-2-yl-propionamide

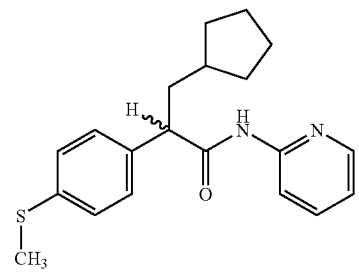

A solution of diisopropylamine (3.2 mL, 23.16 mmol) in dry tetrahydrofuran (10.3 mL) and 1,3-dimethyl-3,4,5,6-tetrahydro-2(1H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio)phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1 h, at which time, a solution of iodomethylcyclopentane (2.55 g, 12.13 mmol) in a small amount of dry tetrahydrofuran was added dropwise. The reaction mixture was then stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ ($M^+$) 264.1184, found 264.1177.

A solution of 3-cyclopentyl-2-(4-methylsulfanyl-phenyl) propionic acid (200 mg, 0.76 mmol) and triphenylphosphine (198 mg, 0.76 mmol) in methylene chloride (2 mL) was cooled to 0° C. and then treated with N-bromosuccinimide (150 mg, 0.84 mmol) in small portions. After the complete addition of N-bromosuccinimide, the reaction mixture was allowed to warm to 25° C. over 30 min. The orange reaction mixture was then treated with 2-aminopyridine (151 mg, 1.60 mmol), and the resulting reaction mixture was stirred at 25° C. for 15 h. The reaction mixture was then concentrated in vacuo to remove methylene chloride. The remaining residue was partitioned between water and ethyl acetate. The organic layer was washed with a 1N aqueous hydrochloric acid solution, washed with a saturated aqueous sodium bicarbonate solution, dried over magnesium sulfate, filtered, and concentrated in vacuo. Flash chromatography (Merck Silica gel 60, 230–400 mesh, 3/1 hexanes/ethyl acetate) afforded 3-cyclopentyl-2-(4-methylsulfanyl-phenyl)-N-pyridin-2-yl-propionamide (83 mg, 32%) as a white solid: mp 127–128° C.; EI-HRMS m/e calcd for $C_{20}H_{24}N_2OS$ ($M^+$) 340.1609, found 340.1611.

EXAMPLE 41

3-Cyclopentyl-N-pyridin-2-yl-2-(4-trifluoromethyl-sulfanyl-phenyl)-propionamide

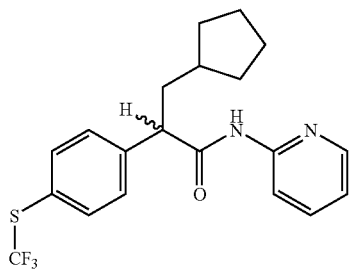

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (59.6 mg, 0.187 mmol) and triphenylphosphine (49.1 mg, 0.187 mmol) in methylene chloride (468 µL) was cooled to 0° C. and then treated with N-bromosuccinimide (36.7 mg, 0.206 mmol) in small portions. After the complete addition of N-bromosuccinimide, the reaction mixture was allowed to warm to 25° C. over 30 min. The orange reaction mixture was then treated with 2-aminopyridine (35.2 mg, 0.374 mmol). The resulting reaction mixture was stirred at 25° C. for 16 h. The reaction mixture was then concentrated in vacuo to remove methylene chloride. The remaining residue was diluted with ethyl acetate (50 mL). The organic layer was washed sequentially with a 10% aqueous hydrochloric acid solution (1×50 mL), a saturated aqueous sodium bicarbonate solution (1×50 mL) and water (1×50 mL), dried over sodium sulfate, filtered, and concentrated in vacuo. Flash chromatography (Merck Silica gel 60, 70–230 mesh, 9/1 hexanes/ethyl acetate) afforded 3-cyclopentyl-N-pyridin-2-yl-2-(4-trifluoromethylsulfanyl-phenyl)-propionamide (25.0 mg, 34%) as a cream solid: mp 101–102° C.; EI-HRMS m/e calcd for $C_{20}H_{21}F_3N_2OS$ ($M^+$) 394.1327, found 394.1321.

EXAMPLE 42

3-Cyclopentyl-2-(4-methanesulfonyl-phenyl)-N-pyridin-2-yl-propionamide

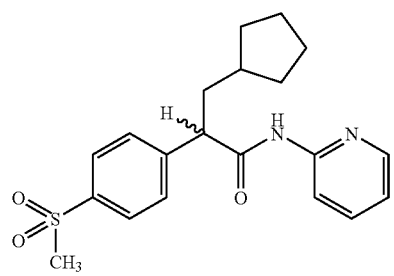

A solution of 2-aminopyridine (95 mg, 1.01 mmol) in acetonitrile (2 mL) was treated with 3-cyclopentyl-2-(4-methanesulfonyl-phenyl)propionic acid (prepared as in Example 3A, 250 mg, 0.84 mmol), triphenylphosphine (243 mg, 0.93 mmol), triethylamine (350 µL, 2.53 mmol), and carbon tetrachloride (1 mL). The resulting reaction mixture was stirred at 25° C. for 15 h. The cloudy reaction mixture was diluted with water and then extracted with methylene chloride. The organic layer was dried over magnesium sulfate, filtered, and concentrated in vacuo. Flash chromatography (Merck Silica gel 60, 230–400 mesh, 1/3 hexanes/ethyl acetate) afforded impure 3-cyclopentyl-2-(4-methanesulfonyl-phenyl)-N-pyridin-2-yl-propionamide.

Recrystallization from hexanes/methylene chloride provided pure 3-cyclopentyl-2-(4-methanesulfonyl-phenyl)-N-pyridin-2-yl-propionamide (170 mg, 54%) as a white solid: mp 172–173° C.; EI-HRMS m/e calcd for $C_{20}H_{24}N_2O_3S$ ($M^+$) 372.1508, found 372.1498.

EXAMPLE 43

3-Cyclopentyl-N-pyridin-2-yl-2-(4-trifluoromethanesulfonyl-phenyl)-propionamide

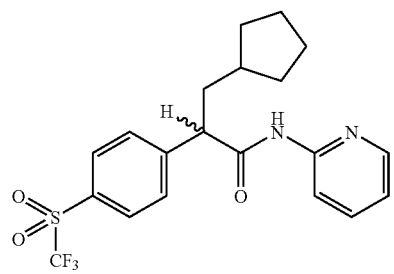

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2 (1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 0.3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL) and a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ ($M^+$) 332.1058, found 332.1052.

A solution of 3-cyclopentyl-2-(4-trifluoromethylsulfanyl-phenyl)propionic acid methyl ester (1.14 g, 3.43 mmol) in methylene chloride (8.6 mL) was treated with 3-chloroperoxybenzoic acid (80–85% grade, 2.00 g based on 80%, 9.26 mmol). The reaction mixture was stirred at 25° C. for 17 h, at which time, thin layer chromatography showed the presence of two new lower $R_f$ products. An additional 2.00 g of 3-chloroperoxybenzoic acid was added to the reaction mixture to drive the conversion of the sulfoxide to the sulfone, and the resulting reaction mixture was stirred at 25° C. for 3 d. The reaction mixture was concentrated in vacuo to remove methylene chloride. The resulting residue was diluted with ethyl acetate (300 mL). The organic phase was washed with a saturated aqueous sodium bicarbonate solution (3×100 mL) and a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-trifluoromethanesulfonyl-phenyl)propionic acid methyl ester (1.19 g, 95%) as a light yellow oil: EI-HRMS m/e calcd for $C_{16}H_{19}F_3O_4S$ ($M^+$) 364.0956, found 364.0965.

A solution of 3-cyclopentyl-2-(4-trifluoromethanesulfonyl-phenyl)propionic acid methyl ester (708.2 mg, 1.94 mmol) in tetrahydrofuran (2.4 mL) was treated with a 0.8M aqueous lithium hydroxide solution (3.6 mL, 2.92 mmol). The reaction mixture was stirred at 25° C. for 23 h and then concentrated in vacuo to remove tetrahydrofuran. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford a cream solid. This solid was purified by triturating with diethyl ether/petroleum ether to provide pure 3-cyclopentyl-2-(4-trifluoromethanesulfonyl-phenyl)propionic acid (527.0 mg, 77%) as a white solid: mp 143–145° C.; EI-HRMS m/e calcd for $C_{15}H_{17}F_3O_4S$ ($M^+$) 350.0800, found 350.0816.

A solution of 3-cyclopentyl-2-(4-trifluoromethanesulfonyl-phenyl)propionic acid (118.9 mg, 0.34 mmol) and triphenylphosphine (133.5 mg, 0.51 mmol) in methylene chloride (848 µL) was cooled to 0° C. and then treated with N-bromosuccinimide (102.7 mg, 0.58 mmol) in small portions. After the complete addition of N-bromosuccinimide, the reaction mixture was allowed to warm to 25° C. where it was stirred for 45 min. The reaction mixture was then treated with 2-aminopyridine (95.8 mg, 1.02 mmol). The resulting reaction mixture was stirred at 25° C. for 22 h. The reaction mixture was then concentrated in vacuo. Flash chromatography (Merck Silica gel 60, 230–400 mesh, 5/1 hexanes/ ethyl acetate) afforded 3-cyclopentyl-N-pyridin-2-yl-2-(4-trifluoromethanesulfonyl-phenyl)-propionamide (37.1 mg, 26%) as a light yellow solid: mp 151–153° C.; EI-HRMS m/e calcd for $C_{20}H_{21}F_3N_2O_3S$ ($M^+$) 426.1225, found 426.1220.

In an analogous manner, there were obtained:
a) From 3-cyclopentyl-2-(4-trifluoromethanesulfonyl-phenyl)propionic acid and 2-amino-5-chloropyridine: N-(5-Chloro-pyridin-2-yl)-3-cyclopentyl-2-(4-trifluoromethane-sulfonyl-phenyl)-propionamide as a cream solid: mp 146–148° C.; EI-HRMS m/e calcd for $C_{20}H_2{}^0ClF_3N_2O_3S$ ($M^+$) 460.0835, found 460.0846.
b) From 3-cyclopentyl-2-(4-trifluoromethanesulfonyl-phenyl)propionic acid and 2-amino-5-methylpyridine: 3-Cyclopentyl-N-(5-methyl-pyridin-2-yl)-2-(4-trifluoro-methanesulfonyl-phenyl)-propionamide as a pale yellow solid: mp 155–157° C.; EI-HRMS m/e calcd for $C_{21}H_{23}F_3N_2O_3S$ ($M^+$) 440.1381, found 440.1376.
c) From 3-cyclopentyl-2-(4-trifluoromethanesulfonyl-phenyl)propionic acid and 6-aminonicotinic acid methyl ester: 6-[3-Cyclopentyl-2-(4-trifluoromethanesulfonyl-phenyl)-propionylamino]-nicotinic acid methyl ester as a yellow foam: mp 58–62° C.; EI-HRMS m/e calcd for $C_{22}H_{23}F_3N_2O_5S$ ($M^+$) 484.1280, found 484.1274.

EXAMPLE 44

3-Cyclopentyl-2-(4-methanesulfonyl-3-nitrophenyl)-N-pyridin-2-yl-propionamide

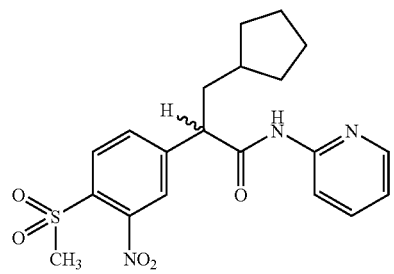

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_9H_8ClNO_4$ ($M^+$) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C. where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_4$ ($M^+$) 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3 mL) was heated at 130° C. for 5 h. The black reaction mixture was then poured over ice (20 g), resulting in the formation of a brown sticky substance. The resulting mixture was then treated with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_6S$ (M+H)+356.1169, found 356.1175.

A solution of 3-cyclopentyl-2-(4-methanesulfonyl-3-nitrophenyl)-propionic acid methyl ester (1.17 g, 3.29 mmol) in tetrahydrofuran (6 mL) was treated with a 0.8M aqueous lithium hydroxide solution (6.17 mL, 4.94 mmol). The reaction mixture was stirred at 25° C. for 3 h. The reaction mixture was then diluted with water (50 mL), a 1N aqueous hydrochloric acid solution (10 mL), and ethyl acetate (50 mL). The layers were separated, and the aqueous layer was back-extracted with ethyl acetate (2×50 mL). The combined organic layers were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid (993 mg, 88%) as a yellow foam which contained a small impurity. A small amount of the yellow foam (50 mg) was re-purified using Biotage chromatography (FLASH 40S, Silica, 3/1 then 1/1 hexanes/ethyl acetate) to afford 3-cyclopentyl-2-(4-methanesulfonyl-3-nitrophenyl)-propionic acid as a white foam: mp 114–118° C. (foam to gel); FAB-HRMS m/e calcd for $C_{15}H_{19}NO_6S$ (M+H)+ 342.1011, found 342.1014.

A solution of triphenylphosphine (138 mg, 0.53 mmol) in methylene chloride (2 mL) was cooled to 0° C. and then slowly treated with N-bromosuccinimide (94 mg, 0.53 mmol) in small portions. The reaction mixture was stirred at 0° C. for 10 min and then treated with 3-cyclopentyl-2-(4-methanesulfonyl-3-nitrophenyl)-propionic acid (150 mg, 0.44 mmol). The resulting reaction mixture was stirred at 0° C. for 5 min and then allowed to warm to 25° C. where it was stirred for 25 min. The reaction mixture was then treated with 2-aminopyridine (91 mg, 0.97 mmol). The resulting reaction mixture was stirred at 25° C. for 15 h. The crude reaction mixture was directly purified by flash chromatography (Merck Silica gel 60, 230–400 mesh, 1/1 hexanes/ethyl acetate) to afford 3-cyclopentyl-2-(4-methanesulfonyl-3-nitrophenyl)-N-pyridin-2-yl-propionamide (106 mg, 58%) as a white foam: mp 92–95° C. (foam to gel); FAB-HRMS m/e calcd for $C_{20}H_{23}N_3O_5S$ (M+H)+ 418.1436, found 418.1430.

EXAMPLE 45

6-[3-Cyclopentyl-2(R)-(3,4-dichloro-phenyl)-propionylamino]-nicotinic Acid Methyl Ester

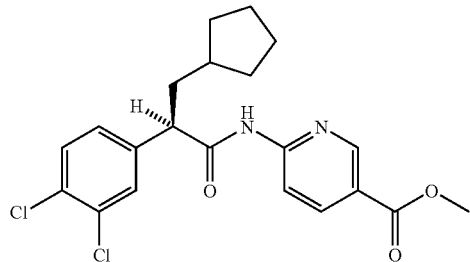

A mixture of 6-aminonicotinic acid (4.0 g, 28.9 mmol), methanol (75 mL), and concentrated hydrochloric acid (4 mL) was heated under reflux for 16 h. The reaction mixture was allowed to cool to 25° C. and then concentrated in vacuo to remove methanol. The resulting solid was treated with water (20 mL) and enough sodium bicarbonate to adjust the pH to pH=8. The solution was then extracted with ethyl acetate (3×25 mL). The combined organic layers were dried over sodium sulfate, filtered, and concentrated in vacuo to afford 6-aminonicotinic acid methyl ester (3.12 g, 71%) as white foam: EI-HRMS m/e calcd for $C_7H_8N_2O_2$ ($M^+$) 152.0586, found 152.0586.

A solution of triphenylphosphine (1.23 g, 4.69 mmol) in methylene chloride (15 mL) was cooled to 0° C. and then treated with N-bromosuccinimide (947 mg, 5.32 mmol). The resulting brown-purple solution was stirred at 0° C. for 5 min and then treated with 3-cyclopentyl-2(R)-(3,4-dichloro-phenyl)-propionic acid (prepared as in Example 54A, 900 mg, 3.13 mmol). The reaction mixture was stirred at 0° C. and then allowed to warm to 25° C. over 45 min. The reaction mixture was then treated with 6-aminonicotinic acid methyl ester (620 mg, 4.07 mmol) and pyridine (0.38 mL, 4.7 mmol), and the reaction mixture was allowed to stir at 25° C. for 20 h. The resulting reaction mixture was diluted with water (15 mL) and then extracted with methylene chloride (3×15 mL). The combined organic layers were dried over sodium sulfate, filtered, and concentrated in vacuo. Flash chromatography (Merck Silica gel 60, 230–400 mesh, 9/1 hexanes/ethyl acetate) afforded 6-[3-cyclopentyl-2(R)-(3,4-dichloro-phenyl)-propionylamino]-nicotinic acid

EXAMPLE 46

6-[3-Cyclopentyl-2-(3,4-dichloro-phenyl)-propionylamino]-nicotinic Acid

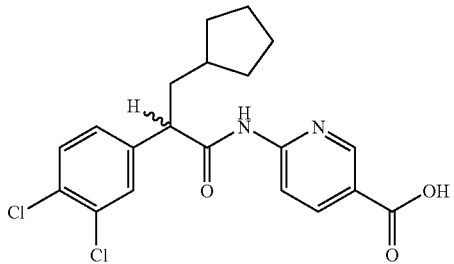

A solution of 3-cyclopentyl-2-(3,4-dichloro-phenyl)-N-(5-carboxymethylpyridin)-2-yl-propionamide (prepared as in Example 38(B)(b), 50 mg, 0.12 mmol) in ethanol (10 mL) at 25° C. was treated with a solution of potassium hydroxide (20 mg, 0.36 mmol) in water (2 mL). The reaction was stirred at 25° C. for 2 h. At this time, the reaction was diluted with water (5 mL). The ethanol was removed in vacuo. The aqueous layer was then acidified to pH=2 with a 1N aqueous hydrochloric acid solution. This solution was extracted with methylene chloride (3×10 mL). The combined organic layers were dried over sodium sulfate, filtered, and concentrated in vacuo. Flash chromatography (Merck Silica gel 60, 230–400 mesh, 80/20 hexanes/ethyl acetate with acetic acid) afforded 6-[3-cyclopentyl-2-(3,4-dichloro-phenyl)-propionylamino]-nicotinic acid (34 mg, 71%) as white foam: EI-HRMS m/e calcd for $C_{20}H_{20}Cl_2N_2O_3$ (M+) 406.0851, found 406.0852.

EXAMPLE 47

6-[2-(4-Chloro-phenyl)-3-cyclopentyl-propionylamino]-nicotinic Acid

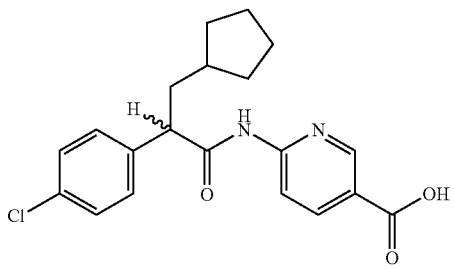

A solution of 6-[2-(4-chloro-phenyl)-3-cyclopentyl-propionylamino]-nicotinic acid methyl ester (prepared as in Example 31(B)(c), 62.6 mg, 0.16 mmol) in tetrahydrofuran/water/methanol (0.40 mL, 3:1:1) was treated with a 2N aqueous sodium hydroxide solution (0.16 mL, 0.32 mmol). The reaction was stirred at 25° C. for 24 h. The reaction mixture was then poured into water and extracted with chloroform (2×30 mL). The aqueous layer was then acidified to pH=1 with a 1N aqueous hydrochloric acid solution. The product was extracted into chloroform/methanol (9:1, 3×25 mL). The combined organic layers were dried over sodium sulfate, filtered, and concentrated in vacuo. Flash chromatography (Merck Silica gel 60, 230–400 mesh, 75/25 hexanes/ethyl acetate w/acetic acid) afforded 6-[2-(4-chloro-phenyl)-3-cyclopentyl-propionylamino]-nicotinic acid (17.0 mg, 31.5%) as a white solid: mp 206–208° C.; EI-HRMS m/e calcd for $C_{20}H_{21}ClN_2O_2$ (M+) 372.1240, found 372.1244.

EXAMPLE 48

6-[3-Cyclopentyl-2-(4-methanesulfonyl-phenyl)-propionylamino]-nicotinic Acid

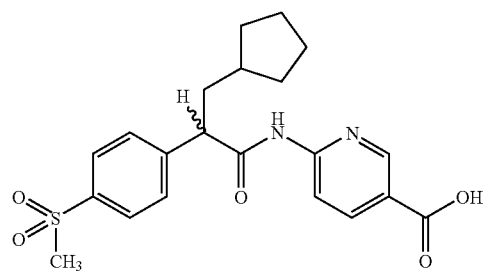

A solution of 6-[3-cyclopentyl-2-(4-methanesulfonyl-phenyl)-propionylamino]-nicotinic acid methyl ester (prepared as in Example 53(B)(a), 100 mg, 0.23 mmol) in tetrahydrofuran (500 μL) was treated with a 0.8M aqueous lithium hydroxide solution (300 μL, 0.23 mmol). The solution was stirred at 25° C. for 4 h. The reaction mixture was then directly purified by column chromatography. Flash chromatography (Merck Silica gel 60, 230–400 mesh, 1/3 methanol/ethyl acetate) afforded 6-[3-cyclopentyl-2-(4-methanesulfonyl-phenyl)-propionylamino]-nicotinic acid (65 mg, 70%) as a white solid: mp 191–193° C.; FAB-HRMS m/e calcd for $C_{21}H_{24}N_2O_5S$ (M+H)+ 417.1484, found 417.1484.

EXAMPLE 49

3-Cyclopentyl-2(3,4-dichloro-phenyl)-N-(5-hydroxymethyl-pyridin-2-yl)-propionamide

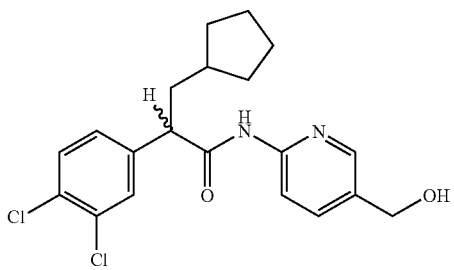

A solution of 3-cyclopentyl-2-(3,4-dichloro-phenyl)-N-(5-carboxymethylpyridin)-2-yl-propionamide (prepared as in Example 38(B)(b), 398 mg, 0.95 mmol) in diethyl ether (30 mL) cooled to 0° C. was treated with lithium aluminum hydride (54 mg, 1.4 mmol). This slurry was allowed to slowly warm to 25° C. The reaction was stirred at 25° C. for 16 h. At this time, the reaction was quenched with water (10 mL) and extracted with ethyl acetate (3×15 mL). The combined organic layers were dried over sodium sulfate, filtered, and concentrated in vacuo. Flash chromatography (Merck Silica gel 60, 230–400 mesh, 50/50 hexanes/ethyl acetate) afforded 3-cyclopentyl-2-(3,4-dichloro-phenyl)-N-(5-hydroxymethyl-pyridin-2-yl)-propionamide (131 mg, 35%) as a white foam: EI-HRMS m/e calcd for $C_{20}H_{22}Cl_2N_2O_2$ ($M^+$) 392.1058, found 392.1062.

EXAMPLE 50

2-(4-Chloro-phenyl)-3-cyclopentyl-N-(5-hydroxymethyl-pyridin-2-yl)-propionamide

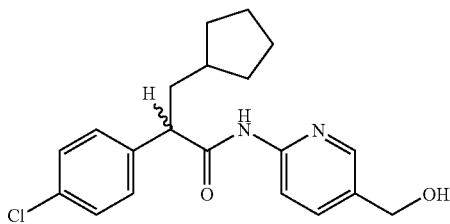

A solution of 6-[2-(4-chloro-phenyl)-3-cyclopentyl-propionylamino]-nicotinic acid methyl ester (prepared as in Example 31(B)(c), 83.3 mg, 0.21 mmol) in tetrahydrofuran (2.1 mL) was added to a cooled (0° C.) slurry of lithium aluminum hydride (12.0 mg, 0.32 mmol) in tetrahydrofuran (1.54 mL). The reaction mixture was stirred at 0° C. for 2.5 h. The reaction was then quenched by the dropwise addition of water (25 mL). The reaction was further diluted with water and was then extracted with ethyl acetate (3×35 mL). The combined organic layers were dried over sodium sulfate, filtered, and concentrated in vacuo. Flash chromatography (Merck Silica gel 60, 230–400 mesh, 70/30 hexanes/ethyl acetate) afforded 2-(4-chloro-phenyl)-3-cyclopentyl-N-(5-hydroxymethyl-pyridin-2-yl)-propionamide (12.5 mg, 16.1%) as a white solid: mp 60–62° C.; EI-HRMS m/e calcd for $C_{20}H_{23}ClN_2O_2$ ($M^+$) 358.1448, found 358.1443.

EXAMPLE 51

3-Cyclopentyl-2-(3,4-dichloro-phenyl)-N-(5-hydroxy-pyridin-2-yl)-propionamide

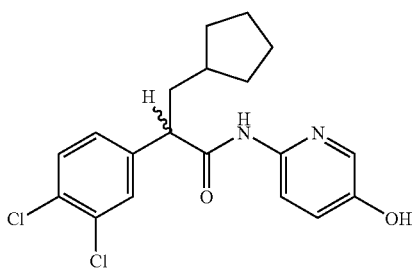

A solution of 3-cyclopentyl-2-(3,4-dichloro-phenyl)-propionic acid (prepared as in Example 38A, 183 mg, 0.63 mmol) in methylene chloride (6.37 mL) was cooled to 0° C. and then treated with a 2.0M solution of oxalyl chloride in methylene chloride (0.35 mL, 0.7 mmol) and a few drops of N,N-dimethylformamide. The reaction mixture was stirred at 0° C. for 10 min and then at 25° C. for 30 min. The reaction mixture was then treated with 5-benzyloxy-pyridin-2-ylamine (281 mg, 1.4 mmol) and N,N-diisopropylethylamine (0.26 mL, 1.5 mmol). The reaction mixture was stirred at 25° C. for 16 h. At this time, the reaction was concentrated in vacuo. Flash chromatography (Merck Silica gel 60, 230–400 mesh, 70/30 hexanes/ethyl acetate) afforded N-(5-benzyloxy-pyridin-2-yl)-3-cyclopentyl-2-(3,4-dichloro-phenyl)-propionamide (150 mg, 50.0%) as a yellow solid: mp 47–49° C.; EI-HRMS m/e calcd for $C_{26}H_{26}Cl_2N_2O_2$ ($M^+$) 469.1449, found 469.1455.

A solution of N-(5-benzyloxy-pyridin-2-yl)-3-cyclopentyl-2-(3,4-dichloro-phenyl)-propionamide (145.3 mg, 0.3 mmol) in methanol (5.1 mL) was treated with 10% palladium on activated carbon. The reaction mixture was stirred under hydrogen gas at 25° C. for 16 h. The catalyst was then filtered off through a pad of celite, which was washed well with ethyl acetate. The resulting filtrate was concentrated in vacuo to give 3-cyclopentyl-2-(3,4-dichloro-phenyl)-N-(5-hydroxy-pyridin-2-yl)-propionamide (92.2 mg, 78.5%) as a tan solid: mp 79–81° C.; EI-HRMS m/e calcd for $C_{19}H_{20}Cl_2N_2O_2$ ($M^+$) 378.0896, found 378.0890.

EXAMPLE 52

3-Cyclopentyl-N-(5-hydroxymethyl-pyridin-2-yl)-2-(4-methanesulfonyl-phenyl)-propionamide

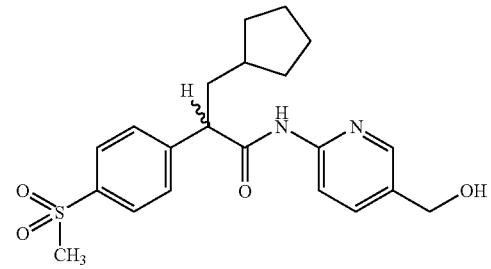

A solution of 6-[3-cyclopentyl-2-(4-methanesulfonyl-phenyl)-propionylamino]-nicotinic acid methyl ester (prepared as in Example 53(B)(a), 110 mg, 0.26 mmol) in diethyl ether (500 μL) was cooled to 0° C. and then slowly treated with lithium aluminum hydride (15 mg, 0.38 mmol). The reaction mixture was stirred at 0° C. for 30 min then allowed to warm to 25° C. After 1 h at 25° C., thin layer chromatography still indicated the presence of the starting material. An additional amount of lithium aluminum hydride (10 mg, 0.26 mmol) was added to the reaction mixture, and the reaction mixture was allowed to stir at 25° C. for 1 h. The reaction mixture was then slowly quenched by the dropwise addition of water (10 mL). The resulting mixture was partitioned between water and ethyl acetate. The organic layer was dried over magnesium sulfate, filtered, and concentrated in vacuo. Flash chromatography (Merck Silica gel 60, 230–400 mesh, 1/3 hexanes/ethyl acetate) afforded the 3-cyclopentyl-N-(5-hydroxymethyl-pyridin-2-yl)-2-(4-methanesulfonyl-phenyl)-propionamide (60 mg, 57%) as a yellow foam: mp 74–77° C.; EI-HRMS m/e calcd for $C_{21}H_{26}N_2O_4S$ ($M^+$) 402.1613, found 402.1617.

EXAMPLE 53

3-Cyclopentyl-2-(4-methanesulfonyl-phenyl)-N-(5-methyl-pyridin-2-yl)-propionamide

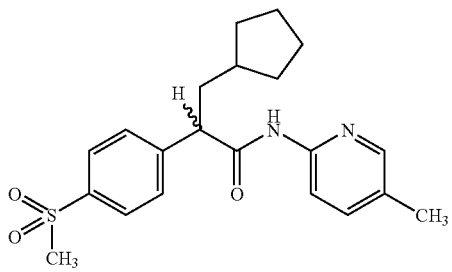

A solution triphenylphosphine (177 mg, 0.68 mmol) in methylene chloride (3 mL) was cooled to 0° C. and then treated with N-bromosuccinimide (132 mg, 0.74 mmol) in small portions. The reaction mixture was allowed to warm to 25° C. over 30 min and then was treated with 3-cyclopentyl-2-(4-methanesulfonyl-phenyl)propionic acid (prepared as in Example 3A, 200 mg, 0.68 mmol). The reaction mixture was stirred at 25° C. for 30 min and then treated with 2-amino-5-methylpyridine (154 mg, 1.42 mmol). The resulting reaction mixture was stirred at 25° C. for 1 h. The crude reaction mixture was directly purified by flash chromatography (Merck Silica gel 60, 230–400 mesh, 1/1 hexanes/ethyl acetate) to afford impure 3-cyclopentyl-2-(4-methanesulfonyl-phenyl)-N-(5-methyl-pyridin-2-yl)-propionamide as a red solid. The impure product was further purified by precipitation from 1/1 hexanes/ethyl acetate to afford pure 3-cyclopentyl-2-(4-methanesulfonyl-phenyl)-N-(5-methyl-pyridin-2-yl)-propionamide (80 mg, 31%) as an off-white solid: mp 184–185° C.; EI-HRMS m/e calcd for $C_{21}H_{26}N_2O_3S$ ($M^+$) 386.1664, found 386.1664.

In an analogous manner, there was obtained:

a) From 3-cyclopentyl-2-(4-methanesulfonyl-phenyl)propionic acid and 6-aminonicotinic acid methyl ester: 6-[3-Cyclopentyl-2-(4-methanesulfonyl-phenyl)-propionylamino]-nicotinic acid methyl ester as a yellow foam: mp 82–85° C.; EI-HRMS m/e calcd for $C_{22}H_{26}N_2O_5S$ ($M^+$) 430.1562, found 430.1571.

EXAMPLE 54

N-(5-Chloro-pyridin-2-yl)-3-cyclopentyl-2(R)-(3,4-dichloro-phenyl)-propionamide

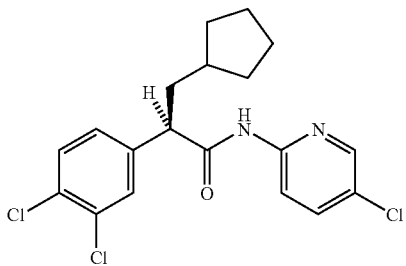

A solution of 3-cyclopentyl-2-(3,4-dichloro-phenyl)-propionic acid (prepared as in Example 38A, 5.00 g, 17.4 mmol) in tetrahydrofuran (150 mL) cooled to −78° C. was treated with triethylamine (2.77 mL, 19.9 mmol) followed by trimethylacetyl chloride (2.24 mL, 18.2 mmol). The resulting white slurry was stirred at −78° C. for 15 min and then at 0° C. for 45 min. In a separate flask, a solution of (S)-4-isopropyl-2-oxazolidinone (2.14 g, 16.57 mmol) in tetrahydrofuran (80 mL) cooled to −78° C. was treated with a 2.0M solution of n-butyllithium in hexanes (8.7 mL, 17.4 mmol). The solution was stirred at −78° C. for 10 min and then allowed to warm to 25° C. where it was stirred for an additional 10 min. At this time, the first reaction mixture was recooled to −78° C. The second reaction mixture was added to the first reaction mixture over a period of 5 min via cannula. The combined reaction was then stirred at −78° C. for 15 min and then allowed to warm to 25° C. where it was stirred for an additional 1.5 h. At this time, the reaction was quenched by the addition of a saturated aqueous sodium bisulfite solution (50 mL) and extracted with ethyl acetate (3×40 mL). The combined organic layers were washed with a saturated aqueous sodium bicarbonate solution (1×20 mL) and a saturated aqueous sodium chloride solution (1×20 mL), dried over sodium sulfate, filtered, and concentrated in vacuo. Flash chromatography (Merck Silica gel 60, 230–400 mesh, 85/15 hexanes/ethyl acetate) afforded two products: (1) 3-[3-cyclopentyl-2(S)-(3,4-dichloro-phenyl)-propionyl]-4(S)-isopropyl-oxazolidin-2-one (2.15 g, 33%) as a clear oil: $[\alpha]^{23}_{589}$=+87.5° (c=0.160, chloroform); EI-HRMS m/e calcd for $C_{20}H_{25}Cl_2NO_3$ ($M^+$) 397.1211, found 397.1215; and (2) 3-[3-cyclopentyl-2(R)-(3,4-dichloro-phenyl)-propionyl]-4(S)-isopropyl-oxazolidin-2-one (1.88 g, 28%) as a white solid: mp 71.9–74.6° C.; $[\alpha]^{23}_{589}$=−27.6° (c=0.188, chloroform); EI-HRMS m/e calcd for $C_{20}H_{25}Cl_2NO_3$ ($M^+$) 397.1211, found 397.1212.

A solution of 3-[3-cyclopentyl-2(R)-(3,4-dichloro-phenyl)-propionyl]-4(S)-isopropyl-oxazolidin-2-one (1.88 g, 4.72 mmol) in tetrahydrofuran (73 mL) and water (22 mL) cooled to 0° C. was treated with a 30% aqueous hydrogen peroxide solution (2.1 mL) and lithium hydroxide (394 mg, 9.4 mmol). The reaction was stirred at 0° C. for 1 h. At this time, the reaction was quenched with a saturated aqueous sodium sulfite solution (16 mL) followed by the addition of a 0.5N aqueous sodium bicarbonate solution (50 mL). The tetrahydrofuran was then removed in vacuo. The residue was diluted with water (40 mL) and extracted with methylene chloride (3×20 mL). The aqueous layer was then acidified to pH=2 with 5N aqueous hydrochloric acid solution and extracted with ethyl acetate (4×25 mL). The combined organic layers were then dried over sodium sulfate, filtered, and concentrated in vacuo to afforded of 3-cyclopentyl-2(R)-(3,4-dichloro-phenyl)-propionic acid (928 mg, 70%) as a white solid: mp 75.1–78.3° C.; $[\alpha]^{23}_{589}$=−50.3° (c=0.100, chloroform); EI-HRMS m/e calcd for $C_{14}H_{16}Cl_2O_2$ ($M^+$) 286.0527, found 286.0535.

A solution of triphenylphosphine (344 mg, 1.31 mmol) in methylene chloride (10 mL) cooled to 0° C. was treated with N-bromosuccinimide (263 mg, 1.48 mmol). The reaction solution was stirred at 0° C. for 5 min. At this time, 3-cyclopentyl-2(R)-(3,4-dichloro-phenyl)propionic acid (250 mg, 0.87 mmol) was added. The reaction was allowed to slowly warm to 25° C. over 45 min. At this time, 5-chloro-2-aminopyridine (145 mg, 1.13 mmol) and pyridine (0.11 mL, 1.31 mmol) were added to the reaction mixture. The reaction was stirred at 25° C. for 20 h. At this time, the reaction was diluted with water (10 mL) and extracted with methylene chloride (3×10 mL). The combined organic layers were dried over sodium sulfate, filtered, and concentrated in vacuo. Flash chromatography (Merck Silica gel 60, 230–400 mesh, 90/10 hexanes/ethyl acetate) afforded N-(5-chloro-pyridin-2-yl)3-cyclopentyl-2-(R)-(3,4-dichloro-phenyl)-propionamide (289 mg, 84%) as a white solid: mp 125–128° C.; $[\alpha]^{23}_{589}$=–65.6° (c=0.16, chloroform); EI-HRMS m/e calcd for $C_{19}H_{19}Cl_3N_2O$ (M$^+$) 396.0563, found 396.0565.

In an analogous manner, there were obtained:

a) From 2-amino pyridine and 3-cyclopentyl-2(R)-(3,4-dichloro-phenyl) propionic acid: 3-Cyclopentyl-2(R)-(3,4-dichloro-phenyl)-N-pyridin-2-yl-propionamide as a white foam: $[\alpha]^{23}_{589}$=–56.2° (c=0.153, chloroform); EI-HRMS m/e calcd for $C_{19}H_{20}Cl_2N_2O$ (M$^+$) 362.0953, found 362.0952.

b) From 2-aminothiazole and 3-cyclopentyl-2(R)-(3,4-dichloro-phenyl) propionic acid: 3-Cyclopentyl-2(R)-(3,4-dichloro-phenyl)-N-thiazol-2-yl-propionamide as a white solid: mp 133.4–136.5° C.; $[\alpha]_{23}^{589}$=–66.0° (c=0.106, chloroform); EI-HRMS m/e calcd for $C_{17}H_{18}Cl_2N_2OS$ (M$^+$) 368.0517, found 368.0519.

c) From 2-(amino-thiazol-5-yl)-oxo-acetic acid ethyl ester and 3-cyclopentyl-2(R)-3-cyclopentyl-2-(3,4-dichlorophenyl)-propionic acid: (2R)-{2-[3-Cyclopentyl-2-(3,4-dichlorophenyl)-propionylamino]-thiazol-5-yl}-oxo-acetic acid ethyl ester as a light yellow foam: mp 117–120° C.; FAB-HRMS m/e calcd for $C_{21}H_{22}Cl_2N_2O_4S$ (M+H)$^+$ 469.0755, found 469.0753.

d) From ethyl 2-amino-4-thiazole glyoxylate and 3-cyclopentyl-2(R)-3-cyclopentyl-2-(3,4-dichlorophenyl)-propionic acid: (2R)-{2-[3-Cyclopentyl-2-(3,4-dichloro-phenyl)-propionylamino]-thiazol-4-yl}-oxo-acetic acid ethyl ester as a white solid: EI-HRMS m/e calcd for $C_{21}H_{22}Cl_2N_2O_4S$ (M$^+$) 468.0677, found 468.0677.

EXAMPLE 55

3-Cyclopentyl-2-(3,4-dichlorophenyl)-N-(1H-imidazol-2-yl)-propionamide

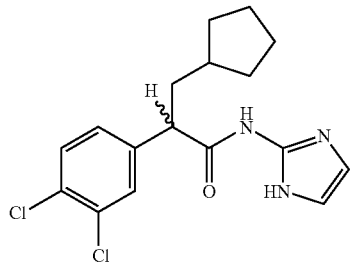

A solution of 3-cyclopentyl-2-(3,4-dichlorophenyl)-propionic acid (prepared as in Example 38A, 200 mg, 0.70 mmol), benzotriazol-1-yloxy-tris(dimethylamino)phosphonium hexafluorophosphate (310 mg, 0.70 mmol), N,N-diisopropylethylamine (244 μL, 1.40 mmol), and 2-aminoimidazole sulfate (140 mg, 1.05 mmol) in dry N,N-dimethylformamide (5 mL) was stirred at 25° C. under nitrogen for 15 h. The reaction mixture was partitioned between water and ethyl acetate. The organic layer was washed sequentially with a 1N aqueous hydrochloric acid solution, water, and a saturated aqueous sodium chloride solution. The organic layer was dried over magnesium sulfate, filtered, and concentrated in vacuo. Flash chromatography (Merck Silica gel 60, 230–400 mesh, 1/3 hexanes/ethyl acetate) afforded 3-cyclopentyl-2-(3,4-dichlorophenyl)-N-(1H-imidazol-2-yl)-propionamide (81.4 mg, 33%) as a white solid: mp 58–60° C.; EI-HRMS m/e calcd for $C_{17}H_{19}Cl_2N_3O$ (M$^+$) 351.0905, found 351.0901.

EXAMPLE 56

3-Cyclopentyl-2-(3,4-dichlorophenyl)-N-(5-methyl-isoxazol-3-yl)-propionamide

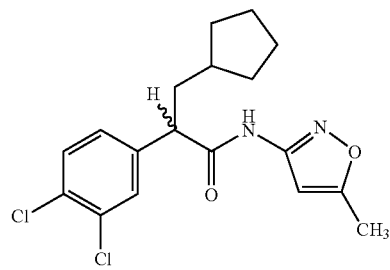

A solution of 3-cyclopentyl-2-(3,4-dichlorophenyl)-propionic acid (prepared as in Example 38A, 70.7 mg, 0.25 mmol) in oxalyl chloride (215 μL, 2.46 mmol) was cooled to 0° C. and then treated with 1 drop of dry N,N-dimethylformamide. The reaction mixture was stirred at 0° C. for 30 min and then stirred at 25° C. for 3 h. The reaction mixture was concentrated in vacuo to afford a yellow oil. This yellow oil was dissolved in a small amount of methylene chloride and then slowly added to a solution of 3-amino-5-methylisoxazole (48.3 mg, 0.49 mmol) and triethylamine (68 mL, 0.49 mmol) in methylene chloride (1.2 mL). The resulting reaction mixture was stirred at 25° C. for 14 h. The reaction mixture was concentrated in vacuo to remove methylene chloride. The resulting residue was diluted with ethyl acetate (100 mL) and then washed with a 10% aqueous hydrochloric acid solution. The organic layer was dried over sodium sulfate, filtered, and concentrated in vacuo. Flash chromatography (Merck Silica gel 60, 230–400 mesh, 3/1 hexanes/ethyl acetate) afforded 3-cyclopentyl-2-(3,4-dichlorophenyl)-N-(5-methyl-isoxazol-3-yl)-propionamide (78.3 mg, 87%) as a yellow glass: mp 84–86° C.; FAB-HRMS m/e calcd for $C_{18}H_{20}Cl_2N_2O_2$ (M+H)$^+$ 367.0981, found 367.0982.

EXAMPLE 57

3-Cyclopentyl-2-(3,4-dichlorophenyl)-N-oxazol-2-yl-propionamide

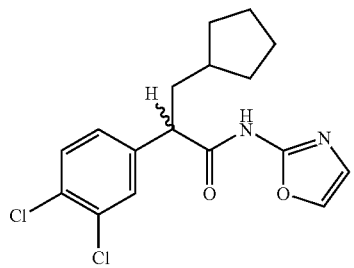

A solution of benzotriazol-1-yloxy-tris(dimethylamino) phosphonium hexafluorophosphate (102 mg, 0.23 mmol), 3-cyclopentyl-2-(3,4-dichlorophenyl)-propionic acid (prepared as in Example 38A, 60 mg, 0.21 mmol), N,N-diisopropylethylamine (73 μL, 0.42 mmol), and 2-aminooxazole (27 mg, 0.31 mmol) in dry N,N-dimethylformamide (1 mL)

was stirred at 25° C. under nitrogen for 15 h. The reaction mixture was partitioned between water and ethyl acetate. The organic layer was washed sequentially with a 1N aqueous hydrochloric acid solution, water, and a saturated aqueous sodium chloride solution. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(3,4-dichlorophenyl)-N-oxazol-2-yl-propionamide (34.9 mg, 47%) as a white solid: mp 134–136° C.; EI-HRMS m/e calcd for $C_{17}H_{18}Cl_2N_2O_2$ (M$^+$) 352.0745, found 352.0750.

EXAMPLE 58

3-Cyclopentyl-2-(3,4-dichlorophenyl)-N-pyridazin-3-yl-propionamide

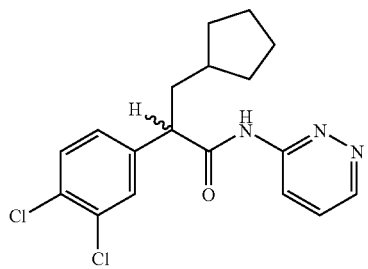

A solution of 3-cyclopentyl-2-(3,4-dichlorophenyl)-propionic acid (prepared as in Example 38A, 625.2 mg, 2.18 mmol), O-benzotriazol-1-yl-N,N,N',N'-tetramethyluronium hexafluorophosphate (908.3 mg, 2.39 mmol), N,N-diisopropylethylamine (1.1 mL, 6.53 mmol), and 3-aminopyridazine (310.6 mg, 3.27 mmol) in dry N,N-dimethylformamide (11 mL) was stirred at 25° C. under nitrogen for 72 h. The reaction mixture was concentrated in vacuo to remove N,N-dimethylformamide. The resulting residue was diluted with ethyl acetate (200 mL). The organic layer was washed with a 10% aqueous hydrochloric acid solution and a saturated aqueous sodium chloride solution. The organic layer was dried over sodium sulfate, filtered, and concentrated in vacuo. Flash chromatography (Merck Silica gel 60, 230–400 mesh, 1/1 hexanes/ethyl acetate) afforded 3-cyclopentyl-2-(3,4-dichlorophenyl)-N-pyridazin-3-yl-propionamide (493.8 mg, 62%) as a white foam: mp 70–71° C.; EI-HRMS m/e calcd for $C_{18}H_{19}Cl_2N_3O$ (M$^+$) 363.0905, found 363.0908.

EXAMPLE 59

3-Cyclopentyl-2-(3,4-dichlorophenyl)-N-pyrimidin-2-yl-propionamide

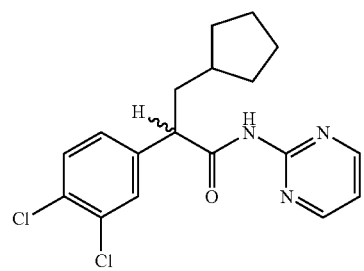

A solution of 3-cyclopentyl-2-(3,4-dichlorophenyl)-propionic acid (prepared as in Example 38A, 100 mg, 0.35 mmol) in methylene chloride (1 mL) was treated with 2 drops of dry N,N-dimethylformamide. The reaction mixture was cooled to 0° C. and then treated dropwise with oxalyl chloride (34 mL, 0.39 mmol). The reaction mixture was stirred at 0° C. for 10 min and then stirred at 25° C. for 2 h. The reaction mixture was concentrated in vacuo. The resulting residue was dissolved in a small amount of methylene chloride and was slowly added to a cooled (0° C.) solution of 2-aminopyrimidine (67 mg, 0.70 mmol) in methylene chloride (1 mL). The resulting reaction mixture was stirred at 0° C. for 30 min and then stirred at 25° C. for 2 h. The reaction mixture was concentrated in vacuo to remove methylene chloride. The resulting residue was diluted with water and extracted with ethyl acetate (3×50 mL). The combined organic extracts were washed with a saturated aqueous sodium chloride solution. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(3,4-dichlorophenyl)-N-pyrimidin-2-yl-propionamide (85.4 mg, 67%) as a white solid: mp 103–105° C.; EI-HRMS m/e calcd for $C_{18}H_{19}Cl_2N_3O$ (M$^+$) 363.0905, found 363.0915.

EXAMPLE 60

3-Cyclopentyl-2(R)-(3,4-dichloro-phenyl)-N-pyrimidine-4-yl-propionamide

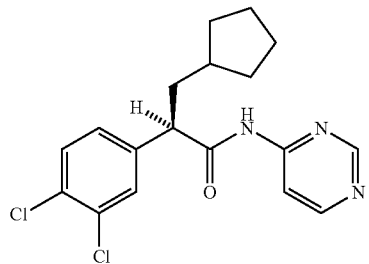

A solution of 3-cyclopentyl-2(R)-(3,4-dichlorophenyl)-propionic acid (prepared as in Example 54A, 200 mg, 0.69 mmol) in methylene chloride (5 mL) was treated with 1 drop of N,N-dimethylformamide and then cooled to 0° C. The reaction mixture was then treated with a 2.0M solution of oxalyl chloride in methylene chloride (0.52 mL, 1.04 mmol). The reaction mixture was stirred at 0° C. for 30 min and then treated with a solution of 4-aminopyrimidine (131 mg, 1.38 mmol) in tetrahydrofuran (10 mL) and pyridine (0.28 mL, 3.45 mmol). The resulting reaction mixture was stirred at 23° C. for 14 h. The reaction mixture was then diluted with water (10 mL) and extracted with methylene chloride (3×15 mL). The combined organic layers were dried over sodium sulfate, filtered, and concentrated in vacuo. Flash chromatography (Merck Silica gel 60, 230–400 mesh, 3/2 hexanes/ethyl acetate) afforded 3-cyclopentyl-2(R)-(3,4-dichlorophenyl)-N-pyrimidin-4-yl-propionamide (147 mg, 60%) as a white solid: mp 166.5–169.3° C.; EI-HRMS m/e calcd for $C_{18}H_{19}Cl_2N_3O$ (M$^+$) 363.0905, found 363.0909.

EXAMPLE 61

3-Cyclopentyl-2-(4-methanesulfinyl-phenyl)-N-thiazol-2-yl-propionamide

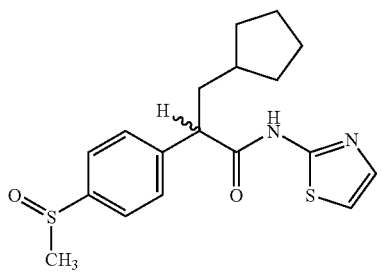

A solution of diisopropylamine (3.2 mL, 23.16 mmol) in dry tetrahydrofuran (10.3 mL) and 1,3-dimethyl-3,4,5,6-tetrahydro-2(1H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio) phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1 h, at which time, a solution of iodomethylcyclopentane (2.55 g, 12.13 mmol) in a small amount of dry tetrahydrofuran was added dropwise. The reaction mixture was then stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ ($M^+$) 264.1184, found 264.1177.

A solution of 3-cyclopentyl-2-(4-methylsulfanyl-phenyl) propionic acid (200 mg, 0.76 mmol) and triphenylphosphine (198 mg, 0.76 mmol) in methylene chloride (2 mL) was cooled to 0° C. and then slowly treated with N-bromosuccinimide (150 mg, 0.84 mmol). After the complete addition of N-bromosuccinimide, the reaction mixture was allowed to warm to 25° C. over 30 min. The reaction mixture was then treated with 2-aminothiazole (160 mg, 1.60 mmol), and the resulting reaction mixture was stirred at 25° C. for 15 h. The reaction mixture was then concentrated in vacuo to remove methylene chloride. The remaining residue was diluted with water and ethyl acetate. The organic layer was washed sequentially with a 1N aqueous hydrochloric acid solution and a saturated aqueous sodium bicarbonate solution, dried over magnesium sulfate, filtered, and concentrated in vacuo. Flash chromatography (Merck Silica gel 60, 230–400 mesh, 2/1 hexanes/ethyl acetate) afforded crude 3-cyclopentyl-2-(4-methylsulfanyl-phenyl)-N-thiazol-2-yl-propionamide as a yellow solid. Recrystallization from 3/1 hexanes/ethyl acetate afforded pure 3-cyclopentyl-2-(4-methylsulfanyl-phenyl)-N-thiazol-2-yl-propionamide (114 mg, 44%) as a white solid: mp 195–196° C.; EI-HRMS m/e calcd for $C_{18}H_{22}N_2OS_2$ ($M^+$) 346.1174, found 346.1171.

A solution 3-cyclopentyl-2-(4-methylsulfanyl-phenyl)-N-thiazol-2-yl-propionamide (75 mg, 0.216 mmol) in methylene chloride (1 mL) was treated with 3-chloroperoxybenzoic acid (75% grade, 50 mg, 0.216 mmol). The reaction mixture was immediately monitored by thin layer chromatography, and the results indicated the immediate absence of starting material. The reaction mixture was partitioned between water and methylene chloride and then washed with a saturated aqueous sodium bicarbonate solution. The organic layer was further washed with water and then dried over magnesium sulfate, filtered, and concentrated in vacuo. Recrystallization from 1/1 hexanes/ethyl acetate afforded 3-cyclopentyl-2-(4-methanesulfinyl-phenyl)-N-thiazol-2-yl-propionamide (25 mg, 32%) as a white solid: mp 170–173° C.; EI-HRMS m/e calcd for $C_{18}H_{22}N_2O_2S_2$ ($M^+$) 362.1123, found 362.1121.

EXAMPLE 62

{2-[3-Cyclopentyl-2-(4-trifluoromethanesulfonyl-phenyl)-propionylamino]-thiazol-4-yl}-acetic Acid Ethyl Ester

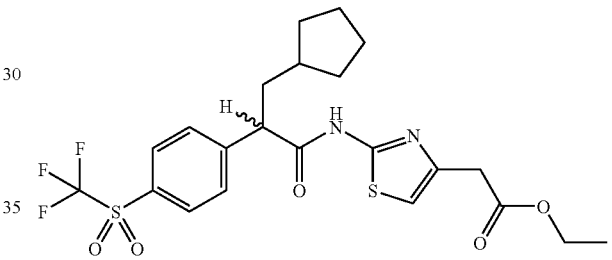

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ ($M^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL) and a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ (M$^+$) 332.1058, found 332.1052.

A solution of 3-cyclopentyl-2-(4-trifluoromethylsulfanyl-phenyl)propionic acid methyl ester (1.14 g, 3.43 mmol) in methylene chloride (8.6 mL) was treated with 3-chloroperoxybenzoic acid (80–85% grade, 2.00 g based on 80%, 9.26 mmol). The reaction mixture was stirred at 25° C. for 17 h, at which time, thin layer chromatography showed the presence of two new lower $R_f$ products. An additional 2.00 g of 3-chloroperoxybenzoic acid was added to the reaction mixture to drive the conversion of the sulfoxide to the sulfone, and the resulting reaction mixture was stirred at 25° C. for 3 d. The reaction mixture was concentrated in vacuo to remove methylene chloride. The resulting residue was diluted with ethyl acetate (300 mL). The organic phase was washed with a saturated aqueous sodium bicarbonate solution (3×100 mL) and a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-trifluoromethanesulfonyl-phenyl)propionic acid methyl ester (1.19 g, 95%) as a light yellow oil: EI-HRMS m/e calcd for $C_{16}H_{19}F_3O_4S$ (M$^+$) 364.0956, found 364.0965.

A solution of 3-cyclopentyl-2-(4-trifluoromethanesulfonyl-phenyl)propionic acid methyl ester (708.2 mg, 1.94 mmol) in tetrahydrofuran (2.4 mL) was treated with a 0.8M aqueous lithium hydroxide solution (3.6 mL, 2.92 mmol). The reaction mixture was stirred at 25° C. for 23 h and then concentrated in vacuo to remove tetrahydrofuran. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford a cream solid. This solid was purified by triturating with diethyl ether/petroleum ether to provide pure 3-cyclopentyl-2-(4-trifluoromethanesulfonyl-phenyl)propionic acid (527.0 mg, 77%) as a white solid: mp 143–145° C.; EI-HRMS m/e calcd for $C_{15}H_{17}F_3O_4S$ (M$^+$) 350.0800, found 350.0816.

A solution of triphenylphosphine (97 mg, 0.371 mmol) in methylene chloride (1.5 mL) was cooled to 0° C. and then slowly treated with N-bromosuccinimide (66 mg, 0.371 mmol). The reaction mixture was stirred at 0° C. for 20 min and then treated with 3-cyclopentyl-2-(4-trifluoromethanesulfonyl-phenyl)propionic acid (100 mg, 0.285 mmol). The resulting reaction mixture was stirred at 0° C. for 10 min, allowed to warm to 25° C., and then treated with ethyl 2-amino-4-thiazoleacetate (123 mg, 0.657 mmol). The resulting reaction mixture was stirred at 25° C. for 3 d. The reaction mixture was then concentrated in vacuo. Flash chromatography (Merck Silica gel 60, 230–400 mesh, 3/1 hexanes/ethyl acetate) afforded {2-[3-cyclopentyl-2-(4-trifluoromethanesulfonyl-phenyl)-propionyl-amino]-thiazol-4-yl}-acetic acid ethyl ester (107 mg, 72%) as a yellow foam: mp 48–51° C.; EI-HRMS m/e calcd for $C_{22}H_{25}F_3N_2O_5S_2$ (M$^+$) 518.1157, found 518.1157.

EXAMPLE 63

N-(5-Bromo-pyridin-2-yl)-3-cyclopentyl-2-(4-trifluoromethanesulfonyl-phenyl)-propionamide

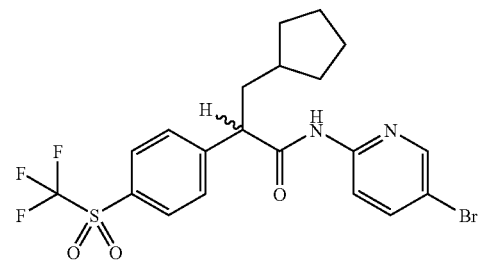

A solution of diisopropylamine (2.4 mL, 16.80 mmol) in dry tetrahydrofuran (7.5 mL) and 1,3-dimethyl-3,4,5,6-tetrahydro-2(1H)-pyrimidinone (2.5 mL) was cooled to −78° C. under nitrogen and then treated with a 2.5M solution of n-butyllithium in hexanes (6.7 mL, 16.80 mmol). The resulting reaction mixture was stirred at −78° C. for 30 min and then treated dropwise with a solution of 4-(trifluoromethylthio)phenylacetic acid (1.89 g, 8.00 mmol) in dry tetrahydrofuran (7.5 mL) and 1,3-dimethyl-3,4,5,6-tetrahydro-2(1H)-pyrimidinone (2.5 mL). The reaction mixture was allowed to stir at −78° C. for 55 min, at which time, a solution of iodomethylcyclopentane (1.85 g, 8.80 mmol) in a small amount of dry tetrahydrofuran was added dropwise. The reaction mixture was allowed to warm to 25° C. where it was stirred for 41 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (1×300 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-trifluoromethylsulfanyl-phenyl)propionic acid (1.47 g, 58%) as a cream solid: mp 69–71° C.; EI-HRMS m/e calcd for $C_{15}H_{17}F_3O_2S$ (M$^+$) 318.0901, found 318.0912.

A solution of 3-cyclopentyl-2-(4-trifluoromethylsulfanyl-phenyl)propionic acid (1.33 g, 4.18 mmol) in methanol (10 mL) was treated slowly with 4 drops of concentrated sulfuric acid. The resulting reaction mixture was heated under reflux for 36 h. The reaction mixture was allowed to cool to 25° C. and then concentrated in vacuo to remove methanol. The residue was diluted with ethyl acetate (200 mL). The organic phase was washed with a saturated aqueous sodium bicarbonate solution (1×100 mL) and a saturated aqueous sodium chloride solution (1×100 mL), dried over sodium sulfate, filtered, and concentrated in vacuo. Flash chromatography (Merck Silica gel 60, 70–230 mesh, 97/3 hexanes/ethyl acetate) afforded 3-cyclopentyl-2-(4-trifluoromethylsulfanyl-phenyl)propionic acid methyl ester (1.37 g, 99%) as a light yellow oil: EI-HRMS m/e calcd for $C_{16}H_{19}F_3O_2S$ (M$^+$) 332.1058, found 332.1052.

A solution of 3-cyclopentyl-2-(4-trifluoromethylsulfanyl-phenyl)propionic acid methyl ester (1.14 g, 3.43 mmol) in methylene chloride (8.6 mL) was treated with 3-chloroperoxybenzoic acid (80–85% grade, 2.00 g based on 80%, 9.26 mmol). The reaction mixture was stirred at 25° C. for 17 h, at which time, thin layer chromatography showed the presence of two new lower $R_f$ products. An additional 2.00 g of 3-chloroperoxybenzoic acid was added to the reaction mixture to drive the conversion of the sulfoxide to the sulfone, and the resulting reaction mixture was stirred at 25° C. for 3 d. The reaction mixture was concentrated in vacuo to remove methylene chloride. The resulting residue was diluted with ethyl acetate (300 mL). The organic phase was washed with a saturated aqueous sodium bicarbonate solution (3×100 mL) and a saturated aqueous sodium chloride solution (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-trifluoromethanesulfonyl-phenyl)propionic acid methyl ester (1.19 g, 95%) as a light yellow oil: EI-HRMS m/e calcd for $C_{16}H_{19}F_3O_4S$ (M$^+$) 364.0956, found 364.0965.

A solution of 3-cyclopentyl-2-(4-trifluoromethanesulfonyl-phenyl)propionic acid methyl ester (708.2 mg, 1.94 mmol) in tetrahydrofuran (2.4 mL) was treated with a 0.8M aqueous lithium hydroxide solution (3.6 mL, 2.92 mmol). The reaction mixture was stirred at 25° C. for 23 h and then concentrated in vacuo to remove tetrahydrofuran. The remaining aqueous layer was acidified to pH=2 with a 10% aqueous hydrochloric acid solution and then extracted with ethyl acetate (2×100 mL). The combined organic layers were washed with a saturated aqueous sodium chloride solution (1×100 mL), dried over sodium sulfate, filtered, and concentrated in vacuo to afford a cream solid. This solid was purified by triturating with diethyl ether/petroleum ether to provide pure 3-cyclopentyl-2-(4-trifluoromethanesulfonyl-phenyl)propionic acid (527.0 mg, 77%) as a white solid: mp 143–145° C.; EI-HRMS m/e calcd for $C_{15}H_{17}F_3O_4S$ (M$^+$) 350.0800, found 350.0816.

A solution of triphenylphosphine (206 mg, 0.785 mmol) in methylene chloride (4 mL) was cooled to 0° C. and then slowly treated with N-bromosuccinimide (140 mg, 0.785 mmol). The reaction mixture was stirred at 0° C. for 10 min and then treated with 3-cyclopentyl-2-(4-trifluoromethanesulfonyl-phenyl)propionic acid (250 mg, 0.710 mmol). The resulting reaction mixture was stirred at 0° C. for 10 min and then allowed to warm to 25° C. where it was stirred for 30 min. The reaction mixture was then treated with 2-amino-5-bromopyridine (271 mg, 1.57 mmol). The resulting reaction mixture was stirred at 25° C. for 15 h. The reaction mixture was then concentrated in vacuo. Flash chromatography (Merck Silica gel 60, 230–400 mesh, 2/1 hexanes/ethyl acetate) afforded the pure N-(5-bromo-pyridin-2-yl)-3-cyclopentyl-2-(4-trifluoromethanesulfonyl-phenyl)-propionamide (226 mg, 63%) as a yellow foam: mp 130–132° C.; EI-HRMS m/e calcd for $C_{20}H_{20}BrF_3N_2O_3S$ (M$^+$) 504.0330, found 504.0325.

EXAMPLE 64

2-(4-Chloro-3-nitro-phenyl)-3-cyclopentyl-N-thiazol-2-yl-propionamide

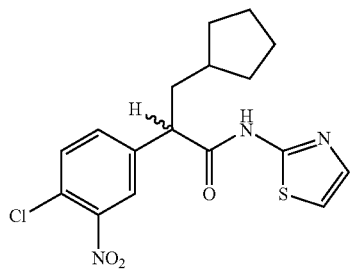

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitro-phenylacetic acid methyl ester (1.91 g, 89%) as a yellow oil: EI-HRMS m/e calcd for $C_9H_8ClNO_4$ (M$^+$) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C., where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitro-phenyl)-3-cyclopentyl-propionic acid methyl ester (2.17 g, 32%) as a yellow oil: EI-HRMS m/e calcd for $C_{15}H_{18}ClNO_4$ (M$^+$) 311.0924, found 311.0927.

A solution of 2-(4-chloro-3-nitro-phenyl)-3-cyclopentyl-propionic acid methyl ester (260 mg, 0.834 mmol) in tetrahydrofuran (3 mL) was treated with a 0.8M aqueous lithium hydroxide solution (1.25 mL, 1.00 mmol). The reaction mixture was stirred at 25° C. for 15 h. The resulting reaction mixture was partitioned between water (50 mL) and ethyl acetate (50 mL) and then treated with a 1N aqueous hydrochloric acid solution (10 mL). The layers were shaken and separated. The aqueous layer was further extracted with ethyl acetate (50 mL). The combined organic layers were dried over magnesium sulfate, filtered, and concentrated in vacuo to afford 2-(4-chloro-3-nitro-phenyl)-3-cyclopentyl-propionic acid (243 mg, 98%) as a yellow solid which was used without further purification: mp 112–115° C.; FAB-HRMS m/e calcd for $C_{14}H_{16}ClNO_4$ (M+H)$^+$ 298.0847, found 298.0851.

A solution of triphenylphosphine (105 mg, 0.403 mmol) in methylene chloride (1 mL) was cooled to 0° C. and then slowly treated with N-bromosuccinimide (72 mg, 0.403 mmol). The reaction mixture was stirred at 0° C. for 20 min and then treated with 2-(4-chloro-3-nitro-phenyl)-3-cyclopentyl-propionic acid (100 mg, 0.336 mmol). The resulting reaction mixture was stirred at 0° C. for 10 min and then allowed to warm to 25° C. where it was stirred for 20 min. The reaction mixture was then treated with 2-aminothiazole (74 mg, 0.739 mmol). The resulting reaction mixture was stirred at 25° C. for 15 h. The crude reaction mixture was treated with a solution of hexanes/ethyl acetate (2 mL, 3:1) and then directly purified by flash chromatography (Merck Silica gel 60, 230–400 mesh, 3/1 hexanes/ethyl acetate). The pure 2-(4-chloro-3-nitro-phenyl)-3-cyclopentyl-N-thiazol-2-yl-propionamide (93 mg, 73%) was obtained as a pale

EXAMPLE 65

2-(4-Chloro-3-nitro-phenyl)-3-cyclopentyl-N-pyridin-2-yl-propionamide

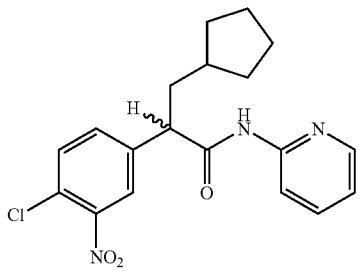

A solution of triphenylphosphine (105 mg, 0.403 mmol) in methylene chloride (1 mL) was cooled to 0° C. and then slowly treated with N-bromosuccinimide (72 mg, 0.403 mmol). The reaction mixture was stirred at 0° C. for 20 min and then treated with 2-(4-chloro-3-nitro-phenyl)-3-cyclopentyl-propionic acid (prepared as in Example 64, 100 mg, 0.336 mmol). The resulting reaction mixture was stirred at 0° C. for 10 min and then allowed to warm to 25° C. where it was stirred for 20 min. The reaction mixture was then treated with 2-aminopyridine (70 mg, 0.739 mmol). The resulting reaction mixture was stirred at 25° C. for 15 h. The crude reaction mixture was treated with a solution of hexanes/ethyl acetate (2 mL, 3:1) and then directly purified by flash chromatography (Merck Silica gel 60, 230–400 mesh, 3/1 hexanes/ethyl acetate). The pure 2-(4-chloro-3-nitro-phenyl)-3-cyclopentyl-N-pyridin-2-yl-propionamide (60 mg, 48%) was obtained as a pale yellow foam: mp 48–52° C. (foam to gel); EI-HRMS m/e calcd for $C_{19}H_{2}^{0}ClN_{3}O_{3}$ (M+) 373.1193, found 373.1185.

EXAMPLE 66

N-(5-Bromo-pyridin-2-yl)-3-cyclopentyl-2-(4-methanesulfonyl-3-nitro-phenyl)-propionamide

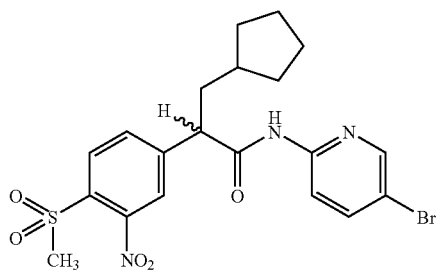

A solution of 4-chloro-3-nitrophenylacetamide (2.00 g, 9.32 mmol) in methanol (40 mL) was treated with Amberlyst® 15 ion exchange resin (15.00 g). The resulting reaction mixture was heated under reflux for 64 h. The reaction mixture was allowed to cool to 25° C. and then filtered to remove the Amberlyst® 15 ion exchange resin. The filtrate was concentrated in vacuo. Flash chromatography (Merck Silica gel 60, 230–400 mesh, 3/1 hexanes/ethyl acetate) afforded 4-chloro-3-nitrophenylacetic acid methyl ester (1.91 g, 89%) as a yellow oil: EI-HRMS m/e calcd for $C_{9}H_{8}ClNO_{4}$ (M+) 229.0142, found 229.0146.

A solution of diisopropylamine (3.35 mL, 23.9 mmol) in dry tetrahydrofuran (45 mL) and 1,3-dimethyl-3,4,5,6-tetrahydro-2(1H)-pyrimidinone (15 mL) was cooled to −78° C. and then treated dropwise with a 2.5M solution of n-butyllithium in hexanes (9.56 mL, 23.9 mmol) over a 10 min period. The pale yellow reaction mixture was stirred at −78° C. for 20 min and then slowly treated with a solution of 4-chloro-3-nitrophenylacetic acid methyl ester (5.00 g, 21.8 mmol) in a small amount of tetrahydrofuran over a 15 min period. The reaction mixture turned deep purple (almost black) in color. The reaction mixture was then stirred at −78° C. for 1 h, at which time, a solution of iodomethylcyclopentane (4.58 g, 21.8 mol) in a small amount of dry tetrahydrofuran was added dropwise. The reaction mixture was then stirred at −78° C. and then allowed to warm to 25° C. where it was stirred for 48 h. The reaction mixture was quenched with a saturated aqueous ammonium chloride solution (50 mL), and the resulting reaction mixture was concentrated in vacuo to remove tetrahydrofuran. The remaining residue was diluted with ethyl acetate (150 mL) and water (50 mL). The organic phase was washed with a saturated aqueous sodium chloride solution, dried over magnesium sulfate, filtered, and concentrated in vacuo. Flash chromatography (Merck Silica gel 60, 230–400 mesh, 4/1 hexanes/ethyl acetate) afforded 2-(4-chloro-3-nitrophenyl)-3-cyclopentyl-propionic acid methyl ester (2.17 g, 32%) as a yellow oil: EI-HRMS m/e calcd for $C_{15}H_{18}ClNO_{4}$ (M+) 311.0924, found 311.0927.

A solution of 2-(4-chloro-3-nitrophenyl)-3-cyclopentyl-propionic acid methyl ester (1.00 g, 3.21 mmol) and sodium methanesulfinate (0.36 g, 3.53 mmol) in dimethyl sulfoxide (3 mL) was heated at 130° C. for 5 h. The black reaction mixture was then poured over ice (20 g), resulting in the formation of a brown sticky substance. The resulting mixture was then treated with ethyl acetate (50 mL) and water (50 mL), and the layers were separated. The aqueous layer was further extracted with ethyl acetate (2×50 mL). The combined organic layers were washed with a saturated aqueous sodium chloride solution, dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid methyl ester (0.95 g, 84%) as a yellow gel: FAB-HRMS m/e calcd for $C_{16}H_{21}NO_{6}S$ (M+H)+ 356.1169, found 356.1175.

A solution of 3-cyclopentyl-2-(4-methanesulfonyl-3-nitrophenyl)-propionic acid methyl ester (1.17 g, 3.29 mmol) in tetrahydrofuran (6 mL) was treated with a 0.8M aqueous lithium hydroxide solution (6.17 mL, 4.94 mmol). The reaction mixture was stirred at 25° C. for 3 h. The reaction mixture was then diluted with water (50 mL), a 1N aqueous hydrochloric acid solution (10 mL), and ethyl acetate (50 mL). The layers were separated, and the aqueous layer was back-extracted with ethyl acetate (2×50 mL). The combined organic layers were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-methanesulfonyl-3-nitrophenyl)-propionic acid (993 mg, 88%) as a yellow foam which contained a small impurity. A small amount of the yellow foam (50 mg) was re-purified using Biotage chromatography (FLASH 40S, Silica, 3/1 then 1/1 hexanes/ethyl acetate) to afford 3-cyclopentyl-2-(4-methanesulfonyl-3-nitrophenyl)- propionic acid as a white foam: mp 114–118° C. (foam to gel); FAB-HRMS m/e calcd for $C_{15}H_{19}NO_6S$ (M+H)+ 342.1011, found 342.1014.

A solution of triphenylphosphine (212 mg, 0.81 mmol) in methylene chloride (3 mL) was cooled to 0° C. and then slowly treated with N-bromosuccinimide (144 mg, 0.81 mmol). The reaction mixture was stirred at 0° C. for 10 min and then treated with 3-cyclopentyl-2-(4-methanesulfonyl-3-nitrophenyl)-propionic acid (250 mg, 0.73 mmol). The resulting reaction mixture was stirred at 0° C. for 5 min and then allowed to warm to 25° C. where it was stirred for 30 min. The reaction mixture was then treated with 2-amino-5-bromopyridine (279 mg, 1.61 mmol). The resulting reaction mixture was stirred at 25° C. for 15 h. The crude reaction mixture was directly purified by flash chromatography, (Merck Silica gel 60, 230–400 mesh, 3/1 hexanes/ethyl acetate), to afford N-(5-bromo-pyridin-2-yl)-3-cyclopentyl-2-(4-methanesulfonyl-3-nitro-phenyl)-propionamide (121 mg, 33%) as a white foam: mp 80–83° C. (foam to gel); FAB-HRMS m/e calcd for $C_{20}H_{22}BrN_3O_5S$ (M+H)+ 496.0542, found 496.0543.

EXAMPLE 67

3-Cyclopentyl-2-(3-hydroxyamino-4-methanesulfonyl-phenyl)-N-thiazol-2-yl-propionamide

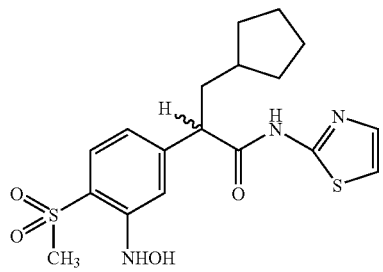

A solution of triphenylphosphine (138 mg, 0.53 mmol) in methylene chloride (2 mL) was cooled to 0° C. and then slowly treated with N-bromosuccinimide (94 mg, 0.53 mmol). The reaction mixture was stirred at 0° C. for 10 min and then treated with 3-cyclopentyl-2-(4-methanesulfonyl-3-nitrophenyl)-propionic acid (prepared as in Example 66, 150 mg, 0.44 mmol). The resulting reaction mixture was stirred at 0° C. for 5 min and then allowed to warm to 25° C. where it was stirred for 25 min. The reaction mixture was then treated with 2-aminothiazole (97 mg, 0.97 mmol). The resulting reaction mixture was stirred at 25° C. for 15 h. The crude reaction mixture was directly purified by flash chromatography, (Merck Silica gel 60, 230–400 mesh, 1/1 hexanes/ethyl acetate), to afford 3-cyclopentyl-2-(4-methanesulfonyl-3-nitrophenyl)-N-thiazol-2-yl-propionamide (96 mg, 52%) as a pale yellow solid: mp 121–124° C.; FAB-HRMS m/e calcd for $C_{18}H_{21}N_3O_5S_2$ (M+H)+ 424.1001, found 424.1000.

A solution of 3-cyclopentyl-2-(4-methanesulfonyl-3-nitrophenyl)-N-thiazol-2-yl-propionamide (150 mg, 0.354 mmol) in methanol (3 mL) was treated with 10% palladium on activated carbon (50 mg). The reaction mixture was stirred under a positive pressure of hydrogen gas (balloon) at 25° C. and atmospheric pressure for 3 h. The catalyst was then filtered off through a pad of celite, and the celite pad was washed well with ethyl acetate. The filtrate was concentrated in vacuo. Flash chromatography (Merck Silica gel 60, 230–400 mesh, 20/1 methylene chloride/methanol) afforded 3-cyclopentyl-2-(3-hydroxyamino-4-methanesulfonyl-phenyl)-N-thiazol-2-yl-propionamide (85 mg, 59%) as a white solid: mp 124–126° C.; EI-HRMS m/e calcd for $C_{18}H_{23}N_3O_4S_2$ (M+) 409.1130, found 409.1131.

EXAMPLE 68

2-(3-Amino-4-methanesulfonyl-phenyl)-3-cyclopentyl-N-thiazol-2-yl-propionamide

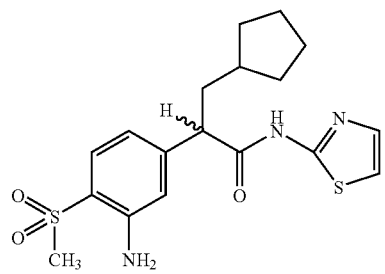

A solution of 3-cyclopentyl-2-(4-methanesulfonyl-3-nitrophenyl)-N-thiazol-2-yl-propionamide (prepared as in Example 67, 100 mg, 0.236 mmol) in methanol (2 mL) was treated with a solution of ammonium chloride (27 mg, 0.500 mmol) in water (200 µL). The reaction mixture was then treated with zinc dust (151 mg, 2.31 mmol). The reaction mixture was heated under reflux for 2 h. The reaction mixture was allowed to cool to 25° C. and then filtered through a pad of celite. The celite pad was washed well with methanol. The filtrate was concentrated in vacuo. Flash chromatography (Merck Silica gel 60, 230–400 mesh, 1/1 hexanes/ethyl acetate) afforded 2-(3-amino-4-methanesulfonyl-phenyl)-3-cyclopentyl-N-thiazol-2-yl-propionamide (40 mg, 43%) as a white solid: mp 207–209° C.; EI-HRMS m/e calcd for $C_{18}H_{23}N_3O_3S_2$ (M+) 393.1181, found 393.1180.

EXAMPLE 69

3-Cyclopentyl-N-thiazol-2-yl-2-(3-trifluoromethanesulfonyl-phenyl)-propionamide

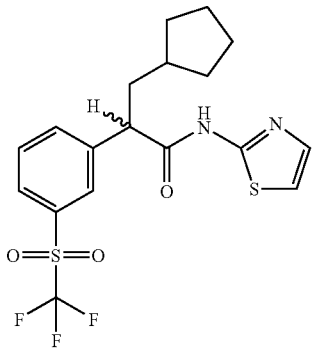

A solution of 3-(trifluoromethylthio)phenylacetic acid (5.00 g, 21.17 mmol) in methanol (50 mL) was treated slowly with 10 drops of concentrated sulfuric acid. The resulting reaction mixture was heated under reflux for 18 h.

The reaction mixture was allowed to cool to 25° C. and then concentrated in vacuo to remove methanol. The residue was diluted with ethyl acetate (100 mL). The organic phase was washed with a saturated aqueous sodium bicarbonate solution (1×100 mL), dried over magnesium sulfate, and filtered. The filtrate was concentrated in vacuo to afford (3-trifluoromethylsulfanyl-phenyl)-acetic acid methyl ester (5.28 g, 99%) as a pale yellow oil which was used without further purification: EI-HRMS m/e calcd for $C_{10}H_9F_3O_2S$ ($M^+$) 250.0275, found 250.0274.

A solution of diisopropylamine (1.5 mL, 10.5 mmol) in dry tetrahydrofuran (27 mL) and 1,3-dimethyl-3,4,5,6-tetrahydro-2(1H)-pyrimidinone (8 mL) was cooled to −78° C. under nitrogen and then treated with a 2.5M solution of n-butyllithium in hexanes (4.2 mL, 10.5 mmol). The resulting reaction mixture was stirred at −78° C. for 30 min and then treated dropwise with a solution of (3-trifluoromethylsulfanyl-phenyl)-acetic acid methyl ester (2.50 g, 10.0 mmol) in a small amount of tetrahydrofuran. The reaction mixture was allowed to stir at −78° C. for 1 h, at which time, a solution of iodomethylcyclopentane (2.10 g, 10.0 mmol) in a small amount of dry tetrahydrofuran was added dropwise. The reaction mixture was allowed to warm to 25° C. where it was stirred for 15 h. The reaction mixture was quenched with water (50 mL) and then partitioned between water (75 mL) and ethyl acetate (75 mL). The layers were shaken and separated. The organic layer was dried over magnesium sulfate, filtered, and concentrated in vacuo. Flash chromatography (Merck Silica gel 60, 230–400 mesh, 8/1 hexanes/ethyl acetate) afforded 3-cyclopentyl-2-(3-trifluoromethylsulfanyl-phenyl)-propionic acid methyl ester (2.95 g, 89%) as a colorless oil: EI-HRMS m/e calcd for $C_{16}H_{19}F_3O_2S$ ($M^+$) 332.1058, found 332.1047.

A solution of 3-cyclopentyl-2-(3-trifluoromethylsulfanyl-phenyl)-propionic acid methyl ester (2.75 g, 8.27 mmol) in methylene chloride (30 mL) was treated with 3-chloroperoxybenzoic acid (80–85% grade, 4.28 g based on 80%, 20.67 mmol). The reaction mixture was stirred at 25° C. for 6 h, at which time, thin layer chromatography showed the presence of two new lower $R_f$ products. An additional 4.00 g of 3-chloroperoxybenzoic acid was added to the reaction mixture to drive the conversion of the sulfoxide to the sulfone, and the resulting reaction mixture was stirred at 40° C. for 3 d. The reaction mixture was allowed to cool to 25° C. and then partitioned between water (100 mL) and methylene chloride (100 mL). The layers were shaken and separated. The organic phase was washed twice with a saturated aqueous sodium bicarbonate solution, washed with water, dried over magnesium sulfate, filtered, and concentrated in vacuo. Flash chromatography (Merck Silica gel 60, 230–400 mesh, 1/1 hexanes/methylene chloride) afforded 3-cyclopentyl-2-(3-trifluoromethanesulfonyl-phenyl)-propionic acid methyl ester (2.07 g, 69%) as a colorless oil: EI-HRMS m/e calcd for $C_{16}H_{19}F_3O_4S$ ($M^+$) 364.0956, found 364.0947.

A solution of 3-cyclopentyl-2-(3-trifluoromethanesulfonyl-phenyl)-propionic acid methyl ester (1.28 g, 3.52 mmol) in tetrahydrofuran (12 mL) was treated with a 0.8M aqueous lithium hydroxide solution (4.9 mL, 3.88 mmol). The reaction mixture was stirred at 25° C. for 24 h and then concentrated in vacuo to remove tetrahydrofuran. The resulting yellow oil was partitioned between water (50 mL) and ethyl acetate (50 mL) and then treated with a 1N aqueous hydrochloric acid solution. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(3-trifluoromethanesulfonyl-phenyl)-propionic acid (1.09 g, 99%) as a viscous yellow oil that solidified upon sitting to a white solid: mp 86–88° C.; EI-HRMS m/e calcd for $C_{15}H_{17}F_3O_4S$ ($M^+$) 350.0800, found 350.0792.

A solution of triphenylphosphine (194 mg, 0.74 mmol) in methylene chloride (3 mL) was cooled to 0° C. and then slowly treated with N-bromosuccinimide (132 mg, 0.74 mmol). The reaction mixture was stirred at 0° C. for 15 min and then treated with 3-cyclopentyl-2-(3-trifluoromethanesulfonyl-phenyl)-propionic acid (200 mg, 0.57 mmol). The resulting reaction mixture was stirred at 0° C. for 5 min and then allowed to warm to 25° C. over 30 min. The reaction mixture was then treated with 2-aminothiazole (143 mg, 1.43 mmol). The resulting reaction mixture was stirred at 25° C. for 15 h. The crude reaction mixture was then directly purified by flash chromatography (Merck Silica gel 60, 230–400 mesh, 3/1 hexanes/ethyl acetate) to afford pure 3-cyclopentyl-N-thiazol-2-yl-2-(3-trifluoromethanesulfonyl-phenyl)-propionamide (178 mg, 72%) as a light yellow foam: mp 61–64° C. (foam to gel); EI-HRMS m/e calcd for $C_{18}H_{19}F_3N_2O_3S_2$ ($M^+$) 432.0789, found 432.0790.

EXAMPLE 70

3-Cyclopentyl-2-(3-fluoro-4-trifluoromethyl-phenyl)-N-thiazol-2-yl-propionamide

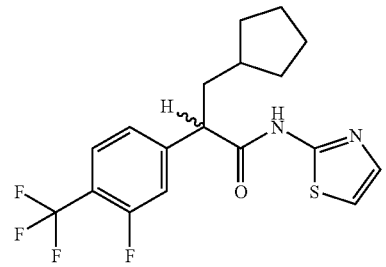

A solution of 3-fluoro-4-(trifluoromethyl)phenylacetic acid (2.50 g, 11.25 mmol) in methanol (25 mL) was treated slowly with 4 drops of concentrated sulfuric acid. The resulting reaction mixture was heated under reflux for 15 h. The reaction mixture was allowed to cool to 25° C. and then concentrated in vacuo to remove methanol. Flash chromatography (Merck Silica gel 60, 230–400 mesh, 1/1 hexanes/ethyl acetate) afforded (3-fluoro-4-trifluoromethyl-phenyl)-acetic acid methyl ester (2.58 g, 97%) as a colorless oil: EI-HRMS m/e calcd for $C_{10}H_8F_4O_2$ ($M^+$) 236.0460, found 236.0457.

A solution of diisopropylamine (1.5 mL, 10.67 mmol) in dry tetrahydrofuran (24 mL) and 1,3-dimethyl-3,4,5,6-tetrahydro-2(1H)-pyrimidinone (8 mL) was cooled to −78° C. under nitrogen and then treated with a 2.5M solution of n-butyllithium in hexanes (4.3 mL, 10.67 mmol). The resulting reaction mixture was stirred at −78° C. for 45 min and then treated dropwise with a solution of (3-fluoro-4-trifluoromethyl-phenyl)-acetic acid methyl ester (2.40 g, 10.16 mmol) in a small amount of tetrahydrofuran. The reaction mixture was allowed to stir at −78° C. for 1 h, at which time, a solution of iodomethylcyclopentane (2.24 g, 10.67 mmol) in a small amount of dry tetrahydrofuran was added dropwise. The reaction mixture was allowed to warm to 25° C. where it was stirred for 15 h. The reaction mixture was quenched with a saturated aqueous ammonium chloride solution (10 mL) and then partitioned between water (75 mL) and ethyl acetate (75 mL). The layers were shaken and separated. The aqueous layer was further extracted with ethyl acetate (1×75 mL). The combined organic layers were washed with a saturated aqueous sodium chloride solution, dried over magnesium sulfate, filtered, and concentrated in vacuo. Flash chromatography (Merck Silica gel 60, 230–400 mesh, 5/1 hexanes/ethyl acetate) afforded 3-cyclopentyl-2-(3-fluoro-4-trifluoromethyl-phenyl)-propionic acid methyl ester (2.69 g, 83%) as a colorless oil: EI-HRMS m/e calcd for $C_{16}H_{18}F_4O_2$ (M$^+$) 318.1243, found 318.1250.

A solution of 3-cyclopentyl-2-(3-fluoro-4-trifluoromethyl-phenyl)-propionic acid methyl ester (1.80 g, 5.69 mmol) in tetrahydrofuran (15 mL) was treated with a 0.8M aqueous lithium hydroxide solution (7.1 mL, 5.69 mmol). The reaction mixture was stirred at 25° C. for 15 h. The reaction mixture was concentrated in vacuo. The resulting residue was diluted with ethyl acetate (100 mL) and then washed with a 5% aqueous hydrochloric acid solution and a saturated aqueous sodium chloride solution. The organic layer was dried over magnesium sulfate, filtered, and concentrated in vacuo. Flash chromatography (Merck Silica gel 60, 230–400 mesh, 2/1 hexanes/ethyl acetate) afforded 3-cyclopentyl-2-(3-fluoro-4-trifluoromethyl-phenyl)-propionic acid (1.11 g, 64%) as a white solid: mp 93–95° C.; FAB-HRMS m/e calcd for $C_{15}H_{16}F_4O_2$ (M+H)$^+$ 305.1165, found 305.1175.

A solution of triphenylphosphine (312 mg, 1.19 mmol) in methylene chloride (5 mL) was cooled to 0° C. and then slowly treated with N-bromosuccinimide (212 mg, 1.19 mmol). The reaction mixture was stirred at 0° C. for 30 min and then treated with 3-cyclopentyl-2-(3-fluoro-4-trifluoromethyl-phenyl)-propionic acid (300 mg, 0.99 mmol). The resulting reaction mixture was stirred at 0° C. for 15 min and then allowed to warm to 25° C. where it was stirred for 30 min. The reaction mixture was then treated with 2-aminothiazole (218 mg, 2.18 mmol). The resulting reaction mixture was stirred at 25° C. for 3 d. The crude reaction mixture was then directly purified by flash chromatography (Merck Silica gel 60, 230–400 mesh, 2/1 hexanes/ethyl acetate) to afford 3-cyclopentyl-2-(3-fluoro-4-trifluoromethyl-phenyl)-N-thiazol-2-yl-propionamide (243 mg, 64%) as a white solid: mp 194–195° C.; EI-HRMS m/e calcd for $C_{18}H_{18}F_4N_2OS$ (M$^+$) 386.1076, found 386.1076.

EXAMPLE 71

3-Cyclo pentyl-2-(3-fluoro-4-trifluoromethyl-phenyl)-N-pyridin-2-yl-propionamide

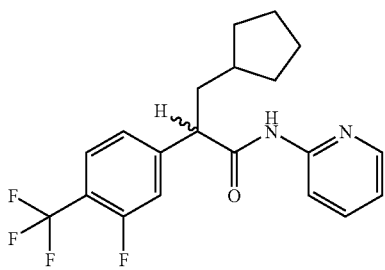

A solution of triphenylphosphine (312 mg, 1.19 mmol) in methylene chloride (5 mL) was cooled to 0° C. and then slowly treated with N-bromosuccinimide (212 mg, 1.19 mmol). The reaction mixture was stirred at 0° C. for 30 min and then treated with 3-cyclopentyl-2-(3-fluoro-4-trifluoromethyl-phenyl)-propionic acid (prepared as in Example 70, 300 mg, 0.99 mmol). The resulting reaction mixture was stirred at 0° C. for 15 min and then allowed to warm to 25° C. where it was stirred for 30 min. The reaction mixture was then treated with 2-aminopyridine (205 mg, 2.18 mmol). The resulting reaction mixture was stirred at 25° C. for 3 d. The crude reaction mixture was then directly purified by flash chromatography (Merck Silica gel 60, 230–400 mesh, 2/1 hexanes/ethyl acetate) to afford 3-cyclopentyl-2-(3-fluoro-4-trifluoromethyl-phenyl)-N-pyridin-2-yl-propionamide (171 mg, 45%) as a pale yellow foam: mp 40–44° C. (foam to gel); EI-HRMS m/e calcd for $C_{20}H_{20}F_4N_2O$ (M$^+$) 380.1512, found 380.1519.

EXAMPLE 72

2-(3-Bromo-4-methanesulfonyl-phenyl)-3-cyclopentyl-N-thiazol-2-yl-propionamide

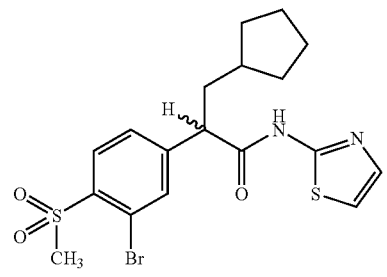

A solution of 4-(methylthio)phenylacetic acid (21.21 g, 116.38 mmol) in methanol (291 mL) was treated slowly with concentrated sulfuric acid (3 mL). The resulting reaction mixture was heated under reflux for 3 d. The reaction mixture was allowed to cool to 25° C. and then concentrated in vacuo to remove methanol. The resulting residue was diluted with diethyl ether (600 mL). The organic layer was washed with a saturated aqueous sodium bicarbonate solution (3×300 mL) and a saturated aqueous sodium chloride solution (1×300 mL). The organic layer was dried over sodium sulfate, filtered, and concentrated in vacuo to afford (4-methylsulfanyl-phenyl)-acetic acid methyl ester (20.95 g, 92%) as a yellow liquid which was used without further purification: EI-HRMS m/e calcd for $C_{10}H_{12}O_2S$ (M$^+$) 196.0558, found 196.0559.

A solution of (4-methylsulfanyl-phenyl)-acetic acid methyl ester (5.11 g, 26.03 mmol) in carbon tetrachloride (130 mL) was slowly treated with bromine (1.74 mL, 33.84 mmol). The reaction mixture was stirred at 25° C. for 4 h, at which time, thin layer chromatography still indicated the presence of a substantial amount of starting material. The reaction mixture was treated with more bromine (1.74 mL, 33.84 mmol). The reaction mixture was stirred an additional 4 h at 25° C. and then quenched with a 10% aqueous sodium bisulfite solution (150 mL). The reaction mixture was concentrated in vacuo to remove carbon tetrachloride. The resulting aqueous layer was extracted with ethyl acetate (3×150 mL). The combined organic layers were dried over sodium sulfate, filtered and concentrated in vacuo. Flash chromatography (Merck Silica gel 60, 70–230 mesh, 9/1 hexanes/ethyl acetate) afforded (3-bromo-4-methylsulfanylphenyl)-acetic acid methyl ester (6.10 g, 85%) as a light yellow oil: EI-HRMS m/e calcd for $C_{10}H_{11}BrO_2S$ (M+) 273.9663, found 273.9661.

A solution of diisopropylamine (3.4 mL, 24.38 mmol) in dry tetrahydrofuran (21 mL) and 1,3-dimethyl-3,4,5,6-tetrahydro-2(1H)-pyrimidinone (7 mL) was cooled to −78° C. under nitrogen and then treated with a 2.5M solution of n-butyllithium in hexanes (9.8 mL, 24.38 mmol). The resulting reaction mixture was stirred at −78° C. for 30 min and then treated dropwise with a solution of (3-bromo-4-methylsulfanyl-phenyl)-acetic acid methyl ester (6.10 g, 22.17 mmol) in dry tetrahydrofuran (21 mL) and 1,3-dimethyl-3,4,5,6-tetrahydro-2(1H)-pyrimidinone (7 mL). The resulting reaction mixture was allowed to stir at −78° C. for 1 h, at which time, a solution of iodomethylcyclopentane (5.59 g, 26.60 mmol) in a small amount of dry tetrahydrofuran was added dropwise. The reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (4.52 g, 57%) as a light yellow oil: EI-HRMS m/e calcd for $C_{16}H_{21}BrO_2S$ (M+) 356.0446, found 356.0435.

A solution of 2-(3-bromo-4-methylsulfanyl-phenyl)-3-cyclopentyl-propionic acid methyl ester (1.07 g, 2.99 mmol) in methylene chloride (15 mL) was treated with 3-chloroperoxybenzoic acid (57–86% grade, 1.81 g based on 57%, 5.99 mmol). The reaction mixture was stirred at 25° C. for 3 h. The reaction mixture was concentrated in vacuo to remove methylene chloride. The resulting residue was diluted with diethyl ether (300 mL). The organic phase was washed with a saturated aqueous sodium bicarbonate solution (3×200 mL) and a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 2-(3-bromo-4-methanesulfonyl-phenyl)-3-cyclopentyl-propionic acid methyl ester (1.09 g, 94%) as a colorless oil: EI-HRMS m/e calcd for $C_{16}H_{19}BrO_4S$ (M+) 388.0344, found 388.0343.

A solution of 2-(3-bromo-4-methanesulfonyl-phenyl)-3-cyclopentyl-propionic acid methyl ester (1.62 g, 4.16 mol) in methanol (10 mL) was treated with a 1N aqueous sodium hydroxide solution (8.7 mL, 8.74 mol). The reaction mixture was stirred at 25° C. for 27 h. The reaction mixture was concentrated in vacuo to remove methanol. The resulting aqueous residue was acidified to pH=2 with a 10% aqueous hydrochloric acid solution and then extracted with ethyl acetate (1×400 mL). The organic layer was washed with water (1×300 mL) and a saturated aqueous sodium chloride solution (1×300 mL). The organic layer was then dried over sodium sulfate, filtered, and concentrated in vacuo to afford 2-(3-bromo-4-methanesulfonyl-phenyl)-3-cyclopentyl-propionic acid (1.39 g, 89%) as a white solid which was used without further purification: mp 149–150° C.; FAB-HRMS m/e calcd for $C_{15}H_{19}BrO_4S$ (M+H)+ 375.0266, found 375.0274.

A solution of triphenylphosphine (168 mg, 0.64 mmol) in methylene chloride (3 mL) was cooled to 0° C. and then slowly treated with N-bromosuccinimide (114 mg, 0.64 mmol). The reaction mixture was stirred at 0° C. for 10 min and then treated with 2-(3-bromo-4-methanesulfonyl-phenyl)-3-cyclopentyl-propionic acid (200 mg, 0.53 mmol). The resulting reaction mixture was stirred at 0° C. for 5 min and then allowed to warm to 25° C. where it was stirred for 25 min. The reaction mixture was then treated with 2-aminothiazole (117 mg, 1.17 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3-bromo-4-methanesulfonyl-phenyl)-3-cyclopentyl-N-thiazol-2-yl-propionamide (214 mg, 88%) as a yellow solid: mp 106–107° C.; EI-HRMS m/e calcd for $C_{18}H_{21}BrN_2O_3S_2$ (M+) 456.0177, found 456.0175.

EXAMPLE 73

2-(3-Bromo-4-methanesulfonyl-phenyl)-3-cyclopentyl-N-pyridin-2-yl-propionamide

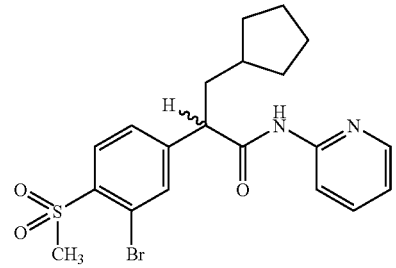

A solution of triphenylphosphine (168 mg, 0.64 mmol) in methylene chloride (3 mL) was cooled to 0° C. and then slowly treated with N-bromosuccinimide (114 mg, 0.64 mmol). The reaction mixture was stirred at 0° C. for 10 min and then treated with 2-(3-bromo-4-methanesulfonyl-phenyl)-3-cyclopentyl-propionic acid (prepared as in Example 72, 200 mg, 0.53 mmol). The resulting reaction mixture was stirred at 0° C. for 5 min and then allowed to warm to 25° C. where it was stirred for 25 min. The reaction mixture was then treated with 2-aminopyridine (110 mg, 1.17 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3-bromo-4-methanesulfonyl-phenyl)-3-cyclopentyl-N-pyridin-2-yl-propionamide (175 mg, 73%) as a white foam: mp 99–101° C.; FAB-HRMS m/e calcd for $C_{20}H_{23}BrN_2O_3S$ (M+H)+ 451.0692, found 451.0689.

EXAMPLE 74

2-(3-Bromo-4-methanesulfonyl-phenyl)-N-(5-bromo-pyridin-2-yl)-3-cyclopentyl-propionamide

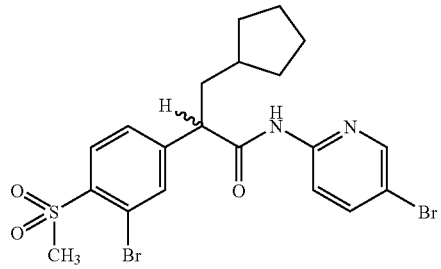

A solution of triphenylphosphine (154 mg, 0.59 mmol) in methylene chloride (3 mL) was cooled to 0° C. and then slowly treated with N-bromosuccinimide (104 mg, 0.59 mmol). The reaction mixture was stirred at 0° C. for 10 min and then treated with 2-(3-bromo-4-methanesulfonyl-phenyl)-3-cyclopentyl-propionic acid (prepared as in Example 72, 200 mg, 0.53 mmol). The resulting reaction mixture was stirred at 0° C. for 5 min and then allowed to warm to 25° C. where it was stirred for 30 min. The reaction mixture was then treated with 2-amino-5-bromopyridine (203 mg, 1.17 mmol). The resulting reaction mixture was stirred at 25° C. for 15 h. The crude reaction mixture was then directly purified by flash chromatography (Merck Silica gel 60, 230–400 mesh, 3/1 hexanes/ethyl acetate) to afford the 2-(3-bromo-4-methanesulfonyl-phenyl)-N-(5-bromo-pyridin-2-yl)-3-cyclopentyl-propionamide (164 mg, 58%) as a white foam: mp 83–86° C. (foam to gel); FAB-HRMS m/e calcd for $C_{20}H_{22}Br_2N_2O_3S$ $(M+H)^+$ 528.9796, found 528.9783.

EXAMPLE 75

2-(3-Cyano-4-methanesulfonyl-phenyl)-3-cyclopentyl-N-thiazol-2-yl-propionamide

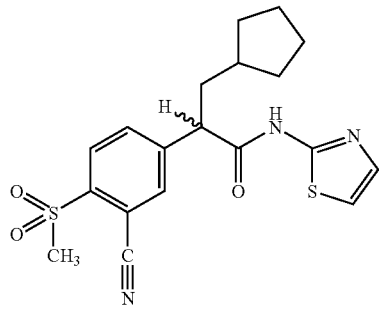

A mixture of 2-(3-bromo-4-methanesulfonyl-phenyl)-3-cyclopentyl-propionic acid methyl ester (prepared as in Example 72, 990.0 mg, 2.54 mmol) and copper(I) cyanide (273.3 mg, 3.05 mmol) in dry N,N-dimethylformamide (2.5 mL) was heated under reflux for 4 h. The reaction was allowed to cool to 25° C., and the crude reaction mixture was directly purified without further chemical work-up. Flash chromatography (Merck Silica gel 60, 70–230 mesh, 100% hexanes then 3/1 hexanes/ethyl acetate) afforded 2-(3-cyano-4-methanesulfonyl-phenyl)-3-cyclopentyl-propionic acid methyl ester (646.5 mg, 76%) as a very light yellow oil: EI-HRMS m/e calcd for $C_{17}H_{21}NO_4S$ $(M^+)$ 335.1191, found 335.1185.

A solution of 2-(3-cyano-4-methanesulfonyl-phenyl)-3-cyclopentyl-propionic acid methyl ester (4.84 g, 14.4 mol) in tetrahydrofuran (25 mL) was treated with a 0.8M aqueous lithium hydroxide solution (27 mL, 21.6 mmol). The reaction mixture was stirred at 25° C. for 2.5 h. The reaction mixture was partitioned between water and ethyl acetate and then acidified to pH=2 with a 10% aqueous hydrochloric acid solution. The layers were shaken and separated. The resulting organic layer was washed with a saturated aqueous sodium chloride solution, dried over magnesium sulfate, filtered, and concentrated in vacuo to afford crude 2-(3-cyano-4-methanesulfonyl-phenyl)-3-cyclopentyl-propionic acid (3.80 g, 82%) as a pale yellow oil that solidified to a pale yellow solid. An analytical sample was obtained by recrystallization from ethyl acetate to afford 2-(3-cyano-4-methanesulfonyl-phenyl)-3-cyclopentyl-propionic acid as a white solid: mp 180–181° C.; EI-HRMS m/e calcd for $C_{16}H_{19}NO_4S$ $(M^+)$ 321.1034, found 321.1039.

A solution of triphenylphosphine (98 mg, 0.37 mmol) in methylene chloride (1 mL) was cooled to 0° C. and then slowly treated with N-bromosuccinimide (67 mg, 0.37 mmol). The reaction mixture was stirred at 0° C. for 15 min and then treated with 2-(3-cyano-4-methanesulfonyl-phenyl)-3-cyclopentyl-propionic acid (100 mg, 0.31 mmol). The resulting reaction mixture was stirred at 0° C. for 5 min and then allowed to warm to 25° C. where it was stirred for 30 min. The reaction mixture was then treated with 2-aminothiazole (68 mg, 0.68 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3-cyano-4-methanesulfonyl-phenyl)-3-cyclopentyl-N-thiazol-2-yl-propionamide (117 mg, 93%) as a white solid: mp 145–148° C.; EI-HRMS m/e calcd for $C_{19}H_{21}N_3O_3S_2$ $(M^+)$ 403.1024, found 403.1023.

EXAMPLE 76

2-(3-Cyano-4-methanesulfonyl-phenyl)-3-cyclopentyl-N-pyridin-2-yl-propionamide

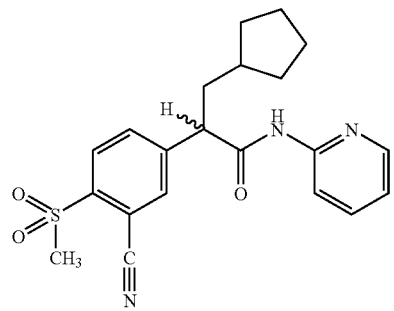

A solution of triphenylphosphine (98 mg, 0.37 mmol) in methylene chloride (1 mL) was cooled to 0° C. and then slowly treated with N-bromosuccinimide (67 mg, 0.37 mmol). The reaction mixture was stirred at 0° C. for 15 min and then treated with 2-(3-cyano-4-methanesulfonyl-phenyl)-3-cyclopentyl-propionic acid (prepared as in Example 75, 100 mg, 0.31 mmol). The resulting reaction mixture was stirred at 0° C. for 5 min and then allowed to warm to 25° C. where it was stirred for 30 min. The reaction mixture was then treated with 2-aminopyridine (64 mg, 0.68 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3-cyano-4-methanesulfonyl-phenyl)-3-cyclopentyl-N-pyridin-2-yl-propionamide (94.5 mg, 76%) as a yellow foam: mp 87–90° C. (foam to gel); EI-HRMS m/e calcd for $C_{21}H_{23}N_3O_3S$ $(M^+)$ 397.1460, found 397.1460.

EXAMPLE 77

3-Cyclopentyl-2-(4-ethanesulfonyl-phenyl)-N-thiazol-2-yl-propionamide

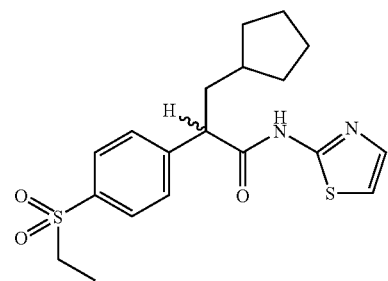

A mixture of aluminum chloride (72.35 g, 0.54 mol) in chloroform (181 mL) was cooled to 0° C. and stirred until the solid material dissolved. The reaction mixture was then slowly treated with ethyl oxalyl chloride (61 mL, 0.54 mol), and the resulting reaction mixture was stirred at 0° C. for 30 min. The reaction mixture was then slowly treated with ethyl phenyl sulfide (25.00 g, 0.18 mol). The solution turned to a wine color and slowly became gum-like. The resulting reaction mixture was then stirred at 0° C. for 2 h. The reaction mixture was slowly poured into a large amount of ice/water. The resulting aqueous layer was extracted with chloroform (3×200 mL). The combined organic layers were dried over sodium sulfate, filtered, and concentrated in vacuo. Flash chromatography (Merck Silica gel 60, 70–230 mesh, 9/1 hexanes/ethyl acetate) afforded (4-ethylsulfanyl-phenyl)-oxo-acetic acid ethyl ester (23.64 g, 55%) as a yellow oil. The material was used without further purification and characterization in subsequent reactions.

A solution of iodomethylcyclopentane (4.60 g, 21.89 mmol) and triphenylphosphine (5.74 g, 21.89 mmol) in acetonitrile (22 mL) was heated under reflux for 2 weeks. The reaction mixture was allowed to cool to 25° C. and then concentrated in vacuo to provide an orange solid. The orange solid was triturated with diethyl ether and then filtered. The solid was washed well with diethyl ether until the washings showed the absence of iodomethylcyclopentane and triphenylphosphine by thin layer chromatography. The solid was allowed to air dry to afford cyclopentylmethyl triphenylphosphonium iodide (8.92 g, 86%) as a light orange solid: mp 195–198° C.; FAB-HRMS m/e calcd for $C_{24}H_{26}P$ $(M+H)^+$ 345.1772, found 345.1784.

A suspension of cyclopentylmethyl triphenylphosphonium iodide (24.48 g, 51.82 mmol) in dry tetrahydrofuran (100 mL) was cooled to 0° C. and then treated dropwise with a 1.0M solution of sodium bis(trimethylsilyl)amide in tetrahydrofuran (52 mL, 51.82 mmol). The bright orange reaction mixture was stirred at 0° C. for 1 h. The reaction mixture was then treated with (4-ethylsulfanyl-phenyl)-oxo-acetic acid ethyl ester (9.50 g, 39.87 mmol). The resulting reaction mixture was allowed to warm to 25° C. where it was stirred for 20 h. The reaction mixture was concentrated in vacuo to remove tetrahydrofuran and then diluted with water (300 mL). The aqueous layer was extracted with ethyl acetate (3×200 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded the 3-cyclopentyl-2-(4-ethylsulfanyl-phenyl)-acrylic acid ethyl ester (6.08 g, 50%) as a yellow oil containing a 1.82:1 mixture of (E):(Z) isomers: FAB-LRMS m/e calcd for $C_{18}H_{24}O_2S$ $(M+H)^+$ integer mass 304, found 305. The isomeric mixture was used without further separation in subsequent reactions.

A solution of 3-cyclopentyl-2-(4-ethylsulfanyl-phenyl)-acrylic acid ethyl ester [5.76 g, 18.92 mmol, (E):(Z)=1.82:1] in methylene chloride (47 mL) was slowly treated with 3-chloroperoxybenzoic acid (57–86% grade, 11.45 g based on 57%, 37.83 mmol). The reaction mixture was stirred at 25° C. for 1 h. The reaction mixture was concentrated in vacuo to remove methylene chloride. The resulting residue was diluted with diethyl ether (300 mL). The organic phase was washed with a saturated aqueous sodium bicarbonate solution (3×200 mL) and a saturated aqueous sodium chloride solution (1×200 mL), dried over sodium sulfate, filtered, and concentrated in vacuo. Flash chromatography (Merck Silica gel 60, 230–400 mesh, 3/1 hexanes/ethyl acetate) afforded 3-cyclopentyl-2-(4-ethanesulfonyl-phenyl)-acrylic acid ethyl ester (4.89 g, 77%) as a colorless oil. The product was a 3:1 mixture of (E):(Z) isomers that was used without further purification and characterization.

A solution of 3-cyclopentyl-2-(4-ethanesulfonyl-phenyl)-acrylic acid ethyl ester [4.89 g, 14.53 mmol, (E):(Z)=3:1] in ethanol (36 mL) was slowly treated with 10% palladium on activated carbon (244.5 mg). The reaction mixture was stirred under a positive pressure of hydrogen gas (balloon) at 25° C. and atmospheric pressure for 44 h. The catalyst was then filtered off through a pad of celite, and the celite pad was washed well with ethyl acetate. The filtrate was concentrated in vacuo. Flash chromatography (Merck Silica gel 60, 70–230 mesh, 3/1 hexanes/ethyl acetate) afforded 3-cyclopentyl-2-(4-ethanesulfonyl-phenyl)-propionic acid ethyl ester (3.50 g, 71%) as a colorless viscous oil: FAB-LRMS m/e calcd for $C_{18}H_{26}O_4S$ $(M+H)^+$ integer mass 338, found 339.

A solution of 3-cyclopentyl-2-(4-ethanesulfonyl-phenyl)-propionic acid ethyl ester (2.50 g, 7.39 mmol) in tetrahydrofuran (30 mL) was treated with a 0.8M aqueous lithium hydroxide solution (11.1 mL, 8.86 mmol). The reaction mixture was stirred at 25° C. for 23 h. The resulting reaction mixture was partitioned between water (75 mL) and ethyl acetate (75 mL) and then treated with a 1N aqueous hydrochloric acid solution (15 mL). The layers were shaken and separated. The organic layer was dried over magnesium sulfate, filtered, and concentrated in vacuo to afford 3-cyclopentyl-2-(4-ethanesulfonyl-phenyl)-propionic acid (2.20 g, 96%) as a white solid which was used without further purification: mp 137–138° C.; FAB-HRMS m/e calcd for $C_{16}H_{22}O_4S$ $(M+H)^+$ 311.1317, found 311.1321.

A solution of triphenylphosphine (279 mg, 1.06 mmol) in methylene chloride (5 mL) was cooled to 0° C. and then slowly treated with N-bromosuccinimide (189 mg, 1.06 mmol). The reaction mixture was stirred at 0° C. for 20 min and then treated with 3-cyclopentyl-2-(4-ethanesulfonyl-phenyl)-propionic acid (300 mg, 0.97 mmol). The resulting reaction mixture was stirred at 0° C. for 10 min and then allowed to warm to 25° C. where it was stirred for 30 min. The reaction mixture was then treated with 2-aminothiazole (213 mg, 2.13 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 3-cyclopentyl-2-(4-ethanesulfonyl-phenyl)-N-thiazol-2-yl-propionamide (330 mg, 87%) as a pale yellow solid: mp 178–179° C.; EI-HRMS m/e calcd for $C_{19}H_{24}N_2O_3S_2$ $(M^+)$ 392.1228, found 392.1230.

EXAMPLE 78

3-Cyclopentyl-2-(4-ethanesulfonyl-phenyl)-N-pyridin-2-yl-propionamide

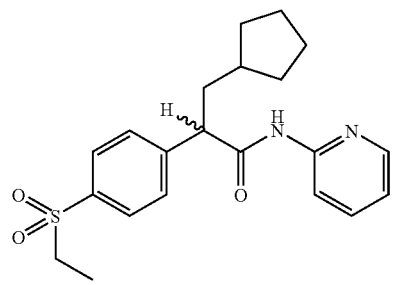

A solution of triphenylphosphine (279 mg, 1.06 mmol) in methylene chloride (5 mL) was cooled to 0° C. and then slowly treated with N-bromosuccinimide (189 mg, 1.06 mmol). The reaction mixture was stirred at 0° C. for 20 min and then treated with 3-cyclopentyl-2-(4-ethanesulfonyl-phenyl)-propionic acid (prepared as in Example 77, 300 mg, 0.97 mmol). The resulting reaction mixture was stirred at 0° C. for 10 min and then allowed to warm to 25° C. where it was stirred for 30 min. The reaction mixture was then treated with 2-aminopyridine (200 mg, 2.13 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 3-cyclopentyl-2-(4-ethanesulfonyl-phenyl)-N-pyridin-2-yl-propionamide (185 mg, 50%) as a pale orange solid: mp 144–145° C.; EI-HRMS m/e calcd for $C_{21}H_{26}N_2O_3S$ ($M^+$) 386.1664, found 386.1660.

EXAMPLE 79

2-(3,4-Bis-methanesulfonyl-phenyl)-3-cyclo pentyl-N-thiazol-2-yl-propionamide

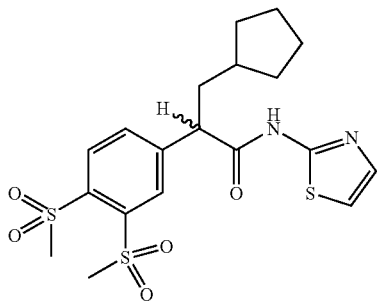

A solution of 3,4-difluorophenylacetic acid (5.00 g, 29.05 mmol) in methanol (73 mL) was slowly treated with concentrated sulfuric acid (4 mL). The resulting reaction mixture was heated under reflux for 65 h. The reaction mixture was allowed to cool to 25° C. and then concentrated in vacuo to remove methanol. The resulting residue was slowly diluted with a saturated aqueous sodium bicarbonate solution (300 mL) and then extracted with ethyl acetate (1×300 mL). The organic layer was dried over magnesium sulfate, filtered, and concentrated in vacuo to afford (3,4-difluoro-phenyl)-acetic acid methyl ester (5.38 g, 99%) as a yellow oil which was used without further purification.

A solution of sodium thiomethoxide (6.39 g, 86.69 mmol) in dimethyl sulfoxide (72 mL) was treated with (3,4-difluoro-phenyl)-acetic acid methyl ester (5.38 g, 28.89 mmol). The reaction mixture was stirred at 25° C. for 2 h then heated at 70° C. for 15 min, at which time, thin layer chromatography indicated the absence of starting material and the presence of a very polar new product. The reaction indicated that the ester hydrolyzed to the acid upon heating. The resulting reaction mixture was allowed to cool to 25° C. The reaction mixture was then treated with a 10% aqueous hydrochloric acid solution (200 mL) and then extracted with chloroform (3×200 mL). The combined organic layers were dried over magnesium sulfate, filtered, and concentrated in vacuo to afford a yellow oil. This yellow oil was dissolved in methanol (100 mL) and then slowly treated with concentrated sulfuric acid (5 mL). The resulting reaction mixture was heated under reflux for 3 h. The reaction mixture was allowed to cool to 25° C. and then concentrated in vacuo to remove methanol. The resulting residue was slowly diluted with a saturated aqueous sodium bicarbonate solution (300 mL) and then extracted with ethyl acetate (1×300 mL). The organic layer was dried over magnesium sulfate, filtered, and concentrated in vacuo to afford an inseparable, isomeric mixture of (3-fluoro-4-methylsulfanyl-phenyl)-acetic acid methyl ester and (4-fluoro-3-methylsulfanyl-phenyl)-acetic acid methyl ester as a yellow oil (4.65 g, 75%) which was used without further purification and characterization.

A solution of the inseparable, isomeric mixture of (3-fluoro-4-methylsulfanyl-phenyl)-acetic acid methyl ester and (4-fluoro-3-methylsulfanyl-phenyl)-acetic acid methyl ester (4.44 g, 20.72 mmol) in methylene chloride (103 mL) was slowly treated with 3-chloroperoxybenzoic acid (57–86% grade, 13.80 g based on 57%, 45.59 mmol). The reaction mixture was stirred at 25° C. for 4 h. The reaction mixture was concentrated in vacuo to remove methylene chloride. The resulting residue was diluted with ethyl acetate (300 mL). The organic phase was washed with a saturated aqueous sodium bicarbonate solution (1×200 mL) and a saturated aqueous sodium chloride solution (1×200 mL), dried over magnesium sulfate, filtered, and concentrated in vacuo. Flash chromatography (Merck Silica gel 60, 70–230 mesh, 20/1 methylene chloride/ethyl acetate) afforded an inseparable, isomeric mixture of (3-fluoro-4-methanesulfonyl-phenyl)-acetic acid methyl ester and (4-fluoro-3-methanesulfonyl-phenyl)-acetic acid methyl ester as a colorless liquid (3.31 g, 65%) which was used without further purification and characterization.

A solution of the inseparable, isomeric mixture of (3-fluoro-4-methanesulfonyl-phenyl)-acetic acid methyl ester and (4-fluoro-3-methanesulfonyl-phenyl)-acetic acid methyl ester (2.28 g, 9.26 mmol) in dimethyl sulfoxide (23 mL) was treated with sodium thiomethoxide (1.37 g, 18.52 mmol). The reaction mixture was stirred at 25° C. for 4 h and then quenched with a 10% aqueous hydrochloric acid solution. The aqueous layer was extracted with chloroform (1×400 mL), dried over magnesium sulfate, filtered, and concentrated in vacuo. Flash chromatography (Merck Silica gel 60, 70–230 mesh, 3/2 hexanes/ethyl acetate) afforded an inseparable, isomeric mixture of (3-methanesulfonyl-4-methylsulfanyl-phenyl)-acetic acid methyl ester and (4-methanesulfonyl-3-methylsulfanyl-phenyl)-acetic acid methyl ester as a yellow liquid (2.19 g, 86%) which was used without further purification and characterization.

A solution of the inseparable, isomeric mixture of (3-methanesulfonyl-4-methylsulfanyl-phenyl)-acetic acid methyl ester and (4-methanesulfonyl-3-methylsulfanyl-phenyl)-acetic acid methyl ester (2.19 g, 7.98 mmol) in methylene chloride (20 mL) was slowly treated with 3-chloroperoxybenzoic acid (57–86% grade, 6.41 g based on 57%, 31.93 mmol). The reaction mixture was stirred at 25° C. for 5 h and then slowly quenched with a 1.5N aqueous sodium sulfite solution. The resulting reaction mixture was extracted with methylene chloride (300 mL). The organic phase was dried over magnesium sulfate, filtered, and concentrated in vacuo. Flash chromatography (Merck Silica gel 60, 70–230 mesh, 10/1 methylene chloride/ethyl acetate) afforded (3,4-bis-methanesulfonyl-phenyl)-acetic acid methyl ester (1.89 g, 77%) as a white solid: mp 157–158° C.; EI-HRMS m/e calcd for $C_{11}H_{14}O_6S_2$ ($M^+$) 306.0232, found 306.0234.

A solution of diisopropylamine (951 µL, 6.79 mmol) in dry tetrahydrofuran (6 mL) and 1,3-dimethyl-3,4,5,6-tetrahydro-2(1H)-pyrimidinone (2 mL) was cooled to −78° C. under nitrogen and then treated with a 2.5M solution of n-butyllithium in hexanes (2.5 mL, 6.79 mmol). The resulting reaction mixture was stirred at −78° C. for 30 min and then treated dropwise with a solution of (3,4-bis-methanesulfonyl-phenyl)-acetic acid methyl ester (1.89 g, 6.17 mmol) in dry tetrahydrofuran (12 mL) and 1,3-dimethyl-3, 4,5,6-tetrahydro-2(1H)-pyrimidinone (4 mL). The resulting reaction mixture was allowed to stir at −78° C. for 1 h, at which time, a solution of iodomethylcyclopentane (1.56 g, 7.40 mmol) in a small amount of dry tetrahydrofuran was added dropwise. The reaction mixture was allowed to warm to 25° C. where it was stirred for 64 h. The reaction mixture was quenched with water (150 mL) and then concentrated in vacuo to remove tetrahydrofuran. The remaining residue was further diluted with water (100 mL) and then extracted with ethyl acetate (1×250 mL). The organic layer was washed with a saturated aqueous sodium chloride solution (1×100 mL), dried over magnesium sulfate, filtered, and concentrated in vacuo. Flash chromatography (Merck Silica gel 60, 70–230 mesh, 3/1 hexanes/ethyl acetate) afforded 2-(3,4-bis-methanesulfonyl-phenyl)-3-cyclopentyl-propionic acid methyl ester (1.61 g, 67%) as a yellow oil: EI-HRMS m/e calcd for $C_{17}H_{24}O_6S_2$ ($M^+$) 388.1014, found 388.1014.

A solution of 2-(3,4-bis-methanesulfonyl-phenyl)-3-cyclopentyl-propionic acid methyl ester (1.17 g, 3.01 mmol) in tetrahydrofuran (12 mL) was treated with a 0.8M aqueous lithium hydroxide solution (5.6 mL, 4.52 mmol). The reaction mixture was stirred at 25° C. for 3 h. The resulting reaction mixture was partitioned between water (75 mL) and ethyl acetate (75 mL) and then treated with a 1N aqueous hydrochloric acid solution (10 mL). The layers were shaken and separated. The organic layer was dried over magnesium sulfate, filtered, and concentrated in vacuo to afford 2-(3,4-bis-methanesulfonyl-phenyl)-3-cyclopentyl-propionic acid (1.10 g, 98%) as a white foam which was used without further purification: mp 64–68° C. (foam to gel); FAB-HRMS m/e calcd for $C_{16}H_{22}O_6S_2$ $(M+H)^+$ 375.0936, found 375.0932.

A solution of triphenylphosphine (154 mg, 0.59 mmol) in methylene chloride (2 mL) was cooled to 0° C. and then slowly treated with N-bromosuccinimide (105 mg, 0.59 mmol). The reaction mixture was stirred at 0° C. for 10 min and then treated with 2-(3,4-bis-methanesulfonyl-phenyl)-3-cyclopentyl-propionic acid (200 mg, 0.53 mmol). The resulting reaction mixture was stirred at 0° C. for 5 min and then allowed to warm to 25° C. where it was stirred for 30 min. The reaction mixture was then treated with 2-aminothiazole (118 mg, 1.18 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3,4-bis-methanesulfonyl-phenyl)-3-cyclopentyl-N-thiazol-2-yl-propionamide (150 mg, 61%) as a pale yellow foam: mp 104–107° C.; EI-HRMS m/e calcd for $C_{19}H_{24}N_2O_5S_3$ ($M^+$) 456.0847, found 456.0846.

EXAMPLE 80

2-(3,4-Bis-methanesulfonyl-phenyl)-3-cyclopentyl-N-pyridin-2-yl-propionamide

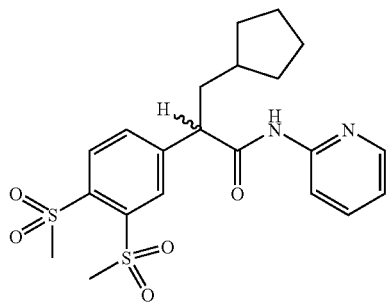

A solution of triphenylphosphine (154 mg, 0.59 mmol) in methylene chloride (2 mL) was cooled to 0° C. and then slowly treated with N-bromosuccinimide (105 mg, 0.59 mmol). The reaction mixture was stirred at 0° C. for 10 min and then treated with 2-(3,4-bis-methanesulfonyl-phenyl)-3-cyclopentyl-propionic acid (prepared as in Example 79, 200 mg, 0.53 mmol). The resulting reaction mixture was stirred at 0° C. for 5 min and then allowed to warm to 25° C. where it was stirred for 30 min. The reaction mixture was then treated with 2-aminopyridine (110 mg, 1.18 mmol). The resulting reaction mixture was stirred at 25° C. for 15 h. The crude reaction mixture was then directly purified by flash chromatography (Merck Silica gel 60, 230–400 mesh, 1/1 hexanes/ethyl acetate) to afford 2-(3,4-bis-methanesulfonyl-phenyl)-3-cyclopentyl-N-pyridin-2-yl-propionamide (117 mg, 49%) as a pale yellow foam: mp 107–110° C.; EI-HRMS m/e calcd for $C_{21}H_{26}N_2O_5S_2$ ($M^+$) 450.1283, found 450.1282.

EXAMPLE 81

3-Cyclopentyl-2-(3,4-dichlorophenyl)-N-[1,2,4]triazin-3-yl-propionamide

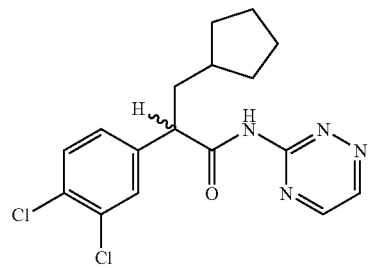

A solution of 3-cyclopentyl-2-(3,4-dichlorophenyl)-propionic acid (prepared as in Example 38A, 400 mg, 1.40 mmol) in dry pyridine (5 mL) was treated with 1,3-dicyclohexylcarbodiimide (316 mg, 1.53 mmol). The reaction mixture was stirred at 25° C. for 3.5 h and then treated with 3-amino-1,2,4-triazine (296 mg, 3.08 mmol) and an additional amount of pyridine (1 mL). The reaction mixture was warmed at 100° C. for 20 h. The reaction mixture was concentrated in vacuo to remove pyridine. The resulting residue was diluted with ethyl acetate then filtered. The filtrate was washed with a 1N aqueous hydrochloric acid solution and washed with water. The organic layer was dried over magnesium sulfate, filtered, and concentrated in vacuo. Flash chromatography (Merck Silica gel 60, 230–400 mesh, 1/1 ethyl acetate/hexanes) afforded 3-cyclopentyl-2-(3,4-dichlorophenyl)-N-[1,2,4]triazin-3-yl-propionamide (40.9 mg, 8%) as a yellow-orange solid: mp 81–83° C.; EI-HRMS m/e calcd for $C_{17}H_{18}Cl_2N_4O$ ($M^+$) 364.0858, found 364.0857.

EXAMPLE 82

3-Cyclopentyl-2-(4-sulfamoyl-phenyl)-N-thiazol-2-yl-propionamide

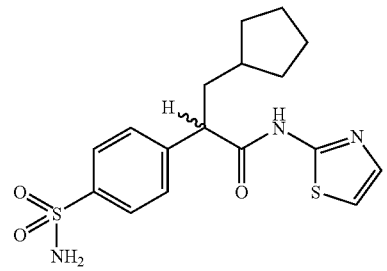

A solution of diisopropylamine (559 μL, 3.99 mmol) in dry tetrahydrofuran (1.2 mL) was cooled to −78° C. under nitrogen and then treated with a 2.5M solution of n-butyllithium in hexanes (1.6 mL, 3.99 mmol). The resulting reaction mixture was allowed to warm to 0° C. and then was treated with 3-cyclopentyl-2-(4-methanesulfonyl-phenyl)-N-thiazol-2-yl-propionamide (prepared as in Example 3A, 463.1 mg, 1.22 mmol) in small portions. The reaction mixture turned orange in color. The reaction mixture was then allowed to warm to 25° C. where it was stirred for 30 min. After 30 min at 25° C., the reaction mixture was cooled back down to 0° C. and then treated with a 1M solution of tributylborane in tetrahydrofuran (1.8 mL, 1.84 mmol). The resulting reaction mixture was stirred at 0° C. for 10 min then allowed to warm to 25° C. The reaction mixture was stirred at 25° C. for 30 min then heated under reflux for 20 h. The reaction mixture was cooled to 0° C. and then treated with water (3 mL) followed by sodium acetate (702.5 mg, 8.56 mmol) and then finally hydroxyamine-O-sulfonic acid (484.2 mg, 4.28 mmol). The resulting reaction mixture was stirred at 0° C. for 30 min then allowed to warm to 25° C. where it was stirred for 44 h. The reaction mixture was concentrated in vacuo to remove tetrahydrofuran. The resulting aqueous residue was diluted with ethyl acetate (150 mL). The organic layer was washed with a saturated aqueous sodium bicarbonate solution (1×100 mL) and a saturated aqueous sodium chloride solution (1×100 mL), dried over sodium sulfate, filtered, and concentrated in vacuo. Flash chromatography (Merck Silica gel 60, 70–230 mesh, 3/2 hexanes/ethyl acetate) afforded 3-cyclopentyl-2-(4-sulfamoyl-phenyl)-N-thiazol-2-yl-propionamide (191.8 mg, 72%) as a white solid: mp 179–181° C.; EI-HRMS m/e calcd for $C_{17}H_{21}N_3O_2S_2$ (M+) 379.1024, found 379.1029.

EXAMPLE 83

3-Cyclopentyl-2-(3,4-dichlorophenyl)-N-[1,3,4]thiadiazol-2-yl-propionamide

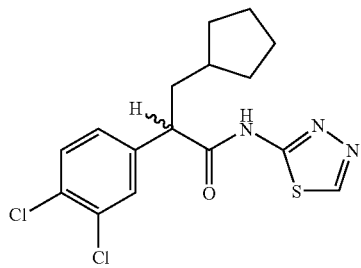

A solution of 3-cyclopentyl-2-(3,4-dichlorophenyl)-propionic acid (prepared as in Example 38A, 200.0 mg, 0.70 mmol), O-benzotriazol-1-yl-N,N,N',N'-tetramethyluronium hexafluorophosphate (316.9 mg, 0.84 mmol), N,N-diisopropylethylamine (365 mL, 2.09 mmol), and 2-amino-1,3,4-thiadiazole (140.8 mg, 1.39 mmol) in dry N,N-dimethylformamide (2 mL) was stirred at 25° C. under nitrogen for 20 h. The reaction mixture was concentrated in vacuo to remove N,N-dimethylformamide. The resulting residue was diluted with ethyl acetate (100 mL). The organic layer was washed sequentially with a saturated aqueous sodium bicarbonate solution (1×50 mL), a 10% aqueous hydrochloric acid solution (1×100 mL), and a saturated aqueous sodium chloride solution (1×100 mL). The organic layer was dried over sodium sulfate, filtered, and concentrated in vacuo. Flash chromatography (Merck Silica gel 60, 230–400 mesh, 2/1 hexanes/ethyl acetate) afforded 3-cyclopentyl-2-(3,4-dichlorophenyl)-N-[1,3,4]thiadiazol-2-yl-propionamide (197.3 mg, 77%) as a white foam: mp 90–91° C.; EI-HRMS m/e calcd for $C_{16}H_{17}Cl_2N_3OS$ (M+) 369.0469, found 369.0476.

EXAMPLE 84

2-(4-Cyano-phenyl)-3-cyclopentyl-N-thiazol-2-yl-propionamide

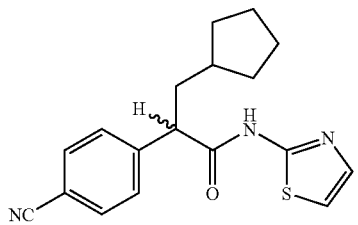

A solution of freshly prepared lithium diisopropylamide (23 mL of a 0.32M stock solution, 7.13 mmol) cooled to −78° C. was treated with (4-bromo-phenyl)-acetic acid methyl ester (1.48 g, 6.48 mmol) in tetrahydrofuran/1,3-dimethyl-3,4,5,6-tetrahydro-2(1H)-pyrimidinone (16.2 mL, 3:1). The resulting solution was stirred at −78° C. for 45 min. Iodomethylcyclopentane (1.49 g, 7.13 mmol) was then added in 1,3-dimethyl-3,4,5,6-tetrahydro-2(1H)-pyrimidinone (2 mL). The reaction mixture was stirred at −78° C. for 4 h. The reaction was then warmed to 25° C. and was stirred at 25° C. for 18 h. The reaction mixture was then quenched by the dropwise addition of a saturated aqueous ammonium chloride solution (10 mL). This mixture was poured into water (100 mL) and extracted with ethyl acetate (3×50 mL). The combined organic layers were washed with a saturated aqueous lithium chloride solution (1×50 mL), dried over sodium sulfate, filtered, and concentrated in vacuo. Flash chromatography (Merck Silica gel 60, 230–400 mesh, 95/5 hexanes/ethyl acetate) afforded 2-(4-bromo-phenyl)-3-cyclopentyl-propionic acid methyl ester (1.60 g, 79.3%) as a clear oil: EI-HRMS m/e calcd for $C_{15}H_{19}O_2Br$ (M+) 310.0568 found 310.0564.

A solution of 2-(4-bromo-phenyl)-3-cyclopentyl-propionic acid methyl ester (500 mg, 1.60 mmol) in N,N-dimethylformamide (4.01 mL) was treated with copper(I) cyanide (144 mg, 1.60 mmol). The mixture was heated at 170° C. for 1 h. At this time, the reaction was cooled to 25° C. and poured into aqueous ammonium hydroxide (5 mL). The solution was diluted with water (25 mL) and extracted with ethyl acetate (3×35 mL). The combined organic layers were dried over sodium sulfate, filtered, and concentrated in vacuo. Flash chromatography (Merck Silica gel 60, 230–400 mesh, 90/10 hexanes/ethyl acetate) afforded 2-(4-cyano-phenyl)-3-cyclopentyl-propionic acid methyl ester (65.6 g, 15.8%) as a clear oil: EI-HRMS m/e calcd for $C_{16}H_{19}NO_2$ (M+) 257.1415 found 257.1406.

A solution of 2-(4-cyano-phenyl)-3-cyclopentyl-propionic acid methyl ester (65.0 mg, 0.25 mmol) in tetrahydrofuran/water/methanol (2.5 mL, 3:1:1) was treated with a 1N aqueous lithium hydroxide solution (0.27 mL, 0.27 mmol). The reaction was stirred at 25° C. for 6 h. At this time, the reaction was acidified to pH=1 with a 1N aqueous hydrochloric acid solution and extracted with chloroform/methanol (9:1, 3×25 mL). The combined organic layers were dried over sodium sulfate, filtered, and concentrated in vacuo.

Flash chromatography (Merck Silica gel 60, 230–400 mesh, 80/20 hexanes/ethyl acetate) afforded 2-(4-cyano-phenyl)-3-cyclopentyl-propionic acid (36.0 mg, 58.6%) as a white solid: mp 126–128° C.; EI-HRMS m/e calcd for $C_{15}H_{17}NO_2$ ($M^+$) 243.1259 found 243.1268.

A solution of 2-(4-cyano-phenyl)-3-cyclopentyl-propionic acid (33.0 mg, 0.13 mmol) in methylene chloride (1.36 mL) was cooled to 0° C. and then treated with a 2.0M solution of oxalyl chloride in methylene chloride (0.07 mL, 0.14 mmol) and a few drops of N,N-dimethylformamide. The reaction mixture was stirred at 0° C. for 10 min and at 25° C. for 30 min. The reaction mixture was then treated with a solution of 2-aminothiazole (30.0 mg, 0.29 mmol) and N,N-diisopropylethylamine (0.05 mL, 0.32 mmol) in tetrahydrofuran (0.67 mL). This solution was stirred at 25° C. for 3 h. At this time, the reaction was concentrated in vacuo. Flash chromatography (Merck Silica gel 60, 230–400 mesh, 50/50 hexanes/ethyl acetate) afforded 2-(4-cyano-phenyl)-3-cyclopentyl-N-thiazol-2-yl-propionamide (44.1 mg, 100%) as a white solid: mp 64–66° C.; EI-HRMS m/e calcd for $C_{18}H_{19}N_3OS$ ($M^+$) 325.1248 found 325.1247.

In an analogous manner, there was obtained:
a) From 2-aminopyridine and 2-(4-cyano-phenyl)-3-cyclopentyl-propionic acid: 2-(4-Cyano-phenyl)-3-cyclopentyl-N-pyridin-2-yl-propionamide as a white solid: mp 61–63° C.; EI-HRMS m/e calcd for $C_{20}H_{21}N_3O$ ($M^+$) 319.1684, found 319.1697.
b) From 2-(4-cyano-phenyl)-3-cyclopentyl-propionic acid and 6-amino-nicotinic acid methyl ester: 6-[2-(4-Cyano-phenyl)-3-cyclopentyl-propionylamino]-nicotinic acid methyl ester as a white solid: mp 62–64° C.; EI-HRMS m/e calcd for $C_{22}H_{23}N_3O_3$ ($M^+$) 377.1739, found 377.1736.

EXAMPLE 85

3-Cyclopentyl-N-pyridin-2-yl-2-(4-trifluoromethyl-phenyl)-propionamide

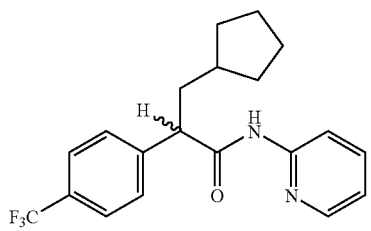

A solution of freshly prepared lithium diisopropylamide (23 mL of a 0.31M stock solution, 7.13 mmol) cooled to −78° C. was treated with (4-trifluoromethyl)phenylacetic acid (693 mg, 3.4 mmol) in tetrahydrofuran/hexamethylphosphoramide (8.5 mL, 3:1). The resulting solution was stirred at −78° C. for 30 min. Iodomethylcyclopentane (784 mg, 3.7 mmol) was then added in hexamethylphosphoramide (1 mL). The reaction mixture was stirred at −78° C. for 4 h. The reaction was then warmed to 25° C. and was stirred at 25° C. for 16 h. The reaction mixture was then quenched by the dropwise addition of saturated aqueous ammonium chloride solution (10 mL). The excess solvent was removed in vacuo. The residue was acidified to pH=1 with a 1N aqueous hydrochloric acid solution. The mixture was poured into water (150 mL) and extracted with ethyl acetate (3×100 mL). The organics were dried over sodium sulfate, filtered, and concentrated in vacuo. Flash chromatography (Merck Silica gel 60, 230–400 mesh, 95/5 hexanes/ethyl acetate) afforded 3-cyclopentyl-2-(4-trifluoromethyl-phenyl)-propionic acid (634.9 mg, 65%) as a white solid: mp 94–95° C.; FAB-HRMS m/e calcd for $C_{15}H_{17}F_3O_2$(M+Na)+309.1079, found 309.1072.

A solution of benzotriazol-1-yloxy-tris(dimethylamino) phosphonium hexafluorophosphate (170 mg, 0.38 mmol), 3-cyclopentyl-2-(4-trifluoromethyl-phenyl)-propionic acid (100 mg, 0.34 mmol), and 2-aminopyridine (36 mg, 0.38 mmol) in N,N-dimethylformamide (1.75 mL) was treated with N,N-diisopropylethylamine (0.12 mL, 0.73 mmol). The reaction mixture was stirred at 25° C. for 18 h. At this time, the reaction was poured into water (50 mL) and extracted with ethyl acetate (3×50 mL). The combined organic layers were washed with a 1N aqueous hydrochloric acid solution (1×50 mL), dried over sodium sulfate, filtered, and concentrated in vacuo. Flash chromatography (Merck Silica gel 60, 230–400 mesh, 90/10 hexanes/ethyl acetate) afforded 3-cyclopentyl-N-pyridin-2-yl-2-(4-trifluoromethyl-phenyl)-propionamide (127 mg, 53.3%) as a white gum: EI-HRMS m/e calcd for $C_{20}H_{21}F_3N_2O$ ($M^+$) 362.1605, found 362.1592.

In an analogous manner, there was obtained:
a) From 6-amino-nicotinic acid methyl ester and 3-cyclopentyl-2-(4-trifluoromethyl-phenyl)-propionic: 6-[3-Cyclopentyl-2-(4-trifluoromethyl-phenyl)-propionylamino]-nicotinic acid methyl ester as a white gum: EI-HRMS m/e calcd for $C_{22}H_{23}F_3N_2O_3$ ($M^+$) 420.1660, found 420.1661.

EXAMPLE 86

2-[4-(Butane-1-sulfonyl)-phenyl]-3-cyclopentyl-N-thiazol-2-yl-propionamide

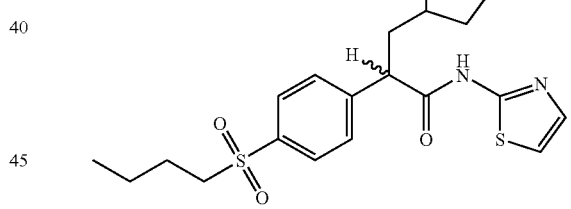

A solution of freshly prepared lithium diisopropylamide (430.55 mL of a 0.3M stock solution, 129.16 mmol) cooled to −78° C. was treated with (4-nitro-phenyl)-acetic acid ethyl ester (prepared as in Example 22A, 26.32 g, 125.83 mmol) in tetrahydrofuran/hexamethylphosphoramide (312.5 mL, 3:1). The resulting solution was stirred at −78° C. for 45 min. Iodomethylcyclopentane (27.75 g, 132.1 mmol) was then added in hexamethylphosphoramide (27.75 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (250 mL). This mixture was concentrated in vacuo. The residue was diluted with water (250 mL) and extracted with ethyl acetate (3×300 mL). The combined organic layers were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate)

afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ (M+) 291.1470, found 291.1470.

A solution of 3-cyclopentyl-2-(4-nitro-phenyl)-propionic acid ethyl ester (7.37 g, 25.3 mmol) in ethyl acetate (316 mL) was treated with 10% palladium on activated carbon. The reaction mixture was stirred under hydrogen gas at 60 psi at 25° C. for 18 h. The catalyst was then filtered off through a pad of celite, which was washed well with ethyl acetate. The resulting filtrate was concentrated in vacuo. Flash chromatography (Merck Silica gel 60, 230–400 mesh, 50/50 hexanes/ethyl acetate) afforded 2-(4-amino-phenyl)-3-cyclopentyl-propionic acid ethyl ester (3.52 mg, 53.3%) as a yellow oil: EI-HRMS m/e calcd for $C_{16}H_{23}NO_2$ (M+) 261.1729 found 261.1727.

A mixture of concentrated hydrochloric acid (0.38 mL) and ice (380 mg) cooled to 0° C. was treated with 2-(4-amino-phenyl)-3-cyclopentyl-propionic acid ethyl ester (497 mg, 1.90 mmol). After 5 min, a solution of sodium nitrite (139 mg, 2.01 mmol) in water (0.31 mL) was added to the reaction mixture. The resulting solution was stirred at 0° C. for 5 min. At this time, the solution was added to a solution of n-butyl mercaptan (0.23 mL, 2.20 mmol) in water (0.41 mL) warmed to 45° C. The reaction was stirred at 45° C. for 3 h. At this time, the reaction was diluted with water (50 mL) and extracted with chloroform (3×50 mL). The organics were dried over sodium sulfate, filtered, and concentrated in vacuo. The crude brown oil (588 mg) in methylene chloride (8.8 mL) was cooled to 0° C. and treated with 3-chloroperoxybenzoic acid (80–85% grade, 1.5 g, 8.78 mmol). The reaction mixture was stirred at 25° C. for 18 h. At this time, the reaction was diluted with water (75 mL) and extracted with chloroform (2×30 mL). The combined organic layers were dried over sodium sulfate, filtered, and concentrated in vacuo. Flash chromatography (Merck Silica gel 60, 230–400 mesh, 80/20 hexanes/ethyl acetate) afforded 2-[4-(butane-1-sulfonyl)-phenyl]-3-cyclopentyl-propionic acid ethyl ester (144.3 mg, 20.7%) as a yellow oil: EI-HRMS m/e calcd for $C_{20}H_{30}O_4S$ (M+) 366.1865 found 366.1858.

A solution of 2-[4-(butane-1-sulfonyl)-phenyl]-3-cyclopentyl-propionic acid ethyl ester (140 mg, 0.38 mmol in tetrahydrofuran/water/methanol (0.95 mL, 3:1:1) was treated with a 1N aqueous lithium hydroxide solution (0.76 mL, 0.76 mmol). The reaction was stirred at 25° C. for 8 h. At this time, the reaction was acidified to pH=1 with a 1N aqueous hydrochloric acid solution and extracted with chloroform (3×50 mL). The combined organic layers were dried over sodium sulfate, filtered, and concentrated in vacuo. Flash chromatography (Merck Silica gel 60, 230–400 mesh, 90/10 chloroform/methanol) afforded 2-[4-(butane-1-sulfonyl)-phenyl]-3-cyclopentyl-propionic acid (88.3 mg, 68.4%) as a clear oil: FAB-HRMS m/e calcd for $C_{18}H_{26}O_4S$ (M+H)+ 339.1631 found 339.1638.

A solution of triphenylphosphine (99 mg, 0.37 mmol) and N-bromosuccinimide (76 mg, 0.42 mmol) in methylene chloride (1.26 mL) cooled to 0° C. was treated with 2-[4-(butane-1-sulfonyl)-phenyl]-3-cyclopentyl-propionic acid (85 mg, 0.25 mmol) in methylene chloride. The reaction mixture was stirred at 25° C. for 45 min. At this time, the reaction was treated with 2-aminothiazole (33 mg, 0.32 mmol) and pyridine (0.03 mL, 0.37 mmol). The reaction was stirred at 25° C. for 18 h. The reaction mixture was then concentrated in vacuo to remove methylene chloride. At this time, the reaction was diluted with water (50 mL) and extracted with chloroform (3×50 mL). The combined organic layers were dried over sodium sulfate, filtered, and concentrated in vacuo. Flash chromatography (Merck Silica gel 60, 70–230 mesh, 50/50 hexanes/ethyl acetate) afforded 2-[4-(butane-1-sulfonyl)-phenyl]-3-cyclopentyl-N-thiazol-2-yl-propionamide (69.3 mg, 65.6%) as an off-white solid: mp 163–165° C.; EI-HRMS m/e calcd for $C_{21}H_{28}N_2O_3S_2$ (M+) 420.1541 found 420.1535.

In an analogous manner, there was obtained:
a) From 2-aminothiazole and 3-cyclopentyl-2-[4-(propane-1-sulfonyl)-phenyl]-propionic acid: 3-Cyclopentyl-2-[4-(propane-1-sulfonyl)-phenyl]-N-thiazol-2-yl-propionamide as a yellow oil: EI-HRMS m/e calcd for $C_{20}H_{26}N_2O_3S_2$ (M+) 406.1385 found 406.1389.

EXAMPLE 87

3-Cyclopentyl-2-(4-fluoro-3-trifluoromethyl-phenyl)-N-thiazol-2-yl-propionamide

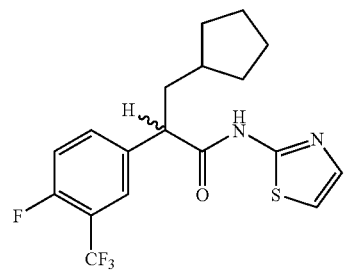

A solution of freshly prepared lithium diisopropylamide (35.32 mL of a 0.31M stock solution, 10.95 mmol) cooled to −78° C. was treated with (4-fluoro-3-trifluoromethyl-phenyl)-acetic acid (1.11 g, 5.0 mmol) in tetrahydrofuran/1,3-dimethyl-3,4,5,6-tetrahydro-2(1H)-pyrimidinone (12.42 mL, 3:1). The resulting solution was then stirred at −78° C. for 1 h. Iodomethylcyclopentane (1.16 g, 5.52 mmol) was then added in 1,3-dimethyl-3,4,5,6-tetrahydro-2(1H)-pyrimidinone (1.2 mL). The reaction mixture was stirred at −78° C. for 4 h. The reaction was then warmed to 25° C. and was stirred at 25° C. for 24 h. This solution was then quenched by the slow addition of the reaction mixture to a 2N aqueous hydrochloric acid solution (50 mL). The product was extracted into ethyl acetate (1×300 mL) and diethyl ether (1×50 mL). The combined organic layers were dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-fluoro-3-trifluoromethyl-phenyl)-propionic acid (1.28 g, 84.3%) as a white solid: mp 65–68° C.; EI-HRMS m/e calcd for $C_{15}H_{16}F_4O_2$ (M+) 305.1165, found 305.1174.

A solution of 3-cyclopentyl-2-(4-fluoro-3-trifluoromethyl-phenyl)-propionic acid (304 mg, 1.0 mmol) in methylene chloride (10 mL) was cooled to 0° C. and then treated with a 2.0M solution of oxalyl chloride in methylene chloride (0.6 mL, 1.2 mmol) and a few drops of N,N-dimethylformamide. The reaction mixture was stirred at 0° C. for 15 min and at 25° C. for 24 h. The reaction mixture was then treated with 2-amino-thiazole (175 mg, 1.75 mmol) and N,N-diisopropylethylamine (0.4 mL, 2.41 mmol). This solution was stirred at 25° C. for 48 h. At this time, the reaction was concentrated in vacuo. High pressure liquid chromatography (Chromegasphere SI-60, 10 µM, 60 Å, 25 cm×23 cm ID, 60/40 heptane/ethyl acetate) afforded 3-cyclopentyl-2-(4-fluoro-3-trifluoromethyl-phenyl)-N-thiazol-2-yl-propionamide (326 mg, 84.5%) as a light yellow solid: mp 125–127° C.; EI-HRMS m/e calcd for $C_{18}H_{18}F_4N_2OS$ (M+) 386.1076, found 386.1086.

In an analogous manner, there was obtained:

a) From ethyl 2-amino-4-thiazole glyoxylate and 3-cyclopentyl-2-(4-fluoro-3-trifluoromethyl-phenyl)-propionic acid: {2-[3-Cyclopentyl-2-(4-fluoro-3-trifluoromethyl-phenyl)-propionylamino]-thiazol-4-yl}-oxo-acetic acid ethyl ester as a light yellow solid: mp 155–158° C.; FAB-HRMS m/e calcd for $C_{22}H_{22}F_4N_2O_4S$ (M+H)+ 487.1314, found 487.1319.

b) From 5-methyl-2-aminopyridine and 3-cyclopentyl-2-(4-fluoro-3-trifluoromethyl-phenyl)-propionic acid: 3-Cyclopentyl-2-(4-fluoro-3-trifluoromethyl-phenyl)-N-(5-methyl-pyridin-2-yl)-propionamide as a white solid: mp 132–133° C.; EI-HRMS m/e calcd for $C_{21}H_{22}F_4N_2O$ (M+) 392.1668, found 392.1669.

c) From 2-aminopyridine and 3-cyclopentyl-2-(4-fluoro-3-trifluoromethyl-phenyl)-propionic acid: 3-Cyclopentyl-2-(4-fluoro-3-trifluoromethyl-phenyl)-N-pyridin-2-yl-propionamide as a light yellow oil: EI-HRMS m/e calcd for $C_{20}H_{20}F_4N_2O$ (M+) 380.1511, found 380.1521.

EXAMPLE 88

3-Cyclopentyl-N-thiazol-2-yl-2-(3-trifluoromethyl-phenyl)-propionamide

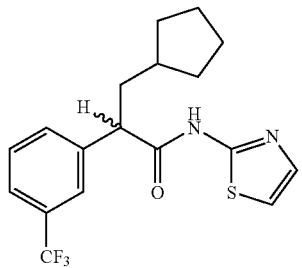

A solution of freshly prepared lithium diisopropylamide (35.32 mL of a 0.31M stock solution, 10.9 mmol) cooled to −78° C. was treated with (3-trifluoromethyl-phenyl)-acetic acid (1.02 g, 5.0 mmol) in tetrahydrofuran/1,3-dimethyl-3,4,5,6-tetrahydro-2(1H)-pyrimidinone (12.4 mL, 3:1). The resulting solution was stirred at −78° C. for 3 h. Iodomethylcyclopentane (1.16 g, 5.52 mmol) was then added in 1,3-dimethyl-3,4,5,6-tetrahydro-2(1H)-pyrimidinone (1.16 mL). The reaction mixture was stirred at −78° C. for 4 h. The reaction was then warmed to 25° C. and was stirred at 25° C. for 48 h. This solution was then quenched by the slow addition of the reaction mixture to a 2N aqueous hydrochloric acid solution (50 mL). The product was extracted into ethyl acetate (3×100 mL) and diethyl ether (1×50 mL). The combined organic layers were washed with a saturated aqueous lithium chloride solution (2×100 mL) and a saturated aqueous sodium chloride solution (1×150 mL), dried over magnesium sulfate and sodium sulfate, filtered, and concentrated in vacuo. Flash chromatography (Merck Silica gel 60, 230–400 mesh, 50/50 hexanes/ethyl acetate with acetic acid) afforded 3-cyclopentyl-2-(3-trifluoromethyl-phenyl)-propionic acid (1.16 g, 80.5%) as an off-white solid: mp 64–65° C.; EI-HRMS m/e calcd for $C_{15}H_{17}F_3O_2$ (M+Na+) 309.1079, found 309.1084.

A solution of 3-cyclopentyl-2-(3-trifluoromethyl-phenyl)-propionic acid (286 mg, 1.0 mmol) in methylene chloride (10 mL) was cooled to 0° C. and then treated with a 2.0M solution of oxalyl chloride in methylene chloride (0.6 mL, 1.2 mmol) and a few drops of N,N-dimethylformamide. The reaction mixture was stirred at 0° C. for 15 min and at 25° C. for 1.25 h. The reaction mixture was then treated with a solution of 2-aminothiazole (175 mg, 1.75 mmol) and N,N-diisopropylethylamine (0.42 mL, 2.41 mmol) in tetrahydrofuran (10 mL). This solution was stirred at 25° C. for 24 h. At this time, the reaction was concentrated in vacuo. High pressure liquid chromatography (Chromegasphere SI-60, 10 μM, 60 Å, 25 cm×23 cm ID, 60/40 heptane/ethyl acetate) afforded 3-cyclopentyl-N-thiazol-2-yl-2-(3-trifluoromethyl-phenyl)-propionamide (299.2 mg, 81.4%) as a light yellow solid: mp 134–136° C.; EI-HRMS m/e calcd for $C_{18}H_{19}F_3N_2OS$ (M+) 368.1170, found 368.1165.

EXAMPLE 89

3-Cyclopentyl-2-(4-methanesulfonyl-3-trifluoromethyl-phenyl)-N-thiazol-2-yl-propionamide

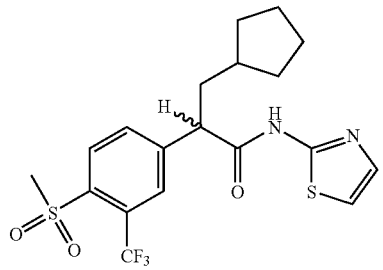

A solution of 3-cyclopentyl-2-(4-fluoro-3-trifluoromethyl-phenyl)-propionic acid (prepared as in Example 87A, 7.77 g, 25.3 mmol) in methanol (50 mL) was treated slowly with concentrated sulfuric acid (0.01 mL). The resulting reaction mixture was heated under reflux for 24 h. The reaction mixture was allowed to cool to 25° C. and then concentrated in vacuo. The residue was dissolved in ethyl acetate (75 mL). The organic layer was washed with a saturated aqueous sodium bicarbonate solution (1×50 mL), water (1×50 mL), and a saturated aqueous sodium chloride solution (4×50 mL). The organic layer was then dried over magnesium sulfate and sodium sulfate, filtered, and concentrated in vacuo to afford 3-cyclopentyl-2-(4-fluoro-3-trifluoromethyl-phenyl)-propionic acid methyl ester (8.48 g, 87.5%) as yellow oil: EI-HRMS m/e calcd for $C_{16}H_{18}F_4O_2$ (M+) 318.1243, found 318.1240.

A solution of 3-cyclopentyl-2-(4-fluoro-3-trifluoromethyl-phenyl)-propionic acid methyl ester (7.0 g, 21.9 mmol) in N,N-dimethylformamide (50 mL) was treated with sodium methanethiolate (2.61 g, 33.0 mmol). The reaction mixture was then heated at 100–110° C. for 24 h. At this time, the reaction was poured onto a mixture of ice and a 2N aqueous hydrochloric acid solution (100 mL). This mixture was extracted into ethyl acetate (3×75 mL) and diethyl ether (1×50 mL). The combined organic layers were then washed with water (1×75 mL) and a saturated aqueous sodium chloride solution (3×100 mL). The organic layer was then dried over magnesium sulfate and sodium sulfate, filtered, and concentrated in vacuo. Flash chromatography (Merck Silica gel 60, 230–400 mesh, 85/15 hexanes/ethyl acetate) afforded 3-cyclopentyl-2-(4-methylsulfanyl-3-trifluoromethyl-phenyl)-propionic acid methyl ester (2.48 g, 35.5%) as a pale yellow oil: EI-HRMS m/e calcd for $C_{17}H_{21}F_3O_2S$ ($M^+$) 346.1214, found 346.1212.

A solution of 3-cyclopentyl-2-(4-methylsulfanyl-3-trifluoromethyl-phenyl)-propionic acid methyl ester (2.36 g, 6.81 mmol) in methylene chloride (75 mL) at 25° C. was treated with 3-chloroperoxybenzoic acid (80–85% grade, 9.69 g, 40.1 mmol). The reaction mixture was stirred at 25° C. for 16 h. At this time, the reaction was diluted with methylene chloride (75 mL). The solution was washed sequentially with a saturated aqueous sodium bisulfite solution (2×50 mL), water (1×50 mL), a saturated aqueous sodium chloride solution (3×75 mL), a saturated aqueous sodium bicarbonate solution (1×75 mL), and a saturated aqueous sodium chloride solution (3×75 mL). The organic layer was then dried over magnesium sulfate and sodium sulfate, filtered, and concentrated in vacuo to afford 3-cyclopentyl-2-(4-methanesulfonyl-3-trifluoromethyl-phenyl)-propionic acid methyl ester (2.88 g) as a clear oil: EI-HRMS m/e calcd for $C_{17}H_{21}F_3O_4S$ ($M^+$) 378.1112 found 378.1116.

A solution of 3-cyclopentyl-2-(4-methanesulfonyl-3-trifluoromethyl-phenyl)-propionic acid methyl ester (395 mg, 1.04 mmol) and 2-aminothiazole (209 mg, 1.38 mmol) in a solution of magnesium methoxide in methanol (7.4 wt %, 2.09 mL, 1.38 mmol) was heated at 110° C. for 24 h. The reaction mixture was then concentrated in vacuo. Flash chromatography (Merck Silica gel 60, 230–400 mesh, 50/50 hexanes/ethyl acetate) afforded the 3-cyclopentyl-2-(4-methanesulfonyl-3-trifluoromethyl-phenyl)-N-thiazol-2-yl-propionamide (256.7 mg, 55.1%) as a white solid: mp 95–100° C.; EI-HRMS m/e calcd for $C_{19}H_{21}F_3N_2O_3S_2$ ($M^+$) 446.0946, found 446.0944.

In an analogous manner, there was obtained:
a) From (2-amino-thiazol-4-yl)-acetic acid methyl ester and 3-cyclopentyl-2-(4-methanesulfonyl-3-trifluoromethyl-phenyl)-propionic acid: {2-[3-Cyclopentyl-2-(4-methanesulfonyl-3-trifluoromethyl-phenyl)-propionylamino]-thiazol-4-yl}-acetic acid methyl ester as a white solid: mp 81–86° C.; FAB-HRMS m/e calcd for $C_{22}H_{25}F_3N_2O_5S_2$ $(M+H)^+$ 518.1157, found 518.1161.
b) From 2-amino-thiazole-4-carboxylic acid methyl ester and 3-cyclopentyl-2-(4-methanesulfonyl-3-trifluoromethyl-phenyl)-propionic acid: 2-[3-Cyclopentyl-2-(4-methanesulfonyl-3-trifluoromethyl-phenyl)-propionylamino]-thiazole-4-carboxylic acid methyl ester as a white solid: mp 117–121° C.; FAB-HRMS m/e calcd for $C_{21}H_{23}F_3N_2O_5S_2$ $(M+H)^+$ 504.1000, found 504.1000.

EXAMPLE 90

3-Cyclopentyl-2-(4-methanesulfonyl-3-trifluoromethyl-phenyl)-N-pyridin-2-yl-propionamide

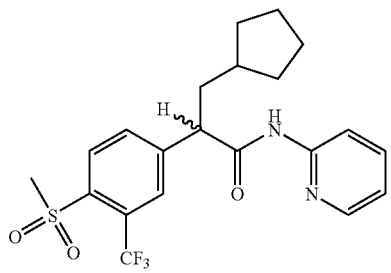

A solution of freshly prepared lithium diisopropylamide (141.28 mL of a 0.31M stock solution, 43.8 mmol) cooled to −78° C. was treated with (4-fluoro-3-trifluoromethyl-phenyl)-acetic acid (4.44 g, 20.0 mmol) in tetrahydrofuran/ 1,3-dimethyl-3,4,5,6-tetrahydro-2(1H)-pyrimidinone (49.68 mL, 3:1). The resulting solution was then stirred at −78° C. for 1 h. At this time, the reaction was treated with a solution of iodomethylcyclopentane (4.64 g, 22.09 mmol) in 1,3-dimethyl-3,4,5,6-tetrahydro-2(1H)-pyrimidinone (4.6 mL). The reaction mixture was stirred at −78° C. for 4 h. The reaction was then warmed to 25° C. and was stirred at 25° C. for 48 h. This solution was then quenched by the slow addition of the reaction mixture to a 2N aqueous hydrochloric acid solution. The product was extracted into ethyl acetate (3×400 mL) and diethyl ether (1×200 mL). The combined organic layers were dried over magnesium sulfate and sodium sulfate, filtered, and concentrated in vacuo. Flash chromatography (Merck Silica gel 60, 230–400 mesh, 50/50 hexanes/ethyl acetate with acetic acid) afforded 3-cyclopentyl-2-(4-fluoro-3-trifluoromethyl-phenyl)-propionic acid (3.37 g, 55.4%) as a white solid: mp 66–68° C.; EI-HRMS m/e calcd for $C_{15}H_{16}F_4O_2$ ($M^+$) 305.1165, found 305.1174.

A solution of 3-cyclopentyl-2-(4-fluoro-3-trifluoromethyl-phenyl)-propionic acid (1.52 g, 5.0 mmol) in N,N-dimethylformamide (10 mL) was treated with sodium methanethiolate (0.59 g, 7.5 mmol). The reaction mixture was then heated to 100–110° C. for 14 h. At this time, the reaction was poured onto a mixture of ice and a 2N aqueous hydrochloric acid solution (25 mL). This mixture was extracted into ethyl acetate (3×35 mL) and diethyl ether (1×25 mL). The combined organic layers were then washed with water (1×50 mL) and a saturated aqueous sodium chloride solution (3×75 mL). The organic layer was then dried over magnesium sulfate and sodium sulfate, filtered, and concentrated in vacuo. Flash chromatography (Merck Silica gel 60, 230–400 mesh, 80/20 hexanes/ethyl acetate w/acetic acid) afforded 3-cyclopentyl-2-(4-methylsulfanyl-3-trifluoromethyl-phenyl)-propionic acid (1.36 g, 83.4%) as a pale yellow oil: EI-HRMS m/e calcd for $C_{16}H_{19}F_3O_2S$ ($M^+$) 332.1058, found 332.1057.

A solution of 3-cyclopentyl-2-(4-methylsulfanyl-3-trifluoromethyl-phenyl)-propionic acid (1.29 g, 3.89 mmol) in ethanol (25 mL) was treated slowly with concentrated sulfuric acid (0.01 mL). The resulting reaction mixture was heated under reflux for 48 h. The reaction mixture was allowed to cool to 25° C. and then concentrated in vacuo. The residue was dissolved in ethyl acetate (35 mL). The organic layer was washed with a saturated aqueous sodium bicarbonate solution (1×15 mL), water (1×15 mL), and a saturated aqueous sodium chloride solution (3×20 mL). The organic layer was then dried over magnesium sulfate and sodium sulfate, filtered, and concentrated in vacuo to afford 3-cyclopentyl-2-(4-methylsulfanyl-3-trifluoromethyl-phenyl)-propionic acid ethyl ester (1.39 g, 94.8%) as yellow oil: EI-HRMS m/e calcd for $C_{18}H_{23}F_3O_2S$ ($M^+$) 360.1370, found 360.1370.

A solution of 3-cyclopentyl-2-(4-methylsulfanyl-3-trifluoromethyl-phenyl)-propionic acid ethyl ester (1.32 g, 3.69 mmol) in methylene chloride (50 mL) at 25° C. was treated with 3-chloroperoxybenzoic acid (80–85% grade, 4.8 g, 19.8 mmol). The reaction mixture was stirred at 25° C. for 4 d. At this time, the reaction was diluted with methylene chloride (25 mL). This solution was washed sequentially with a saturated aqueous sodium bisulfite solution (1×50 mL), water (1×50 mL), a saturated aqueous sodium bicarbonate solution (1×50 mL), water (1×50 mL), and a saturated aqueous sodium chloride solution (3×50 mL). The organic layer was dried over magnesium sulfate and sodium sulfate, filtered, and concentrated in vacuo. Flash chromatography (Merck Silica gel 60, 230–400 mesh, 70/30 hexanes/ethyl acetate with acetic acid) afforded 3-cyclopentyl-2-(4-methanesulfonyl-3-trifluoromethyl-phenyl)-propionic acid ethyl ester (1.28 g, 89.0%) as a clear oil: EI-HRMS m/e calcd for $C_{18}H_{23}F_3O_4S$ (M+) 392.1269 found 392.1268.

A solution of 3-cyclopentyl-2-(4-methanesulfonyl-3-trifluoromethyl-phenyl)-propionic acid ethyl ester (707 mg, 1.80 mmol in tetrahydrofuran/water (24 mL, 3:1) was treated with lithium hydroxide (166 mg, 3.97 mmol). The reaction was stirred at 25° C. for 24 h. At this time, the reaction concentrated in vacuo. The residue was diluted with water (25 mL) and extracted with diethyl ether (1×15 mL). The aqueous layer was acidified to pH=1 with a 2N aqueous hydrochloric acid solution, and extracted with chloroform (3×25 mL). The combined organic layers were washed with water (1×25 mL) and a saturated aqueous sodium chloride solution (3×25 mL), dried over magnesium sulfate, filtered, and concentrated in vacuo to afford 3-cyclopentyl-2-(4-methanesulfonyl-3-trifluoromethyl-phenyl)-propionic acid (426.7 mg, 65%) as a white solid: mp 122–123° C.; EI-HRMS m/e calcd for $C_{16}H_{19}F_3O_4S$ (M+) 364.0956 found 364.0956.

A solution of 3-cyclopentyl-2-(4-methanesulfonyl-3-trifluoromethyl-phenyl)-propionic acid (73 mg, 0.2 mmol) and triphenylphosphine (79 mg, 0.3 mmol) in methylene chloride (5.0 mL) was cooled to 0° C. and then treated with N-bromosuccinimide (60.5 mg, 0.34 mmol). After the complete addition of N-bromosuccinimide, the reaction mixture was allowed to warm to 25° C. over 30 min. The reaction mixture was then treated with 2-aminopyridine (28.2 mg, 0.3 mmol) and pyridine (1 drop). The resulting reaction mixture was stirred at 25° C. for 48 h. The reaction mixture was then diluted with methylene chloride (50 mL). The organic layer was washed with water (1×50 mL) and a saturated aqueous sodium chloride solution (2×25 mL), dried over magnesium sulfate and sodium sulfate, filtered, and concentrated in vacuo. High pressure liquid chromatography (Chromegasphere SI-60, 10 µM, 60 Å, 25 cm×23 cm ID, 50/50 heptane/ethyl acetate) afforded 3-cyclopentyl-2-(4-methanesulfonyl-3-trifluoromethyl-phenyl)-N-pyridin-2-yl-propionamide (54.2 mg, 61.5%) as a white solid: mp 86–89° C.; EI-HRMS m/e calcd for $C_{21}H_{23}F_3N_2O_3S$ (M+) 440.1383, found 440.1381.

EXAMPLE 91

3-Cyclopentyl-2-(4-methylsulfanyl-3-trifluoromethyl-phenyl)-N-thiazol-2-yl-propionamide

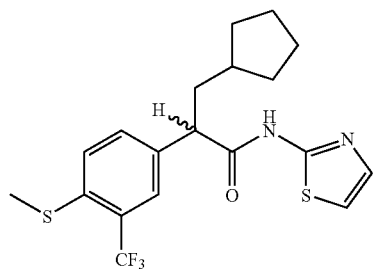

A solution of 3-cyclopentyl-2-(4-fluoro-3-trifluoromethyl-phenyl)-propionic acid (prepared as in Example 87A, 1.52 g, 5.0 mmol) in N,N-dimethylformamide (10 mL) was treated with sodium methanethiolate (593 mg, 7.5 mmol). The reaction mixture was then heated to 100–110° C. for 14 h. At this time, the reaction was cooled to 25° C. and poured onto a 1N aqueous hydrochloric acid solution (25 mL) and extracted into ethyl acetate (3×25 mL) and diethyl ether (1×25 mL). The combined organic layers were then washed with water (1×50 mL) and a saturated aqueous sodium chloride solution (3×75 mL), dried over magnesium sulfate and sodium sulfate, filtered, and concentrated in vacuo. Flash chromatography (Merck Silica gel 60, 230–400 mesh, 80/20 hexanes/ethyl acetate) afforded 3-cyclopentyl-2-(4-methylsulfanyl-3-trifluoromethyl-phenyl)-propionic acid (1.37 g, 82.4%) as a pale yellow oil: EI-HRMS m/e calcd for $C_{16}H_{19}F_3O_2S$ (M+) 332.1058, found 332.1057.

A solution of benzotriazol-1-yloxy-tris(dimethylamino) phosphonium hexafluorophosphate (188 mg, 0.42 mmol) and 3-cyclopentyl-2-(4-methylsulfanyl-3-trifluoromethyl-phenyl)-propionic acid (94 mg, 0.28 mmol) in N,N-dimethylformamide (5 mL) was treated with N,N-diisopropylethylamine (150 mL, 0.85 mmol) and 2-aminothiazole (42.5 mg, 0.42 mmol). The mixture was stirred at 25° C. for 48 h. At this time, the reaction mixture was poured into cold water (25 mL) containing a 1N aqueous hydrochloric acid solution (50 mL) and extracted into ethyl acetate (2×75 mL) and diethyl ether (1×25 mL). The combined organic layers were then washed with water (2×75 mL) and a saturated aqueous sodium chloride solution (3×75 mL), dried over magnesium sulfate and sodium sulfate, filtered, and concentrated in vacuo. Flash chromatography (Merck Silica gel 60, 230–400 mesh, 50/50 hexanes/ethyl acetate) afforded 3-cyclopentyl-2-(4-methylsulfanyl-3-trifluoromethyl-phenyl)-N-thiazol-2-yl-propionamide (50.5 mg, 43.1%) as a clear oil: FAB-HRMS m/e calcd for $C_{19}H_{21}F_3N_2OS_2$ (M+H)+ 415.1125, found 415.1123.

EXAMPLE 92

2-(3-Chloro-4-methanesulfonyl-phenyl)-3-cyclopentyl-N-pyridin-2-yl-propionamide

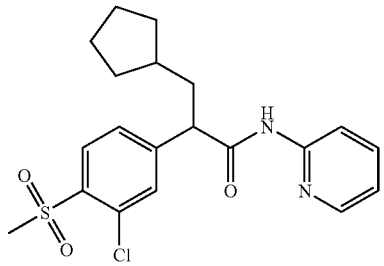

A solution of aluminum chloride (34.8 g, 261.4 mmol) in chloroform (120 mL) under argon was cooled to 0° C. and then treated dropwise with a solution of ethyl oxalyl chloride (18.7 mL, 167.5 mmol) in chloroform (120 mL). The reaction mixture was stirred at 0° C. for 30 min and then treated dropwise with a solution of 2-chlorothioanisole (25.0 g, 156.5 mmol) in chloroform (120 mL). The resulting reaction mixture turned red in color. The reaction mixture was allowed to warm to 25° C. where it was stirred for an additional 3.5 h. The reaction mixture was then slowly quenched with water (500 mL), and upon addition of the water, the reaction mixture turned yellow in color. The resulting solution was then extracted with chloroform (3×50 mL). The combined organic layers were dried over sodium sulfate, filtered, and concentrated in vacuo. Flash chromatography (Merck Silica gel 60, 230–400 mesh, 80/20 hexanes/ethyl acetate) afforded (3-chloro-4-methylsulfanyl-phenyl)-oxo-acetic acid ethyl ester (31.37 g, 77%) as a yellow oil.

A solution of iodomethylcyclopentane (129.38 g, 0.616 mol) and triphenylphosphine (161.54 g, 0.616 mol) in acetonitrile (308 mL) was heated under reflux for 9 d. The reaction mixture was allowed to cool to 25° C. and then concentrated in vacuo to provide a solid. The solid was triturated with diethyl ether and then filtered. The solid was washed well with diethyl ether until the washings showed the absence of iodomethylcyclopentane and triphenylphosphine by thin layer chromatography. The resulting solid was allowed to air dry to afford cyclopentylmethyl triphenylphosphonium iodide (266.92 g, 92%) as a light yellow solid: mp 195–198° C.; FAB-HRMS m/e calcd for $C_{24}H_{26}P$ $(M+H)^+$ 345.1772, found 345.1784.

A suspension of cyclopentylmethyl triphenylphosphine iodide (725 mg, 1.53 mmol) in tetrahydrofuran (10 mL) was cooled to 0° C. and then treated with a 1.0M solution of sodium bis(trimethylsilyl)amide in tetrahydrofuran (2.14 mL, 2.14 mmol). The resulting red reaction mixture was stirred at 0° C. for 45 minutes and then slowly treated with a solution of (3-chloro-4-methylsulfanyl-phenyl)-oxo-acetic acid ethyl ester (355 mg, 1.37 mmol) in tetrahydrofuran (5 mL). The reaction mixture was warmed to 25° C. where it was stirred for 20 h. The reaction mixture was then diluted with water (50 mL) and extracted with diethyl ether (3×25 mL). The combined organic layers were dried over sodium sulfate, filtered, and concentrated in vacuo. Biotage chromatography (Flash 12M, Silica, 80/20 hexanes/ethyl acetate) afforded 2-(3-chloro-4-methylsulfanyl-phenyl)-3-cyclopentyl-acrylic acid ethyl ester (267 mg, 60%) as a yellow oil consisting of a 2:1 mixture of (E):(Z) isomers. The isomeric mixture was used without further separation and characterization.

A solution of the isomeric mixture of 2-(3-chloro-4-methylsulfanyl-phenyl)-3-cyclopentyl-acrylic acid ethyl ester (100 mg, 0.31 mmol) in methylene chloride (5 mL) was cooled to 0° C. and then treated with 3-chloroperoxybenzoic acid (80% grade, 157 mg, 0.729 mmol). The reaction mixture was stirred at 0° C. for 3.5 h and then diluted with methylene chloride (25 mL). The organic phase was washed with a saturated aqueous sodium carbonate solution (2×10 mL) and a saturated aqueous sodium chloride solution (2×10 mL). The organic layer was dried over sodium sulfate, filtered, and concentrated in vacuo. Biotage chromatography (Flash 12M, Silica, 80/20 hexanes/ethyl acetate) afforded 2-(3-chloro-4-methanesulfonyl-phenyl)-3-cyclopentyl-acrylic acid ethyl ester (95 mg, 86%) as a colorless oil consisting of a 2:1 mixture of (E):(Z) isomers. The isomeric mixture was used without further separation and characterization.

A solution of the isomeric mixture of 2-(3-chloro-4-methanesulfonyl-phenyl)-3-cyclopentyl-acrylic acid ethyl ester (1.04 g, 2.91 mmol) and nickel chloride hexahydrate (69 mg, 0.29 mmol) in methanol (25 mL) was slowly treated with sodium borohydride (221 mg, 5.83 mmol) in small portions. If necessary, an ice bath was used to keep the temperature at 20° C. The initial green solution turned black in color, and a fine precipitate formed after addition of the sodium borohydride. The reaction mixture was then stirred at 25° C. for 1.5 h. The reaction mixture was then filtered through celite and washed with methanol. The filtrate and washings were combined and concentrated in vacuo to reduce the volume. The residual solution was then diluted with water (15 mL) and extracted with ethyl acetate (3×15 mL). The combined organic layers were dried over sodium sulfate, filtered, and concentrated in vacuo. Flash chromatography (Merck Silica gel 60, 230–400 mesh, 75/25 hexanes/ethyl acetate) afforded a mixture of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (937 mg, transesterification occurred under the reaction conditions) as a clear colorless oil. This mixture was used without further separation and characterization.

The mixture of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (937 mg) was dissolved in ethanol (30 mL). This solution was then treated with a solution of potassium hydroxide (733 mg, 13.1 mmol) in water (7 mL). The resulting yellow solution was stirred at 25° C. for 3 h and then concentrated in vacuo to remove ethanol. The aqueous residue was treated with a 1N aqueous hydrochloric acid solution until the pH=2. The product was then extracted into methylene chloride (3×15 mL). The combined organic layers were dried over sodium sulfate, filtered, and concentrated in vacuo. Flash chromatography (Merck Silica gel 60, 230–400 mesh, 75/25 hexanes/ethyl acetate plus 1% acetic acid) afforded 2-(3-chloro-4-methanesulfonyl-phenyl)-3-cyclopentyl-propionic acid (787 mg, 82% for two steps) as a white solid: mp 123.9–126.2° C.; FAB-HRMS m/e calcd for $C_{15}H_{19}ClO_4S$ $(M+H)^+$ 331.0771, found 331.0776.

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2-(3-chloro-4-methanesulfonyl-phenyl)-3-cyclopentyl-propionic acid (200 mg, 0.61 mmol). The reaction mixture was stirred at 0° C. for 20 min and then allowed to warm to 25° C. where it was stirred for 30 min. The reaction mixture was then treated with 2-aminopyridine (85 mg, 0.91 mmol) and pyridine (0.088 mL, 1.09 mmol), and then the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Flash chromatography (Merck Silica gel 60, 230–400 mesh, 60/40 hexanes/ethyl acetate) afforded 2-(3-chloro-4-methanesulfonyl-phenyl)-3-cyclopentyl-N-pyridin-2-yl-propionamide (210 mg, 85%) as a colorless oil: EI-HRMS m/e calcd for $C_{20}H_{23}N_2O_3SCl$ $(M^+)$ 406.1118, found 406.1120.

EXAMPLE 93

N-(5-Bromo-pyridin-2-yl)-2-(3-chloro-4-methanesulfonyl-phenyl)-3-cyclopentyl-propionamide

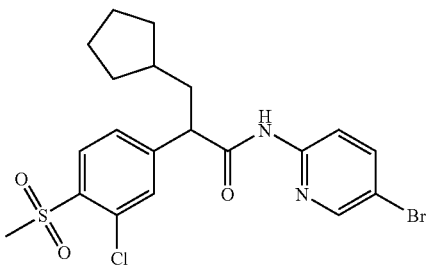

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2-(3-chloro-4-methanesulfonyl-phenyl)-3-cyclopentyl-propionic acid (prepared as in Example 92, 200 mg, 0.61 mmol) and stirred at 0° C. for 20 min and then warmed to 25° C. where it was stirred for 30 min. After such time, the reaction mixture was treated with 2-amino-5-bromopyridine (157 mg, 0.91 mmol) and pyridine (0.088 mL, 1.09 mmol), and reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Flash chromatography (Merck Silica gel 60, 230–400 mesh, 70/30 hexanes/ethyl acetate) afforded 2-(3-chloro-4-methanesulfonyl-phenyl)-3-cyclopentyl-N-(5-bromo-pyridin-2-yl)-propionamide (245 mg, 83%) as a white foam: EI-HRMS m/e calcd for $C_{20}H_{22}Br\ ClN_2O_3S$ ($M^+$) 484.0223, found 484.0222.

EXAMPLE 94

N-(5-Chloro-pyridin-2-yl)-2-(3-chloro-4-methanesulfonyl-phenyl)-3-cyclopentyl-propionamide

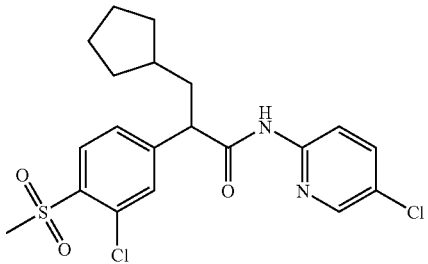

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2-(3-chloro-4-methanesulfonyl-phenyl)-3-cyclopentyl-propionic acid (prepared as in Example 92, 200 mg, 0.61 mmol) and stirred at 0° C. for 20 min and then warmed to 25° C. where it was stirred for 30 min. After such time, the reaction mixture was treated with 2-amino-5-chloropyridine (117 mg, 0.91 mmol) and pyridine (0.088 mL, 1.09 mmol), and the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Flash chromatography (Merck Silica gel 60, 230–400 mesh, 80/20 hexanes/ethyl acetate) afforded 2-(3-chloro-4-methanesulfonyl-phenyl)-3-cyclopentyl-N-(5-chloro-pyridin-2-yl)-propionamide (110 mg, 41%) as a yellow foam: EI-HRMS m/e calcd for $C_{20}H_{22}Cl_2N_2O_3S$ ($M^+$) 440.0728, found 440.0728.

EXAMPLE 95

2-(3-Chloro-4-methanesulfonyl-phenyl)-3-cyclopentyl-N-(5-trifluoromethyl-pyridin-2-yl)-propionamide

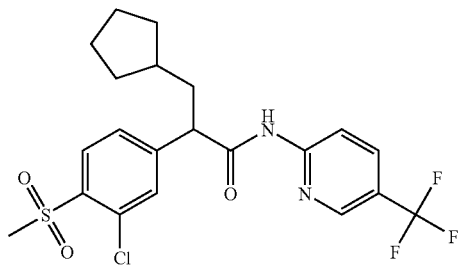

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2-(3-chloro-4-methanesulfonyl-phenyl)-3-cyclopentyl-propionic acid (prepared as in Example 92, 200 mg, 0.61 mmol) and stirred at 0° C. for 20 min and then warmed to 25° C. where it was stirred for 30 min. After such time, the reaction mixture was treated with 2-amino-5-trifluoromethyl-pyridine (147 mg, 0.91 mmol) and pyridine (0.088 mL, 1.09 mmol), and the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Flash chromatography (Merck Silica gel 60, 230–400 mesh, 60/40 hexanes/ethyl acetate) afforded 2-(3-chloro-4-methanesulfonyl-phenyl)-3-cyclopentyl-N-(5-trifluoromethyl-pyridin-2-yl)-propionamide (122 mg, 43%) as a white foam: EI-HRMS m/e calcd for $C_{20}H_{22}ClF_3N_2O_3S$ ($M^+$) 474.0992, found 474.0990.

EXAMPLE 96

{2-[2-(3-Chloro-4-methanesulfonyl-phenyl)-3-cyclopentyl-propionylamino]-thiazol-4-yl}-oxo-acetic Acid Ethyl Ester

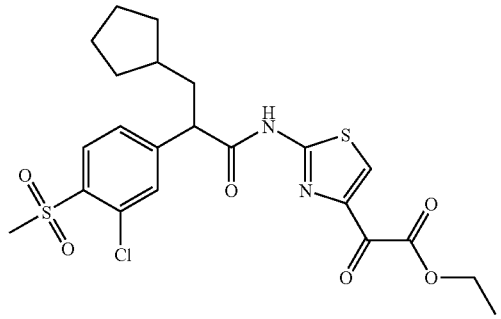

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2-(3-chloro-4-methanesulfonyl-phenyl)-3-cyclopentyl-propionic acid (prepared as in Example 92, 200 mg, 0.61 mmol) and stirred at 0° C. for 20 min and then warmed to 25° C. where it was stirred for 30 min. After such time, the reaction mixture was treated with 2-(amino-thiazol-4-yl)-oxo-acetic acid ethyl ester (182 mg, 0.91 mmol) and pyridine (0.088 mL, 1.09 mmol), and the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Flash chromatography (Merck Silica gel 60, 230–400 mesh, 75/25 hexanes/ethyl acetate) afforded {2-[2-(3-chloro-4-methanesulfonyl-phenyl)-3-cyclopentyl-propionylamino]-thiazol-4-yl}-oxo-acetic acid ethyl ester (208 mg, 67%) as a clear colorless oil: EI-HRMS m/e calcd for $C_{22}H_{25}ClN_2O_6S_2$ ($M^+$) 513.0921, found 513.0919.

EXAMPLE 97

2(R)-(3-Chloro-4-methanesulfonyl-phenyl)-3-cyclopentyl-N-thiazol-2-yl-propionamide

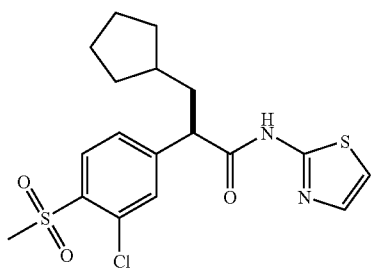

A mixture of 2-(3-chloro-4-methanesulfonyl-phenyl)-3-cyclopentyl-propionic acid (prepared as in Example 92, 6.07 g, 18.35 mmol), (R)-(+)-4-benzyl-2-oxazolidinone (2.83 g, 15.96 mmol), and triethylamine (6.68 mL, 47.71 mmol) in toluene (50 mL) was heated at 80° C. under argon until a homogeneous solution was obtained. The reaction mixture was then treated with trimethylacetyl chloride (3.55 mL, 28.81 mmol) in toluene (10 mL), and the reaction became yellow in color and a precipitate formed. The reaction mixture was then heated at 80° C. for 36 h. The reaction was cooled to 25° C. and then the toluene was removed in vacuo. The residue was diluted with ethyl acetate (150 mL). The organic layer was washed sequentially with a 1N aqueous hydrochloric solution (1×100 mL), a 10% aqueous sodium carbonate solution (1×100 mL), and a saturated aqueous sodium chloride solution (1×100 mL). The organic layer was then dried over magnesium sulfate, filtered, and concentrated in vacuo. Flash chromatography (Merck Silica gel 60, 230–400 mesh, 90/5/5 methylene chloride/hexanes/ethyl acetate) afforded two products: (1) 4(R)-benzyl-3-[2(S)-(3-chloro-4-methanesulfonyl-phenyl)-3-cyclopentyl-propionyl]-oxazolidin-2-one (2.08 g, 23%) as a white foam: $[\alpha]^{23}_{589}=+10.4°$ (c=0.144, chloroform); FAB-HRMS m/e calcd for $C_{25}H_{28}ClNO_5S$ (M+H)$^+$ 490.1455, found 490.1457; and (2) 4(R)-benzyl-3-[2(R)-(3-chloro-4-methanesulfonyl-phenyl)-3-cyclopentyl-propionyl]-oxazolidin-2-one (2.20 g, 25%) as a white foam: $[\alpha]^{23}_{589}=-93.9°$ (c=0.165, chloroform); FAB-HRMS m/e calcd for $C_{25}H_{28}ClNO_5S$ (M+H)$^+$ 490.1455, found 490.1443.

A solution of lithium hydroxide (215 mg, 9.0 mmol) in water (2.8 mL) was treated with a 30% aqueous hydrogen peroxide solution (2.0 mL, 18 mmol). This freshly prepared lithium hydroperoxide solution was then cooled to 0° C. and then slowly added to a cooled (0° C.) solution of 4(R)-benzyl-3-[2(R)-(3-chloro-4-methanesulfonyl-phenyl)-3-cyclopentyl-propionyl]-oxazolidin-2-one (2.20 g, 4.5 mmol) in tetrahydrofuran (18 mL) and water (5.8 mL). After 1.5 h at 0° C., the reaction was quenched with a 1.5N aqueous sodium sulfite solution (25 mL) and was diluted with water (150 mL). The aqueous layer was extracted with diethyl ether (3×50 mL). The aqueous layer was then acidified with a 1N aqueous hydrochloric acid solution to pH=2 and extracted with ethyl acetate (3×50 mL). The combined organic layers were dried over sodium sulfate, filtered, and concentrated in vacuo. Flash chromatography (Merck Silica gel 60, 230–400 mesh, 75/25 hexanes/ethyl acetate with 1% acetic acid) afforded 2(R)-(3-chloro-4-methanesulfonyl-phenyl)-3-cyclopentyl-propionic acid (1.26 g, 85%) as a white solid: mp 106.1–108.8° C.; $[\alpha]^{23}_{589}=-43.0°$ (c=0.172, chloroform); EI-HRMS m/e calcd for $C_{15}H_{19}ClO_4S$ (M$^+$) 330.0692, found 330.0690.

A solution of triphenylphosphine (248 mg, 0.94 mmol) in methylene chloride (9 mL) was cooled to 0° C. and then treated with N-bromosuccinimide (190 mg, 1.07 mmol). The reaction mixture was stirred at 0° C. until it was completely dissolved and became light purple in color. The reaction mixture was then treated with 2(R)-(3-chloro-4-methanesulfonyl-phenyl)-3-cyclopentyl-propionic acid (208 mg, 0.63 mmol). The reaction mixture was stirred at 0° C. for 20 min and then warmed to 25° C. where it was stirred for 30 min. After such time, the reaction mixture was treated with 2-aminothiazole (95 mg, 0.94 mmol) and pyridine (0.092 mL, 1.13 mmol), and the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Biotage chromatography (FLASH 40S, Silica, 65/35 hexanes/ethyl acetate) afforded 2(R)-(3-chloro-4-methanesulfonyl-phenyl)-3-cyclopentyl-N-thiazol-2-yl-propionamide (210 mg, 81%) as a white foam: $[\alpha]^{23}_{589}=-54.3°$ (c=0.081, chloroform); EI-HRMS m/e calcd for $C_{18}H_{21}ClN_2O_3S_2$ (M$^+$) 412.0682, found 412.0679.

EXAMPLE 98

2(R)-(3-Chloro-4-methanesulfonyl-phenyl)-3-cyclopentyl-N-pyridin-2-yl-propionamide

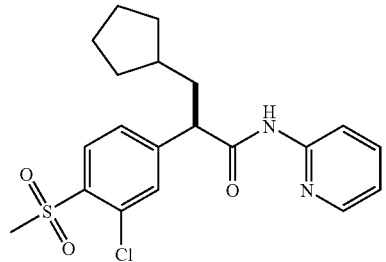

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2(R)-(3-chloro-4-methanesulfonyl-phenyl)-3-cyclopentyl-propionic acid (prepared as in Example 97, 200 mg, 0.61 mmol). The reaction mixture was stirred at 0° C. for 20 min and then warmed to 25° C. where it was stirred for 30 min. After such time, the reaction mixture was treated with 2-aminopyridine (85 mg, 0.91 mmol) and pyridine (0.088 mL, 1.09 mmol), and the reaction mixture was stirred at 25° C. for 16 h. The reaction was then diluted with water (10 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded 2(R)-(3-chloro-4-methanesulfonyl-phenyl)-3-cyclopentyl-N-pyridin-2-yl-propionamide (202 mg, 81.5%) as a white foam: $[\alpha]^{23}_{589}=-41.8°$ (c=0.098, chloroform); EI-HRMS m/e calcd for $C_{20}H_{23}ClN_2O_3S$ (M$^+$) 406.1118, found 406.1119.

EXAMPLE 99

N-(5-Bromo-pyridin-2-yl)-2(R)-(3-chloro-4-methanesulfonyl-phenyl)-3-cyclopentyl-propionamide

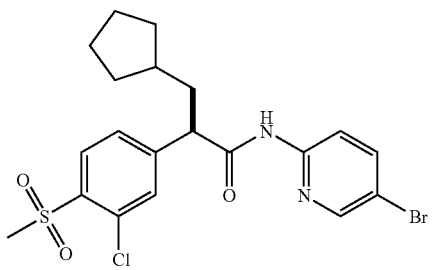

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it was completely dissolved and became light purple in color. The reaction mixture was then treated with 2(R)-(3-chloro-4-methanesulfonyl-phenyl)-3-cyclopentyl-propionic acid (prepared as in Example 97, 200 mg, 0.61 mmol). The reaction mixture was stirred at 0° C. for 20 min and then warmed to 25° C. where it was stirred for 30 min. After such time, the reaction mixture was treated with 2-aminopyridine (85 mg, 0.91 mmol) and pyridine (0.088 mL, 1.09 mmol), and the reaction mixture was stirred at 25° C. for 16 h. The reaction was then diluted with water (10 mL) and then extracted with methylene chloride (3×15 mL). The combined organic layers were then dried over sodium sulfate, filtered, and concentrated in vacuo. Biotage chromatography (FLASH 40S, Silica, 60/40 hexanes/ethyl acetate) afforded N-(5-bromo-pyridin-2-yl)-2(R)-(3-chloro-4-methanesulfonyl-phenyl)-3-cyclopentyl-propionamide (222 mg, 76%) as an off-white foam: $[\alpha]^{23}_{589}$=−48.6° (c=0.105, chloroform); EI-HRMS m/e calcd for $C_{20}H_{22}BrClN_2O_3S$ (M+) 484.0223, found 484.0223.

EXAMPLE 100

N-(5-Cyano-pyridin-2-yl)-3-cyclopentyl-2-(3,4-dichloro-phenyl)-propionamide

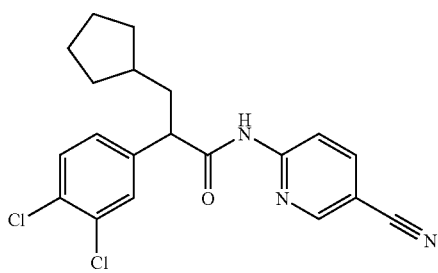

A solution of nickel(II) bromide (253 mg, 1.16 mmol), triphenylphosphine (1.15 g, 4.39 mmol), and zinc powder (113 mg, 1.73 mmol) in acetonitrile (11 mL) was stirred under argon at 60° C. for 1 h. The reaction turned dark brown in color. After such time, the reaction mixture was treated with sodium cyanide (578 mg, 11.8 mmol) and 2-amino-5-bromopyridine (2.00 g, 11.6 mmol), and the reaction mixture was stirred at 60° C. for 16 h. The reaction mixture was then cooled to 25° C., diluted with ethyl acetate (50 mL), and then filtered through celite. The filtrate was concentrated in vacuo. Flash chromatography (Merck Silica gel 60, 230–400 mesh, 100% ethyl acetate) afforded 6-amino-nicotinonitrile (577 mg, 42%) as a white solid: mp 156.8–158.5° C.; EI-HRMS m/e calcd for $C_6H_5N_3$ (M+) 119.0483, found 119.0480.

A solution of triphenylphosphine (1.23 g, 4.70 mmol) in methylene chloride (26 mL) was cooled to 0° C. and then treated with N-bromosuccinimide (948 mg, 5.33 mmol). The reaction mixture was stirred at 0° C. until it was completely dissolved and became light purple in color. The reaction mixture was then treated with 3-cyclopentyl-2-(3,4-dichloro-phenyl)-propionic acid (prepared as in Example 38A, 900 mg, 3.13 mmol). The reaction mixture was stirred at 0° C. for 20 min and then warmed to 25° C. where it stirred for 30 min. After such time, the reaction mixture was treated with 6-amino-nicotinonitrile (560 mg, 4.70 mmol) and pyridine (0.46 mL, 5.64 mmol), and the reaction mixture was stirred at 25° C. for 16 h. The reaction was then diluted with water (25 mL) and then extracted with methylene chloride (3×25 mL). The combined organic layers were dried over sodium sulfate, filtered, and concentrated in vacuo. Flash chromatography (Merck Silica gel 60, 230–400 mesh, 85/15 hexanes/ethyl acetate) afforded N-(5-cyano-pyridin-2-yl)-3-cyclopentyl-2-(3,4-dichloro-phenyl)-propionamide (882 mg, 73%) as a pink foam: EI-HRMS m/e calcd for $C_{20}H_{19}Cl_2N_3O$ (M+) 387.0905, found 387.0905.

EXAMPLE 101

3-Cyclopentyl-2(R)-(3,4-dichloro-phenyl)-N-(5-trifluoromethyl-pyridin-2-yl)-propionamide

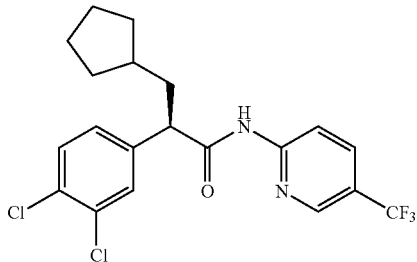

A solution of 3-cyclopentyl-2(R)-(3,4-dichloro-phenyl)-propionic acid (prepared as in Example 54A, 200 mg, 0.69 mmol) in methylene chloride (10 mL) and one drop of N,N-dimethylformamide was cooled to 0° C. and then treated with a 2.0M solution of oxalyl chloride in methylene chloride (0.42 mL, 0.84 mmol). Gas evolution began immediately. The reaction mixture was allowed to warm slowly to 25° C. where it was stirred for 30 min. After this time, the reaction mixture was treated with a solution of N,N-diisopropylethylamine (0.24 mL, 1.39 mmol) and 5-trifluoromethyl-2-aminopyridine (150 mg, 0.905 mmol) in tetrahydrofuran (4 mL) in one portion. The resulting reaction mixture was stirred for 16 h at 25° C. After such time, the reaction was diluted with water (15 mL) and was extracted with methylene chloride (3×15 mL). The combined organic layers were dried over sodium sulfate, filtered, and concentrated in vacuo. Flash chromatography (Merck Silica gel 60, 230–400 mesh, 90/10 hexanes/ethyl acetate) afforded the 3-cyclopentyl-2(R)-(3,4-dichloro-phenyl)-N-(5-trifluoromethyl-pyridin-2-yl)-propionamide (77 mg, 26%) as a white solid: mp 113.8–117.5° C.; EI-HRMS m/e calcd for $C_{20}H_{19}Cl_2F_3N_2O$ (M+) 430.0826, found 430.0835.

EXAMPLE 102

6-[3-Cyclopentyl-2(R)-(3,4-dichloro-phenyl)-propionylamino]-nicotinic Acid

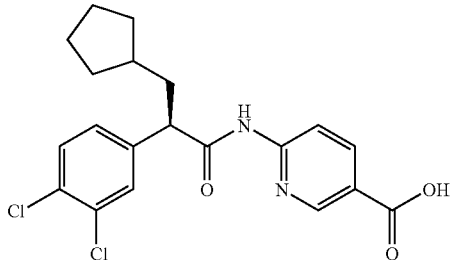

A solution of 6-[3-cyclopentyl-2(R)-(3,4-dichloro-phenyl)-propionylamino]-nicotinic acid methyl ester (prepared as in Example 45, 188 mg, 0.45 mmol) in tetrahydrofuran (3 mL) was treated with a 3N aqueous hydrochloric acid solution (3 mL). The resulting reaction mixture was heated under reflux at 60° C. for 4 h. After such time, the reaction was cooled to 25° C., diluted with water (5 mL), and then extracted with ethyl acetate (3×20 mL). The combined organic layers were dried over sodium sulfate, filtered, and concentrated in vacuo. Flash chromatography (Merck Silica gel 60, 230–400 mesh, 90/10 hexanes/ethyl acetate with 1% acetic acid) afforded 6-[3-cyclopentyl-2(R)-(3,4-dichloro-phenyl)-propionylamino]-nicotinic acid (8 mg, 4%) as a white solid: $[\alpha]^{23}_{589}$=−41.4° (c=0.099, chloroform); FAB-HRMS m/e calcd for $C_{20}H_{20}Cl_2N_2O_3$ (M+H)$^+$ 407.0930, found 407.0928.

EXAMPLE 103

6-[3-Cyclopentyl-2-(3,4-dichloro-phenyl)-propionylamino]-N-methyl-nicotinamide

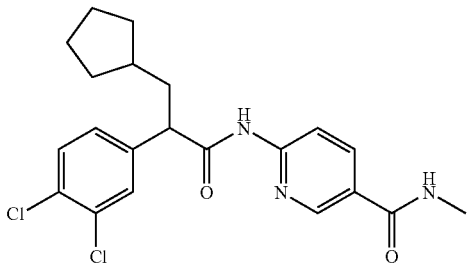

A solution of 6-[3-cyclopentyl-2-(3,4-dichloro-phenyl)-propionylamino]-nicotinic acid (prepared as in Example 46, 125 mg, 0.31 mmol), N,N-diisopropylethylamine (0.10 mL, 0.61 mmol), and benzotriazol-1-yloxy-tris(dimethylamino)phosphonium hexafluorophosphate (142 mg, 0.32 mmol) in N,N-dimethylformamide (15 mL) at 25° C. was treated dropwise with a 2.0M solution of methylamine in tetrahydrofuran (0.16 mL, 0.32 mmol). The resulting reaction mixture was stirred at 25° C. for 16 h. The reaction mixture was then diluted with water (10 mL) and extracted with ethyl acetate (3×10 mL). The combined organic layers were dried over sodium sulfate, filtered, and concentrated in vacuo. Flash chromatography (Merck Silica gel 60, 230–400 mesh, 50/50 hexanes/ethyl acetate) afforded 6-[3-cyclopentyl-2-(3,4-dichloro-phenyl)-propionylamino]-N-methyl-nicotinamide (83 mg, 64%) as white solid: mp 229.1–231.7° C.; FAB-HRMS m/e calcd for $C_{21}H_{23}Cl_2N_3O_2$ (M+H)$^+$ 420.1245, found 420.1247.

EXAMPLE 104

3-Cyclopentyl-2-(3,4-dichloro-phenyl)-N-pyrazin-2-yl-propionamide

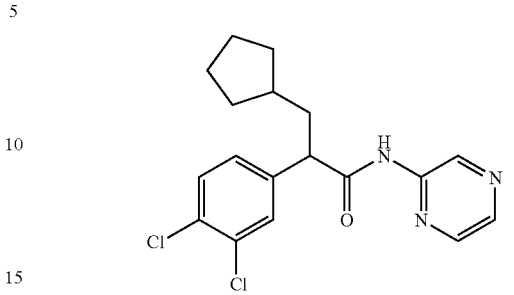

A solution of 3-cyclopentyl-2-(3,4-dichloro-phenyl)-propionic acid (prepared as in Example 38A, 100 mg, 0.35 mmol) in methylene chloride (5 mL) and one drop of N,N-dimethylformamide was cooled to 0° C. and then treated with a 2.0M solution of oxalyl chloride in methylene chloride (0.20 mL, 0.39 mmol). Gas evolution began immediately. The reaction mixture was stirred for 30 min at 0° C. After this time, the reaction mixture was treated with a solution of N,N-diisopropylethylamine (0.15 mL, 0.84 mmol) and 2-aminopyrazine (69 mg, 0.73 mmol) in tetrahydrofuran (4 mL) in one portion. The resulting reaction mixture was stirred for 16 h at 25° C. The reaction mixture was then diluted with water (10 mL) and extracted with methylene chloride (3×15 mL). The combined organic layers were dried over sodium sulfate, filtered, and concentrated in vacuo. Flash chromatography (Merck Silica gel 60, 230–400 mesh, 90/10 hexanes/ethyl acetate) afforded 3-cyclopentyl-2-(3,4-dichloro-phenyl)-N-pyrazin-2-yl-propionamide (38 mg, 30%) as a yellow solid: mp 46.5–51.3° C.; EI-HRMS m/e calcd for $C_{18}H_{19}Cl_2N_3O$ (M$^+$) 363.0905, found 363.0907.

EXAMPLE 105

N-(5-Bromo-pyridin-2-yl)-3-cyclopentyl-2(R)-(3,4-dichloro-phenyl)-propionamide

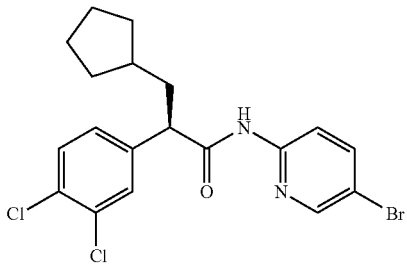

A solution of triphenylphosphine (411 mg, 1.57 mmol) in methylene chloride (15 mL) was cooled to 0° C. and then treated with N-bromosuccinimide (316 mg, 1.78 mmol). The reaction mixture was stirred at 0° C. until it was completely dissolved and became light purple in color. The reaction mixture was then treated with 3-cyclopentyl-2(R)-(3,4-dichloro-phenyl)-propionic acid (prepared as in Example 54A, 300 mg, 1.05 mmol). The reaction mixture was stirred at 0° C. for 20 min and then warmed to 25° C. where it was stirred for 30 min. After such time, the reaction mixture was treated with 2-amino-5-bromopyridine (271 mg, 1.57 mmol) and pyridine (0.15 mL, 1.88 mmol). The resulting reaction mixture was stirred at 25° C. for 16 h. The reaction was then diluted with water (10 mL) and extracted with methylene chloride (3×15 mL). The combined organic layers were dried over sodium sulfate, filtered, and concentrated in vacuo. Flash chromatography (Merck Silica gel 60, 230–400 mesh, 90/10 hexanes/ethyl acetate) afforded N-(5-bromo-pyridin-2-yl)-3-cyclopentyl-2(R)-(3,4-dichloro-phenyl)-propionamide (448 mg, 97%) as a white solid: mp 107.3–109.9° C.; $[\alpha]^{23}_{589}$=–66.7° (c=0.084, chloroform); EI-HRMS m/e calcd for $C_9H_{19}BrCl_2N_2O$ (M$^+$) 440.0058, found 440.0056.

EXAMPLE 106

3-Cyclopentyl-2(R)-(3,4-dichloro-phenyl)-N-(5-hydroxymethyl-pyridin-2-yl)propionamide

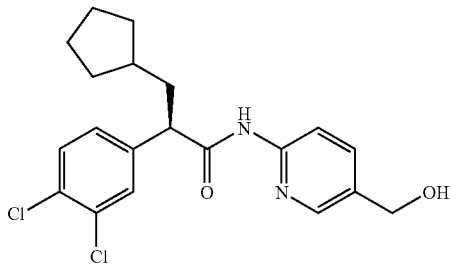

A solution of 6-[3-cyclopentyl-2(R)-(3,4-dichloro-phenyl)-propionylamino]-nicotinic acid methyl ester (prepared as in Example 45, 398 mg, 0.95 mmol) in diethyl ether (30 mL) was cooled to 0° C. and then treated with lithium aluminum hydride (54 mg, 1.4 mmol) in one portion. There was immediate gas evolution. The reaction mixture was allowed to slowly warm to 25° C. and was stirred at 25° C. 16 h. After such time, the reaction mixture was diluted with water (10 mL) and then extracted with ethyl acetate (3×15 mL). The combined organic layers were dried over sodium sulfate, filtered, and concentrated in vacuo. Flash chromatography (Merck Silica gel 60, 230–400 mesh, 90/10 hexanes/ethyl acetate) afforded 3-cyclopentyl-2-(3,4-dichloro-phenyl)-N-(5-hydroxymethyl-pyridin-2-yl) propionamide (131 mg, 35%) as a white foam: FAB-HRMS m/e calcd for $C_{20}H_{22}Cl_2N_2O_2$ (M+H)$^+$ 392.1058, found 392.1062.

EXAMPLE 107

3-Cycloheptyl-2-(4-methanesulfonyl-phenyl)-N-thiazol-2-yl-propionamide

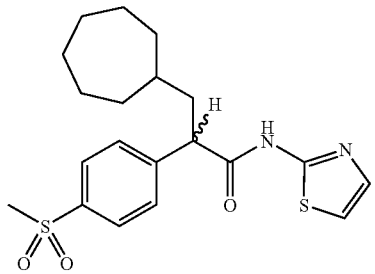

A mixture of magnesium metal (4.81 g, 200 mmol) and dry tetrahydrofuran (10 mL) under argon was treated with a solution of 1,2-dibromoethane (0.94 g, 5 mmol) in dry tetrahydrofuran (5 mL). The resulting reaction mixture was stirred for 10 min to activate the magnesium metal. The reaction mixture was then treated dropwise with a solution of cycloheptyl bromide (17.7 g, 100 mmol) in dry tetrahydrofuran (30 mL), one-fifth portion over a period of 5 min. The resulting reaction mixture was stirred for 5–10 min to initiate the exothermic reaction. The remaining portion of the cycloheptyl bromide solution was then added dropwise while controlling the inside temperature below 50° C. After complete addition, the solution was stirred for 1 h and then diluted with dry tetrahydrofuran (80 mL). In a separate reaction flask, a mixture of lithium chloride (8.48 g, 200 mmol, predried at 130° C. under high vacuum for 3 h) and copper(I) cyanide (8.96 g, 100 mmol) in dry tetrahydrofuran (110 mL) was stirred at 25° C. under argon for 10 min to obtain a clear solution. The reaction mixture was cooled to –70° C. and then slowly treated with the freshly prepared cycloheptylmagnesium bromide. After the addition, the reaction mixture was allowed to warm to –10° C. where it was stirred for 5 min. The resulting reaction mixture was again cooled back to –70° C. and then treated with methyl propiolate (7.57 g, 90 mmol). The reaction mixture was stirred for 15 h at –70° C. to –50° C. and then slowly treated with a solution of iodine (34.3 g, 135 mmol) in dry tetrahydrofuran (30 mL) while maintaining the temperature at –70° C. to –60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×200 mL). The combined organic extracts were successively washed with a saturated aqueous sodium thiosulfate solution (1×400 mL) and a saturated aqueous sodium chloride solution (1×400 mL). The organic layer was then dried over anhydrous magnesium sulfate, filtered, and concentrated in vacuo. Flash chromatography (Merck Silica gel 60, 230–400 mesh, 20/1 to 10/1 hexanes/diethyl ether) afforded (E)-3-cycloheptyl-2-iodo-acrylic acid methyl ester (17.86 g, 64%) as a colorless oil: EI-HRMS m/e calcd for $C_{11}H_{17}IO_2$ (M$^+$) 308.0273, found 308.0273.

A mixture of zinc dust (2.6 g, 40 mmol, Aldrich, –325 mesh) and dry tetrahydrofuran (3 mL) under argon was treated with 1,2-dibromoethane (0.38 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (220 mg, 2 mmol), and the suspension was stirred for 15 min at 25° C. The reaction mixture was then treated dropwise with a solution of (E)-3-cycloheptyl-2-iodo-acrylic acid methyl ester (6.16 g, 20 mmol) in dry tetrahydrofuran (5 mL) over 10 min. The reaction mixture was then stirred at 40–45° C. for 1 h and then stirred overnight at 25° C. The reaction mixture was then diluted with dry tetrahydrofuran (10 mL), and the stirring was stopped to allow the excess zinc dust to settle down (~2 h). In a separate reaction flask; bis(dibenzylideneacetone)palladium(0) (270 mg, 0.5 mmol) and triphenylphosphine (520 mg, 2 mmol) in dry tetrahydrofuran (25 mL) was stirred at 25° C. under argon for 10 min and then treated with 4-bromophenyl methyl sulfone (4.23 g, 18 mmol) and the freshly prepared zinc compound in tetrahydrofuran. The resulting brick red solution was heated at 50° C. for 24 h. The reaction mixture was cooled to 25° C. and then poured into a saturated aqueous ammonium chloride solution (150 mL), and the organic compound was extracted into ethyl acetate (3×150 mL). The combined organic extracts were washed with a saturated aqueous sodium chloride solution (1×300 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cycloheptyl-2-(4-methanesulfonyl-phenyl)-acrylic acid methyl ester (6.01 g, 99%) as a viscous yellow oil: EI-HRMS m/e calcd for $C_{18}H_{24}O_4S$ (M+) 336.1395, found 336.1395.

A solution of nickel(II) chloride hexahydrate (7.8 mg, 0.033 mmol) and (E)-3-cycloheptyl-2-(4-methanesulfonyl-phenyl)-acrylic acid methyl ester (111 mg, 0.33 mmol) in methanol (3 mL) was cooled to 0° C. and then treated with sodium borohydride (25 mg, 0.66 mmol) in two portions. After the addition, the black reaction mixture was stirred for 15 min at 0° C. and then allowed to warm to 25° C. where it was stirred for 15 h. The black solid was filtered using filter paper and washed with methanol. The combined solvents were concentrated in vacuo, and the residue was diluted with water (25 mL) and ethyl acetate (25 mL). The two layers were separated, and the aqueous layer was extracted with ethyl acetate (1×15 mL). The combined organic extracts were washed with a saturated aqueous sodium chloride solution (1×50 mL), dried over anhydrous magnesium sulfate, filtered, and concentrated in vacuo to afford racemic 3-cycloheptyl-2-(4-methanesulfonyl-phenyl)-propionic acid methyl ester (101 mg, 91%) as a colorless oil: EI-HRMS m/e calcd for $C_{18}H_{26}O_4S$ (M+) 338.1552, found 338.1555.

A solution of 3-cycloheptyl-2-(4-methanesulfonyl-phenyl)-propionic acid methyl ester (95 mg, 0.28 mmol) in ethanol (2 mL) was treated with a 1N aqueous sodium hydroxide solution (1.5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (10 mL) and extracted with diethyl ether (1×20 mL) to remove any neutral impurities. The aqueous layer was then acidified with a 1N aqueous hydrochloric acid solution, and the resulting acid was extracted into ethyl acetate (2×15 mL). The combined organic layers were washed with a saturated aqueous sodium chloride solution (1×50 mL), dried over anhydrous magnesium sulfate, filtered, and concentrated in vacuo to afford 3-cycloheptyl-2-(4-methanesulfonyl-phenyl)-propionic acid (78 mg, 86%) as a white solid: EI-HRMS m/e calcd for $C_{17}H_{24}O_4S$ (M+H)+ 325.1474, found 325.1478.

A solution of triphenylphosphine (116 mg, 0.44 mmol) in methylene chloride (2 mL) was cooled to 0° C. and then treated with N-bromosuccinimide (78 mg, 0.44 mmol). The reaction mixture was stirred at 0° C. for 30 min and then treated with a solution of 3-cycloheptyl-2-(4-methanesulfonyl-phenyl)-propionic acid (72 mg, 0.22 mmol) in methylene chloride (2 mL). The clear solution was stirred for 10 min at 0° C. and then allowed to warm to 25° C. where it was stirred for 1.5 h. The reaction mixture was then treated with 2-aminothiazole (66 mg, 0.66 mmol), and the resulting suspension was stirred for 20 h at 25° C. The reaction mixture was then concentrated in vacuo to remove methylene chloride, and the residue was diluted with ethyl acetate (30 mL) and a 1N aqueous hydrochloric acid solution (30 mL). The two layers were separated, and the aqueous layer was extracted with ethyl acetate (1×10 mL). The combined organic extracts were successively washed with a saturated aqueous sodium bicarbonate solution (1×20 mL) and a saturated aqueous sodium chloride solution (1×30 mL), dried over anhydrous magnesium sulfate, filtered, and concentrated in vacuo. Biotage chromatography (FLASH 40S, Silica, 4/1 to 1/1 hexanes/ethyl acetate) afforded 3-cycloheptyl-2-(4-methanesulfonyl-phenyl)-N-thiazol-2-yl-propionamide (68 mg, 76%) as an amorphous solid: EI-HRMS m/e calcd for $C_{20}H_{26}N_2O_3S_2$ (M+) 406.1426, found 406.1424.

EXAMPLE 108

3-Cyclohexyl-2-(4-methanesulfonyl-phenyl)-N-thiazol-2-yl-propionamide

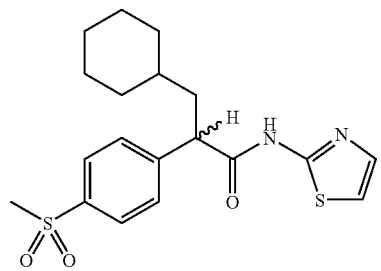

A mixture of zinc dust (16.34 g, 250 mmol, Aldrich, −325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C. The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper(I) cyanide (8.95 g, 100 mmol) in dry tetrahydrofuran (110 mL) was stirred for 10 min at 25° C. to obtain a clear solution. The reaction mixture was cooled to −70° C. and then slowly treated with the freshly prepared zinc solution using a syringe. After the addition, the reaction mixture was allowed to warm to 0° C. where it was stirred for 5 min. The reaction mixture was again cooled back to −70° C. and then slowly treated with methyl propiolate (7.56 g, 90 mmol). The resulting reaction mixture was stirred for 15 h at −70° C. to −50° C. and then slowly treated with a solution of iodine (34.26 g, 135 mmol) in dry tetrahydrofuran (30 mL) while maintaining the temperature at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-HRMS m/e calcd for $C_{10}H_{15}IO_2$ ($M^+$) 294.0117, found 294.0114.

A mixture of zinc dust (2.6 g, 40 mmol, Aldrich, –325 mesh) and dry tetrahydrofuran (3 mL) under argon was treated with 1,2-dibromoethane (0.37 g, 2 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (217 mg, 2 mmol), and the suspension was stirred for 15 min at 25° C. The reaction mixture was then treated dropwise with a solution of (E)-3-cyclohexyl-2-iodo-acrylic acid methyl ester (5.88 g, 20 mmol) in dry tetrahydrofuran (5 mL) over 5 min. During the addition, the temperature rose to 50° C. The reaction mixture was then stirred at 40–45° C. for 1 h and then stirred overnight at 25° C. The reaction mixture was then diluted with dry tetrahydrofuran (10 mL), and the stirring was stopped to allow the excess zinc dust to settle down (~2 h). In a separate reaction flask, bis(dibenzylideneacetone)palladium(0) (270 mg, 0.5 mmol) and triphenylphosphine (520 mg, 2 mmol) in dry tetrahydrofuran (25 mL) was stirred at 25° C. under argon for 10 min and then treated with 4-bromophenyl methyl sulfone (4.23 g, 18 mmol) and the freshly prepared zinc compound in tetrahydrofuran. The resulting brick red solution was heated at 50° C. for 24 h, at which time, thin layer chromatography analysis of the reaction mixture indicated the absence of starting material. The reaction mixture was cooled to 25° C. and then poured into a saturated aqueous ammonium chloride solution (150 mL), and the organic compound was extracted into ethyl acetate (3×100 mL). The combined organic extracts were washed with a saturated aqueous sodium chloride solution (1×200 mL), dried over anhydrous magnesium sulfate, filtered, and concentrated in vacuo. Flash chromatography (Merck Silica gel 60, 230–400 mesh, 3/2 hexanes/ethyl acetate) afforded (E)-3-cyclohexyl-2-(4-methanesulfonyl-phenyl)-acrylic acid methyl ester (5.79 g, 99%) as a low melting white solid: EI-HRMS m/e calcd for $C_{17}H_{22}O_4S$ ($M^+$) 322.1238, found 322.1236.

A solution of nickel(II) chloride hexahydrate (157 mg, 0.66 mmol) and (E)-3-cyclohexyl-2-(4-methanesulfonyl-phenyl)-acrylic acid methyl ester (1.07 g, 3.31 mmol) in methanol (30 mL) was cooled to 0° C. and then treated with sodium borohydride (380 mg, 10 mmol) in four portions. After the addition, the black reaction mixture was stirred for 15 min at 0° C. and then allowed to warm to 25° C. where it was stirred for 15 h. The black solid was filtered using filter paper and washed with methanol. The combined solvents were concentrated in vacuo, and the residue was diluted with water (50 mL) and ethyl acetate (50 mL). The two layers were separated, and the aqueous layer was extracted with ethyl acetate (1×25 mL). The combined organic extracts were washed with a saturated aqueous sodium chloride solution (1×50 mL), dried over anhydrous magnesium sulfate, filtered, and concentrated in vacuo to afford racemic 3-cyclohexyl-2-(4-methanesulfonyl-phenyl)-propionic acid methyl ester (1.04 g, 97%) as an amorphous white solid: EI-HRMS m/e calcd for $C_{17}H_{24}O_4S$ ($M^+$) 324.1395, found 324.1395.

A solution of 3-cyclohexyl-2-(4-methanesulfonyl-phenyl)-propionic acid methyl ester (1.00 g, 3.08 mmol) in ethanol (15 mL) was treated with a 1N aqueous sodium hydroxide solution (6 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (20 mL) and extracted with diethyl ether (1×40 mL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×50 mL), dried over anhydrous magnesium sulfate, filtered, and concentrated in vacuo to afford 3-cyclohexyl-2-(4-methanesulfonyl-phenyl)-propionic acid (570 mg, 60%) as a white solid: mp 139–143° C.; EI-HRMS m/e calcd for $C_{16}H_{22}O_4S$ ($M^+$) 310.1239, found 310.1241.

A solution of triphenylphosphine (416 mg, 1.58 mmol) in methylene chloride (8 mL) was cooled to 0° C. and then treated with N-bromosuccinimide (281 mg, 1.58 mmol). The reaction mixture was stirred at 0° C. for 30 min and then treated with a solution of 3-cyclohexyl-2-(4-methanesulfonyl-phenyl)-propionic acid (290 mg, 0.93 mmol) in methylene chloride (5 mL). The clear solution was stirred for 15 min at 0° C. and then allowed to warm to 25° C. where it was stirred for 1.5 h. The reaction mixture was then treated with 2-aminothiazole (233 mg, 2.32 mmol), and the resulting suspension was stirred for 20 h at 25° C. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and, concentrated in vacuo. Biotage chromatography (FLASH 40S, Silica, 4/1 to 1/1 hexanes/ethyl acetate) afforded 3-cyclohexyl-2-(4-methanesulfonyl-phenyl)-N-thiazol-2-yl-propionamide (337 mg, 92%) as an amorphous solid: EI-HRMS m/e calcd for $C_{19}H_{24}N_2O_3S_2$ ($M^+$) 392.1228, found 392.1230.

EXAMPLE 109

3-Cyclopentyl-2-(3-nitrophenyl)-N-thiazol-2-yl-propionamide

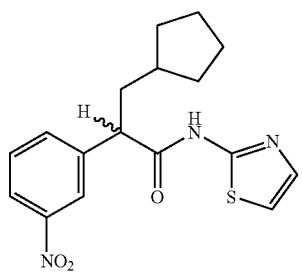

A solution of (3-nitro-phenyl)-acetic acid (5.0 g, 27.6 mmol) in methanol (50 mL) was treated with a catalytic amount of sulfuric acid. The reaction mixture was heated under reflux for 48 h. The reaction was then concentrated in vacuo. The residue was dissolved in methylene chloride (50 mL). The organic layer was washed with a saturated aqueous sodium bicarbonate solution (2×25 mL), water (1×50 mL), and a saturated aqueous sodium chloride solution (1×50 mL). The combined organic layers were dried over sodium sulfate, filtered, and concentrated in vacuo to give (4-nitrophenyl)-acetic acid methyl ester (5.27 g, 97.9%) as a pale yellow solid: mp 29–30° C.; EI-HRMS m/e calcd for $C_9H_9NO_4$ ($M^+$) 195.0531, found 195.0532.

A solution of freshly prepared lithium diisopropylamide (43.3 mL of a 0.3M stock solution, 12.99 mmol) cooled to −78° C. was treated with (3-nitro-phenyl)-acetic acid methyl ester (2.45 g, 12.56 mmol) in tetrahydrofuran/1,3-dimethyl-3,4,5,6-tetrahydro-2(1H)-pyrimidinone (32 mL, 3:1). The resulting solution was stirred at −78° C. for 45 min. At this time, the reaction was treated with a solution of iodomethylcyclopentane (2.78 g, 13.23 mmol) in 1,3-dimethyl-3,4,5,6-tetrahydro-2(1H)-pyrimidinone (2.78 mL), and the mixture was stirred at −78° C. for 3 h. The reaction was warmed to 25° C. and was stirred at 25° C. for 16 h. The reaction mixture was then quenched by the dropwise addition of a saturated aqueous ammonium chloride solution (25 mL) and was concentrated in vacuo. The residue was diluted with water (50 mL) and extracted with ethyl acetate (3×50 mL). The combined organic layers were washed with a saturated aqueous lithium chloride solution (2×25 mL), dried over sodium sulfate, filtered, and concentrated in vacuo. Flash chromatography (Merck Silica gel 60, 230–400 mesh 80/20 hexanes/ethyl acetate) afforded 3-cyclopentyl-2-(3-nitrophenyl)-propionic acid methyl ester (1.63 g, 46.8%) as pale yellow oil: EI-HRMS m/e calcd for $C_{15}H_{19}NO_4$ ($M^+$) 277.1314, found 277.1317.

A solution of 3-cyclopentyl-2-(3-nitro-phenyl)-propionic acid methyl ester (0.55 g, 2.0 mmol) in tetrahydrofuran/water (12 mL, 3:1) was treated with lithium hydroxide (185 mg, 4.40 mmol). The reaction was stirred at 25° C. for 48 h. The tetrahydrofuran was then removed in vacuo. The residue was diluted with water (25 mL) and extracted with ether (1×20 mL). The aqueous layer was acidified to pH=2 with a 3N aqueous hydrochloric acid solution. The solution was extracted with methylene chloride (3×25 mL). The combined organic layers were washed with a saturated aqueous sodium chloride solution (2×25 mL), dried over sodium sulfate, filtered, and concentrated in vacuo to give 3-cyclopentyl-2-(3-nitro-phenyl)-propionic acid (0.48 g, 91.9%) as a tan solid: mp 95–99° C.; EI-HRMS m/e calcd for $C_{14}H_{17}NO_4$ ($M^+$) 263.1157, found 263.1156.

A solution of 3-cyclopentyl-2-(3-nitro-phenyl)-propionic acid (432 mg, 1.64 mmol) in methylene chloride (16 mL) was cooled to 0° C. and then treated with a 2.0M solution of oxalyl chloride in methylene chloride (0.90 mL, 1.80 mmol) and a few drops of N,N-dimethylformamide. The reaction mixture was stirred at 0° C. for 15 min and at 25° C. for 1.2 h. The reaction mixture was then treated with a solution of 2-aminothiazole (361.4 mg, 3.61 mmol) and N,N-diisopropylethylamine (0.70 mL, 3.93 mmol) in tetrahydrofuran (16 mL). The reaction mixture was stirred at 25° C. for 6 h. At this time, the reaction was concentrated in vacuo. Flash chromatography (Merck Silica gel 60, 230–400 mesh 70/30 hexanes/ethyl acetate) afforded 3-cyclopentyl-2-(nitrophenyl)-N-thiazol-2-yl-propionamide (409.3 mg, 72.2%) as a tan solid: mp 171–174° C.; EI-HRMS m/e calcd for $C_{17}H_{19}N_3O_3S$ ($M^+$) 345.1147, found 345.1153.

EXAMPLE 110

3-Cyclopentyl-2-(3-methoxy-phenyl)-N-thiazol-2-yl-propionamide

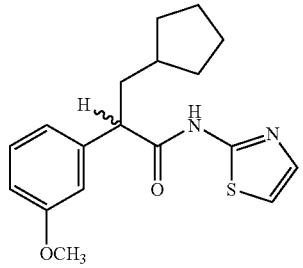

A solution of freshly prepared lithium diisopropylamide (23 mL of a 0.31M stock solution, 7.13 mmol) cooled to −78° C. was treated with (3-methoxy-phenyl)-acetic acid methyl ester (1.07 g, 5.94 mmol) in tetrahydrofuran/1,3-dimethyl-3,4,5,6-tetrahydro-2(1H)-pyrimidinone (14.8 mL, 3:1). The resulting solution was stirred at −78° C. for 45 min. At this time, the reaction was treated with a solution of iodomethylcyclopentane (1.37 g, 6.53 mmol) in 1,3-dimethyl-3,4,5,6-tetrahydro-2(1H)-pyrimidinone (1.16 mL). The reaction mixture was stirred at −78° C. for 3 h. The reaction was then warmed to 25° C. and was stirred at 25° C. for 16 h. At this time, the reaction was quenched by the dropwise addition of a saturated aqueous ammonium chloride solution. This solution was diluted with water (100 mL) and extracted into ethyl acetate (3×50 mL). The combined organic layers were washed with a saturated aqueous lithium chloride solution (1×75 mL), dried over sodium sulfate, filtered, and concentrated in vacuo. Flash chromatography (Merck Silica gel 60, 230–400 mesh, 95/5 hexanes/ethyl acetate) afforded 3-cyclopentyl-2-(3-methoxy-phenyl)-propionic acid methyl ester (1.39 g, 89.1%) as a clear oil: EI-HRMS m/e calcd for $C_{16}H_{22}O_3$ ($M^+$) 262.1568, found 262.1561.

A solution of 3-cyclopentyl-2-(3-methoxy-phenyl)-propionic acid methyl ester (1.39 g, 5.29 mmol) in tetrahydrofuran/water/methanol (13.2 mL, 3:1:1) at 25° C. was treated with a 2N aqueous sodium hydroxide solution (3.97 mL, 7.94 mmol). The reaction was stirred at 25° C. for 48 h. At this time, the reaction mixture was poured into water (50 mL) and extracted with chloroform (3×25 mL). The aqueous layer was acidified to pH=1 with a 1N aqueous hydrochloric acid solution. The aqueous layer was extracted with a solution of chloroform/methanol (9:1). The combined organic layers were dried over sodium sulfate, filtered, and concentrated in vacuo. Flash chromatography (Merck Silica gel 60, 230–400 mesh, 70/30 hexanes/ethyl acetate with glacial acetic acid) afforded 3-cyclopentyl-2-(3-methoxy-phenyl)-propionic acid (1.05 g, 79.8%) as a clear wax: EI-HRMS m/e calcd for $C_{15}H_{20}O_3$ ($M^+$) 248.1412, found 248.1409.

A solution of 3-cyclopentyl-2-(3-methoxy-phenyl)-propionic acid (500 mg, 2.0 mmol) in methylene chloride (20 mL) cooled to 0° C. was treated with a 2.0M solution of oxalyl chloride in methylene chloride (1.1 mL, 2.20 mmol) and a few drops of N,N-dimethylformamide. The reaction mixture was stirred at 0° C. for 10 min then at 25° C. for 30 min. The reaction mixture was then treated with 2-aminothiazole (444 mg, 4.42 mmol) and N,N-diisopropylethylamine (0.84 mL, 4.83 mmol) in tetrahydrofuran (10.1 mL). This solution was stirred at 25° C. for 18 h. At this time, the reaction was concentrated in vacuo. Flash chromatography (Merck Silica gel 60, 230–400 mesh, 80/20 hexanes/ethyl acetate) afforded 3-cyclopentyl-2-(3-methoxy-phenyl)-N-thiazol-2-yl-propionamide (549 mg, 82.6%) as a white solid: mp 44–45° C.; EI-HRMS m/e calcd for $C_{18}H_{22}N_2O_2S$ (M$^+$) 330.1402 found 330.1398.

EXAMPLE 111

3-Cyclopentyl-2-(3-hydroxy-phenyl)-N-thiazol-2-yl-propionamide

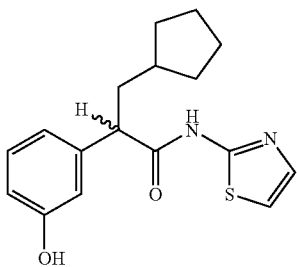

A 1.0M solution of boron tribromide in methylene chloride (3.53 mL, 3.53 mmol) at 25° C. was treated with a solution of 3-cyclopentyl-2-(3-methoxy-phenyl)-N-thiazol-2-yl-propionamide (prepared as in Example 110, 0.11 g, 0.35 mmol) in methylene chloride (3.5 mL). This solution was stirred at 25° C. for 1 h. At this time, the reaction was cooled to 0° C. and treated with a dilute aqueous ammonium hydroxide solution. This mixture was stirred at 0° C. for 15 min. At this time, the aqueous layer was separated from the organic layer. The aqueous layer was extracted with chloroform (3×50 mL). The combined organic layers were dried over sodium sulfate, filtered, and concentrated in vacuo. Flash chromatography (Merck Silica gel 60, 230–400 mesh, 50/50 hexanes/ethyl acetate) afforded 3-cyclopentyl-2-(3-hydroxy-phenyl)-N-thiazol-2-yl-propionamide (50 mg, 44.7%) as a white solid: mp 177–179° C.; EI-HRMS m/e calcd for $C_{17}H_{20}N_2O_2S$ (M$^+$) 316.1245 found 316.1244.

EXAMPLE 112

3-Cyclopentyl-N-thiazol-2-yl-2-(4-trifluoromethoxy-phenyl)-propionamide

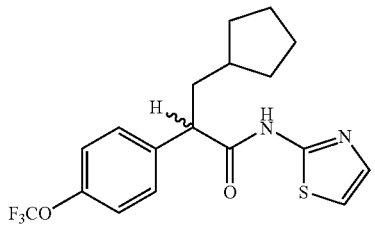

A solution of freshly prepared lithium diisopropylamide (23 mL of a 0.31M stock solution, 7.13 mmol) cooled to −78° C. was treated with (4-trifluoromethoxy-phenyl)-acetic acid (0.74 g, 3.39 mmol) in tetrahydrofuran/1,3-dimethyl-3,4,5,6-tetrahydro-2(1H)-pyrimidinone (8.5 mL, 3:1). The resulting solution was stirred at −78° C. for 45 min. At this time, the reaction was treated with a solution of iodomethylcyclopentane (0.78 g, 3.73 mmol) in 1,3-dimethyl-3,4,5,6-tetrahydro-2(1H)-pyrimidinone (1 mL). The reaction mixture was stirred at −78° C. for 4 h. The reaction was then warmed to 25° C. and was stirred at 25° C. for 18 h. The reaction mixture was then quenched by the dropwise addition of saturated aqueous ammonium chloride solution (10 mL). The resulting mixture was concentrated in vacuo to remove the excess solvent. The residue was diluted with water (100 mL) and acidified to pH=1 with a 1N aqueous hydrochloric acid solution. This solution was extracted with ethyl acetate (3×50 mL). The combined organic layers were washed with a saturated aqueous lithium chloride solution (1×100 mL), dried over sodium sulfate, filtered, and concentrated in vacuo. Flash chromatography (Merck Silica gel 60, 230–400 mesh, 50/50 hexanes/ethyl acetate) afforded 3-cyclopentyl-2-(4-trifluoromethoxy-phenyl)-propionic acid (0.31 g, 30.6%) as a tan solid: mp 62–64° C.; EI-HRMS m/e calcd for $C_{15}H_{17}F_3O_3$ (M$^+$) 302.1129 found 302.1131.

A solution of 3-cyclopentyl-2-(4-trifluoromethoxy-phenyl)-propionic acid (0.16 g, 0.52 mmol) in methylene chloride (5.3 mL) cooled to 0° C. was treated with a 2.0M solution of oxalyl chloride in methylene chloride (0.29 mL, 0.58 mmol) and a few drops of N,N-dimethylformamide. The reaction mixture was stirred at 0° C. for 10 min and at 25° C. for 30 min. The reaction mixture was then treated with a solution of 2-aminothiazole (0.11 g, 1.16 mmol) and N,N-diisopropylethylamine (0.22 mL, 1.27 mmol) in tetrahydrofuran (2.65 mL). The reaction mixture was stirred at 25° C. for 18 h. At this time, the reaction was concentrated in vacuo. Flash chromatography (Merck Silica gel 60, 230–400 mesh 80/20 hexanes/ethyl acetate) afforded 3-cyclopentyl-N-thiazol-2-yl-2-(4-trifluoromethoxy-phenyl)-propionamide (203.8 mg, 100%) as a white solid: mp 168–170° C.; EI-HRMS m/e calcd for $C_{18}H_{19}F_3N_2O_2S$ (M$^+$) 384.1119, found 384.1118.

EXAMPLE 113

3-Cyclopentyl-2-(3,4-dimethoxy-phenyl)-N-thiazol-2-yl-propionamide

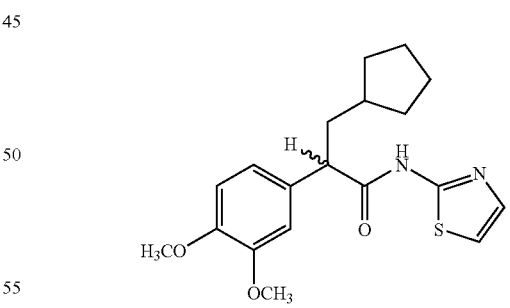

A solution of freshly prepared lithium diisopropylamide (58.5 mL of a 0.91M stock solution, 53.2 mmol) cooled to −78° C. was treated with (3,4-dimethoxy-phenyl)-acetic acid (4.97 g, 25.3 mmol) in tetrahydrofuran/1,3-dimethyl-3,4,5,6-tetrahydro-2(1H)-pyrimidinone (25.3 mL, 3:1). The resulting solution was stirred at −78° C. for 45 min and at 25° C. for 15 min. At this time, the reaction was cooled to 0° C. and was treated with a solution of iodomethylcyclopentane (5.87 g, 27.8 mmol) in 1,3-dimethyl-3,4,5,6-tetrahydro-2(1H)-pyrimidinone (1 mL). The reaction mixture was stirred at 0° C. for 30 min. The reaction was then warmed to 25° C. and was stirred at 25° C. for 18 h. The reaction mixture was then quenched by the dropwise addition of saturated aqueous ammonium chloride solution (10 mL). The resulting mixture was concentrated in vacuo. The residue was diluted with water (100 mL) and acidified to pH=1 with a 1N aqueous hydrochloric acid solution. This solution was extracted with ethyl acetate (3×50 mL). The combined organic layers were washed with a saturated aqueous lithium chloride solution (1×100 mL), dried over sodium sulfate, filtered, and concentrated in vacuo. Flash chromatography (Merck Silica gel 60, 230–400 mesh, 70/30 hexanes/ethyl acetate) afforded 3-cyclopentyl-2-(3,4-dimethoxy-phenyl)-propionic acid (4.5 g, 63.8%) as a yellow solid: mp 111–112° C.; EI-HRMS m/e calcd for $C_{16}H_{22}O_4$ (M+) 278.1518 found 278.1517.

A solution of 3-cyclopentyl-2-(3,4-dimethoxy-phenyl)-propionic acid (0.50 g, 1.79 mmol) in methylene chloride (17.9 mL) cooled to 0° C. was treated with a 2.0M solution of oxalyl chloride in methylene chloride (1.0 mL, 1.97 mmol) and a few drops of N,N-dimethylformamide. The reaction mixture was stirred at 0° C. for 10 min and at 25° C. for 30 min. The reaction mixture was then treated with a solution of 2-aminothiazole (0.39 g, 3.95 mmol) and N,N-diisopropylethylamine (0.76 mL, 4.3 mmol) in tetrahydrofuran (8.98 mL). The reaction mixture was stirred at 25° C. for 18 h. At this time, the reaction was concentrated in vacuo. Flash chromatography (Merck Silica gel 60, 230–400 mesh 80/20 hexanes/ethyl acetate) afforded 3-cyclopentyl-2-(3,4-dimethoxy-phenyl)-N-thiazol-2-yl-propionamide (665 mg, 100%) as a pale yellow solid: mp 50–52° C.; EI-HRMS m/e calcd for $C_{19}H_{24}N_2O_3S$ (M+) 360.1507, found 360.1516.

EXAMPLE 114

3-Cyclopentyl-2-(3,4-dihydroxy-phenyl)-N-thiazol-2-yl-propionamide

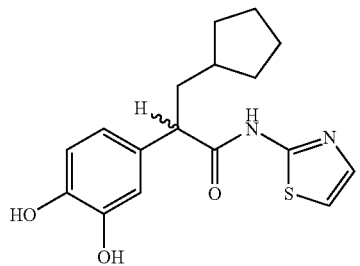

A 1.0M solution of boron tribromide in methylene chloride (7.43 mL, 7.43 mmol) at 25° C. was treated with a solution of 3-cyclopentyl-2-(3,4-dimethoxy-phenyl)-N-thiazol-2-yl-propionamide (prepared as in Example 113, 0.27 g, 0.74 mmol) in methylene chloride (7.43 mL). This solution was stirred at 25° C. for 1 h. At this time, the reaction was cooled to 0° C. and treated with a dilute aqueous ammonium hydroxide solution. This mixture was stirred at 0° C. for 20 min. At this time, the reaction was poured into water and was extracted with chloroform (3×50 mL). The combined organic layers were dried over sodium sulfate, filtered, and concentrated in vacuo. Flash chromatography (Merck Silica gel 60, 230–400 mesh, 70/30 hexanes/ethyl acetate) afforded 3-cyclopentyl-2-(3,4-dihydroxy-phenyl)-N-thiazol-2-yl-propionamide (38.8 mg, 15.7%) as a white solid: mp 170–173° C.; EI-HRMS m/e calcd for $C_{17}H_{20}N_2O_3S$ (M+) 332.1194 found 332.1192.

EXAMPLE 115

3-Cyclopentyl-2-(4-methoxy-phenyl)-N-thiazol-2-yl-propionamide

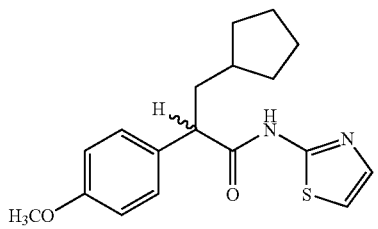

A solution of freshly prepared lithium diisopropylamide (58.5 mL of a 0.93M stock solution, 53.2 mmol) cooled to −78° C. was treated with (4-methoxy-phenyl)-acetic acid (4.21 g, 25.35 mmol) in tetrahydrofuran/1,3-dimethyl-3,4,5,6-tetrahydro-2(1H)-pyrimidinone (25.3 mL, 3:1). The resulting solution was stirred at −78° C. for 45 min. At this time, the reaction was treated with a solution of iodomethylcyclopentane (5.85 g, 27.8 mmol) in 1,3-dimethyl-3,4,5,6-tetrahydro-2(1H)-pyrimidinone (1 mL). The reaction mixture was stirred at −78° C. for 45 min and at 0° C. for 1 h. The reaction was then warmed to 25° C. and was stirred at 25° C. for 16 h. The reaction mixture was then quenched by the dropwise addition of saturated aqueous ammonium chloride solution (10 mL). The excess solvent was removed in vacuo. The residue was acidified to pH=1 with a 1N aqueous hydrochloric acid solution. This mixture was poured into water (50 mL) and extracted with ethyl acetate (3×50 mL). The combined organic layers were washed with a saturated aqueous lithium chloride solution (1×100 mL), dried over sodium sulfate, filtered, and concentrated in vacuo. Flash chromatography (Merck Silica gel 60, 230–400 mesh, 70/30 hexanes/ethyl acetate) afforded 3-cyclopentyl-2-(4-methoxy-phenyl)-propionic acid (2.76 g, 43.8%) as a yellow solid: mp 119–121° C.; EI-HRMS m/e calcd for $C_{15}H_{20}O_3$ (M+) 248.1412 found 248.1415.

A solution of 3-cyclopentyl-2-(4-methoxy-phenyl)-propionic acid (500 mg, 2.0 mmol) in methylene chloride (20.1 mL) cooled to 0° C. was treated with a 2.0M solution of oxalyl chloride in methylene chloride (1.1 mL, 2.21 mmol) and a few drops of N,N-dimethylformamide. The reaction mixture was stirred at 0° C. for 10 min then at 25° C. for 30 min. The reaction mixture was then treated with a solution of 2-aminothiazole (444 mg, 4.42 mmol) and N,N-diisopropylethylamine (0.84 mL, 4.83 mmol) in tetrahydrofuran (10.1 mL). This solution was stirred at 25° C. for 18 h. At this time, the reaction was concentrated in vacuo. Flash chromatography (Merck Silica gel 60, 230–400 mesh, 50/50 hexanes/ethyl acetate) afforded 3-cyclopentyl-2-(4-methoxy-phenyl)-N-thiazol-2-yl-propionamide (638 mg, 95.8%) as a pale yellow solid: mp 166–167° C.; EI-HRMS m/e calcd for $C_{18}H_{22}N_2O_2S$ (M+) 330.1402 found 330.1398.

EXAMPLE 116

3-Cyclopentyl-2-(4-hydroxy-phenyl)-N-thiazol-2-yl-propionamide

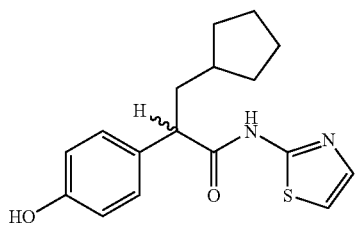

A solution 3-cyclopentyl-2-(4-methoxy-phenyl)-N-thiazol-2-yl-propionamide (prepared as in Example 115, 1.03 g, 3.12 mmol) in methylene chloride (31.26 mL) at 25° C. was treated with a 1.0M solution of boron tribromide in methylene chloride (31.26 mL, 31.26 mmol). This solution was stirred at 25° C. for 4 h. At this time, the reaction was cooled to 0° C. and was then quenched by the dropwise addition of a dilute aqueous ammonium hydroxide solution. The resulting solution was stirred at 0° C. for 15 min. This mixture was then poured into water (50 mL) and extracted with ethyl acetate (3×30 mL). The combined organic layers were dried over sodium sulfate, filtered, and concentrated in vacuo. Flash chromatography (Merck Silica gel 60, 230–400 mesh, 70/30 hexanes/ethyl acetate) afforded 3-cyclopentyl-2-(4-hydroxy-phenyl)-N-thiazol-2-yl-propionamide (626.8 mg, 63.4%) as a off-white solid: mp 198–200° C.; EI-HRMS m/e calcd for $C_{17}H_{20}N_2O_2S$ (M$^+$) 316.1245 found 316.1256.

EXAMPLE 117

4-[2-Cyclopentyl-1-(thiazol-2-ylcarbamoyl)-ethyl]-benzoic Acid Methyl Ester

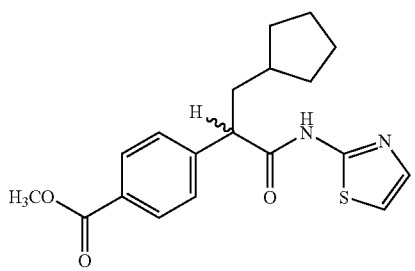

A solution of 4-methyl-benzoic acid (10 g, 73.4 mmol) in benzene (133 mL) was treated with benzoyl peroxide (72 mg, 0.29 mmol). This mixture was heated at reflux until it became homogeneous. At this time, the reaction was treated with N-bromosuccinimide (13 g, 73.4 mmol) and additional benzoyl peroxide (72 mg, 0.29 mmol). This mixture was heated at reflux for 2.5 h. At this time, the reaction was cooled to 25° C. The resulting precipitate was collected by filtration and washed with hot water (50 mL). The solid was taken up in water (150 mL). This slurry was heated at 80° C. and then filtered while hot. The solid that was collected was dried in vacuo to afford 4-bromomethyl-benzoic acid (12.3, 77.9%) as a white solid: mp 224–226° C.; EI-HRMS m/e calcd for $C_8H_7BrO_2$ (M$^+$) 213.9629, found 213.9628.

A solution of 4-bromomethyl-benzoic acid (4.0 g, 18.6 mmol) in acetonitrile (186 mL) was treated with a solution of sodium cyanide (1.0 g, 20.4 mmol) and sodium hydroxide (0.74 g, 18.6 mmol) in water (24 mL). The reaction mixture was heated at reflux for 2 h. At this time, the reaction was cooled to 25° C. and concentrated in vacuo. The resulting solution was washed with chloroform (1×50 mL). The aqueous layer was acidified to pH=3 with a 1N aqueous hydrochloric acid solution. The aqueous layer was extracted with a solution of chloroform/methanol (9:1, 3×100 mL). The combined organic layers were dried over sodium sulfate, filtered, and concentrated in vacuo to afford 4-cyanomethyl-benzoic acid (0.79 g, 26.3%) as a white solid: mp 193–195° C.; EI-HRMS m/e calcd for $C_9H_7NO_2$ (M$^+$) 161.0476, found 161.0483.

A solution of 4-cyanomethyl-benzoic acid (0.53 g, 3.31 mmol) in a 50% aqueous hydrochloric acid solution (42.8 mL) was heated at 80° C. for 16 h. At this time, the reaction was cooled to 25° C. and adjusted to pH=3 by the dropwise addition of a 50% aqueous sodium hydroxide solution. The resulting mixture was diluted with water and extracted with butanol (2×50 mL). The combined organic layers were then extracted with water (5×50 mL, pH=6–7). The aqueous extracts were adjusted to pH=3 with a 3M aqueous hydrochloric acid solution and concentrated in vacuo to afford 4-carboxymethyl-benzoic acid (70 mg, 11.7%) as a white solid: mp 235–237° C.; EI-HRMS m/e calcd for $C_9H_8O_4$ (M$^+$) 180.0422, found 180.

A mixture of 4-carboxymethyl-benzoic acid (0.20 g, 1.11 mmol) and nickel(II) chloride hexahydrate (27 mg, 0.11 mol) in methanol (1.11 mL) was heated at 120° C. for 24 h. At this time, the reaction mixture was cooled to 25° C. and concentrated in vacuo. Flash chromatography (Merck Silica gel 60, 230–400 mesh, 70/30 hexanes/ethyl acetate) afforded 4-methoxycarbonylmethyl-benzoic acid methyl ester (66.7 mg, 28.8%) as a clear oil: EI-HRMS m/e calcd for $C_{11}H_{12}O_4$ (M$^+$) 208.0735, found 208.0733.

A solution of freshly prepared lithium diisopropylamide (2.3 mL of a 0.31M stock solution, 0.71 mmol) cooled to −78° C. was treated with a solution of 4-methoxycarbonylmethyl-benzoic acid methyl ester (66 mg, 0.31 mmol) in tetrahydrofuran/1,3-dimethyl-3,4,5,6-tetrahydro-2(1H)-pyrimidinone (0.85 mL, 3:1). The resulting solution was stirred at −78° C. for 45 min. At this time, the reaction was treated with a solution of iodomethylcyclopentane (86 mg, 0.40 mmol) in 1,3-dimethyl-3,4,5,6-tetrahydro-2(1H)-pyrimidinone (1 mL). The reaction mixture was then stirred at −78° C. for 4 h. The reaction was then warmed to 25° C. and stirred at 25° C. for 18 h. At this time, the reaction mixture was quenched by the slow addition of a saturated aqueous ammonium chloride solution (10 mL). The reaction mixture was then poured into water (50 mL). This solution was extracted into ethyl acetate (3×25 mL). The combined organic layers were dried over sodium sulfate, filtered, and concentrated in vacuo. Flash chromatography (Merck Silica gel 60, 230–400 mesh, 80/20 hexanes/ethyl acetate) afforded 4-(2-cyclopentyl-1-methoxycarbonyl-ethyl)-benzoic acid methyl ester (60.5 mg, 65.7%) as a clear oil: EI-HRMS m/e calcd for $C_{17}H_{22}O_4$ (M$^+$) 290.1518, found 290.1518.

A solution of 4-(2-cyclopentyl-1-methoxycarbonyl-ethyl)-benzoic acid methyl ester (0.40 g, 1.37 mmol) in tetrahydrofuran/water/methanol (13.7 mL, 3:1:1) was treated with a 1N aqueous lithium hydroxide solution. The reaction mixture was stirred at 25° C. for 1 h. At this time, the reaction was poured into water. The aqueous layer was acidified to pH=1 with a 1N aqueous hydrochloric acid solution and extracted with a solution of chloroform/methanol (9:1, 4×25 mL). The combined organic layers were dried over sodium sulfate, filtered, and concentrated in vacuo. Flash chromatography (Merck Silica gel 60, 230–400 mesh, 50/50 hexanes/ethyl acetate) afforded a mixture of 4-(1-carboxy-2-cyclopentyl-ethyl)-benzoic acid methyl ester and 4-(1-carboxy-2-cyclopentyl-ethyl)-benzoic acid methyl ester (161.8 mg, 42.5%) as a clear oil: EI-HRMS m/e calcd for $C_{16}H_{20}O_4$ ($M^+$) 276.1361, found 276.1364.

A solution of the mixture of 4-(1-carboxy-2-cyclopentyl-ethyl)-benzoic acid methyl ester and 4-(1-carboxy-2-cyclopentyl-ethyl)-benzoic acid methyl ester (24.2 mg, 0.08 mmol) in methylene chloride (0.87 mL) cooled to 0° C. was treated with a 2.0M solution of oxalyl chloride in methylene chloride (0.05 mL, 0.10 mmol) and a few drops of N,N-dimethylformamide. The reaction mixture was stirred at 0° C. for 10 min and at 25° C. for 30 min. The reaction mixture was then treated with a solution of 2-aminothiazole (19.3 mg, 0.19 mmol) and N,N-diisopropylethylamine (0.04 mL, 0.21 mmol) in tetrahydrofuran (0.44 mL). The reaction mixture was stirred at 25° C. for 4 h. At this time, the reaction was concentrated in vacuo. Flash chromatography (Merck Silica gel 60, 230–400 mesh, 50/50 hexanes/ethyl acetate) afforded 4-[2-cyclopentyl-1-(thiazol-2-ylcarbamoyl)-ethyl]-benzoic acid methyl ester (18.1 mg, 57.6%) as an off-white solid: mp 54–56° C.; EI-HRMS m/e calcd for $C_{19}H_{22}N_2O_3S$ ($M^+$) 358.1351, found 358.1346.

EXAMPLE 118

3-Cyclopentyl-2-(3-fluoro-4-methoxy-phenyl)-N-thiazol-2-yl-propionamide

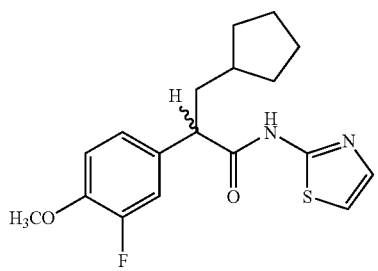

A solution of (3-fluoro-4-hydroxy-phenyl)-acetic acid (1.0 g, 5.87 mmol) in methanol (20 mL) was treated with a catalytic amount of sulfuric acid. The reaction was heated at 120° C. for 6 h. At this time, the reaction was concentrated in vacuo. Flash chromatography (Merck Silica gel 60, 230–400 mesh, 50/50 hexanes/ethyl acetate) afforded (3-fluoro-4-hydroxy-phenyl)-acetic acid methyl ester (1.05 g, 97.6%) as a white solid: mp 34–36° C.: EI-HRMS m/e calcd for $C_9H_9FO_3$ ($M^+$) 184.0535, found 184.0533.

A mixture of 3-fluoro-4-hydroxy-phenyl)-acetic acid methyl ester (1.0 g, 5.43 mmol), potassium carbonate (1.87 g, 13.57 mmol), and methyl iodide (1.12 g, 8.14 mmol) in acetone (27.1 mL) was heated at 90° C. for 4 h. At this time, the potassium carbonate was removed by filtration. The filtrate was concentrated in vacuo. Flash chromatography (Merck Silica gel 60, 230–400 mesh, 80/20 hexanes/ethyl acetate) afforded (3-fluoro-4-methoxy-phenyl)-acetic acid methyl ester (1.01 g, 94.3%) as a clear oil: EI-HRMS m/e calcd for $C_{10}H_{11}FO_3$($M^+$) 198.0692, found 198.0693.

A solution of freshly prepared lithium diisopropylamide (21.6 mL of 0.31M stock solution, 6.69 mmol) cooled to −78° C. was treated with a solution of (3-fluoro-4-methoxy-phenyl)-acetic acid methyl ester (1.26 g, 6.38 mmol) in tetrahydrofuran/1,3-dimethyl-3,4,5,6-tetrahydro-2(1H)-pyrimidinone (16 mL, 3:1). The resulting solution was stirred at −78° C. for 45 min. At this time, the reaction was treated with a solution of iodomethylcyclopentane (1.47 g, 7.02 mmol) in 1,3-dimethyl-3,4,5,6-tetrahydro-2(1H)-pyrimidinone (2 mL). The reaction mixture was stirred at −78° C. for 4 h. The reaction was warmed to 25° C. and stirred at 25° C. for 48 h. The reaction mixture was then quenched by the slow addition of a saturated aqueous ammonium chloride solution (10 mL). The reaction mixture was then poured into water (100 mL) and extracted with ethyl acetate (3×50 mL). The combined organic layers were washed with a saturated aqueous lithium chloride solution (1×50 mL), dried over sodium sulfate, filtered, and concentrated in vacuo. Flash chromatography (Merck Silica gel 60, 230–400 mesh, 90/10 hexanes/ethyl acetate) afforded 3-cyclopentyl-2-(3-fluoro-4-methoxy-phenyl)-propionic acid methyl ester (1.50 g, 83.8%) as a clear oil: EI-HRMS m/e calcd for $C_{16}H_{21}FO_3$ ($M^+$) 280.1477 found 280.1474.

A solution of 3-cyclopentyl-2-(3-fluoro-4-methoxy-phenyl)-propionic acid methyl ester (1.04 g, 3.73 mmol) in tetrahydrofuran/water/methanol (9.3 mL, 3:1:1) was treated with a 1N aqueous lithium hydroxide solution (3.73 mL, 3.73 mmol). The reaction was stirred at 25° C. for 18 h. At this time, the reaction was acidified to pH=1 with a 1N aqueous hydrochloric acid solution and extracted with ethyl acetate (3×50 mL). The combined organic layers were dried over sodium sulfate, filtered, and concentrated in vacuo. Flash chromatography (Merck Silica gel 60, 230–400 mesh, 50/50 hexanes/ethyl acetate) afforded 3-cyclopentyl-2-(3-fluoro-4-methoxy-phenyl)-propionic acid (707.8 mg, 71.3%) as a white solid: mp 149–151° C.; EI-HRMS m/e calcd for $C_{15}1H_{19}FO_3$ ($M^+$) 266.1318 found 266.1317.

A solution of 3-cyclopentyl-2-(3-fluoro-4-methoxy-phenyl)-propionic acid (400.0 mg, 1.50 mmol) in methylene chloride (5.0 mL) cooled to 0° C. was treated with a 2.0M solution of oxalyl chloride in methylene chloride (0.82 mL, 1.65 mmol) and a few drops of N,N-dimethylformamide. The reaction mixture was stirred at 0° C. for 10 min and at 25° C. for 30 min. The reaction mixture was then treated with a solution of 2-aminothiazole (331 mg, 3.30 mmol) and N,N-diisopropylethylamine (0.62 mL, 3.60 mmol) in tetrahydrofuran (7.5 mL). This solution was stirred at 25° C. for 18 h. At this time, the reaction was concentrated in vacuo. Flash chromatography (Merck Silica gel 60, 230–400 mesh, 80/20 hexanes/ethyl acetate) afforded 3-cyclopentyl-2-(3-fluoro-4-methoxy-phenyl)-N-thiazol-2-yl-propionamide (538.4 mg, 100%) as a white solid: mp 51–53° C.: EI-HRMS m/e calcd for $C_{18}H_{21}FN_2O_2S$ ($M^+$) 348.1307 found 348.1312.

EXAMPLE 119

3-Cyclopentyl-2-(3-fluoro-4-hydroxy-phenyl)-N-thiazol-2-yl-propionamide

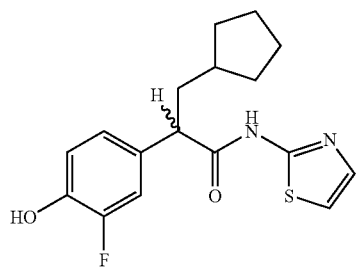

A solution of 3-cyclopentyl-2-(3-fluoro-4-methoxy-phenyl)-N-thiazol-2-yl-propionamide (prepared as in Example 118, 305.4 mg, 0.87 mmol) in methylene chloride (8.7 mL) at 25° C. was treated with a 1.0M solution of boron tribromide in methylene chloride (8.75 mL, 8.75 mmol). This solution was stirred at 25° C. for 5 h. At this time, the reaction was cooled to 0° C. and quenched by the dropwise addition of a dilute aqueous ammonium hydroxide solution. The resulting solution was stirred at 0° C. for 15 min. This mixture was then poured into water (50 mL) and extracted with ethyl acetate (3×30 mL). The combined organic layers were dried over sodium sulfate, filtered, and concentrated in vacuo. Flash chromatography (Merck Silica gel 60, 230–400 mesh, 50/50 hexanes/ethyl acetate) afforded 3-cyclopentyl-2-(3-fluoro-4-hydroxy-phenyl)-N-thiazol-2-yl-propionamide (212.7 mg, 72.5%) as a white solid: mp 199–201° C.: EI-HRMS m/e calcd for $C_{17}H_{19}FN_2O_2S$ (M+) 334.1151 found 334.1152.

EXAMPLE 120

6-[2-(3-Chloro-phenyl)-3-cyclopentyl-propionylamino]-nicotinic Acid

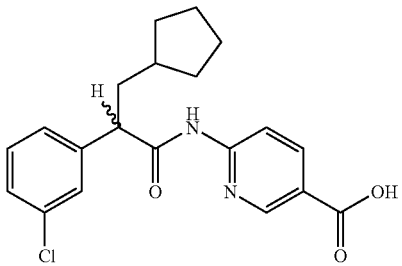

A solution of freshly prepared lithium diisopropylamide (141.3 mL of a 0.32M stock solution, 45.0 mmol) cooled to −78° C. was treated with (3-chloro-phenyl)-acetic acid (3.41 g, 20.0 mmol) in tetrahydrofuran/1,3-dimethyl-3,4,5,6-tetrahydro-2(1H)-pyrimidinone (49.7 mL, 3:1). The resulting solution was stirred at −78° C. for 1 h. At this time, the reaction was treated with a solution of iodomethylcyclopentane (4.64 g, 22.08 mmol) in 1,3-dimethyl-3,4,5,6-tetrahydro-2(1H)-pyrimidinone (4.64 mL). The reaction mixture was stirred at −78° C. for 4 h. The reaction was then warmed to 25° C. and was stirred at 25° C. for 48 h. This solution was then quenched by the slow addition of the reaction mixture to a 2N aqueous hydrochloric acid solution (50 mL). The product was extracted into ethyl acetate (1×150 mL). The organic layer was dried over sodium sulfate, filtered, and concentrated in vacuo. Flash chromatography (Merck Silica gel 60, 230–400 mesh, 85/15 hexanes/ethyl acetate) afforded 2-(3-chloro-phenyl)-3-cyclopentyl-propionic acid (3.68 g, 72.9%) as a yellow solid: mp 70–72° C.; EI-HRMS m/e calcd for $C_{14}H_{17}ClO_2$ (M+) 252.0917, found 252.0915.

A solution of 2-(3-chloro-phenyl)-3-cyclopentyl-propionic acid (504 mg, 2.0 mmol) in methylene chloride (20 mL) cooled to 0° C. was treated with a 2.0M solution of oxalyl chloride in methylene chloride (1.1 mL, 2.2 mmol) and a few drops of N,N-dimethylformamide. The reaction mixture was stirred at 0° C. for 15 min and at 25° C. for 2 h. The reaction mixture was then treated with 6-amino-nicotinic acid methyl ester (532 mg, 3.5 mmol) and N,N-diisopropylethylamine (0.84 mL, 4.8 mmol). This solution was stirred at 25° C. for 18 h. At this time, the reaction was concentrated in vacuo. Flash chromatography (Merck Silica gel 60, 230–400 mesh, 50/50 hexanes/ethyl acetate) afforded 6-[2-(3-chloro-phenyl)-3-cyclopentyl-propionylamino]-nicotinic acid methyl ester (151.9 mg, 19.7%) as a colorless oil: EI-HRMS m/e calcd for $C_{21}H_{23}ClN_2O_3$ (M+) 386.1397, found 386.1398.

A solution of 6-[2-(3-chloro-phenyl)-3-cyclopentyl-propionylamino]-nicotinic acid methyl ester (146.9 mg, 0.38 mmol) in tetrahydrofuran/water/methanol (10 mL, 3:1:1) at 25° C. was treated with a 2N aqueous sodium hydroxide solution (0.4 mL, 0.80 mmol). The reaction mixture was stirred at 25° C. for 4 d. At this time, the reaction was concentrated in vacuo. The residue was diluted with water (50 mL) and extracted with diethyl ether (1×50 mL). The aqueous layer was acidified to pH=1 by the dropwise addition of a 3N aqueous hydrochloric acid solution. This solution was extracted with a solution of methylene chloride/methanol (3:1, 3×75 mL). The combined organic layers were dried over magnesium sulfate, filtered, and concentrated in vacuo. The resulting solid was triturated with diethyl ether/hexanes (2:1) to afford 6-[2-(3-chloro-phenyl)-3-cyclopentyl-propionylamino]-nicotinic acid (63.6 mg, 44.4%) as a white solid: mp 251–255° C.; EI-HRMS m/e calcd for $C_{20}H_{21}ClN_2O_3$ (M+) 372.1240, found 372.1250.

EXAMPLE 121

6-[3-Cyclopentyl-2-(4-nitro-phenyl)-propionylamino]-nicotinic Acid Methyl Ester

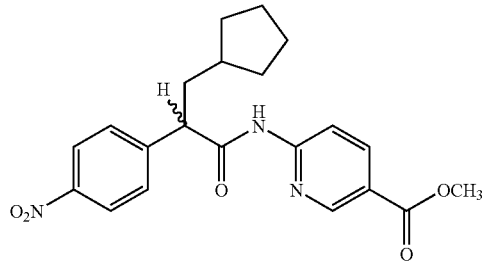

A solution of 3-cyclopentyl-2-(4-nitro-phenyl)-propionic acid (prepared as in Example 22A, 526 mg, 2.0 mmol) in methylene chloride (20 mL) cooled to 0° C. was treated with a 2.0M solution of oxalyl chloride in methylene chloride (1.2 mL, 2.4 mmol) and a few drops of N,N-dimethylformamide. The reaction mixture was stirred at 0° C. for 15 min and at 25° C. for 30 min. The reaction mixture was then treated with a solution of 6-amino-nicotinic acid methyl ester (532 mg, 3.5 mmol) in tetrahydrofuran (10 mL) and N,N-diisopropylethylamine (0.84 mL, 4.8 mmol). This solution was stirred at 25° C. for 48 h. At this time, the reaction was concentrated in vacuo. Flash chromatography (Merck Silica gel 60, 230–400 mesh, 80/20 hexanes/ethyl acetate) afforded 6-[3-cyclopentyl-2-(4-nitro-phenyl)-propionylamino]-nicotinic acid methyl ester (353.9 mg, 44.6%) as a pale orange glass: EI-HRMS m/e calcd for $C_{21}H_{23}N_3O_5$ (M+) 397.1637, found 397.1631.

EXAMPLE 122

2-(4-Amino-phenyl)-3-cyclopentyl-N-pyridin-2-yl-propionamide

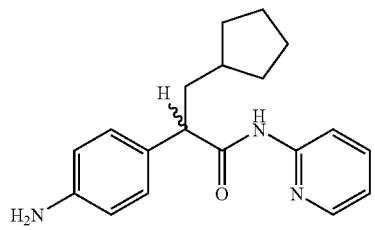

A solution of 3-cyclopentyl-2-(4-nitro-phenyl)-propionic acid (prepared as in Example 22A, 263 mg, 1.0 mmol) in methylene chloride (10 mL) cooled to 0° C. was treated with a 2.0M solution of oxalyl chloride in methylene chloride (0.6 mL, 1.2 mmol) and a few drops of N,N-dimethylformamide. The reaction mixture was stirred at 0° C. for 15 min and at 25° C. for 30 min. The reaction mixture was then treated with a solution of 2-aminopyridine (200.6 mg, 2.14 mmol) in tetrahydrofuran (5 mL) and N,N-diisopropylethylamine (0.42 mL, 2.4 mmol). This solution was stirred at 25° C. for 48 h. At this time, the reaction was concentrated in vacuo. Flash chromatography (Merck Silica gel 60, 230–400 mesh, 80/20 hexanes/ethyl acetate) afforded 3-cyclopentyl-2-(4-nitro-phenyl)-N-pyridin-2-yl-propionamide (138.6 mg, 40.9%) as a pale yellow glass: EI-HRMS m/e calcd for $C_{19}H_{21}N_3O_3$ (M+) 339.1581, found 339.1582.

A mixture of 3-cyclopentyl-2-(4-nitro-phenyl)-N-pyridin-2-yl-propionamide (130 mg, 0.38 mmol) in ethyl acetate (50 mL) and methanol (5 mL) was treated with a catalytic amount of 10% palladium on activated carbon (50 mg). The resulting mixture was shaken at 25° C. under 60 psi of hydrogen gas in a Parr apparatus for 24 h. At this time, the catalyst was removed by filtration through a plug of celite. The filtrate was concentrated in vacuo to afford 2-(4-amino-phenyl)-3-cyclopentyl-N-pyridin-2-yl-propionamide (99.9 mg, 84.3%) as a tan oil: EI-HRMS m/e calcd for $C_{19}H_{23}N_3O$ (M+) 309.1834, found 309.1849.

EXAMPLE 123

6-[2-(4-Amino-phenyl)-3-cyclopentyl-propionylamino]-nicotinic Acid Methyl Ester

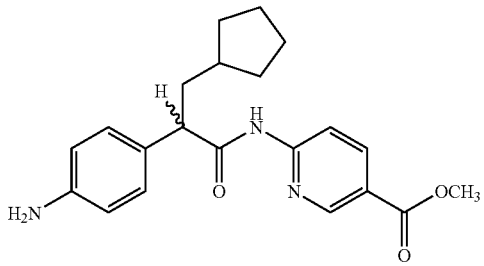

A solution of 3-cyclopentyl-2-(4-nitro-phenyl)-propionic acid (prepared as in Example 22A, 526 mg, 2.0 mmol) in methylene chloride (20 mL) cooled to 0° C. was treated with a 2.0M solution of oxalyl chloride in methylene chloride (1.2 mL, 2.4 mmol) and a few drops of N,N-dimethylformamide. The reaction mixture was stirred at 0° C. for 15 min and at 25° C. for 30 min. The reaction mixture was then treated with a solution of 6-amino-nicotinic acid methyl ester (532 mg, 3.5 mmol) in tetrahydrofuran (10 mL) and N,N-diisopropylethylamine (0.84 mL, 4.8 mmol). This solution was stirred at 25° C. for 48 h. At this time, the reaction was concentrated in vacuo. Flash chromatography (Merck Silica gel 60, 230–400 mesh, 80/20 hexanes/ethyl acetate) afforded 6-[3-cyclopentyl-2-(4-nitro-phenyl)-propionylamino]-nicotinic acid methyl ester (353.9 mg, 44.6%) as a pale orange glass: EI-HRMS m/e calcd for $C_{21}H_{23}N_3O_5$ (M+) 397.1637, found 397.1631.

A mixture of 6-[3-cyclopentyl-2-(4-nitro-phenyl)-propionylamino]-nicotinic acid methyl ester (300 mg, 0.75 mmol) in ethyl acetate (30 mL) was treated with a catalytic amount of 10% palladium on activated carbon (30 mg). The resulting mixture was shaken at 25° C. under 60 psi of hydrogen gas in a Parr apparatus for 24 h. At this time, the catalyst was removed by filtration through a plug of celite. The filtrate was concentrated in vacuo to afford 6-[2-(4-amino-phenyl)-3-cyclopentyl-propionylamino]-nicotinic acid methyl ester (262.8 mg, 94.7%) as a pale yellow glass: EI-HRMS m/e calcd for $C_{21}H_{25}N_3O_3$ (M+) 367.1895, found 367.1899.

EXAMPLE 124

3-Cyclohexyl-2-(4-methanesulfonyl-3-trifluoromethyl-phenyl)-N-thiazol-2-yl-propionamide

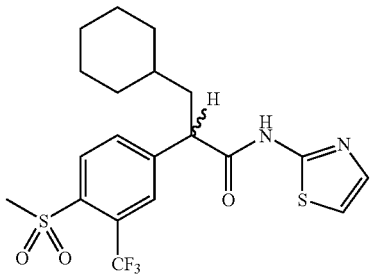

A solution of isoamyl nitrite (4.02 mL, 30 mmol) in dimethyl disulfide (19.8 mL, 220 mmol) at 25° C. was slowly treated with 4-bromo-2-(trifluoromethyl)aniline (4.8 g, 20 mmol). The reaction was exothermic with gas evolution. The resulting brown reaction mixture was heated to 80–90° C. for 2 h, at which time, thin layer chromatography analysis of the reaction mixture indicated the absence of starting material. The reaction mixture was cooled to 25° C. and then concentrated in vacuo. The resulting residue was dissolved in ethyl acetate (200 mL). The organic layer was washed successively with a 1N aqueous hydrochloric acid solution (1×200 mL) and a saturated aqueous sodium chloride solution (1×200 mL), dried over anhydrous magnesium sulfate, filtered, and concentrated in vacuo. Biotage chromatography (FLASH 40M, Silica, 8/1 hexanes/ethyl acetate) afforded 4-bromo-1-methylsulfanyl-2-trifluoromethyl-benzene (4.73 g, 87%) as a brown oil: EI-HRMS m/e calcd for $C_8H_6BrF_3S$ (M+) 269.9326, found 269.9327.

A solution of 4-bromo-1-methylsulfanyl-2-trifluoromethyl-benzene (4.71 g, 17.4 mmol) in methylene chloride (100 mL) was cooled to −10° C. and then treated with 3-chloroperoxybenzoic acid (86% grade, 9.0 g, 52.2 mmol). The reaction mixture was stirred at −10° C. for 10 min and then allowed to warm to 25° C. where it was stirred overnight. At this time, thin layer chromatography analysis of the reaction mixture indicated the absence of starting material. The reaction mixture was then filtered, and the solids were washed with methylene chloride (1×50 mL). The filtrate was concentrated in vacuo. The resulting residue was dissolved in ethyl acetate (100 mL). The organic layer was washed successively with a saturated aqueous sodium bicarbonate solution (2×100 mL) and a saturated aqueous sodium chloride solution (1×100 mL), dried over anhydrous magnesium sulfate, filtered, and concentrated in vacuo to afford a yellow solid. Recrystallization from methylene chloride (20 mL), diethyl ether (10 mL), and hexanes afforded 4-bromo-1-methanesulfonyl-2-trifluoromethyl-benzene (3.46 g, 57%) as a white solid: mp 110–112° C.; EI-HRMS m/e calcd for $C_8H_6BrF_3O_2S$ (M+) 301.9224, found 301.9223.

A mixture of zinc dust (1.3 g, 20 mmol, Aldrich, −325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (prepared as in Example 108, 2.5 g, 8.5 mmol) in dry tetrahydrofuran (3 mL) over 5 min. After the addition, the reaction mixture was stirred for 1 h at 40–45° C. and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone)palladium(0) (108 mg, 0.2 mmol) and triphenylphosphine (209 mg, 0.8 mmol) in dry tetrahydrofuran (10 mL) was stirred at 25° C. under argon for 10 min and then treated with 4-bromo-1-methanesulfonyl-2-trifluoromethyl-benzene (2.12 g, 7 mmol) and the freshly prepared zinc compound in tetrahydrofuran. The resulting brick red solution was heated at 40–45° C. for 2 d. The reaction mixture was cooled to 25° C. and then poured into a saturated aqueous ammonium chloride solution (100 mL), and the organic compound was extracted into ethyl acetate (3×75 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 9/1 to 3/1 hexanes/ethyl acetate) afforded (E)-3-cyclohexyl-2-(4-methanesulfonyl-3-trifluoromethyl-phenyl)-acrylic acid methyl ester (2.7 g, 99%) as a viscous oil: EI-HRMS m/e calcd for $C_{18}H_{21}F_3O_4S$ (M$^+$) 391.1191, found 391.1200.

A solution of nickel(II) chloride hexahydrate (36.6 mg, 0.154 mmol) and (E)-3-cyclohexyl-2-(4-methanesulfonyl-3-trifluoromethyl-phenyl)-acrylic acid methyl ester (302 mg, 0.77 mmol) in methanol (8 mL) was cooled to 0° C. and then treated with sodium borohydride (87 mg, 2.29 mmol) in four portions. After the addition, the black reaction mixture was stirred for 15 min at 0° C. and then allowed to warm to 25° C. where it was stirred for 15 h. The black solid was filtered using filter paper and washed with methanol. The combined solvents were concentrated in vacuo, and the residue was diluted with ethyl acetate (50 mL). The organic layer was washed successively with a 3N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo to afford racemic 3-cyclohexyl-2-(4-methanesulfonyl-3-trifluoromethyl-phenyl)-propionic acid methyl ester (280 mg, 93%) as a viscous oil: EI-HRMS m/e calcd for $C_{18}H_{23}F_3O_4S$ (M$^+$) 392.1269, found 392.1276.

A solution of 3-cyclohexyl-2-(4-methanesulfonyl-3-trifluoromethyl-phenyl)-propionic acid methyl ester (265 mg, 0.67 mmol) in ethanol (5 mL) was treated with a 1N aqueous sodium hydroxide solution (1.5 mL). The solution was heated at 45–50° C. for 5 h, at which time, thin layer chromatography analysis of the mixture indicated the absence of starting material. The reaction mixture was then concentrated in vacuo to remove ethanol, and the residue was diluted with water (20 mL) and extracted with diethyl ether (1×40 mL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×50 mL), dried over anhydrous magnesium sulfate, filtered, and concentrated in vacuo to afford 3-cyclohexyl-2-(4-methanesulfonyl-3-trifluoromethyl-phenyl)-propionic acid (249 mg, 97%) as a viscous oil: EI-HRMS m/e calcd for $C_{17}H_{21}F_3O_4S$ (M$^+$) 378.1113, found 378.1121.

A solution of triphenylphosphine (279 mg, 1.06 mmol) in methylene chloride (5 mL) was cooled to 0° C. and then treated with N-bromosuccinimide (188.7 mg, 1.06 mmol). The reaction mixture was stirred at 0° C. for 30 min and then treated with a solution of 3-cyclohexyl-2-(4-methanesulfonyl-3-trifluoromethyl-phenyl)-propionic acid (237 mg, 0.626 mmol) in methylene chloride (4 mL). The clear solution was stirred for 15 min at 0° C. and then allowed to warm to 25° C. where it was stirred for 2 h. The reaction mixture was then treated with 2-aminothiazole (188 mg, 1.88 mmol), and the resulting suspension was stirred for 15 h at 25° C. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 4/1 to 2/1 hexanes/ethyl acetate) afforded 3-cyclohexyl-2-(4-methanesulfonyl-3-trifluoromethyl-phenyl)-N-thiazol-2-yl-propionamide (83 mg, 29%) as an amorphous solid: EI-HRMS m/e calcd for $C_{20}H_{23}F_3N_2O_3S_2$ (M$^+$) 460.1102, found 460.1100.

EXAMPLE 125

3-Cyclopentyl-2-(4-methoxymethanesulfonyl-phenyl)-N-thiazol-2-yl-propionamide

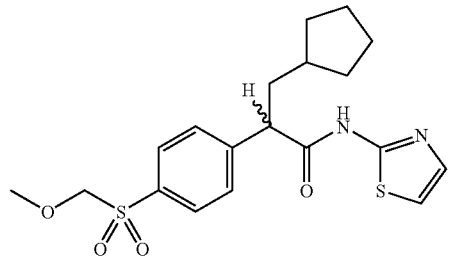

A solution of (4-mercapto-phenyl)-acetic acid (1.00 g, 5.94 mmol) in methanol (10 mL) was treated with a catalytic amount of concentrated sulfuric acid (2 drops). The reaction was heated under reflux for 2 h. At this time, the reaction mixture was concentrated in vacuo. The residue was re-dissolved in chloroform and washed with a saturated aqueous sodium bicarbonate solution. The organic layer was dried over magnesium sulfate, filtered, and concentrated in vacuo to afford (4-mercapto-phenyl)-acetic acid methyl ester (1.04 g, 96%) as a colorless oil: EI-HRMS m/e calcd for $C_9H_{10}O_2S$ (M$^+$) 182.0402, found 182.0405.

A solution of (4-mercapto-phenyl)-acetic acid methyl ester (500 mg, 2.7 mmol) and chloromethyl methyl ether (331 mg, 4.1 mmol) in acetonitrile (3 mL) and pyridine (1 mL) was heated under reflux for 16 h. At this time, the reaction was concentrated in vacuo. The residue was re-dissolved in ethyl acetate (10 mL) and was washed with a 1N aqueous hydrochloric acid solution (2×25 mL) and a saturated aqueous sodium chloride solution. The organic layer was dried over magnesium sulfate, filtered and concentrated in vacuo. Flash chromatography (Merck Silica gel 60, 230–400 mesh, 90/10 hexanes/ethyl acetate) afforded (4-methoxymethylsulfanyl-phenyl)-acetic acid methyl ester (482 mg, 77.6%) as a clear oil: EI-HRMS m/e calcd for $C_{11}H_{14}O_3S$ (M+) 226.0664, found 226.0664.

A solution of (4-methoxymethylsulfanyl-phenyl)-acetic acid methyl ester (441 mg, 1.90 mmol) in methanol (1 mL), water (0.5 mL), and tetrahydrofuran (0.5 mL) was treated with lithium hydroxide (51 mg, 2.1 mmol). The reaction mixture was stirred at 25° C. for 20 h. At this time, the reaction was concentrated in vacuo. The residue was re-dissolved in water and extracted with ethyl acetate. The aqueous layer was then acidified to pH=1 with a 1N aqueous hydrochloric acid solution. This solution was extracted with ethyl acetate. The combined organic extracts were dried over sodium sulfate, filtered, and concentrated in vacuo to afford (4-methoxymethylsulfanyl-phenyl)-acetic acid (402 mg, 100%) as a clear oil which was used without further purification.

A solution of diisopropylamine (0.37 mL, 2.62 mmol) in tetrahydrofuran (2 mL) was cooled to −78° C. and then treated with a 2.5M solution of n-butyllithium in hexanes (1.05 mL, 2.62 mmol). This solution was stirred at −78° C. for 30 min and then treated with a solution of (4-methoxymethylsulfanyl-phenyl)-acetic acid (223 mg, 1.05 mmol) in tetrahydrofuran (1.5 mL) and 1,3-dimethyl-3,4,5,6-tetrahydro-2(1H)-pyrimidinone (0.5 mL). The reaction mixture was allowed to stir at −78° C. for 1 h. At this time, the reaction was treated with iodomethylcyclopentane (328 mg, 1.56 mmol). The reaction mixture was allowed to slowly warm to 25° C. where it was stirred for 18 h. At this time, the reaction, mixture was quenched with a saturated aqueous sodium bicarbonate solution and then concentrated in vacuo. The residue was treated with a 1N aqueous sodium hydroxide solution and extracted with ethyl acetate. The aqueous layer was then acidified with concentrated hydrochloric acid. This solution was extracted with ethyl acetate. The combined organic extracts were dried over magnesium sulfate, filtered, and concentrated in vacuo. Biotage chromatography (FLASH 12M, Silica, 80/20 hexanes/ethyl acetate) afforded 3-cyclopentyl-2-(4-methoxymethylsulfanyl-phenyl)-propionic acid (202 mg, 65%) as an off-white solid: mp 167–170° C.; EI-HRMS m/e calcd for $C_{16}H_{22}O_3S$ (M+) 294.1290, found 294.1288.

A solution of 3-cyclopentyl-2-(4-methoxymethylsulfanyl-phenyl)-propionic acid (50 mg, 0.17 mmol) in methanol (1 mL), water (0.2 mL), and pH=4 phosphate buffer (0.5 mL) at 25° C. was treated with oxone (314 mg, 0.51 mmol). The reaction was stirred at 25° C. for 6 h. At this time, the reaction was concentrated in vacuo. The residue was dissolved in ethyl acetate and washed with a 1N aqueous hydrochloric acid solution (2×25 mL). The organic layer was then dried over magnesium sulfate, filtered, and concentrated in vacuo to afford 3-cyclopentyl-2-(4-methoxymethanesulfonyl-phenyl)-propionic acid (35 mg, 63.2%) as a white solid: mp 184–187° C.; EI-HRMS m/e calcd for $C_{16}H_{22}O_5S$ (M+) 326.1188, found 326.1189.

A solution of 3-cyclopentyl-2-(4-methoxymethanesulfonyl-phenyl)-propionic acid (31 mg, 0.09 mmol), benzotriazol-1-yloxytris(dimethylamino)phosphonium hexafluorophosphate (67 mg, 0.15 mmol), and 2-aminothiazole (15 mg, 0.15 mmol) in methylene chloride (1 mL) at 25° C. was treated with triethylamine (0.04 mL, 0.29 mmol). The reaction was stirred at 25° C. for 20 h. At this time, the reaction was treated with a saturated aqueous sodium bicarbonate solution. The resulting organic layer was washed with a 1N aqueous hydrochloric acid solution, dried over magnesium sulfate, filtered, and concentrated in vacuo. Flash chromatography (Merck Silica gel 60, 230–400 mesh, 80/20 hexanes/ethyl acetate) afforded 3-cyclopentyl-2-(4-methoxymethanesulfonyl-phenyl)-N-thiazol-2-yl-propionamide (23 mg, 59.2%) as a white solid: mp 157–160° C.; EI-HRMS m/e calcd for $C_{19}H_{24}N_2O_4S_2$ (M+) 408.1178, found 408.1178.

EXAMPLE 126

3-Cyclopentyl-2(R)-(4-methylsulfanyl-phenyl)-N-pyrazin-2-yl-propionamide

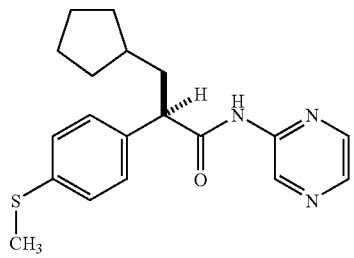

A mixture of 4-(methylthio)phenylacetic acid (50 g, 272 mmol) in tetrahydrofuran (250 mL) was treated with freshly powdered potassium carbonate (93.8 g, 679 mmol). A very mild exotherm ensued, and the resulting white suspension was stirred at 25–26° C. for 30 min. The reaction mixture was then cooled to −10° C. and treated with trimethylacetyl chloride (35.5 mL, 285 mmol) over 30 min. After completion of the addition, the reaction mixture was then stirred at −10° C. to −5° C. for 30 min and then treated with (1R, 2R)-(−)-pseudoephedrine (59.5 g, 353 mmol) in portions over 15 min while maintaining the temperature of the reaction mixture between −10° C. and −4° C. The reaction mixture was then stirred at −7° C. to 0° C. for 3 h. The reaction mixture was then quenched at 0° C. by the addition of water (150 mL). After vigorously stirring for 10 min, toluene (150 mL) was added, and the reaction mixture was stirred for 5 min. The organic layer was separated and washed with water (2×100 mL). The combined aqueous layers were back-extracted with toluene (1×50 mL). The combined organic layers were washed with a 1N aqueous sulfuric acid solution (1×200 mL), a saturated aqueous sodium bicarbonate solution (1×200 mL), and a solution of water/saturated aqueous sodium chloride solution (1:1, 1×50 mL). The resulting organic layer was then concentrated in vacuo to afford a white solid. This white solid was dried overnight under high vacuum (0.4 mm Hg) to afford crude N-[2(R)-hydroxy-1(R)-methyl-2(R)-phenyl-ethyl]-N-methyl-2-(4-methylsulfanyl-phenyl)-acetamide (82.8 g, 92.6% pure by HPLC analysis). This material was dissolved in toluene (225 mL) at reflux. After standing in a refrigerator over the weekend, the resulting crystalline material was collected by filtration, washed with cold toluene (3×35 mL), and dried under high vacuum to afford N-[2(R)-hydroxy-1(R)-methyl-2(R)-phenyl-ethyl]-N-methyl-2-(4-methylsulfanyl-phenyl)-acetamide (66.1 g, 73.1%) as white crystals: mp 112–113° C.; 99.6% pure by HPLC analysis. HPLC conditions as follows:

| Column: | ES Si, 3 μ, 5 × 150 mm |
|---|---|
| Mobile Phase: | 30% THF in heptane at 1 mL/min |
| Detection: | UV, 259 nm |
| Retention Time: | 20 min |

A solution of triphenylphosphine (28.80 g, 109.8 mmol) and imidazole (14.9 g, 219.6 mmol) in methylene chloride (160 mL) was cooled to 0° C. and then slowly treated with iodine (27.87 g, 109.8 mmol). The reaction mixture was then treated dropwise with a solution of cyclopentylmethanol (10.00 g, 99.8 mmol) in methylene chloride (10 mL). The resulting reaction mixture was allowed to warm to 25° C. where it was stirred for for 4 h. The reaction mixture was then diluted with water (50 mL), and the reaction mixture was further extracted with methylene chloride (3×20 mL). The combined organic layers were dried over sodium sulfate, filtered, and concentrated in vacuo at 25° C. The resulting solid was washed with pentane (4×50 mL) and filtered through a silica gel plug. The filtrate was concentrated in vacuo at 25° C. to afford iodomethylcyclopentane (18.48 g, 88%) as a clear colorless liquid: EI-HRMS m/e calcd for $C_6H_{11}I$ ($M^+$) 209.9906, found 209.9911.

A solution of 1,1,1,3,3,3-hexamethyldisilazane (98.4 mL, 457 mmol) in tetrahydrofuran (400 mL) was cooled to −20° C. and then treated with a 2.29M solution of n-butyllithium in hexanes (182 mL, 418 mmol) over 35 min while maintaining the temperature between −20° C. and −15° C. The reaction mixture was stirred at −20° C. for 30 min and then was treated with a solution of N-[2(R)-hydroxy-1 (R)-methyl-2(R)-phenyl-ethyl]-N-methyl-2-(4-methylsulfanyl-phenyl)-acetamide (66.1 g, 201 mmol) in tetrahydrofuran (500 mL) over 50 min while maintaining the temperature between −20° C. and −15° C. The resulting yellow solution was stirred at 0° C. for 30 min and then treated with a premixed solution of 1,3-dimethyl-3,4,5,6-tetrahydro-2 (1H)-pyrimidinone (51 mL, 418 mmol) and iodomethylcyclopentane (50.6 g, 239 mmol) over 30 min. The resulting reaction mixture was stirred at 0° C. for 4 h, at which time, thin layer chromatography analysis indicated that the reaction was complete. The reaction mixture was then poured into toluene (400 mL). The organic phase was washed sequentially with a solution of water/saturated aqueous sodium chloride solution (1:1, 1×1000 mL), a solution of water/saturated aqueous sodium chloride solution (1:2, 1×1000 mL), a 1M aqueous sulfuric acid solution (1×800 mL), water (1×200 mL), and a saturated aqueous sodium bicarbonate solution (1×1000 mL). The resulting organic layer was concentrated in vacuo to afford crude 3-cyclopentyl-N-[2(R)-hydroxy-1(R)-methyl-2(R)-phenyl-ethyl]-N-methyl-2(R)-(4-methylsulfanyl-phenyl)-propionamide as an oily yellow residue (98.5% de by HPLC analysis). This material was dissolved in ethyl acetate (70 mL) and subsequently treated with hexanes (200 mL). The solution was stored in a freezer over the weekend. The resulting solid was collected by filtration, washed with cold hexanes (ca. −10° C., 3×30 mL), and then dried under high vacuum to afford 3-cyclopentyl-N-[2(R)-hydroxy-1 (R)-methyl-2(R)-phenyl-ethyl]-N-methyl-2(R)-(4-methylsulfanyl-phenyl)-propionamide (48.8 g, 59%) as a white solid: mp 82–84° C.; 100% de by HPLC analysis. The combined filtrate and washes were concentrated in vacuo, and the residue (34.4 g) was placed on top of a plug of thin layer chromatography grade silica gel (2–25μ, 70 g). The silica gel plug was then washed with a solution of hexanes/ethyl acetate (4:1, 1.5 L), and the combined eluates were concentrated in vacuo. The resulting pale-yellow oil was dissolved in ethyl acetate (35 mL) and subsequently treated with hexanes (100 mL). The solution was stored in a refrigerator overnight. The resulting solid was collected by filtration, washed with cold hexanes (ca. −10° C., 3×25 mL), and dried under high vacuum to afford 3-cyclopentyl-N-[2(R)-hydroxy-1(R)-methyl-2(R)-phenyl-ethyl]-N-methyl-2(R)-(4-methylsulfanyl-phenyl)-propionamide (17.3 g, 20.9%) as a white solid: mp 83–85° C.; 99.6% de by HPLC analysis. These two crops were combined to afford the desired diastereomer, 3-cyclopentyl-N-[2(R)-hydroxy-1 (R)-methyl-2(R)-phenyl-ethyl]-N-methyl-2(R)-(4-methylsulfanyl-phenyl)-propionamide (66.1 g, 79.9%), as a white solid. HPLC conditions as follows:

| Column: | ES Si, 3 μ, 5 × 150 mm |
|---|---|
| Mobile Phase: | 20% THF in heptane at 1 mL/min |
| Detection: | UV, 259 nm |
| Retention Time: | 9.2 min (undesired diastereomer) and 14.4 min (desired diastereomer) |

A solution of 3-cyclopentyl-N-[2(R)-hydroxy-1(R)-methyl-2(R)-phenyl-ethyl]-N-methyl-2(R)-(4-methylsulfanyl-phenyl)-propionamide (4.00 g, 9.72 mmol) in dioxane (8 mL) was treated with a 9N aqueous sulfuric acid solution (7.7 mL). The two-phase mixture was heated at reflux, resulting in a homogeneous colorless solution. After heating at reflux for 16 h, the reaction mixture was cooled to 5° C. with an ice-water bath and then treated dropwise with water (20 nL) to precipitate the product. After the resulting suspension was stirred for 1 h with ice-water cooling, the solid was collected by filtration, washed with water (4×10 mL), and dried by suction to afford crude 3-cyclopentyl-2R-(4-methylsulfanyl-phenyl)-propionic (2.57 g, 96.6%, 96.3% ee by chiral HPLC analysis) as a light tan solid. This material was dissolved in glacial acetic acid (5 mL) at reflux and then treated with water (1 mL) to initiate crystallization. The heating bath was removed, and then water (4 mL) was added dropwise to the suspension to complete the crystallization. The mixture was allowed to cool to ambient temperature. After stirring for 1 h, the solid was collected by filtration. The solid was washed with a solution of acetic acid/water (1:1, 10 mL) and water (4×10 mL), and then dried to afford 3-cyclopentyl-2(R)-(4-methylsulfanyl-phenyl)-propionic (2.24 g, 87.2%) as a white solid: mp 75–76° C.; 96.4% ee by chiral HPLC analysis. Chiral HPLC conditions as follows:

| Column: | Chiralpak AS, 5 μ, 5 × 250 mm |
|---|---|
| Mobile Phase: | 6% isopropanol in hexane + 0.1% TFA at 0.5 mL/min |
| Detection: | UV, 259 nm |
| Retention Time: | 13.2 min (desired R-isomer) and 17.1 min (S-isomer) |

A solution of 3-cyclopentyl-2(R)-(4-methylsulfanyl-phenyl)-propionic acid (529 mg, 2.0 mmol) and triphenylphosphine (892 mg, 3.4 mmol) in methylene chloride (10 mL) was cooled to 0° C. and then treated with N-bromosuccinimide (605 mg, 3.4 mmol) in small portions. The reaction mixture color changed from light yellow to a darker yellow then to brown. After the complete addition of the N-bromosuccinimide, the reaction mixture was allowed to warm to 25° C. over 30 min. The brown reaction mixture was then treated with 2-aminopyrazine (476 mg, 5.0 mmol). The resulting reaction mixture was stirred at 25° C. for 19 h. The reaction mixture was then concentrated in vacuo to remove methylene chloride. The remaining black residue was diluted with a 10% aqueous hydrochloric acid solution (40 mL) and then extracted with ethyl acetate (3×25 mL). The combined organic layers were washed with a saturated aqueous sodium chloride solution (1×20 mL), dried over sodium sulfate, filtered, and concentrated in vacuo. Biotage chromatography (FLASH 40M, Silica, 65/35 hexanes/ethyl acetate) afforded 3-cyclopentyl-2(R)-(4-methylsulfanyl-phenyl)-N-pyrazin-2-yl-propionamide (102 mg, 15%) as a white solid: mp 128–130° C., $[\alpha]^{23}_{589}$=−103.1° (c=0.032, chloroform); EI-HRMS m/e calcd for $C_{19}H_{23}N_3OS$ ($M^+$) 341.1562, found 341.1563.

EXAMPLE 127

3-Cyclopentyl-2(R)-(4-methylsulfonyl-phenyl)-N-pyrazin-2-yl-propionamide

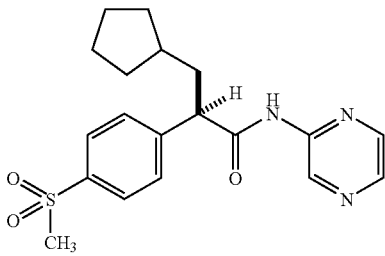

A solution of 3-cyclopentyl-2(R)-(4-methylsulfanyl-phenyl)-N-pyrazin-2-yl-propionamide (prepared as in Example 126, 68 mg, 0.20 mmol) in formic acid (0.24 mL) was cooled to 0° C. and then treated with a 30% aqueous hydrogen peroxide solution (0.11 mL, 1.0 mmol). The resulting solution was stirred at 0° C. for 3 h. The reaction was then concentrated in vacuo. Biotage chromatography (FLASH 12M, Silica, 1/1 hexanes/ethyl acetate) afforded 3-cyclopentyl-2(R)-(4-methylsulfonyl-phenyl)-N-pyrazin-2-yl-propionamide (58 mg, 77%) as a white foam: mp 75–80° C., $[\alpha]^{23}_{589}$=−29.4° (c=0.034, chloroform); EI-HRMS m/e calcd for $C_{19}H_{23}N_3O_3S$ ($M^+$) 373.1460, found 373.1451.

EXAMPLE 128

3-Cyclopentyl-2(R)-(4-methanesulfonyl-phenyl)-N-(4-methyl-thiazol-2-yl)-propionamide

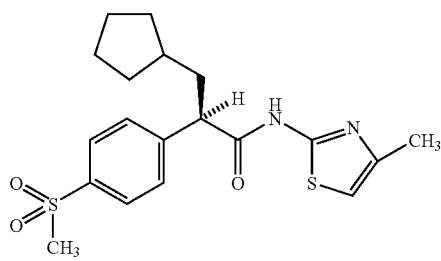

A solution of 3-cyclopentyl-2(R)-(4-methylsulfanyl-phenyl)-propionic (prepared as in Example 126, 50.03 g, 189.21 mmol) in formic acid (189 mL) was cooled to 0° C. and then slowly treated with a 30% aqueous hydrogen peroxide solution (58 mL, 567.64 mmol). The resulting reaction mixture was allowed to stir at 0° C. for 1 h and then allowed to warm to 25° C. where it was stirred for 3 h. The reaction mixture was re-cooled to 0° C. and then slowly quenched with a saturated aqueous sodium bisulfite solution (500 mL). A precipitate formed. The resulting suspension was stirred at 0° C. for 1 h and then the solid was filtered. The solid was washed with cold water (4×700 mL) and dried by suction to afford 3-cyclopentyl-2(R)-(4-methanesulfonylphenyl)propionic acid as a cream solid: mp 138–140° C.; $[\alpha]^{23}_{589}$=−50.0° (c=0.02, chloroform); EI-HRMS m/e calcd for $C_{15}H_{20}O_4S$ ($M^+$) 296.1082, found 296.1080.

A solution of triphenylphosphine (345 mg, 1.31 mmol) in methylene chloride (4 mL) was cooled to 0° C. and then treated with N-bromosuccinimide (234 mg, 1.31 mmol). The reaction mixture was stirred at 0° C. for 15 min and then treated with 3-cyclopentyl-2(R)-(4-methanesulfonylphenyl) propionic acid (300 mg, 1.01 mmol). The resulting reaction mixture was stirred at 0° C. for 5 min and then allowed to warm to 25° C. where it was stirred for 25 min. The reaction mixture was then treated with 2-amino-4-methylthiazole (288 mg, 2.52 mmol). The resulting reaction mixture was allowed to stir at 25° C. for 20 h. The reaction mixture was then diluted with water (30 mL), a 1N aqueous hydrochloric acid solution (5 mL), and ethyl acetate (30 mL). The layers were separated, and the organic layer was dried over magnesium sulfate, filtered, and concentrated in vacuo. Biotage chromatography (FLASH 40S, Silica, 1/1 hexanes/ethyl acetate) afforded 3-cyclopentyl-2(R)-(4-methanesulfonyl-phenyl)-N-(4-methyl-thiazol-2-yl)-propionamide (192 mg, 48%) as an off-white foam: mp 83–87° C. (foam to gel); $[\alpha]^{23}_{589}$=−35.7° (c=1.01, chloroform); EI-HRMS m/e calcd for $C_{19}H_{24}N_2O_3S_2$ ($M^+$) 392.1228, found 392.1227.

EXAMPLE 129

3-Cyclopentyl-2(R)-(4-methanesulfonyl-phenyl)-N-(5-methyl-thiazol-2-yl)-propionamide

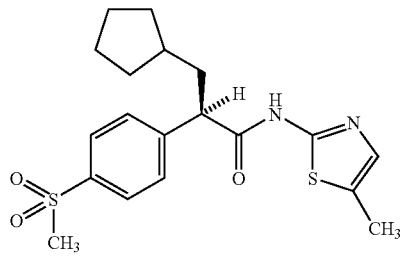

A solution of triphenylphosphine (345 mg, 1.31 mmol) in methylene chloride (4 mL) was cooled to 0° C. and then treated with N-bromosuccinimide (234 mg, 1.31 mmol). The reaction mixture was stirred at 0° C. for 15 min and then treated with 3-cyclopentyl-2(R)-(4-methanesulfonylphenyl) propionic acid (prepared as in Example 128, 300 mg, 1.01 mmol). The resulting reaction mixture was stirred at 0° C. for 5 min and then allowed to warm to 25° C. where it was stirred for 25 min. The reaction mixture was then treated with 2-amino-5-methylthiazole (288 mg, 2.52 mmol). The resulting reaction mixture was allowed to stir at 25° C. for 20 h. The reaction mixture was then diluted with water (30 mL), a 1N aqueous hydrochloric acid solution (5 mL), and ethyl acetate (30 mL). The layers were separated, and the organic layer was dried over magnesium sulfate, filtered, and concentrated in vacuo. Biotage chromatography (FLASH 40S, Silica, 1/1 hexanes/ethyl acetate) afforded 3-cyclopentyl-2(R)-(4-methanesulfonyl-phenyl)-N-(5-methyl-thiazol-2-yl)-propionamide (223 mg, 56%) as a pale yellow foam: mp 81–85° C. (foam to gel); $[\alpha]^{23}_{589}$=–40.4° (c=1.01, chloroform); EI-HRMS m/e calcd for $C_{19}H_{24}N_2O_3S_2$ (M$^+$) 392.1228, found 392.1225.

EXAMPLE 130

N-(5-Chloro-thiazol-2-yl)-3-cyclopentyl-2-(4-methanesulfonyl-phenyl)-propionamide

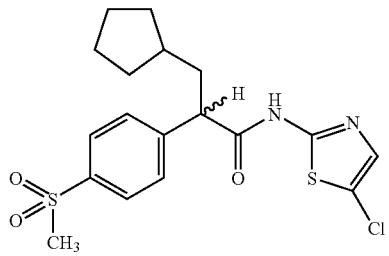

A solution of diisopropylamine (3.3 mL, 23.5 mmol) in dry tetrahydrofuran (50 mL) and 1,3-dimethyl-3,4,5,6-tetrahydro-2(1H)-pyrimidinone (10 mL) was cooled to –78° C. under nitrogen and then treated with a 10M solution of n-butyllithium in hexanes (2.35 mL, 23.5 mmol). The yellow reaction mixture was stirred at –78° C. for 30 min and then treated dropwise with a solution of 4-methylsulfonylphenylacetic acid (2.40 g, 11.2 mmol) in a small amount of dry tetrahydrofuran. After approximately one-half of the 4-methylsulfonylphenylacetic acid in dry tetrahydrofuran was added, a precipitate formed. Upon further addition of the remaining 4-methylsulfonylphenylacetic acid in dry tetrahydrofuran, the reaction mixture became thick in nature. After complete addition of the 4-methylsulfonylphenylacetic acid in dry tetrahydrofuran, the reaction mixture was very thick and became difficult to stir. An additional amount of dry tetrahydrofuran (20 mL) was added to the thick reaction mixture, and the reaction mixture was then stirred at –78° C. for 45 min. The reaction mixture was then treated with a solution of iodomethylcyclopentane (2.35 g, 11.2 mmol) in a small amount of dry tetrahydrofuran was added dropwise. The reaction mixture was allowed to warm to 25° C. where it was stirred for 15 h. The reaction mixture was quenched with water (100 mL), and the resulting yellow reaction mixture was concentrated in vacuo to remove tetrahydrofuran. The aqueous residue was acidified to pH=2 using concentrated hydrochloric acid. The aqueous layer was extracted with ethyl acetate. The organic phase was dried over magnesium sulfate, filtered, and concentrated in vacuo. Flash chromatography (Merck Silica gel 60, 230–400 mesh, 1/3 hexanes/ethyl acetate) afforded 3-cyclopentyl-2-(4-methanesulfonyl-phenyl)propionic acid (1.80 g, 52%) as a white solid: mp 152–154° C.; EI-HRMS m/e calcd for $C_{15}H_{20}O_4S$ (M$^+$) 296.1082, found 296.1080.

A solution of 3-cyclopentyl-2-(4-methanesulfonyl-phenyl)-propionic acid (300 mg, 1.01 mmol) and dry N,N-dimethylformamide (2 drops) in methylene chloride (3 mL) was cooled to 0° C. and then treated dropwise with oxalyl chloride (115 μL, 1.32 mmol). The reaction mixture was stirred at 0° C. for 10 min and then stirred at 25° C. for 1 h. The reaction mixture was concentrated in vacuo. The resulting yellow oil was dissolved in a small amount of methylene chloride and then slowly added to a solution of 2-amino-5-chlorothiazole hydrochloride (259 mg, 1.52 mmol) and triethylamine (424 μL, 3.04 mmol) in N,N-dimethylformamide (3 mL). The resulting reaction mixture was then stirred at 25° C. for 15 h. The reaction mixture was then partitioned between water (50 mL) and ethyl acetate (50 mL), and the layers were separated. The aqueous layer was back-extracted with ethyl acetate (50 mL). The combined organic layers were then dried over magnesium sulfate, filtered, and concentrated in vacuo. Flash chromatography (Merck Silica gel 60, 230–400 mesh, 1/1 hexanes/ethyl acetate) afforded the N-(5-chloro-thiazol-2-yl)-3-cyclopentyl-2-(4-methanesulfonyl-phenyl)-propionamide (106 mg, 25%) as a tan foam: mp 76–79° C. (foam to gel); EI-HRMS m/e calcd for $C_{18}H_{21}ClN_2O_3S_2$ (M$^+$) 412.0682, found 412.0683.

EXAMPLE 131

N-(5-Chloro-thiazol-2-yl)-3-cyclopentyl-2(R)-(4-methanesulfonyl-phenyl)-propionamide

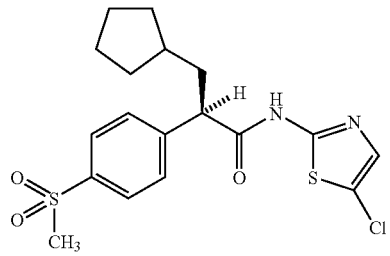

A solution of triphenylphosphine (4.60 g, 17.55 mmol) in methylene chloride (50 mL) was cooled to 0° C. and then treated with N-bromosuccinimide (3.12 g, 17.55 mmol). The reaction mixture was stirred at 0° C. for 25 min and then treated with 3-cyclopentyl-2(R)-(4-methanesulfonylphenyl) propionic acid (prepared as in Example 128, 4.00 g, 13.50 mmol). The resulting reaction mixture was stirred at 0° C. for 15 min and then allowed to warm to 25° C. where it was stirred for 30 min. The reaction mixture was then treated with a solution of 2-amino-5-chlorothiazole hydrochloride (5.77 g, 33.75 mmol) and pyridine (4.37 mL, 54.03 mmol) in methylene chloride. The resulting reaction mixture was allowed to stir at 25° C. overnight. The reaction mixture was then diluted with water (150 mL), a 1N aqueous hydrochloric acid solution (50 mL), and ethyl acetate (100 mL). The layers were separated. The organic layer was washed with a saturated aqueous sodium bicarbonate solution (2×50 mL) and then dried over magnesium sulfate, filtered, and concentrated in vacuo. Flash chromatography (Merck Silica gel 60, 230–400 mesh, 1/1 hexanes/ethyl acetate) afforded N-(5-chloro-thiazol-2-yl)-3-cyclopentyl-2(R)-(4-methanesulfonyl-phenyl)-propionamide (2.24 g, 40%) as a yellow foam: mp 83–88° C. (foam to gel); $[\alpha]^{23}_{589}$=–73.3° (c=1, chloroform); EI-HRMS m/e calcd for $C_{18}H_{21}ClN_2O_3S_2$ (M$^+$) 412.0682, found 412.0692.

EXAMPLE 132

N-(5-Bromo-thiazol-2-yl)-3-cyclopentyl-2-(4-methanesulfonyl-phenyl)-propionamide

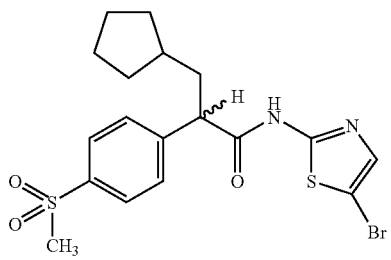

A solution of 3-cyclopentyl-2-(4-methanesulfonyl-phenyl)-propionic acid (prepared in Example 130, 300 mg, 1.01 mmol) and dry N,N-dimethylformamide (2 drops) in methylene chloride (3 mL) was cooled to 0° C. and then treated dropwise with oxalyl chloride (115 µL, 1.32 mmol). The reaction mixture was stirred at 0° C. for 10 min and then stirred at 25° C. for 1 h. The reaction mixture was concentrated in vacuo. The resulting yellow oil was dissolved in a small amount of methylene chloride and then slowly added to a solution of 2-amino-5-bromothiazole monohydrobromide (395 mg, 1.52 mmol) and triethylamine (424 µL, 3.04 mmol) in N,N-dimethylformamide (3 mL). The resulting reaction mixture was then stirred at 25° C. for 15 h. The resulting reaction mixture was partitioned between water (50 mL) and ethyl acetate (50 mL), and the layers were separated. The aqueous layer was further extracted with ethyl acetate (50 mL). The combined organic layers were then dried over magnesium sulfate, filtered, and concentrated in vacuo. Flash chromatography (Merck Silica gel 60, 230–400 mesh, 1/1 hexanes/ethyl acetate) afforded the N-(5-bromo-thiazol-2-yl)-3-cyclopentyl-2-(4-methanesulfonyl-phenyl)-propionamide (160 mg, 35%) as a tan foam: mp 73–75° C. (foam to gel); EI-HRMS m/e calcd for $C_{18}H_{21}BrN_2O_3S_2$ (M$^+$) 456.0177, found 456.0176.

EXAMPLE 133

N-(5-Bromo-thiazol-2-yl)-3-cyclopentyl-2(R)-(4-methanesulfonyl-phenyl)-propionamide

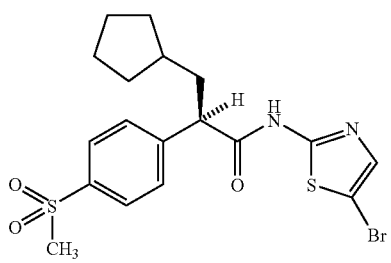

A solution of triphenylphosphine (3.35 g, 12.79 mmol) in methylene chloride (19 mL) was cooled to 0° C. and then slowly treated with N-bromosuccinimide (2.28 g, 12.79 mmol) in small portions. The reaction mixture was stirred at 0° C. for 30 min, and during this time period, the color of the reaction mixture changed from light yellow to a darker yellow then to a purple color. The cooled purple reaction mixture was then treated with 3-cyclopentyl-2(R)-(4-methanesulfonylphenyl)propionic acid (prepared as in Example 128, 2.23 g, 7.52 mmol). The resulting reaction mixture was then allowed to warm to 25° C. over 45 min. The reaction mixture was then treated with 2-aminothiazole (1.88 g, 18.81 mmol). The resulting reaction mixture was stirred at 25° C. for 12 h. The reaction mixture was then concentrated in vacuo to remove methylene chloride. The remaining black residue was diluted with ethyl acetate (300 mL). The organic layer was washed sequentially with a 10% aqueous hydrochloric acid solution (2×100 mL), a 5% aqueous sodium bicarbonate solution (3×100 mL), and a saturated aqueous sodium chloride solution (1×200 mL). The organic layer was then dried over sodium sulfate, filtered, and concentrated in vacuo. Flash chromatography (Merck Silica gel 60, 70–230 mesh, 9/1, 3/1, and then 11/9 hexanes/ethyl acetate) afforded 3-cyclopentyl-2(R)-(4-methanesulfonylphenyl)-N-thiazol-2-yl-propionamide (2.10 g, 74%) as a white foam: mp 78–80° C. (foam to gel); $[\alpha]^{23}_{589}$=−70.4° (c=0.027, chloroform); EI-HRMS m/e calcd for $C_{18}H_{22}N_2O_3S_2$ (M$^+$) 378.1072, found 378.1081.

A suspension of 3-cyclopentyl-2(R)-(4-methanesulfonyl-phenyl)-N-thiazol-2-yl-propionamide (1.0 g, 2.64 mmol) and N-bromosuccinimide (470 mg, 2.64 mmol) in carbon tetrachloride (5 mL) at 25° C. was treated with benzoyl peroxide (32 mg, 0.132 mmol). The resulting reaction mixture was heated to 90° C. where it was stirred at this temperature overnight. The reaction mixture was allowed to cool to 25° C. and then concentrated in vacuo. The resulting residue was dissolved in ethyl acetate (60 mL). The organic phase was then washed with water (1×100 mL) and a saturated aqueous sodium chloride solution (1×100), dried over anhydrous magnesium sulfate, filtered, and concentrated in vacuo. Biotage chromatography (FLASH 40M, Silica, 2/1 to 1/1 hexanes/ethyl acetate) afforded N-(5-bromo-thiazol-2-yl)-3-cyclopentyl-2(R)-(4-methanesulfonyl-phenyl)-propionamide (546 mg, 45%) as an amorphous solid: EI-HRMS m/e calcd for $C_{18}H_{21}BrN_2O_3S_2$ (M$^+$) 456.1077, found 456.1077.

EXAMPLE 134

2-[3-Cyclopentyl-2-(4-methanesulfonyl-phenyl)-propionylamino]-thiazole-5-carboxylic Acid Amide

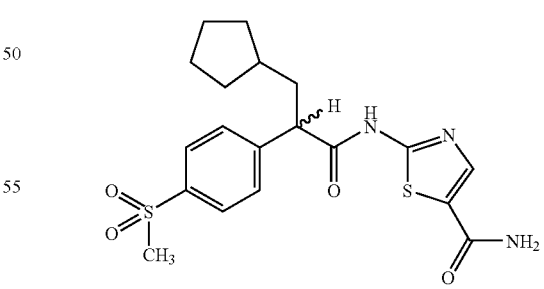

A solution of diisopropylamine (3.2 mL, 23.16 mmol) in dry tetrahydrofuran (10.3 mL) and 1,3-dimethyl-3,4,5,6-tetrahydro-2(1H)-pyrimidinone (3.4 mL) was cooled to −78° C. under nitrogen and then treated with a 10M solution of n-butyllithium in hexanes (2.3 mL, 23.16 mmol). The resulting reaction mixture was stirred at −78° C. for 30 min and then treated dropwise with a solution of 4-(methylthio)

phenylacetic acid (2.01 g, 11.03 mmol) in dry tetrahydrofuran (10.3 mL) and 1,3-dimethyl-3,4,5,6-tetrahydro-2(1H)-pyrimidinone (3.4 mL). The reaction mixture was allowed to stir at −78° C. for 1 h, at which time, a solution of iodomethylcyclopentane (2.55 g, 12.13 mmol) in a small amount of dry tetrahydrofuran was added dropwise. The reaction mixture was then stirred at −78° C. for 30 min and then allowed to warm to 25° C. where it was stirred for 24 h. The reaction mixture was quenched with water and then concentrated in vacuo to remove tetrahydrofuran. The remaining aqueous phase was acidified to pH=2 with a 10% aqueous hydrochloric acid solution and then extracted with ethyl acetate (200 mL). The organic layer was washed with a saturated aqueous sodium chloride solution (1×100 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-methylsulfanyl-phenyl)propionic acid (1.01 g, 35%) as a cream solid: mp 91–93° C.; EI-HRMS m/e calcd for $C_{15}H_{20}O_2S$ (M$^+$) 264.1184, found 264.1177.

A solution of 3-cyclopentyl-2-(4-methylsulfanyl-phenyl) propionic acid (2.54 g, 9.60 mmol) in formic acid (7 mL) was cooled to 0° C. and then treated with a 30% aqueous hydrogen peroxide solution (8.3 mL, 20.0 mmol). The resulting solution was allowed to warm to 25° C. where it was stirred for 1 h. The reaction was then re-cooled to 0° C., and the product was precipitated by the addition of water (30 mL). The solid was filtered off and dried to afford pure 3-cyclopentyl-2-(4-methanesulfonylphenyl)propionic acid (2.48 g, 87%) as a white solid which was used without further purification: mp 154–159° C.; EI-HRMS m/e calcd for $C_{15}H_{20}O_4S$ (M$^+$) 296.1082, found 296.1080.

A solution of 3-cyclopentyl-2-(4-methanesulfonyl-phenyl)-propionic acid (300 mg, 1.01 mmol), benzotriazol-1-yloxy-tris(dimethylamino)phosphonium hexafluorophosphate (717 mg, 1.62 mmol), triethylamine (420 μL, 3.03 mmol), and 2-amino-thiazole-5-carboxylic acid ethyl ester: (279 mg, 1.62 mmol) in methylene chloride (10 mL) was stirred at 25° C. under nitrogen for 14 h. The reaction mixture was partitioned between water and methylene chloride. The organic layer was sequentially washed with a 1N aqueous hydrochloric acid solution (1×10 mL), water (1×10 mL), and a saturated aqueous sodium bicarbonate solution (1×10 mL). The organic layer was dried over magnesium sulfate, filtered, and concentrated in vacuo. Biotage chromatography (FLASH 40S, Silica, 10/11 hexanes/ethyl ether) afforded 2-[3-cyclopentyl-2-(4-methanesulfonyl-phenyl)-propionylamino]-thiazole-5-carboxylic acid ethyl ester (448 mg, 98%) as a white solid: mp 100–103° C.; EI-HRMS m/e calcd for $C_{21}H_{26}N_2O_5S_2$(M$^+$) 450.1283, found 450.1285.

A solution of 2-[3-cyclopentyl-2-(4-methanesulfonyl-phenyl)-propionylamino]-thiazole-5-carboxylic acid ethyl ester (430 mg, 0.95 mmol) in ethanol (10 mL) and water (2 mL) was treated with lithium hydroxide (46 mg, 1.9 mmol). The reaction mixture was stirred at 25° C. for 14 h. The reaction mixture was then concentrated in vacuo to remove methanol. The resulting aqueous residue was diluted with water (20 mL) and then washed ethyl acetate (1×20 mL). The aqueous layer was then acidified to pH=2 with a 10% aqueous hydrochloric acid solution and then extracted with ethyl acetate (3×40 mL). The combined organic layers were then dried over magnesium sulfate, filtered, and concentrated in vacuo to afford 2-[3-cyclopentyl-2-(4-methanesulfonyl-phenyl)-propionylamino]-thiazole-5-carboxylic acid (386 mg, 96%) as a white solid which was used without further purification: mp 172–176° C.

A solution of 2-[3-cyclopentyl-2-(4-methanesulfonyl-phenyl)-propionylamino]-thiazole-5-carboxylic acid (100 mg, 0.24 mmol) in dry tetrahydrofuran (3 mL) under argon was treated with N-methylmorpholine (0.04 mL, 0.36 mmol) followed by iso-butylchloroformate (50 μL, 0.36 mmol). The reaction was stirred at 25° C. for 2 h, after which time, a concentrated aqueous ammonium hydroxide solution (0.2 mL) was added. The resulting reaction mixture was stirred at 25° C. for 2 h. The reaction mixture was then treated with water (5 mL), and the tetrahydrofuran was concentrated in vacuo. The product was then extracted with ethyl acetate (3×10 mL). The combined organic layers were dried over magnesium sulfate, filtered, and concentrated in vacuo. Flash chromatography (Merck Silica gel 60, 70–230 mesh, 9/1 chloroform/methanol) afforded 2-[3-cyclopentyl-2-(4-methanesulfonyl-phenyl)-propionylamino]-thiazole-5-carboxylic acid amide (68 mg, 67%) as a white solid: mp 155–160° C.; EI-HRMS m/e calcd for $C_{19}H_{23}N_3O_4S_2$ (M$^+$) 421.1130, found 421.1135.

EXAMPLE 135

3-Cyclopentyl-2-(3-fluoro-4-methanesulfonyl-phenyl)-N-thiazol-2-yl-propionamide

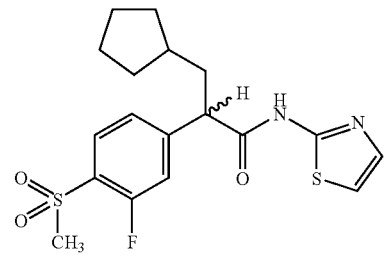

A solution of 3-cyclopentyl-2-(4-methanesulfonyl-3-nitrophenyl)-propionic acid methyl ester (prepared as in Example 14, 1.50 g, 4.22 mmol) in methanol (30 mL) was treated with a solution of ammonium chloride (474 mg, 8.86 mmol) in water (3 mL). The reaction mixture was stirred at 25° C. for 5 min and then treated with zinc dust (2.70 g, 41.36 mmol). The reaction mixture was heated under reflux for 2 h. The reaction mixture was allowed to cool to 25° C. and then filtered through a pad of celite. The filtrate was concentrated in vacuo. The resulting orange oil was dissolved in ethyl acetate, dried over magnesium sulfate, filtrated, and concentrated in vacuo. Flash chromatography (Merck Silica gel 60, 230–400 mesh, 2/1 hexanes/ethyl acetate) afforded 2-(3-amino-4-methanesulfonyl-phenyl)-3-cyclopentyl-propionic acid methyl ester (1.49 g, 98%) as a white solid: mp 98–100° C.; EI-HRMS m/e calcd for $C_{16}H_{23}NO_4S$ (M$^+$) 325.1348, found 325.1358.

A slurry of nitrosonium tetrafluoroborate (215 mg, 1.84 mmol) in methylene chloride (6 mL) was cooled to 0° C. and then treated dropwise with a solution of 2-(3-amino-4-methanesulfonyl-phenyl)-3-cyclopentyl-propionic acid methyl ester (500 mg, 1.54 mmol) in a small amount of methylene chloride. The resulting reaction mixture was stirred at 0° C. for 1 h. The reaction mixture was then allowed to warm to 25° C. and was treated with 1,2-dichlorobenzene (6 mL). The resulting reaction mixture was heated at 100° C. for 1 h, during which time, the methylene chloride was distilled off. After 1 h at 100° C., the reaction mixture was allowed to cool to 25° C. The crude reaction mixture was directly purified by flash chromatography (Merck Silica gel 60, 230–400 mesh, 9/1 hexanes/ethyl acetate to elute 1,2-dichlorobenzene then 2/1 hexanes/ethyl acetate) to afford impure 3-cyclopentyl-2-(3-fluoro-4-methanesulfonyl-phenyl)-propionic acid methyl ester as a yellow oil. Repurification by flash chromatography (Merck Silica gel 60, 230–400 mesh, 3/1 hexanes/ethyl acetate) afforded pure 3-cyclopentyl-2-(3-fluoro-4-methanesulfonyl-phenyl)-propionic acid methyl ester (214 mg, 42%) as a pale yellow oil which solidified upon sitting at 25° C. to a pale yellow solid: mp 66–68° C.; EI-HRMS m/e calcd for $C_{16}H_{21}FO_4S$ (M+) 328.1144, found 328.1148.

A solution of 3-cyclopentyl-2-(3-fluoro-4-methanesulfonyl-phenyl)-propionic acid methyl ester (110 mg, 0.335 mmol) in tetrahydrofuran (1 mL) was treated with a 0.8M aqueous lithium hydroxide solution (630 μL, 0.502 mmol). The reaction mixture was stirred at 25° C. for 2 h and then treated with water (30 mL), a 1N aqueous hydrochloric acid solution (2 mL), and ethyl acetate (30 mL). The layers were separated, and the resulting aqueous layer was back-extracted with ethyl acetate (30 mL). The combined organic layers were dried over magnesium sulfate, filtered, and concentrated in vacuo to afford 3-cyclopentyl-2-(3-fluoro-4-methanesulfonyl-phenyl)-propionic acid as a pale yellow oil which solidified to a pale yellow solid upon sitting at 25° C. The pale yellow solid corresponding to 3-cyclopentyl-2-(3-fluoro-4-methanesulfonyl-phenyl)-propionic acid (106 mg, 98%) was used without further purification: mp 115–117° C.; EI-HRMS m/e calcd for $C_{15}H_{19}FO_4S$ (M+) 314.0988, found 314.0986.

A solution of triphenylphosphine (48 mg, 0.183 mmol) in methylene chloride (700 μL) was cooled to 0° C. and then slowly treated with N-bromosuccinimide (33 mg, 0.183 mmol). The reaction mixture was stirred at 0° C. for 10 min and then treated with 3-cyclopentyl-2-(3-fluoro-4-methanesulfonyl-phenyl)-propionic acid (50 mg, 0.159 mmol). The resulting reaction mixture was stirred at 0° C. for 5 min and then allowed to warm to 25° C. where it was stirred for 30 min. The reaction mixture was then treated with 2-aminothiazole (35 mg, 0.35 mmol). The resulting reaction mixture was stirred at 25° C. for 15 h. The crude reaction mixture was directly purified by flash chromatography (Merck Silica gel 60, 230–400 mesh, 1/1 hexanes/ethyl acetate) to afford 3-cyclopentyl-2-(3-fluoro-4-methanesulfonyl-phenyl)-N-thiazol-2-yl-propionamide (40.4 mg, 64%) as a pink solid: mp 200–202° C.; EI-HRMS m/e calcd for $C_{18}H_{21}FN_2O_3S_2$ (M+) 396.0978, found 396.0976.

EXAMPLE 136

3-Cyclopentyl-2-(3-fluoro-4-methanesulfonyl-phenyl)-N-pyridin-2-yl-propionamide

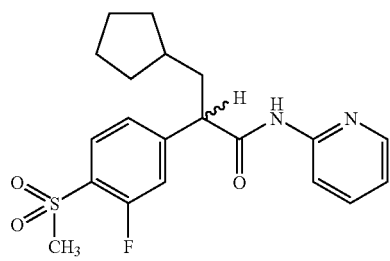

A solution of triphenylphosphine (48 mg, 0.183 mmol) in methylene chloride (700 μL) was cooled to 0° C. and then slowly treated with N-bromosuccinimide (33 mg, 0.183 mmol). The reaction mixture was stirred at 0° C. for 10 min and then treated with 3-cyclopentyl-2-(3-fluoro-4-methanesulfonyl-phenyl)-propionic acid (prepared as in Example 135, 50 mg, 0.159 mmol). The resulting reaction mixture was stirred at 0° C. for 5 min and then allowed to warm to 25° C. where it was stirred for 30 min. The reaction mixture was then treated with 2-aminopyridine (33 mg, 0.35 mmol). The resulting reaction mixture was stirred at 25° C. for 15 h. The crude reaction mixture was directly purified by flash chromatography (Merck Silica gel 60, 230–400 mesh, 2/1 hexanes/ethyl acetate) to afford 3-cyclopentyl-2-(3-fluoro-4-methanesulfonyl-phenyl)-N-pyridin-2-yl-propionamide (23.7 mg, 38%) as a pink solid: mp 76–79° C.; EI-HRMS m/e calcd for $C_{20}H_{23}FN_2O_3S$ (M+) 390.1413, found 390.1420.

EXAMPLE 137

N-(5-Bromo-thiazol-2-yl)-2(R)-(3-chloro-4-methanesulfonyl-phenyl)-3-cyclopentyl-propionamide

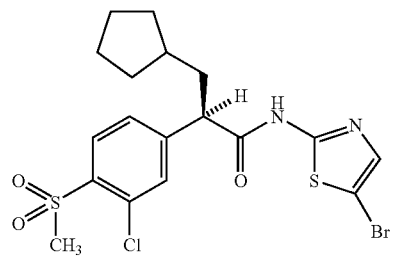

A solution of aluminum trichloride (54.9 g, 412 mmol) in chloroform (180 mL) under argon was cooled to 0° C. and then treated dropwise with a solution of methyl chlorooxoacetate (24.3 mL, 264 mmol) in chloroform (180 mL). The reaction mixture was stirred at 0° C. for 30 min and then was treated dropwise with a solution of 2-chlorothioanisole (39.4 g, 247 mmol) in chloroform (180 mL). The reaction mixture turned red in color. The resulting reaction mixture was allowed to warm to 25° C. where it was stirred for 4 h. The reaction mixture was then slowly poured onto ice (700 mL). The resulting yellow mixture was stirred for 15 min and then was filtered through celite to remove the aluminum salts. The filtrate was then extracted with methylene chloride (3×50 mL). The combined organic layers were washed with a saturated aqueous sodium bicarbonate solution (1×50 mL). The organic layer was then dried over magnesium sulfate, filtered, and concentrated in vacuo to afford (3-chloro-4-methylsulfanyl-phenyl)-oxo-acetic acid methyl ester (36.4 g, 60%) as a light yellow oil: EI-HRMS m/e calcd for $C_{10}H_9ClSO_3$ (M+) 243.9961, found 243.9958.

A solution of (3-chloro-4-methylsulfanyl-phenyl)-oxo-acetic acid methyl ester (61.7 g, 252 mmol) in toluene (120 mL) was heated at 50° C. This heated solution was then treated dropwise with a 3M aqueous sodium hydroxide solution (105 mL, 313 mmol) via a dropping funnel, taking care to keep the temperature below 60° C. After the addition was complete, the reaction mixture was stirred at 50° C. for another 1.5 h, during which time, a yellow precipitate began to form. After this time, the heat was removed, and the warm solution was treated dropwise with concentrated hydrochloric acid (10.6 mL, 290 mmol). The resulting reaction mixture was allowed to cool to 25° C. and then was stirred at 25° C. for 16 h. The solid was filtered and then washed with water (50 mL) and toluene (50 mL). The solid was dried by suction for 1 h and then dried in a high vacuum desiccator to afford (3-chloro-4-methylsulfanyl-phenyl)-oxo-acetic acid (57.22 g, 98%) as a white solid: mp 166° C. (dec); FAB-HRMS m/e calcd for $C_9H_7ClSO_3$ (M+Na)$^+$ 252.9702, found 252.9700.

A reaction flask equipped with mechanical stirrer was charged with hydrazine hydrate (8.5 mL, 273 mmol). The hydrazine hydrate was cooled to −50° C. and then treated with (3-chloro-4-methylsulfanyl-phenyl)-oxo-acetic acid (12.6 g, 54.6 mmol) in one portion. An exotherm ensued that raised the temperature. The resulting white milky mixture was then heated to 80° C. After reaching 80° C., the heating element was removed, and the reaction mixture was then treated with potassium hydroxide (2.09 g, 31.7 mmol) in one portion. An exotherm was observed. The reaction was then stirred at 25° C. until the reaction temperature cooled back to 80° C. At this time, another portion of potassium hydroxide (2.09 g, 31.7 mmol) was added. Again, an exotherm was observed, and the resulting reaction mixture was allowed to cool back to 80° C. Once at 80° C., a third portion of potassium hydroxide (2.09 g, 31.7 mmol) was added to the reaction mixture. Another exotherm was observed, and after cooling back to 80° C., the fourth and final portion of potassium hydroxide (2.09 g, 31.7 mmol) was added. At this point, the heating element was added, and the reaction mixture was heated at 100° C. for 16 h. The resulting homogenous reaction mixture was cooled to 25° C. and then diluted with water (12 mL). The reaction mixture was then transferred to a separatory funnel, rinsing with additional water (12 mL) and diethyl ether (40 mL). The layers were separated, and the aqueous layer was transferred to a flask. The organic layer was extracted with water (2×15 mL) The aqueous layers were combined and treated with heptane (20 mL), and the resulting reaction mixture was vigourously stirred. This stirred solution was then treated dropwise with concentrated hydrochloric acid (26 mL) over 30 min while the temperature was kept under 50° C. with an ice bath. A cloudy suspension formed, and this suspension was stirred at 25° C. for 3 h. The solid that formed was collected by filtration and then washed sequentially with a 1N aqueous hydrochloric acid solution (2×6 mL), heptane (1×12 mL), and a solution of heptane/diethyl ether (15 mL, 4:1). The resulting solid was dried under high vacuum to afford (3-chloro-4-methylsulfanyl-phenyl)-acetic acid (10.48 g, 89%) as an off-white solid: mp 105.6–108.4° C.; EI-HRMS m/e calcd for $C_9H_9ClSO_2$ (M$^+$) 216.0012, found 216.0022.

A mixture of (3-chloro-4-methylsulfanyl-phenyl)-acetic acid (10.48 g, 48.4 mmol) and potassium carbonate (20.1 g, 145.1 mmol) in acetone (65 mL) was cooled to −10° C. The pale yellow slurry was then treated dropwise with trimethylacetyl chloride (6.25 mL, 50.8 mmol) while maintaining the temperature below −10° C. The resulting reaction mixture was stirred at −10° C. for 15 min and then allowed to warm to 0° C. where it was stirred for 10 min. The reaction mixture was re-cooled to −10° C. and then treated with (1R,2R)-(−)-pseudoephedrine (11.99 g, 72.5 mmol), resulting in an exotherm. The reaction mixture was stirred −10° C. for 10 min and then warmed to 25° C. where it was stirred for 1 h. After such time, thin layer chromatography analysis indicated that the reaction was complete. The reaction mixture was then quenched with water (50 mL) and then extracted with ethyl acetate (1×100 mL). The organic layer was washed with water (2×40 mL). The aqueous layers were combined and back-extracted with ethyl acetate (2×50 mL). The combined organic layers were dried over magnesium sulfate, filtered, and concentrated in vacuo. The crude material was recrystallized from ethyl acetate (45 mL) and hexanes (80 mL) to afford 2-(3-chloro-4-methylsulfanyl-phenyl)-N-[2(R)-hydroxy-1 (R)-methyl-2(R)-phenyl-ethyl]-N-methyl-acetamide (13.75 g, 78%) as a light yellow solid: mp 111.5–112.9° C.; $[\alpha]^{23}_{589}$=−97.2° (c=0.104, chloroform); FAB-HRMS m/e calcd for $C_{19}H_{22}ClNSO_2$ (M+H)$^+$ 364.1138, found 364.1142.

A solution of 1,1,1,3,3,3-hexamethyldisilazane (17.9 mL, 85 mmol) in tetrahydrofuran (90 mL) was cooled to −78° C. and then treated with a 2.34M solution of n-butyllithium in hexanes (33.9 mL, 79.3 mmol). The reaction mixture was stirred at −78° C. for 15 min and then slowly treated with a solution of 2-(3-chloro-4-methylsulfanyl-phenyl)-N-[2(R)-hydroxy-1 (R)-methyl-2(R)-phenyl-ethyl]-N-methyl-acetamide (13.75 g, 37.8 mmol) in tetrahydrofuran (90 mL) while maintaining the temperature below −65° C. The resulting yellow-orange reaction mixture was stirred at −78° C. for 15 min and then allowed to warm to 0° C. where it was stirred for 20 min. The reaction mixture was then re-cooled to −78° C. and then treated with a solution of iodomethylcyclopentane (11.9 g, 56.7 mmol) in 1,3-dimethyl-3,4,5,6-tetrahydro-2(1H)-pyrimidinone (9.6 mL, 79.3 mmol). The resulting reaction mixture was stirred at −78° C. for 30 min and then allowed to warm to 25° C. where it was stirred for 16 h. The reaction mixture was diluted with ethyl acetate (200 mL) and then washed with a saturated aqueous ammonium chloride solution (1×100 mL). The aqueous layer was then extracted with ethyl acetate (2×50 mL). The combined organic layers were washed with a saturated aqueous sodium chloride solution (1×50 mL), dried over sodium sulfate, filtered, and concentrated in vacuo. The resulting material was then re-dissolved in ethyl acetate. This organic phase was washed with a 10% aqueous sulfuric acid solution (2×100 mL) and a 10% aqueous sodium bicarbonate solution (2×100 mL), dried over magnesium sulfate, filtered, and concentrated in vacuo. The crude material was recrystallized from ethyl acetate/hexanes to afford 2(R)-(3-chloro-4-methylsulfanyl-phenyl)-3-cyclopentyl-N-[2(R)-hydroxy-1(R)-methyl-2(R)-phenyl-ethyl]-N-methyl-propionamide (11.36 g, 67%) as a light yellow solid: mp 113.8–117.6° C.; $[\alpha]^{23}_{589}$=−100.3° (c=0.09, chloroform); FAB-HRMS m/e calcd for $C_{25}H_{32}ClNSO_2$ (M−H)$^+$ 444.1764, found 444.1765.

A solution of 2(R)-(3-chloro-4-methylsulfanyl-phenyl)-3-cyclopentyl-N-[2(R)-hydroxy-1(R)-methyl-2(R)-phenyl-ethyl]-N-methyl-propionamide (11.36 g, 25.5 mmol) in dioxane (45 mL) was treated with a 9N aqueous sulfuric acid solution (28 mL). The resulting reaction mixture was then heated at 105° C. for 16 h. The reaction mixture was then cooled to 0° C. with an ice bath, and the product was precipitated by adding water (200 mL). The suspension was stirred at 0° C. until the supernatant, which was initially turbid, became clear and light yellow in color. The solid was filtered off and dried by suction. The solid material was dissolved in hot glacial acetic acid (15 mL), and the hot solution was treated with water (10 mL) to initiate crystallization. The mixture was allowed to cool to 25° C. and then treated with an additional amount of water (20 mL). After stirring at 25° C. for 1 h, the solid was collected by filtration. The solid was dried in a high vacuum desiccator with phosphourous pentoxide to afford 2(R)-(3-chloro-4-methylsulfanyl-phenyl)-3-cyclopentyl-propionic acid (7.46 g, 98%) as a white solid: mp 116.9–119.2° C.; $[\alpha]^{23}_{589}$=−55.8° (c=0.104, chloroform); EI-HRMS m/e calcd for $C_{15}H_{19}ClSO_2$ (M)$^+$ 298.0794, found 298.0804.

A slurry of 2(R)-(3-chloro-4-methylsulfanyl-phenyl)-3-cyclopentyl-propionic acid (15.68 g, 52.5 mmol) in formic acid (10 mL) was cooled to 0° C. and then treated with a 30% aqueous hydrogen peroxide solution (30 mL). The resulting solution was allowed to warm to 25° C. where it was stirred for 16 h. The product was precipitated by the addition of water (120 mL). The solid was filtered off, washed with water, and dried by suction. Flash chromatography (Merck Silica gel 60, 230–400 mesh, 50/50 hexanes/ ethyl acetate plus 1% acetic acid) afforded 2(R)-(3-chloro-4-methanesulfonyl-phenyl)-3-cyclopentyl-propionic acid (13.93 g, 80%) as a white solid: mp 123.9–126.2° C.; $[\alpha]^{23}_{589}=-41.5°$ (c=0.176, chloroform); FAB-HRMS m/e calcd for $C_{15}H_{19}ClO_4S$ (M+H)$^+$ 331.0771, found 331.0776.

A solution of triphenylphosphine (595 mg, 2.27 mmol) in methylene chloride (20 mL) was cooled to 0° C. and then treated with N-bromosuccinimide (457 mg, 2.57 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (500 mg, 1.51 mmol). The reaction mixture was stirred at 0° C. for 20 min and then allowed to warm to 25° C. where it was stirred for 30 min. The reaction mixture was then treated with 2-amino-5-bromothiazole monohydrobromide (589 mg, 2.27 mmol) and pyridine (0.37 mL, 4.53 mmol), and then the reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 55/45 hexanes/ethyl acetate) afforded N-(5-bromo-thiazol-2-yl)-2(R)-(3-chloro-4-methanesulfonyl-phenyl)-3-cyclopentyl-propionamide (375 mg, 51%) as a light green foam: $[\alpha]^{23}_{589}=-110.3°$ (c=0.068, chloroform); EI-HRMS m/e calcd for $C_{18}H_{20}ClBrN_2O_3S_2$ (M$^+$) 489.9787, found 489.9792.

EXAMPLE 138

2(R)-(3-Chloro-4-methanesulfonyl-phenyl)-3-cyclopentyl-N-(5-methyl-thiazol-2-yl)-propionamide

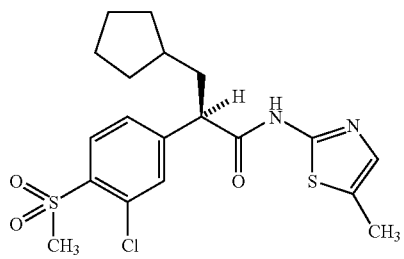

A solution of triphenylphosphine (238 mg, 0.91 mmol) in methylene chloride (6 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (prepared as in Example 137, 200 mg, 0.61 mmol). The reaction mixture was stirred at 0° C. for 20 min and then allowed to warm to 25° C. where it was stirred for 30 min. The reaction mixture was then treated with 2-amino-5-methylthiazole (104 mg, 0.91 mmol) and pyridine (0.15 mL, 1.82 mmol), and the resulting reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 55/45 hexanes/ethyl acetate) afforded 2(R)-(3-chloro-4-methanesulfonyl-phenyl)-3-cyclopentyl-N-(5-methyl-thiazol-2-yl)-propionamide (201 mg, 78%) as a orange foam: $[\alpha]^{23}_{589}=-72.7°$ (c=0.055, chloroform); EI-HRMS m/e calcd for $C_{19}H_{23}ClN_2O_3S_2$(M$^+$) 426.0838, found 426.0837.

EXAMPLE 139

2(R)-(3-Chloro-4-methanesulfonyl-phenyl)-3-cyclopentyl-N-(4-methyl-thiazol-2-yl)-propionamide

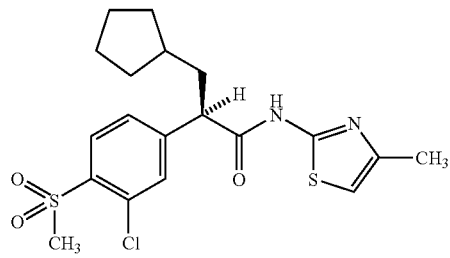

A solution of triphenylphosphine (238 mg, 0.91 mmol) in methylene chloride (6 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (prepared as in Example 137, 200 mg, 0.61 mmol). The reaction mixture was stirred at 0° C. for 20 min and then allowed to warm to 25° C. where it was stirred for 30 min. The reaction mixture was then treated with 2-amino-4-methylthiazole (104 mg, 0.91 mmol) and pyridine (0.15 mL, 1.82 mmol), and the resulting reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 70/30 hexanes/ethyl acetate) afforded 2(R)-(3-chloro-4-methanesulfonyl-phenyl)-3-cyclopentyl-N-(4-methyl-thiazol-2-yl)-propionamide (118 mg, 46%) as an off-white foam: $[\alpha]^{23}_{589}=-44.4°$ (c=0.024, chloroform); EI-HRMS m/e calcd for $C_{19}H_{23}ClN_2O_3S_2$(M$^+$) 426.0838, found 426.0837.

EXAMPLE 140

2(R)-(3-Chloro-4-methanesulfonyl-phenyl)-3-cyclopentyl-N-(5-methyl-pyridin-2-yl)-propionamide

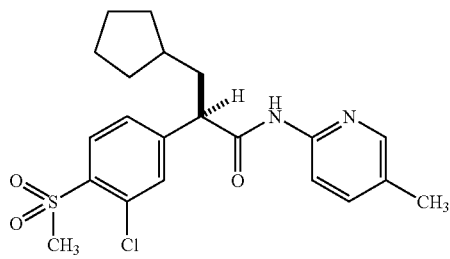

A solution of triphenylphosphine (238 mg, 0.91 mmol) in methylene chloride (10 mL) was cooled to 0° C. and then treated with N-bromosuccinimide (183 mg, 1.03 mmol). The reaction mixture was stirred at 0° C. until it became homogeneous. The resulting light purple reaction mixture was then treated with 2(R)-(3-chloro-4-methanesulfonyl-phenyl)-3-cyclopentyl-propionic acid (prepared as in Example 137, 200 mg, 0.61 mmol). The reaction mixture was stirred at 0° C. for 20 min and then allowed to warm to 25° C. where it was stirred for 30 min. The reaction mixture was then treated with 2-amino-5-picoline (98.1 mg, 0.91 mmol) and pyridine (0.15 mL, 1.82 mmol), and the reaction mixture was stirred at 25° C. for 16 h. The reaction was then diluted with water (15 mL) and then extracted with methylene chloride (3×15 mL). The combined organic layers were dried over sodium sulfate, filtered, and concentrated in vacuo. Biotage chromatography (FLASH 40S, Silica, 60/40 hexanes/ethyl acetate) afforded 2(R)-(3-chloro-4-methanesulfonyl-phenyl)-3-cyclopentyl-N-(5-methyl-pyridin-2-yl)-propionamide (197 mg, 77%) as a white foam: $[\alpha]^{23}{}_{589}=-47.8°$ (c=0.046, chloroform); EI-HRMS m/e calcd for $C_{21}H_{25}ClN_2O_3S$ (M+) 420.1274, found 420.1273.

EXAMPLE 141

2-(3-Chloro-4-methanesulfonyl-phenyl)-3-cyclopentyl-N-pyrimidin-4-yl-propionamide

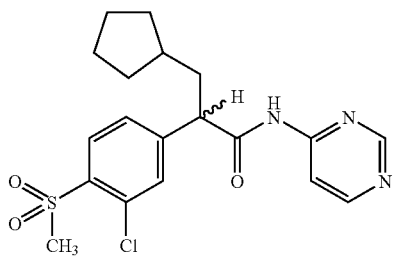

A solution of 2-(3-chloro-4-methanesulfonyl-phenyl)-3-cyclopentyl-propionic acid (prepared as in Example 143, 50 mg, 0.15 mmol) in methylene chloride (1.5 mL) was treated with N,N-dimethylformamide (1 drop) and then cooled to 0° C. The reaction mixture was then treated dropwise with a 2M solution of oxalyl chloride in methylene chloride (0.11 mL, 0.23 mmol) and stirred at 0° C. for 30 min. The reaction mixture was then treated with a solution of 4-aminopyrimidine (29 mg, 0.30 mmol) and pyridine (0.06 mL, 0.76 mmol) in tetrahydrofuran (2.5 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 20/80 hexanes/ethyl acetate) afforded 2-(3-chloro-4-methanesulfonyl-phenyl)-3-cyclopentyl-N-pyrimidin-2-yl-propionamide (47 mg, 76%) as a white foam: EI-HRMS m/e calcd for $C_{19}H_{22}ClN_3O_3S$ (M+) 407.1070, found 407.1080.

EXAMPLE 142

2(R)-(3-Chloro-4-methanesulfonyl-phenyl)-3-cyclopentyl-N-pyrimidin-4-yl-propionamide

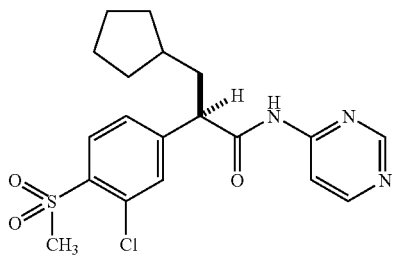

A solution of 2(R)-(3-chloro-4-methanesulfonyl-phenyl)-3-cyclopentyl-propionic acid (prepared as in Example 137, 200 mg, 0.61 mmol) in methylene chloride (5 mL) was treated with N,N-dimethylformamide (1 drop) and then cooled to 0° C. The reaction mixture was then treated dropwise with a 2M solution of oxalyl chloride in methylene chloride (0.45 mL, 0.91 mmol) and stirred at 0° C. for 30 min. The reaction mixture was then treated with a solution of 4-aminopyrimidine (115 mg, 1.21 mmol) and pyridine (0.245 mL, 3.03 mmol) in tetrahydrofuran (10 mL). The resulting reaction mixture was allowed to warm to 25° C. where it was stirred for 16 h. The reaction mixture was then diluted with water (10 mL) and extracted with methylene chloride (3×15 mL). The combine organic layers were dried over sodium sulfate, filtered, and concentrated in vacuo. Biotage chromatography (FLASH 40S, Silica, 20/80 hexanes/ethyl acetate) afforded 2(R)-(3-chloro-4-methanesulfonyl-phenyl)-3-cyclopentyl-N-pyrimidin-4-yl-propionamide (105 mg, 43%, 80% R-isomer) as a white foam: $[\alpha]^{23}{}_{589}=-38.0°$ (c=0.050, chloroform); EI-HRMS m/e calcd for $C_{19}H_{22}ClN_3O_3S$ (M+) 407.1070, found 407.1072.

EXAMPLE 143

2-(3-Chloro-4-methanesulfonyl-phenyl)-3-cyclopentyl-N-(2-methyl-pyrimidin-4-yl)-propionamide

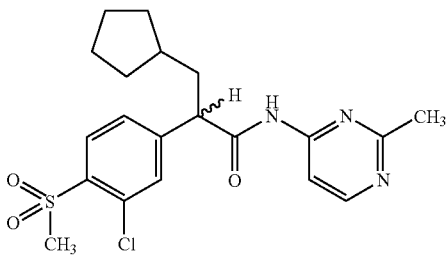

A mixture of acetamidine hydrochloride (2.00 g, 21.2 mmol) in a 0.5M solution of sodium methoxide in methanol (42.3 mL, 21.2 mmol) was stirred at 25° C. for 30 min. After this time, the sodium chloride was collected by filtration, and the filtrate was concentrated in vacuo. The resulting residue was diluted with 3-ethoxyacrylonitrile (2.18 ml, 21.2 mmol), and the reaction mixture was heated at 160° C. for 3 h. After this time, ethanol evolution stopped, and the melt began to crystallize. The red-brown solution was cooled to 25° C. A small amount of methanol was added, and the solid was filtered. The solid was then washed with methanol to afford 4-amino-2-methylpyrimidine (1.03 g, 44%) as an off-white solid: mp>200° C.; EI-HRMS m/e calcd for $C_5H_7N_3$ (M+) 109.0640, found 109.0640.

A solution of aluminum chloride (34.8 g, 261.4 mmol) in chloroform (120 mL) under argon was cooled to 0° C. and then treated dropwise with a solution of ethyl oxalyl chloride (18.7 mL, 167.5 mmol) in chloroform (120 mL). The reaction mixture was stirred at 0° C. for 30 min and then treated dropwise with a solution of 2-chlorothioanisole (25.0 g, 156.5 mmol) in chloroform (120 mL). The resulting reaction mixture turned red in color. The reaction mixture was allowed to warm to 25° C. where it was stirred for an additional 3.5 h. The reaction mixture was then slowly quenched with water (500 mL), and upon addition of the water, the reaction mixture turned yellow in color. The resulting solution was then extracted with chloroform (3×50 mL). The combined organic layers were dried over sodium sulfate, filtered, and concentrated in vacuo. Flash chromatography (Merck Silica gel 60, 230–400 mesh, 80/20 hexanes/ethyl acetate) afforded (3-chloro-4-methylsulfanyl-phenyl)-oxo-acetic acid ethyl ester (31.37 g, 77%) as a yellow oil.

A solution of iodomethylcyclopentane (129.38 g, 0.616 mol) and triphenylphosphine (161.54 g, 0.616 mol) in acetonitrile (308 mL) was heated under reflux for 9 d. The reaction mixture was allowed to cool to 25° C. and then concentrated in vacuo to provide a solid. The solid was triturated with diethyl ether and then filtered. The solid was washed well with diethyl ether until the washings showed the absence of iodomethylcyclopentane and triphenylphosphine by thin layer chromatography. The resulting solid was allowed to air dry to afford cyclopentylmethyl triphenylphosphonium iodide (266.92 g, 92%) as a light yellow solid: mp 195–198° C.; FAB-HRMS m/e calcd for $C_{24}H_{26}P$ $(M+H)^+$ 345.1772, found 345.1784.

A suspension of cyclopentylmethyl triphenylphosphine iodide (725 mg, 1.53 mmol) in tetrahydrofuran (10 mL) was cooled to 0° C. and then treated with a 1.0M solution of sodium bis(trimethylsilyl)amide in tetrahydrofuran (2.14 mL, 2.14 mmol). The resulting red reaction mixture was stirred at 0° C. for 45 minutes and then slowly treated with a solution of (3-chloro-4-methylsulfanyl-phenyl)-oxo-acetic acid ethyl ester (355 mg, 1.37 mmol) in tetrahydrofuran (5 mL). The reaction mixture was warmed to 25° C. where it was stirred for 20 h. The reaction mixture was then diluted with water (50 mL) and extracted with diethyl ether (3×25 mL). The combined organic layers were dried over sodium sulfate, filtered, and concentrated in vacuo. Biotage chromatography (Flash 12M, Silica, 80/20 hexanes/ethyl acetate) afforded 2-(3-chloro-4-methylsulfanyl-phenyl)-3-cyclopentyl-acrylic acid ethyl ester (267 mg, 60%) as a yellow oil consisting of a 2:1 mixture of (E):(Z) isomers. The isomeric mixture was used without further separation and characterization.

A solution of the isomeric mixture of 2-(3-chloro-4-methylsulfanyl-phenyl)-3-cyclopentyl-acrylic acid ethyl ester (100 mg, 0.31 mmol) in methylene chloride (5 mL) was cooled to 0° C. and then treated with 3-chloroperoxybenzoic acid (80% grade, 157 mg, 0.729 mmol). The reaction mixture was stirred at 0° C. for 3.5 h and then diluted with methylene chloride (25 mL). The organic phase was washed with a saturated aqueous sodium carbonate solution (2×10 mL) and a saturated aqueous sodium chloride solution (2×10 mL). The organic layer was dried over sodium sulfate, filtered, and concentrated in vacuo. Biotage chromatography (Flash 12M, Silica, 80/20 hexanes/ethyl acetate) afforded 2-(3-chloro-4-methanesulfonyl-phenyl)-3-cyclopentyl-acrylic acid ethyl ester (95 mg, 86%) as a colorless oil consisting of a 2:1 mixture of (E):(Z) isomers. The isomeric mixture was used without further separation and characterization.

A solution of the isomeric mixture of 2-(3-chloro-4-methanesulfonyl-phenyl)-3-cyclopentyl-acrylic acid ethyl ester (1.04 g, 2.91 mmol) and nickel chloride hexahydrate (69 mg, 0.29 mmol) in methanol (25 mL) was slowly treated with sodium borohydride (221 mg, 5.83 mmol) in small portions. If necessary, an ice bath was used to keep the temperature at 20° C. The initial green solution turned black in color, and a fine precipitate formed after addition of the sodium borohydride. The reaction mixture was then stirred at 25° C. for 1.5 h. The reaction mixture was then filtered through celite and washed with methanol. The filtrate and washings were combined and concentrated in vacuo to reduce the volume. The residual solution was then diluted with water (15 mL) and extracted with ethyl acetate (3×15 mL). The combined organic layers were dried over sodium sulfate, filtered, and concentrated in vacuo. Flash chromatography (Merck Silica gel 60, 230–400 mesh, 75/25 hexanes/ethyl acetate) afforded a mixture of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (937 mg, transesterification occurred under the reaction conditions) as a clear colorless oil. This mixture was used without further separation and characterization.

The mixture of 2-(3-chloro-4-methanesulfonyl-phenyl)-3-cyclopentyl-propionic acid methyl ester and 2-(3-chloro-4-methanesulfonyl-phenyl)-3-cyclopentyl-propionic acid ethyl ester (937 mg) was dissolved in ethanol (30 mL). This solution was then treated with a solution of potassium hydroxide (733 mg, 13.1 mmol) in water (7 mL). The resulting yellow solution was stirred at 25° C. for 3 h and then concentrated in vacuo to remove ethanol. The aqueous residue was treated with a 1N aqueous hydrochloric acid solution until the pH=2. The product was then extracted into methylene chloride (3×15 mL). The combined organic layers were dried over sodium sulfate, filtered, and concentrated in vacuo. Flash chromatography (Merck Silica gel 60, 230–400 mesh, 75/25 hexanes/ethyl acetate plus 1% acetic acid) afforded 2-(3-chloro-4-methanesulfonyl-phenyl)-3-cyclopentyl-propionic acid (787 mg, 82% for two steps) as a white solid: mp 123.9–126.2° C.; FAB-HRMS m/e calcd for $C_{15}H_{19}ClO_4S$ $(M+H)^+$ 331.0771, found 331.0776.

A solution of 2-(3-chloro-4-methanesulfonyl-phenyl)-3-cyclopentyl-propionic acid (200 mg, 0.61 mmol) in methylene chloride (2 mL) was treated with N,N-dimethylformamide (I drop) and then cooled to 0° C. The reaction mixture was then treated dropwise with a 2M solution of oxalyl chloride in methylene chloride (0.45 mL, 0.91 mmol) and stirred at 0° C. for 30 min. The resulting reaction mixture was then treated with a solution of 4-amino-2-methylpyrimidine (98.9 mg, 0.91 mmol) and pyridine (0.25 mL, 3.03 mmol) in N,N-dimethylformamide (5 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 55/45 hexanes/ethyl acetate) afforded 2-(3-chloro-4-methanesulfonyl-phenyl)-3-cyclopentyl-N-(2-methyl-pyrimidin-4-yl)-propionamide (64 mg, 25%) as a colorless oil: EI-HRMS m/e calcd for $C_{20}H_{24}ClN_3O_3S$ $(M^+)$ 421.1227, found 421.1230.

EXAMPLE 144

2(R)-(3-Chloro-4-methanesulfonyl-phenyl)-3-cyclopentyl-N-(2-methyl-pyrimidin-4-yl)-propionamide

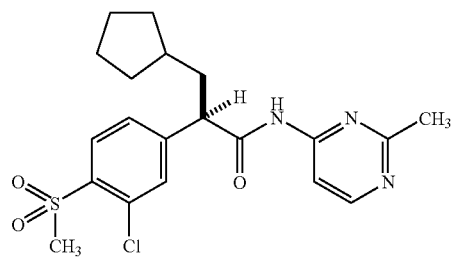

A slurry of 4-amino-2-methylpyrimidine (2.04 g, 18.69 mmol) in 1,1,1,3,3,3-hexamethyldisilazane (40 mL) and chlorotrimethylsilane (0.36 mL, 2.8 mmol) was heated at 150° C. for 8 h. At this time, the reaction mixture was close to a homogeneous solution. The resulting slightly orange solution was then filtered to remove any remaining solids. The filtrate was concentrated in vacuo to afford 4-(1,1,1,3,3,3-hexamethyl-disilazan-2-yl)-2-methyl-pyrimidine as an off-white solid (2.18 g).

A solution of 2(R)-(3-chloro-4-methanesulfanyl-phenyl)-3-cyclopentyl-propionic acid (prepared as in Example 137, 1.20 g, 4.02 mmol) in methylene chloride (5 mL) was treated with N,N-dimethylformamide (1 drop) and then cooled to 0° C. The reaction mixture was then treated dropwise with a 2M solution of oxalyl chloride in methylene chloride (2.21 mL, 4.42 mmol) and stirred at 0° C. for 30 min. The resulting reaction mixture was then treated with a solution of the 4-(1,1,1,3,3,3-hexamethyl-disilazan-2-yl)-2-methyl-pyrimidine (2.04 g, 8.03 mmol) and pyridine (1.3 mL, 16.06 mmol) in tetrahydrofuran (25 mL). The resulting reaction mixture was allowed to warm to 25° C. where it was stirred for 16 h. The reaction mixture was then diluted with methylene chloride (30 mL) and then washed with a 1N aqueous hydrochloric acid solution (30 mL). The aqueous layer was back-extracted with methylene chloride (3×30 mL). The combined organic layers were washed with a saturated aqueous sodium chloride solution (1×30 mL), dried over sodium sulfate, filtered, and concentrated in vacuo. Biotage chromatography (FLASH 40M, Silica, 60/40 hexanes/ethyl acetate) afforded the 2(R)-(3-chloro-4-methylsulfanyl-phenyl)-3-cyclopentyl-N-(2-methyl-pyrimidin-4-yl)-propionamide (1.11 g, 71%) as an off-white foam: $[\alpha]^{23}_{589}$=−65.7° (c=0.067, chloroform).

A solution of 2(R)-(3-chloro-4-methylsulfanyl-phenyl)-3-cyclopentyl-N-(2-methyl-pyrimidin-4-yl)-propionamide (119 mg, 0.31 mmol) in methanol (7 mL) was treated with a solution of sodium periodate (117 mg, 0.55 mmol) in water (3.5 mL). The resulting reaction mixture was stirred at 25° C. for 8 h. After this time, the precipitate was filtered and washed with methylene chloride (15 mL). The organic layer was separated and set aside. The aqueous layer was extracted with methylene chloride (3×15 mL). The combined organic layers were dried over sodium sulfate, filtered, and concentrated in vacuo to afford the sulfoxide product (123 mg) which was used without further purification. The resulting crude sulfoxide was dissolved in methanol (5 mL) at 25° C. This solution was then treated with a solution of potassium permanganate (57 mg, 0.36 mmol) in water (1.5 mL), and the reaction mixture was stirred at 25° C. for 30 min. The reaction mixture was then filtered, and the cake was washed with methylene chloride (10 mL). The filtrate was then washed with a saturated aqueous sodium bicarbonate solution (1×10 mL) and a saturated aqueous sodium chloride solution (1×10 mL), dried over sodium sulfate, filtered, and concentrated in vacuo. Biotage chromatography (FLASH 12M, Silica, 50/50 hexanes/ethyl acetate) afforded 2(R)-(3-chloro-4-methanesulfonyl-phenyl)-3-cyclopentyl-N-(2-methyl-pyrimidin-4-yl)-propionamide (65 mg, 51% for two steps) as a white foam: $[\alpha]^{23}_{589}$=−40.3° (c=0.062, chloroform); EI-HRMS m/e calcd for $C_{20}H_{24}ClN_3O_3S$ (M$^+$) 421.1227, found 421.1224.

EXAMPLE 145

2(R)-(3-Chloro-4-methanesulfonyl-phenyl)-3-cyclopentyl-N-(2-oxo-1,2-dihydro-pyrimidin-4-yl)-propionamide

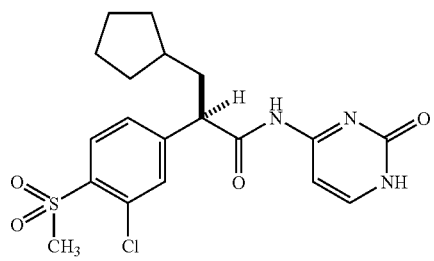

A solution of 2(R)-(3-chloro-4-methanesulfonyl-phenyl)-3-cyclopentyl-propionic acid (prepared as in Example 137, 200 mg, 0.61 mmol) in methylene chloride (4 mL) was treated with N,N-dimethylformamide (1 drop) and then cooled to 0° C. The reaction mixture was then treated dropwise with a 2M solution of oxalyl chloride in methylene chloride (0.45 mL, 0.91 mmol) and stirred at 0° C. for 30 min. The resulting reaction mixture was then treated with a solution of cytosine (101 mg, 0.91 mmol) and pyridine (0.245 mL, 3.03 mmol) in N,N-dimethylformamide (10 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 95/5 methylene chloride/methanol) afforded 2(R)-(3-chloro-4-methanesulfonyl-phenyl)-3-cyclopentyl-N-(2-oxo-1,2-dihydro-pyrimidin-4-yl)-propionamide (145 mg, 57%) as a white solid: mp>200° C.; EI-HRMS m/e calcd for $C_{19}H_{22}ClN_3O_4S$ (M$^+$) 423.1019, found 423.1015.

EXAMPLE 146

2-(3-Chloro-4-methanesulfonyl-phenyl)-3-cyclopentyl-N-pyrazin-2-yl-propionamide

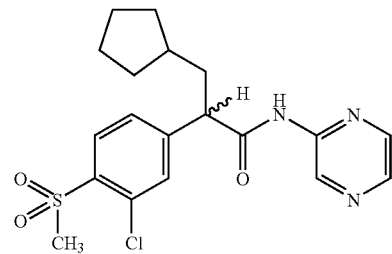

A solution of 2-(3-chloro-4-methanesulfonyl-phenyl)-3-cyclopentyl-propionic acid (prepared as in Example 143, 50 mg, 0.15 mmol) in methylene chloride (2 mL) was treated with N,N-dimethylformamide (1 drop) and then cooled to 0° C. The reaction mixture was then treated dropwise with a 2M solution of oxalyl chloride in methylene chloride (0.11 mL, 0.23 mmol) and stirred at 0° C. for 30 min. The reaction mixture was then treated with a solution of 2-aminopyrazine (29 mg, 0.30 mmol) and pyridine (0.06 mL, 0.76 mmol) in tetrahydrofuran (2.5 mL). The resulting reaction mixture was allowed to warm to 25° C. where it was stirred for 16 h. The reaction mixture was then diluted with water (10 mL) and extracted with ethyl acetate (3×15 mL). The combined organic layers were dried over sodium sulfate, filtered, and concentrated in vacuo. Biotage chromatography (FLASH 40S, Silica, 50/50 hexanes/ethyl acetate) afforded 2-(3-chloro-4-methanesulfonyl-phenyl)-3-cyclopentyl-N-pyrazin-2-yl-propionamide (53 mg, 86%) as a white foam: EI-HRMS m/e calcd for $C_{19}H_{22}ClN_3O_3S$ (M$^+$) 407.1070, found 407.1073.

EXAMPLE 147

2(R)-(3-Chloro-4-methanesulfonyl-phenyl)-3-cyclopentyl-N-pyrazin-2-yl-propionamide

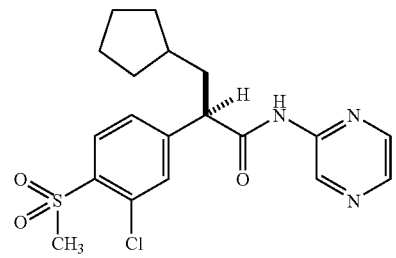

A solution of 2(R)-(3-chloro-4-methanesulfonyl-phenyl)-3-cyclopentyl-propionic acid (prepared as in Example 137, 200 mg, 0.61 mmol) in methylene chloride (5 mL) was treated with N,N-dimethylformamide (1 drop) and then cooled to 0° C. The reaction mixture was then treated dropwise with a 2M solution of oxalyl chloride in methylene chloride (0.45 mL, 0.91 mmol) and stirred at 0° C. for 30 min. The reaction mixture was then treated with a solution of 2-aminopyrazine (115 mg, 1.21 mmol) and pyridine (0.245 mL, 3.03 mmol) in tetrahydrofuran (10 mL). The resulting reaction mixture was allowed to warm to 25° C. where it was stirred for 16 h. The reaction mixture was then diluted with water (10 mL) and extracted with methylene chloride (3×15 mL). The combine organic layers were dried over sodium sulfate, filtered, and concentrated in vacuo. Biotage chromatography (FLASH 40S, Silica, 50/50 hexanes/ethyl acetate) afforded 2(R)-(3-chloro-4-methanesulfonyl-phenyl)-3-cyclopentyl-N-pyrazin-2-yl-propionamide (172 mg, 70%) as a white foam: $[\alpha]^{23}_{589}=-46.8°$ (c=0.047, chloroform); EI-HRMS m/e calcd for $C_{19}H_{22}ClN_3O_3S$ (M$^+$) 407.1070, found 407.1068.

EXAMPLE 148

2-(3-Bromo-4-methanesulfonyl-phenyl)-3-cyclopentyl-N-pyrimidin-4-yl-propionamide

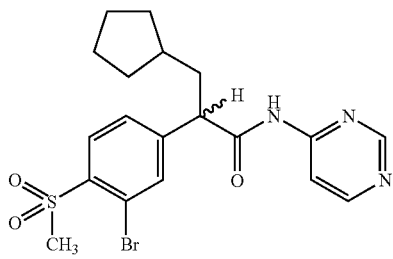

A solution of 4-(methylthio)phenylacetic acid (6.91 g, 37.9 mmol) in methanol (100 mL) was treated slowly with concentrated sulfuric acid (1 mL). The resulting reaction mixture was heated under reflux for 19 h. The reaction mixture was allowed to cool to 25° C. and then concentrated in vacuo to remove methanol. The resulting residue was diluted with ethyl acetate (200 mL). The organic layer was washed with a saturated aqueous sodium bicarbonate solution (3×300 mL) and a saturated aqueous sodium chloride solution (1×100 mL). The organic layer was dried over sodium sulfate, filtered, and concentrated in vacuo to afford (4-methylsulfanyl-phenyl)-acetic acid methyl ester (7.28 g, 98%) as a yellow liquid which was used without further purification: EI-HRMS m/e calcd for $C_{10}H_{12}O_2S$ (M$^+$) 196.0558, found 196.0559.

A solution of (4-methylsulfanyl-phenyl)-acetic acid methyl ester (7.28 g, 37.1 mmol) in carbon tetrachloride (150 mL) was slowly treated with bromine (2.5 mL, 48.23 mmol). The reaction mixture was stirred at 25° C. for 3 h, at which time, thin layer chromatography still indicated the presence of a substantial amount of starting material. The reaction mixture was treated with more bromine (2.5 mL, 48.23 mmol). The reaction mixture was stirred an additional 1 h at 25° C. and then quenched with a 10% aqueous sodium bisulfite solution (200 mL). The reaction mixture was concentrated in vacuo to remove carbon tetrachloride. The resulting aqueous layer was extracted with ethyl acetate (3×200 mL). The combined organic layers were dried over sodium sulfate, filtered, and concentrated in vacuo. Flash chromatography (Merck Silica gel 60, 70–230 mesh, 9/1 hexanes/ethyl acetate) afforded (3-bromo-4-methylsulfanyl-phenyl)-acetic acid methyl ester (8.57 g, 84%) as a light yellow oil: EI-HRMS m/e calcd for $C_{10}H_{11}BrO_2S$ (M$^+$) 273.9663, found 273.9661.

A solution of diisopropylamine (4.8 mL, 34.27 mmol) in dry tetrahydrofuran (30 mL) and 1,3-dimethyl-3,4,5,6-tetrahydro-2(1H)-pyrimidinone (10 mL) was cooled to −78° C. under nitrogen and then treated with a 2.5M solution of n-butyllithium in hexanes (13.8 mL, 34.27 mmol). The resulting reaction mixture was stirred at −78° C. for 30 min and then treated dropwise with a solution of (3-bromo-4-methylsulfanyl-phenyl)-acetic acid methyl ester (8.57 g, 31.15 mmol) in dry tetrahydrofuran (30 mL) and 1,3-dimethyl-3,4,5,6-tetrahydro-2(1H)-pyrimidinone (10 mL). The resulting reaction mixture was allowed to stir at −78° C. for 1 h, at which time, a solution of iodomethylcyclopentane (7.85 g, 37.38 mmol) in a small amount of dry tetrahydrofuran was added dropwise. The reaction mixture was allowed to warm to 25° C. where it was stirred for 15 h. The reaction mixture was quenched with water (300 mL) and then concentrated in vacuo to remove tetrahydrofuran. The remaining aqueous phase was extracted with ethyl acetate (3×150 mL). The combined organic layers were washed with a saturated aqueous sodium chloride solution (1×200 mL), dried over sodium sulfate, filtered, and concentrated in vacuo. Flash chromatography (Merck Silica gel 60, 70–230 mesh, 19/1 hexanes/ethyl acetate) afforded 2-(3-bromo-4-methylsulfanyl-phenyl)-3-cyclopentyl-propionic acid methyl ester (9.20 g, 83%) as a light yellow oil: EI-HRMS m/e calcd for $C_{16}H_{21}BrO_2S$ (M$^+$) 356.0446, found 356.0435.

A solution of 2-(3-bromo-4-methylsulfanyl-phenyl)-3-cyclopentyl-propionic acid methyl ester (9.20 g, 25.75 mmol) in formic acid (30 mL) was cooled to 0° C. and then treated with a 30% aqueous hydrogen peroxide solution (15.0 mL, 386.25 mmol). The resulting solution was allowed to warm to 25° C. where it was stirred for 1.5 h. An additional amount of 30% aqueous hydrogen peroxide solution (5.0 mL, 43.00 mmol) was then added, and the reaction was stirred at 25° C. for 3 h. The reaction was then re-cooled to 0° C., quenched with a saturated aqueous sodium bisulfite solution, and then extracted with ethyl acetate (2×300 mL). The combined organic layers were then washed with a saturated aqueous sodium bicarbonate solution (2×200 mL), dried over sodium sulfate, filtered, and concentrated in vacuo to afford 2-(3-bromo-4-methanesulfonyl-phenyl)-3-cyclopentyl-propionic acid methyl ester (10.02 g, 100%) as a colorless gum which was used without further purification: EI-HRMS m/e calcd for $C_{16}H_{19}BrO_4S$ (M$^+$) 388.0344, found 388.0343.

A solution of 2-(3-bromo-4-methanesulfonyl-phenyl)-3-cyclopentyl-propionic acid methyl ester (10.02 g, 25.75 mol) in methanol (100 mL) and water (100 mL) was treated with lithium hydroxide (15.4 g, 515 mmol). The reaction mixture was stirred at 25° C. for 2 h. The reaction mixture was then concentrated in vacuo to remove methanol. The resulting aqueous residue was acidified to pH=2 with a 10% aqueous hydrochloric acid solution and then extracted with ethyl acetate (1×400 mL). The organic layer was washed with water (1×300 mL) and a saturated aqueous sodium chloride solution (1×300 mL). The organic layer was then dried over sodium sulfate, filtered, and concentrated in vacuo to afford 2-(3-bromo-4-methanesulfonyl-phenyl)-3-cyclopentyl-propionic acid (9.58 g, 99%) as a white solid which was used without further purification: mp 149–150° C.; FAB-HRMS m/e calcd for $C_{15}H_{19}BrO_4S$ (M+H)+ 375.0266, found 375.0274.

A solution of 2-(3-bromo-4-methanesulfonyl-phenyl)-3-cyclopentyl-propionic acid (100 mg, 0.266 mmol) in methylene chloride (8 mL) was treated with dry N,N-dimethylformamide (2 drops). The reaction mixture was cooled to 0° C. and then treated dropwise with a 2M solution of oxalyl chloride in methylene chloride (0.15 mL, 0.29 mmol). The reaction mixture was stirred at 0° C. for 10 min and then stirred at 25° C. for 30 min. The reaction mixture was then treated with N,N-diisopropylethylamine (0.11 mL, 0.63 mmol) followed by a solution of 4-aminpyrimidine (53 mg, 0.56 mmol) in dry tetrahydrofuran (3 mL). The resulting reaction mixture was stirred at 25° C. for 17 h. The reaction mixture was concentrated in vacuo. The resulting residue was adsorbed onto silica gel (Merck Silica gel 60, 230–400 mesh) and then purified via Biotage chromatography (FLASH 40S, Silica, 2/3 hexanes/ethyl acetate) to afford 2-(3-bromo-4-methanesulfonyl-phenyl)-3-cyclopentyl-N-pyrimidin-4-yl-propionamide (110 mg, 92%) as a white solid: mp 75–80° C.; EI-HRMS m/e calcd for $C_{19}H_{22}BrN_3O_3S$ (M+) 451.0565, found 451.0558.

In an analogous manner, there was obtained:
a) From 2-(3-bromo-4-methanesulfonyl-phenyl)-3-cyclopentyl-propionic acid and 4-amino-2-methylpyrimidine: 2-(3-Bromo-4-methanesulfonyl-phenyl)-3-cyclopentyl-N-(2-methyl-pyrimidin-4-yl)-propionamide as a white foam: EI-HRMS m/e calcd for $C_{22}H_{23}BrN_2O_3S_2$(M+) 465.0722, found 465.0723.

EXAMPLE 149

2-(3-Bromo-4-methanesulfonyl-phenyl)-3-cyclopentyl-N-pyrazin-2-yl-propionamide

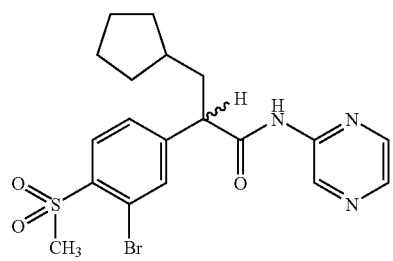

A solution of 2-(3-bromo-4-methanesulfonyl-phenyl)-3-cyclopentyl-propionic acid (prepared as in Example 148A, 375 mg, 1.0 mmol) and triphenylphosphine (446 mg, 1.7 mmol) in methylene chloride (5 mL) was cooled to 0° C. and then treated with N-bromosuccinimide (303 mg, 1.7 mmol) in small portions. The reaction mixture color changed from light yellow to a darker yellow then to brown. After the complete addition of the N-bromosuccinimide, the reaction mixture was allowed to warm to 25° C. over 30 min. The brown reaction mixture was then treated with 2-aminopyrazine (238 mg, 2.5 mmol). The resulting reaction mixture was stirred at 25° C. for 19 h. The reaction mixture was then concentrated in vacuo to remove methylene chloride. Biotage chromatography (FLASH 40S, Silica, 2/3 hexanes/ethyl acetate) afforded 2-(3-bromo-4-methanesulfonyl-phenyl)-3-cyclopentyl-N-pyrazin-2-yl-propionamide (72 mg, 16%) as pink foam: EI-HRMS m/e calcd for $C_{19}H_{22}BrN_3O_3S$ (M+) 451.0565, found 451.0547.

EXAMPLE 150

2-(3-Bromo-4-methanesulfonyl-phenyl)-3-cyclopentyl-N-(1H-imidazol-2-yl)-propionamide

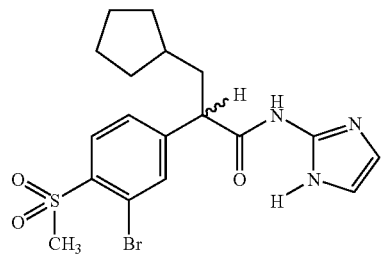

A solution of 2-(3-bromo-4-methanesulfonyl-phenyl)-3-cyclopentyl-propionic acid (prepared as in Example 148A, 100 mg, 0.266 mmol), benzotriazol-1-yloxy-tris(dimethylamino)phosphonium hexafluorophosphate (187 mg, 0.42 mmol), triethylamine (115 µL, 1.064 mmol), and 2-aminoimidazole sulfate (56 mg, 0.42 mmol) in methylene chloride (10 mL) was stirred at 25° C. for 15 h. The reaction mixture was partitioned between water and methylene chloride. The organic layer was washed sequentially with a 1N aqueous hydrochloric acid solution (1×10 mL) and water (1×10 mL). The organic layer was dried over magnesium sulfate, filtered, and concentrated in vacuo. Biotage chromatography (FLASH 40M, Silica, ethyl acetate) afforded 2-(3-bromo-4-methanesulfonyl-phenyl)-3-cyclopentyl-N-(1H-imidazol-2-yl)-propionamide (69 mg, 53%) as a white solid: mp>210° C. (dec); EI-HRMS m/e calcd for $C_{18}H_{22}BrN_3O_3S$(M+) 439.0565, found 439.0566.

EXAMPLE 151

2-(3-Cyano-4-methanesulfonyl-phenyl)-3-cyclopentyl-N-pyrimidin-4-yl-propionamide

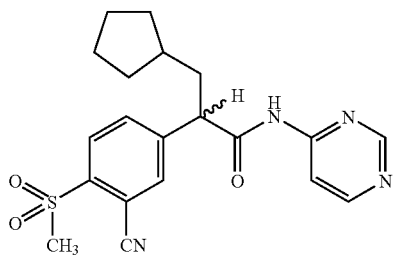

A solution of 2-(3-cyano-4-methanesulfonyl-phenyl)-3-cyclopentyl-propionic acid (prepared as in Example 75, 125 mg, 0.389 mmol) in methylene chloride (3 mL) was treated with N,N-dimethylformamide (1 drop) and then cooled to 0° C. The reaction mixture was then treated with oxalyl chloride (0.050 mL, 0.583 mmol). The resulting reaction mixture was allowed to warm to 25° C. where it was stirred for 1 h. The reaction mixture was then concentrated in vacuo. The resulting yellow gel was diluted with methylene chloride (2 mL) and then slowly added to a solution of 4-aminopyrimidine (56 mg, 0.583 mmol) and triethylamine (0.108 mL, 0.778 mmol) in N,N-dimethylformamide (3 mL). The resulting reaction mixture was stirred at 25° C. for 20 h. The reaction mixture was then diluted with water (25 mL), a 1N aqueous hydrochloric acid solution (5 mL), and ethyl acetate (25 mL). The layers were separated, and the organic layer was dried over magnesium sulfate, filtered, and concentrated in vacuo. Biotage chromatography (FLASH 40S, Silica, 1/1 then 1/3 hexanes/ethyl acetate) afforded 2-(3-cyano-4-methanesulfonyl-phenyl)-3-cyclopentyl-N-pyrimidin-4-yl-propionamide (34.7 mg, 22%) as a pale yellow foam: mp 79–84° C. (foam to gel); EI-HRMS m/e calcd for $C_{20}H_{22}N_4O_3S$ (M$^+$) 398.1413, found 398.1411.

EXAMPLE 152

2-(3-Cyano-4-methanesulfonyl-phenyl)-3-cyclopentyl-N-(2-methyl-pyrimidin-4-yl)-propionamide

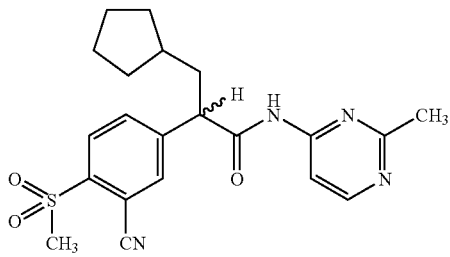

A solution of 2-(3-cyano-4-methanesulfonyl-phenyl)-3-cyclopentyl-propionic acid (prepared as in Example 75, 200 mg, 0.622 mmol) in methylene chloride (5 mL) was treated with N,N-dimethylformamide (2 drops) and then cooled to 0° C. The reaction mixture was then treated with oxalyl chloride (0.081 mL, 0.933 mmol). The resulting reaction mixture was allowed to warm to 25° C. where it was stirred for 1 h. The reaction mixture was then concentrated in vacuo. The resulting yellow gel was diluted with methylene chloride (2 mL) and then slowly added to a mixture of 4-amino-2-methylpyrimidine (102 mg, 0.933 mmol) and triethylamine (0.173 mL, 1.24 mmol) in N,N-dimethylformamide (3 mL). The resulting reaction mixture was stirred at 25° C. for 24 h. The crude reaction mixture was directly purified by Biotage chromatography (FLASH 40S, Silica, 19/1 methylene chloride/methanol) to afford 2-(3-cyano-4-methanesulfonyl-phenyl)-3-cyclopentyl-N-(2-methyl-pyrimidin-4-yl)-propionamide (15 mg, 6%) as a white foam: mp 89–94° C. (foam to gel); EI-HRMS m/e calcd for $C_{21}H_{24}N_4O_3S$ (M$^+$) 412.1569, found 412.1568.

EXAMPLE 153

2-(3-Cyano-4-methanesulfonyl-phenyl)-3-cyclopentyl-N-pyrazin-2-yl-propionamide

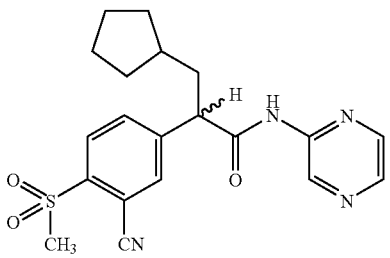

A solution of 2-(3-cyano-4-methanesulfonyl-phenyl)-3-cyclopentyl-propionic acid (prepared as in Example 75, 200 mg, 0.622 mmol) in methylene chloride (5 mL) was treated with N,N-dimethylformamide (2 drops) and then cooled to 0° C. The reaction mixture was then treated with oxalyl chloride (0.081 mL, 0.933 mmol). The resulting reaction mixture was allowed to warm to 25° C. where it was stirred for 1 h. The reaction mixture was then concentrated in vacuo. The resulting yellow gel was diluted with methylene chloride (2 mL) and then slowly added to a mixture of 2-aminopyrazine (89 mg, 0.933 mmol) and triethylamine (0.173 mL, 1.24 mmol) in N,N-dimethylformamide (3 mL). The resulting reaction mixture was stirred at 25° C. for 24 h. The reaction mixture was then diluted with water (30 mL), a 1N aqueous hydrochloric acid solution (5 mL), and ethyl acetate (30 mL). The layers were separated, and the organic layer was dried over magnesium sulfate, filtered, and concentrated in vacuo. Biotage chromatography (FLASH 40S, Silica, 19/1 methylene chloride/methanol) afforded 2-(3-cyano-4-methanesulfonyl-phenyl)-3-cyclopentyl-N-pyrazin-2-yl-propionamide as an impure orange foam. Repurification by flash chromatography (Merck Silica gel 60, 230–400 mesh, 1/1 hexanes/ethyl acetate) afforded 2-(3-cyano-4-methanesulfonyl-phenyl)-3-cyclopentyl-N-pyrazin-2-yl-propionamide (8 mg, 3%) as a yellow foam: mp 88–93° C. (foam to gel); EI-HRMS m/e calcd for $C_{20}H_{22}N_4O_3S$ (M$^+$) 398.1413, found 398.1413.

EXAMPLE 154

3-Cyclopentyl-2-(4-methylsulfanyl-3-trifluoromethyl-phenyl)-N-(5-nitro-pyridin-2-yl)-propionamide

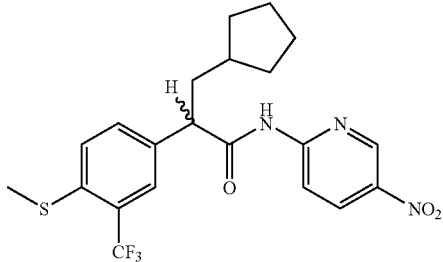

A solution of 3-cyclopentyl-2-(4-methylsulfanyl-3-trifluoromethyl-phenyl)-propionic acid methyl ester (prepared as in Example 89, 1.73 g, 5 mmol) in tetrahydrofuran/water (20 mL, 3:1) was treated with lithium hydroxide (419 mg, 10 mmol). The reaction was stirred at 25° C. for 24 h. At this time, the reaction was diluted with water (50 mL) and extracted with ether (1×50 mL). The aqueous layer was acidified to pH=2 with a 2N aqueous hydrochloric acid solution. The product was extracted into methylene chloride (3×75 mL). The combined organic layers were washed with a saturated aqueous sodium chloride solution (3×100 mL), dried over magnesium sulfate and sodium sulfate, filtered, and concentrated in vacuo. The residue was triturated with 90/10 hexanes/ether to afford 3-cyclopentyl-2-(4-methylsulfanyl-3-trifluoromethyl-phenyl)-propionic acid (1.05 g, 63.65%) as a white solid: mp 105–106° C.; EI-HRMS m/e calcd for $C_{16}H_{19}F_3O_2S$ (M$^+$) 332.1058, found 332.1055.

A solution of triphenylphosphine (393 mg, 1.5 mmol) in methylene chloride (10.0 mL) was cooled to 0° C. and then treated with N-bromosuccinimide (303 mg, 1.7 mmol). After stirring at 0° C. for 10 min, the reaction mixture was treated with 3-cyclopentyl-2-(4-methylsulfanyl-3-trifluoromethyl-phenyl)-propionic acid (332 mg, 1.0 mmol). The reaction mixture was stirred at 0° C. for 20 min and at 25° C. for 30 min. At this time, the reaction mixture was treated with 2-amino-5-nitropyridine (290 mg, 1.5 mmol) and pyridine (0.14 mL, 1.8 mmol). The resulting reaction mixture was stirred at 25° C. for 20 h. The reaction mixture was then concentrated in vacuo. Flash chromatography (Merck Silica gel 60, 200–400 mesh, 90/10 hexane s/ethyl acetate) afforded 3-cyclopentyl-2-(4-methylsulfanyl-3-trifluoromethyl-phenyl)-N-(5-nitro-pyridin-2-yl)-propionamide (425 mg, 60%) as an off-white solid: mp 109–110° C.; EI-HRMS m/e calcd for $C_{21}H_{22}F_3N_3O_3S$ (M$^+$) 453.1334, found 453.1334.

In an analogous manner, there were obtained:
a) From 2-amino-5-bromopyridine and 3-cyclopentyl-2-(4-methylsulfanyl-3-trifluoromethyl-phenyl)-propionic acid: N-(5-Bromo-pyridin-2-yl)-3-cyclopentyl-2-(4-methylsulfanyl-3-trifluoromethyl-phenyl)-propionamide as an off-white solid: mp 108–110° C.; EL-HRMS m/e calcd for $C_{21}H_{22}BrF_3N_2OS$ (M$^+$) 486.0588, found 486.0587.
b) From 2-amino-5-cyanopyridine and 3-cyclopentyl-2-(4-methylsulfanyl-3-trifluoromethyl-phenyl)-propionic acid: N-(5-Cyano-pyridin-2-yl)-3-cyclopentyl-2-(4-methylsulfanyl-3-trifluoromethyl-phenyl)-propionamide as a pale yellow oil: EI-HRMS m/e calcd for $C_{22}H_{22}F_3N_3OS$ (M$^+$) 433.1435, found 433.1429.

EXAMPLE 155

3-Cyclopentyl-2-(4-methanesulfonyl-3-trifluoromethyl-phenyl)-N-(2-oxo-2,3-dihydro-pyrimidin-4-yl)-propionamide

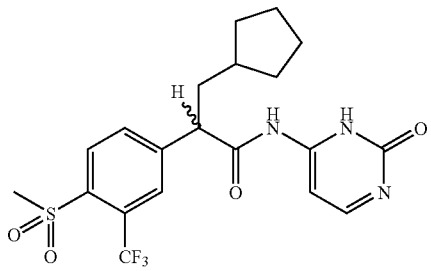

A solution of 3-cyclopentyl-2-(4-methanesulfonyl-3-trifluoromethyl-phenyl)-propionic acid methyl ester (prepared as in Example 89A, 2.92 g, 7.72 mmol) in tetrahydrofuran/water (88 mL, 3:1) was treated with lithium hydroxide (647 mg, 15.43 mmol). The reaction was stirred at 25° C. for 3 d. The tetrahydrofuran was then removed in vacuo. The residue was diluted with water (50 mL) and extracted with ether (25 mL). The aqueous layer was acidified to pH=1 with a 3N aqueous hydrochloric acid solution. The product was extracted into ethyl acetate (3×75 mL) and ether (1×50 mL). The combined organic layers were washed with a saturated aqueous sodium chloride solution (2×100 mL), dried over magnesium sulfate and sodium sulfate, filtered, and concentrated in vacuo to give 3-cyclopentyl-2-(4-methanesulfonyl-3-trifluoromethyl-phenyl)-propionic acid (2.37 g, 84.5%) as a pale-yellow semi-solid: EI-HRMS m/e calcd for $C_{16}H_{19}F_3O_4S$ (M$^+$) 364.0956, found 364.0958.

A solution of 3-cyclopentyl-2-(4-methanesulfonyl-3-trifluoromethyl-phenyl)-propionic acid (183 mg, 0.50 mmol) in methylene chloride (5 mL) cooled to 0° C. was treated with a 2.0M solution of oxalyl chloride in methylene chloride (0.30 mL, 0.56 mmol) and a few drops of N,N-dimethylformamide. The reaction mixture was stirred at 0° C. for 15 min and at 25° C. for 30 min. The reaction mixture was then treated with a solution of cytosine (116.7 mg, 1.06 mmol) in tetrahydrofuran (2.0 mL) and N,N-dimethylformamide (2.0 mL) followed by N,N-diisopropylethylamine (0.20 mL, 1.20 mmol). This solution was stirred at 25° C. for 18 h. At this time, the reaction was concentrated in vacuo. Biotage chromatography (FLASH 40S, Silica, 90/10 methylene chloride/methanol) afforded 3-cyclopentyl-2-(4-methanesulfonyl-3-trifluoromethyl-phenyl)-N-(2-oxo-2,3-dihydro-pyrimidin-4-yl)-propionamide (100 mg, 53.7%) as a white solid: mp 236–238° C.; EI-HRMS m/e calcd for $C_{20}H_{22}F_3N_3O_4S$ (M$^+$) 457.1283, found 457.1291.

In an analogous manner, there were obtained:
a) From 4-aminopyrimidine and 3-cyclopentyl-2-(4-methanesulfonyl-3-trifluoromethyl-phenyl)-propionic acid: 3-Cyclopentyl-2-(4-methanesulfonyl-3-trifluoromethyl-phenyl)-N-pyrimidin-4-yl-propionamide as a pale-yellow solid: mp 85–90° C.; EI-HRMS m/e calcd for $C_{20}H_{22}F_3N_3O_3S$ (M$^+$) 441.1334, found 441.1354.
b) From 2-aminopyrazine and 3-cyclopentyl-2-(4-methanesulfonyl-3-trifluoromethyl-phenyl)-propionic acid: 3-Cyclopentyl-2-(4-methanesulfonyl-3-trifluoromethyl-phenyl)-N-pyrazin-2-yl-propionamide as a white semi-solid: EI-HRMS m/e calcd for $C_{20}H_{22}F_3N_3O_3S$ (M$^+$) 441.1334, found 441.1325.
c) From 4-amino-2-methylpyrimidine and 3-cyclopentyl-2-(4-methanesulfonyl-3-trifluoromethyl-phenyl)-propionic acid: 3-Cyclopentyl-2-(4-methanesulfonyl-3-trifluoromethyl-phenyl)-N-(2-methyl-pyrimidin-4-yl)-propionamide as a pale-yellow oil: EI-HRMS m/e calcd for $C_{21}H_{24}F_3N_3O_3S$ (M$^+$) 455.1490, found 455.1486.

EXAMPLE 156

N-(5-Bromo-pyridin-2-yl)-3-cyclopentyl-2-(4-methanesulfonyl-3-trifluoromethyl-phenyl)-propionamide

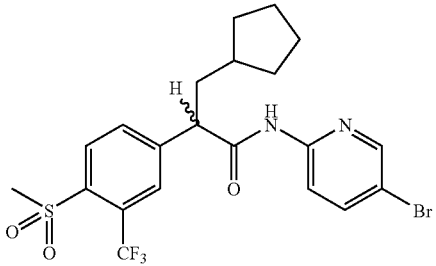

A solution of 3-cyclopentyl-2-(4-methanesulfonyl-3-trifluoromethyl-phenyl)-propionic acid (prepared as in Example 155A, 73 mg, 0.07 mmol) and triphenylphosphine (79 mg, 0.08 mmol) in methylene chloride (5.0 mL) was cooled to 0° C. and then treated with N-bromosuccinimide (60.5 mg, 0.34 mmol). The reaction mixture was stirred at 0° C. for 15 min and at 25° C. for 30 min. At this time, reaction mixture was treated with 2-amino-5-bromopyridine (52 mg, 0.30 mmol) and a few drops of pyridine. The resulting reaction mixture was stirred at 25° C. for 18 h. The reaction mixture was then diluted with methylene chloride (50 mL). The organic phase was washed with water (1×35 mL) and a saturated aqueous sodium chloride solution (3×35 mL), dried over magnesium sulfate and sodium sulfate, treated with charcoal, filtered through a pad of celite, and concentrated in vacuo. Flash chromatography (Merck Silica gel 60, 70–230 mesh, 70/30 hexanes/ethyl acetate) afforded N-(5-bromo-pyridin-2-yl)-3-cyclopentyl-2-(4-methanesulfonyl-3-trifluoromethyl-phenyl)-propionamide (128.3 mg, quant) as a white solid: mp 81–85° C.; EI-HRMS m/e calcd for $C_{21}H_{22}BrF_3N_2O_3S$ (M$^+$) 518.0486, found 518.0489.

In an analogous coupling procedure, there was obtained:
a) From 2-aminothiazole and 3-cyclopentyl-2(R)-(4-methanesulfonyl-3-trifluoromethyl-phenyl)-propionic acid (prepared as in Example 157A): 3-Cyclopentyl-2(R)-(4-methanesulfonyl-3-trifluoromethyl-phenyl)-N-thiazol-2-yl-propionamide as a clear oil: $[\alpha]^{23}{}_{589}$=−17.21° (c=0.122, chloroform); EI-HRMS m/e calcd for $C_{19}H_{21}F_3N_2O_3S_2$ (M+H$^+$) 447.1018, found 447.1022.

EXAMPLE 157

3-Cyclopentyl-2(R)-(4-methanesulfonyl-3-trifluoromethyl-phenyl)-N-pyrimidin-4-yl-propionamide

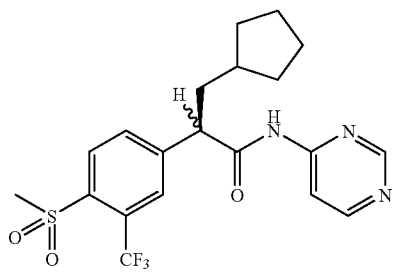

A mixture of (4-fluoro-3-trifluoromethyl-phenyl)-acetic acid (27.0 g, 121.54 mmol) and potassium carbonate (41.85 g, 302.8 mmol) in tetrahydrofuran (112 mL) cooled to −10° C. was treated with trimethylacetyl chloride (15.75 mL, 127.5 mmol). The resulting reaction mixture was stirred at −10° C. for 30 min. The reaction mixture was then treated with a solution of (1R,2R)-(−)-pseudoephedrine (26.5 g, 160.4 mmol) in tetrahydrofuran (100 mL). The resulting reaction was stirred at 0° C. for 3.5 h. At this time, the reaction mixture was poured into water (135 mL) and then extracted with ethyl acetate (3×125 mL) and diethyl ether (1×75 mL). The combined organic layers were washed with a 1N aqueous hydrochloric acid solution (1×125 mL), water (1×125 mL), a saturated aqueous sodium bicarbonate solution (3×200 mL), and a saturated aqueous sodium chloride solution (3×200 mL). The combined organic layers were dried over magnesium sulfate and sodium sulfate, filtered, and concentrated in vacuo. Flash chromatography (Merck Silica gel 60, 230–400 mesh, 50/50 hexanes/ethyl acetate) afforded 2-(4-fluoro-3-trifluoromethyl-phenyl)-N-[2(R)-hydroxy-1(R)-methyl-2(R)-phenyl-ethyl]-N-methyl-acetamide (34.65 g, 77.19%) as a clear oil: EI-HRMS m/e calcd for $C_{19}H_{19}F_4NO_2$(M−H$_2$O)+351.1246, found 351.1243.

A solution of 2-(4-fluoro-3-trifluoromethyl-phenyl)-N-[2(R)-hydroxy-1(R)-methyl-2(R)-phenyl-ethyl]-N-methyl-acetamide (34.65 g, 93.81 mmol) in N,N-dimethylformamide (330 mL) was treated with sodium methanethiolate (11.14 g, 140.85 mmol). The reaction mixture was then heated at 100–110° C. for 24 h. At this time, the reaction was poured onto a mixture of ice and a 1.5N aqueous hydrochloric acid solution (150 mL). This mixture was extracted with ethyl acetate (3×150 mL) and diethyl ether (1×100 mL). The combined organic layers were then washed with water (1×300 mL) and a saturated aqueous sodium chloride solution (3×100 mL). The organic layer was dried over magnesium sulfate and sodium sulfate, treated with charcoal, filtered, and concentrated in vacuo. Flash chromatography (Merck Silica gel 60, 230–400 mesh, 33/67 hexanes/ethyl acetate) afforded N-[2(R)-hydroxy-1(R)-methyl-2(R)-phenyl-ethyl]-N-methyl-2-(4-methylsulfanyl-3-trifluoromethyl-phenyl)-acetamide (24.87 g, 66.7%) as a clear oil: $[\alpha]^{23}{}_{589}$=−91.35° (c=0.243, chloroform); EI-HRMS m/e calcd for $C_{20}H_{22}F_3NO_2S$ (M−H$_2$O)$^+$ 379.1217, found 379.1218.

A solution of 1,1,1,3,3,3-hexamethyldisilazane (27.87 mL, 132.1 mmol) in tetrahydrofuran (113 mL) cooled to −20° C. was treated with a 2.5M solution of n-butyllithium in hexanes (47.4 mL, 118.5 mmol). The resulting reaction mixture was stirred at −20° C. for 30 min. At this time, the reaction mixture was treated with a solution of N-[2(R)-hydroxy-1(R)-methyl-2(R)-phenyl-ethyl]-N-methyl-2-(4-methylsulfanyl-3-trifluoromethyl-phenyl)-acetamide (22.68 g, 57.0 mmol) in tetrahydrofuran (143 mL). The resulting solution was stirred at −20° C. for 30 min and then allowed to warm to 0° C. At this time, the reaction mixture was treated with a solution of iodomethylcyclopentane (14.37 g, 68.4 mmol) in 1,3-dimethyl-3,4,5,6-tetrahydro-2(1H)-pyrimidinone (14.3 mL). The resulting reaction mixture was stirred at 0° C. for 4 h. The reaction was then stored in the freezer overnight. At this time, the reaction mixture was poured into a saturated aqueous sodium chloride solution (250 mL) and ethyl acetate (250 mL). The organic layer was separated. The aqueous phase was back-extracted with ethyl acetate (2×125 mL) and ether (1×100 mL). The combined organic layers were washed with a 1N aqueous hydrochloric acid solution (1×150 mL), water (1×150 mL), a saturated aqueous sodium bicarbonate solution (2×200 mL), a saturated aqueous sodium chloride solution (3×250 mL), and a saturated aqueous lithium chloride solution (1×150 mL). The organic layer was then dried over magnesium sulfate and sodium sulfate, treated with charcoal, filtered, and concentrated in vacuo. The crude material was recrystallized from ethyl acetate to afford 3-cyclopentyl-N-[2(R)-hydroxy-1(R)-methyl-2(R)-phenyl-ethyl]-N-methyl-2(R)-(4-methylsulfanyl-3-trifluoromethyl-phenyl)-propionamide (21.07 g, 77.1%) as a white solid: mp 145–146° C.; $[\alpha]^{23}{}_{589}$=−80.54° (c=0.149, chloroform); FAB-HRMS m/e calcd for $C_{26}H_{32}F_3NO_2S$ (M−H$_2$O)$^+$ 461.2000, found 461.1995.

A solution of 3-cyclopentyl-N-[2(R)-hydroxy-1(R)-methyl-2(R)-phenyl-ethyl]-N-methyl-2(R)-(4-methylsulfanyl-3-trifluoromethyl-phenyl)-propionamide (21.01 g, 43.8 mmol) in dioxane (105 mL) was treated with an 18N aqueous sulfuric acid solution (35 mL). The resulting reaction mixture was then heated at 115° C. for 16 h. The reaction mixture was then cooled to 25° C., poured onto ice water (500 mL), and extracted with ethyl acetate (3×250 mL) and ether (1×125 mL). The combined organic layers were washed with water (1×500 mL) and a saturated aqueous sodium chloride solution (3×500 mL), dried over magnesium sulfate and sodium sulfate, treated with charcoal, filtered through a pad of celite, and concentrated in vacuo. Flash chromatography (Merck Silica gel 60, 230–400 mesh, 80/20 hexanes/ethyl acetate) afforded 3-cyclopentyl-2(R)-(4-methylsulfanyl-3-trifluoromethyl-phenyl)-propionic acid (12.14 g, 83.4%) as a pale-yellow solid: mp 78–80° C.; $[\alpha]^{23}{}_{589}$=−46.49° (c=0.185, chloroform); EI-HRMS m/e calcd for $C_{16}H_{19}F_3O_2S$ (M)$^+$ 332.1058, found 332.1068.

A slurry of 3-cyclopentyl-2(R)-(4-methylsulfanyl-3-trifluoromethyl-phenyl)-propionic acid (6.65 g, 20.0 mmol) in formic acid (3.8 mL) cooled to 0° C. was treated with a 30% aqueous hydrogen peroxide solution (11.4 mL). The resulting solution was stirred at 0° C. for 15 min and at 25° C. for 18 h. At this time, the reaction was treated with tetrahydrofuran (5 mL), cooled to 0° C., and then treated with an additional amount of 30% aqueous hydrogen peroxide solution (11.4 mL). The reaction was then stirred at 25° C. for 4 h. At this time, the reaction was poured onto a slurry of ice water (125 mL) and then extracted into methylene chloride (3×125 mL). The combined organic layers were washed with a saturated aqueous sodium chloride solution (3×25 mL), dried over sodium sulfate and magnesium sulfate, filtered, and concentrated in vacuo. The residue was then retreated under the same reaction conditions and work up procedure to complete the conversion of the sulfoxide to the desired sulfone. Biotage chromatography (FLASH 40M, Silica, 100% ethyl acetate) afforded 3-cyclopentyl-2(R)-(4-methanesulfonyl-3-trifluoromethyl-phenyl)-propionic acid (7.29 g, quant.) as a white solid: mp 100–102° C.; $[\alpha]^{23}_{589}$=–27.63° (c=0.351, chloroform); FAB-HRMS m/e calcd for $C_{16}H_{19}F_3O_4S$ (M)$^+$ 364.0956, found 364.0954.

A solution of 3-cyclopentyl-2(R)-(4-methanesulfonyl-3-trifluoromethyl-phenyl)-propionic acid (8.32 g, 20.0 mmol) in methylene chloride (100 mL) cooled to 0° C. was treated with a 2.0M solution of oxalyl chloride in methylene chloride (11.14 mL, 22.28 mmol) and N,N-dimethylformamide (0.5 mL). The reaction mixture was stirred at 0° C. for 45 min and at 25° C. for 1 h. The reaction mixture was then cooled to 0° C. and treated with a solution of 4-aminopyrimidine (4.02 g, 4.28 mmol) in tetrahydrofuran (60 mL) followed by pyridine (6.0 mL, 74.2 mmol). This solution was stirred at 0° C. for 15 min and at 25° C. for 16 h. At this time, the reaction was poured onto a slurry of ice water (100 g) and then extracted with ethyl acetate (3×250 mL) and ether (1×200 mL). The combined organic layers were washed with water (1×500 mL) and a saturated aqueous sodium chloride solution (3×300 mL). The organic layer was then dried over sodium sulfate and magnesium sulfate, treated with charcoal, filtered through a pad of celite, and concentrated in vacuo. Flash chromatography (Merck Silica gel 60, 230–400 mesh, 50/50 hexanes/ethyl acetate) afforded 3-cyclopentyl-2(R)-(4-methanesulfonyl-3-trifluoromethyl-phenyl)-N-pyrimidin-4-yl-propionamide (6.36 g, 72.1%) as a white solid: mp 85–90° C.; $[\alpha]^{23}_{589}$=–32.53° (c=0.166, chloroform); EI-HRMS m/e calcd for $C_{20}H_{22}F_3N_3O_3S$ (M$^+$) 441.1334, found 441.1333.

In an analogous manner, there were obtained:
a) From 2-aminopyrazine and 3-cyclopentyl-2(R)-(4-methanesulfonyl-3-trifluoromethyl-phenyl)-propionic acid: 3-Cyclopentyl-2(R)-(4-methanesulfonyl-3-trifluoromethyl-phenyl)-N-pyrazin-2-yl-propionamide as an off-white solid: mp 78–80° C.; $[\alpha]^{23}_{589}$=–27.32° (c=0.183, chloroform); EI-HRMS m/e calcd for $C_{20}H_{22}F_3N_3O_3S$ (M$^+$) 441.1334, found 441.1342.
b) From 4-(1,1,1,3,3,3-hexamethyl-disilazan-2-yl)-2-methyl-pyrimidine (prepared as in Example 144) and 3-cyclopentyl-2(R)-(4-methanesulfonyl-3-trifluoromethyl-phenyl)-propionic acid: 3-Cyclopentyl-2(R)-(4-methanesulfonyl-3-trifluoromethyl-phenyl)-N-(2-methyl-pyrimidin-4-yl)-propionamide as a pale-yellow oil: $[\alpha]^{23}_{589}$=–12.450 (c=0.273, chloroform); EI-HRMS m/e calcd for $C_{21}H_{24}F_3N_3O_3S$ (M$^+$) 455.1490, found 455.1499.

EXAMPLE 158

3-Cyclopentyl-2-(4-methanesulfonyl-3-nitro-phenyl)-N-pyrimidin-4-yl-propionamide

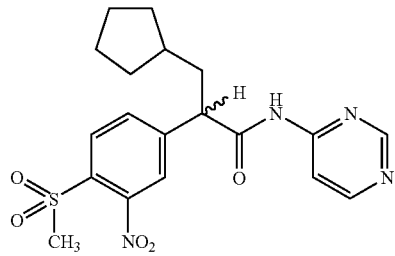

A solution of 3-cyclopentyl-2-(4-methanesulfonyl-3-nitrophenyl)-propionic acid (prepared as in Example 14, 150 mg, 0.439 mmol), triethylamine (0.184 mL, 1.32 mmol), benzotriazol-1-yloxy-tris(dimethylamino)phosphonium hexafluorophosphate (291 mg, 0.659 mmol), and 4-aminopyrimidine (63 mg, 0.659 mmol) in methylene chloride (4 mL) was stirred at 25° C. overnight. The crude reaction mixture was directly purified by Biotage chromatography (FLASH 40M, Silica, 1/2 hexanes/ethyl acetate) to afford 3-cyclopentyl-2-(4-methanesulfonyl-3-nitro-phenyl)-N-pyrimidin-4-yl-propionamide (56 mg, 30%) as a pale yellow foam: mp 91–95° C. (foam to gel); EI-HRMS m/e calcd for $C_{19}H_{22}N_4O_5S$ (M$^+$) 418.1311, found 418.1310.

EXAMPLE 159

3-Cyclopentyl-2-(4-methanesulfonyl-3-nitro-phenyl)-N-(2-methyl-pyrimidin-4-yl)-propionamide

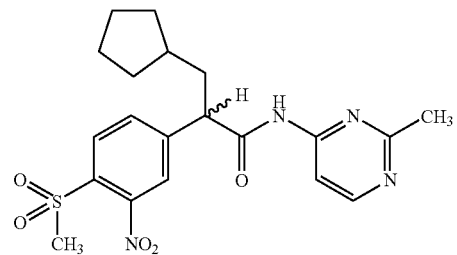

A mixture of 3-cyclopentyl-2-(4-methanesulfonyl-3-nitrophenyl)-propionic acid (prepared as in Example 14, 250 mg, 0.732 mmol), triethylamine (0.306 mL, 2.19 mmol), benzotriazol-1-yloxy-tris(dimethylamino)phosphonium hexafluorophosphate (487 mg, 1.10 mmol), and 4-amino-2-methylpyrimidine (120 mg, 1.10 mmol) in methylene chloride (5 mL) was stirred at 25° C. for 24 h. The reaction mixture was then diluted with water (25 mL), a 1N aqueous hydrochloric acid solution (5 mL), and ethyl acetate (25 mL). The layers were separated, and the organic layer was dried over magnesium sulfate, filtered, and concentrated in vacuo. Biotage chromatography (FLASH 40S, Silica, 1/3 hexanes/ethyl acetate) afforded impure 3-cyclopentyl-2-(4-methanesulfonyl-3-nitro-phenyl)-N-(2-methyl-pyrimidin-4-yl)-propionamide. Re-purification by flash chromatography (Merck Silica gel 60, 230–400 mesh, 1/1 then 1/3 hexanes/ethyl acetate) afforded 3-cyclopentyl-2-(4-methanesulfonyl-3-nitro-phenyl)-N-(2-methyl-pyrimidin-4-yl)-propionamide (59 mg, 18%) as a white foam: mp 96–99° C. (foam to gel); EI-HRMS m/e calcd for $C_{20}H_{24}N_4O_5S$ (M$^+$) 432.1467, found 432.1470.

EXAMPLE 160

3-Cyclopentyl-2-(4-methanesulfonyl-3-nitro-phenyl)-N-(2-oxo-1,2-dihydro-pyrimidin-4-yl)-propionamide

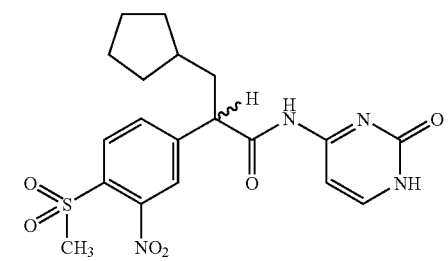

A solution of 3-cyclopentyl-2-(4-methanesulfonyl-3-nitrophenyl)-propionic acid (prepared as in Example 14, 150 mg, 0.439 mmol) in methylene chloride (2 mL) was treated with N,N-dimethylformamide (2 drops) and then cooled to 0° C. The reaction mixture was then treated with oxalyl chloride (0.042 mL, 0.483 mmol). The resulting reaction mixture was allowed to warm to 25° C. where it was stirred for 30 min. The reaction mixture was then treated with a mixture of cytosine (102 mg, 0.922 mmol) and N,N-diisopropylethylamine (0.191 mL, 1.098 mmol) in N,N-dimethylformamide (2 mL). The resulting reaction mixture was allowed to stir at 25° C. overnight. The reaction mixture was then diluted with water (30 mL), a 1N aqueous hydrochloric acid solution (5 mL), and ethyl acetate (30 mL). The layers were separated, and the organic layer was dried over magnesium sulfate, filtered, and concentrated in vacuo. Biotage chromatography (FLASH 40S, Silica, 20/1 methylene chloride/methanol) afforded impure 3-cyclopentyl-2-(4-methanesulfonyl-3-nitro-phenyl)-N-(2-oxo-1,2-dihydro-pyrimidin-4-yl)-propionamide (25 mg) as a pale yellow solid. Re-purification by recrystallization from chloroform afforded 3-cyclopentyl-2-(4-methanesulfonyl-3-nitro-phenyl)-N-(2-oxo-1,2-dihydro-pyrimidin-4-yl)-propionamide (12 mg, 6.5%) as a white solid: mp 256–258° C. (dec); FAB-HRMS m/e calcd for $C_{19}H_{22}N_4O_6S$ (M+H)$^+$ 435.1338, found 435.1334.

EXAMPLE 161

3-Cyclopentyl-2-(4-methanesulfonyl-3-nitro-phenyl)-N-pyrazin-2-yl-propionamide

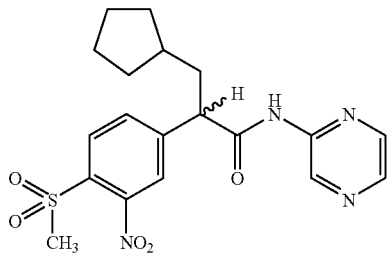

A mixture of 3-cyclopentyl-2-(4-methanesulfonyl-3-nitrophenyl)-propionic acid (prepared as in Example 14, 250 mg, 0.732 mmol), triethylamine (0.306 mL, 2.19 mmol), benzotriazol-1-yloxy-tris(dimethylamino)phosphonium hexafluorophosphate (487 mg, 1.10 mmol), and 2-aminopyrazine (105 mg, 1.10 mmol) in methylene chloride (5 mL) was stirred at 25° C. for 18 h. The reaction mixture was then diluted with water (25 mL), a 1N aqueous hydrochloric acid solution (5 mL), and ethyl acetate (25 mL). The layers were separated, and the organic layer was dried over magnesium sulfate, filtered, and concentrated in vacuo. Biotage chromatography (FLASH 40S, Silica, 19/1 methylene chloride/methanol) afforded impure 3-cyclopentyl-2-(4-methanesulfonyl-3-nitro-phenyl)-N-pyrazin-2-yl-propionamide as a white foam. This white foam was dissolved in ethyl acetate (2 mL) and then added to hexanes (50 mL). A white precipitate formed, and the solid was collected by filtration to afford 3-cyclopentyl-2-(4-methanesulfonyl-3-nitro-phenyl)-N-pyrazin-2-yl-propionamide (23.3 mg, 7.6%) as a white solid: mp 104–108° C. (gel formation); EI-HRMS m/e calcd for $C_{19}H_{22}N_4O_5S$ (M$^+$) 418.1311, found 418.1309.

EXAMPLE 162

3-Cyclopentyl-N-(1H-imidazol-2-yl)-2-(4-methanesulfonyl-3-nitro-phenyl)-propionamide

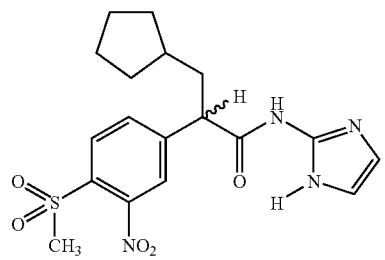

A mixture of 3-cyclopentyl-2-(4-methanesulfonyl-3-nitrophenyl)-propionic acid (prepared as in Example 14, 150 mg, 0.439 mmol), triethylamine (0.184 mL, 1.32 mmol), benzotriazol-1-yloxy-tris(dimethylamino)phosphonium hexafluorophosphate (291 mg, 0.659 mmol), and 2-aminoimidazole sulfate (87 mg, 0.659 mmol) in methylene chloride (4 mL) and N,N-dimethylformamide (1.5 mL) was stirred at 25° C. for 48 h. The reaction mixture was then diluted with water (25 mL), a 1N aqueous hydrochloric acid solution (5 mL), and ethyl acetate (25 mL). The layers were separated, and the organic layer was dried over magnesium sulfate, filtered, and concentrated in vacuo to afford a yellow gel. This yellow gel was diluted with methylene chloride (5 mL), and an off-white solid precipitated. The off-white solid was collected by filtration, and then treated with acetone (5 mL). The acetone mixture was heated to a boil, allowed to cool, and then filtered to afford 3-cyclopentyl-N-(1H-imidazol-2-yl)-2-(4-methanesulfonyl-3-nitro-phenyl)-propionamide (25 mg, 14%) as a white solid: mp 243–244° C.; EI-HRMS m/e calcd for $C_{18}H_{22}N_4O_5S$ (M$^+$) 406.1311, found 406.1311.

EXAMPLE 163

3-Cyclopentyl-2(R)-(3,4-dichloro-phenyl)-N-pyrazin-2-yl-propionamide

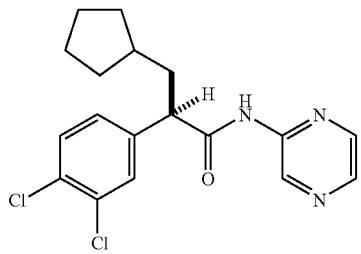

A solution of 3-cyclopentyl-2(R)-(3,4-dichlorophenyl)-propionic acid (prepared as in Example 54A, 200 mg, 0.70 mmol) in methylene chloride (5 mL) was cooled to 0° C. and then treated with a 2M solution of oxalyl chloride in methylene chloride (0.52 mL, 1.0 mmol) and N,N-dimethylformamide (1 drop). The reaction mixture was stirred at 0° C. for 30 min and then treated with a solution of 2-aminopyrazine (133 mg, 1.4 mmol) in tetrahydrofuran (10 mL) followed by pyridine (0.28 ml, 3.5 mmol). The resulting reaction mixture was stirred at 25° C. for 16 h. The reaction mixture was then diluted with water (10 mL) and extracted with methylene chloride (3×15 mL). The combined organic layers were dried over sodium sulfate, filtered, and concentrated in vacuo. Biotage chromatography (FLASH 40S, Silica, 70/30 hexanes/ethyl acetate) afforded 3-cyclopentyl-2(R)-(3,4-dichloro-phenyl)-N-pyrazin-2-yl-propionamide (192 mg, 76%) as a colorless oil: $[\alpha]^{23}_{589}$=−62.1° (c=0.095, chloroform); EI-HRMS m/e calcd for $C_{18}H_{19}N_3OCl_2$ (M+) 363.0905, found 363.0893.

EXAMPLE 164

N-(5-Bromo-pyridin-2-yl)-2-(4-chloro-3-nitro-phenyl)-3-cyclopentyl-propionamide

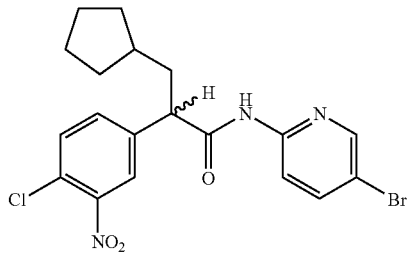

A solution of triphenylphosphine (241 mg, 0.92 mmol) in methylene chloride (3 mL) was cooled to 0° C. and then slowly treated with N-bromosuccinimide (164 mg, 0.92 mmol). The reaction mixture was stirred at 0° C. for 10 min and then treated with 2-(4-chloro-3-nitro-phenyl)-3-cyclopentyl-propionic acid (prepared as in Example 64, 250 mg, 0.84 mmol). The resulting reaction mixture was stirred at 0° C. for 5 min and then allowed to warm to 25° C. where it was stirred for 30 min. The reaction mixture was then treated with 2-amino-5-bromopyridine (320 mg, 1.85 mmol). The crude reaction mixture was then directly purified by flash chromatography (Merck Silica gel 60, 230–400 mesh, 3/1 hexanes/ethyl acetate) to afford N-(5-bromo-pyridin-2-yl)-2-(4-chloro-3-nitro-phenyl)-3-cyclopentyl-propionamide (216 mg, 57%) as a pale yellow solid: mp 128–130° C.; EI-HRMS m/e calcd for $C_{19}H_{19}BrClN_3O_3$ (M+) 451.0298, found 451.0300.

EXAMPLE 165

3-Cyclopentyl-N-pyrimidin-4-yl-2-(3-trifluoromethyl-phenyl)-propionamide

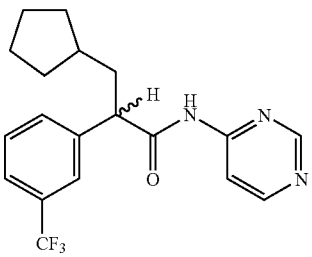

A solution of 3-cyclopentyl-2-(3-trifluoromethyl-phenyl)-propionic acid (prepared as in Example 88, 152 mg, 0.532 mmol) in methylene chloride (10 mL) was treated with dry N,N-dimethylformamide (3 drops). The reaction mixture was cooled to 0° C. and then treated dropwise with a 2M solution of oxalyl chloride in methylene chloride (0.30 mL, 0.58 mmol). The reaction mixture was stirred at 0° C. for 10 min and then stirred at 25° C. for 30 min. The reaction mixture was then treated with N,N-diisopropylethylamine (0.22 mL, 1.26 mmol) followed by a solution of 4-aminopyrimidine (106 mg, 1.12 mmol) in dry tetrahydrofuran (5 mL). The resulting reaction mixture was stirred at 25° C. for 17 h. The reaction mixture was concentrated in vacuo. The resulting residue was adsorbed onto silica gel (Merck Silica gel 60, 230–400 mesh) and then purified via Biotage chromatography (FLASH 40S, Silica, 1/1 hexanes/ethyl acetate) to afford 3-cyclopentyl-N-pyrimidin-4-yl-2-(3-trifluoromethyl-phenyl)-propionamide (170 mg, 88%) as a white solid: mp 113–115° C.; EI-HRMS m/e calcd for $C_{19}H_{20}F_3N_3O$ (M+) 363.1558, found 363.1553.

In an analogous manner, there were obtained:

a) From 3-cyclopentyl-2-(3-trifluoromethyl-phenyl)-propionic acid and 4-amino-2-methylpyrimidine: 3-Cyclopentyl-N-(2-methyl-pyrimidin-4-yl)-2-(3-trifluoromethyl-phenyl)-propionamide as a colorless gum: EI-HRMS m/e calcd for $C_{20}H_{22}F_3N_3O$ (M+) 377.1715, found 377.1715.

b) From 3-cyclopentyl-2-(3-trifluoromethyl-phenyl)-propionic acid and 2-aminopyrazine: 3-Cyclopentyl-N-pyrazin-2-yl-2-(3-trifluoromethyl-phenyl)-propionamide as a pale yellow gum: EI-HRMS m/e calcd for $C_{29}H_{20}F_3N_3O$ (M+) 363.1558, found 363.1558.

EXAMPLE 166

{2-[3-Cyclopentyl-2-(4-fluoro-3-trifluoromethyl-phenyl)-propionylamino]-thiazol-4-yl}-acetic Acid Ethyl Ester

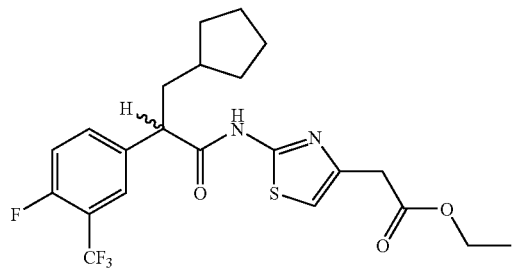

A solution of 3-cyclopentyl-2-(4-fluoro-3-trifluoromethyl-phenyl)-propionic acid (prepared as in Example 87, 250 mg, 0.82 mmol) in methylene chloride (8.22 mL) cooled to 0° C. was treated with a 2.0M solution of oxalyl chloride in methylene chloride (0.45 mL, 0.90 mmol) and a few drops of N,N-dimethylformamide. The reaction mixture was stirred at 0° C. for 10 min and at 25° C. for 20 min. The reaction mixture was then treated with a solution of (2-amino-thiazol-4-yl)-acetic acid ethyl ester (337 mg, 1.81 mmol) in tetrahydrofuran (4.11 mL) and N,N-diisopropylethylamine (0.34 mL, 1.97 mmol). This solution was stirred at 25° C. for 18 h. At this time, the reaction was concentrated in vacuo. Flash chromatography (Merck Silica gel 60, 230–400 mesh, 75/25 hexanes/ethyl acetate) afforded {2-[3-cyclopentyl-2-(4-fluoro-3-trifluoromethyl-phenyl)-propionylamino]-thiazol-4-yl}-acetic acid ethyl ester (208.7 mg, 53.7%) as a pale-yellow gum: EI-HRMS m/e calcd for $C_{21}H_{22}F_4N_2O_3S$ (M+) 472.1444, found 472.1442.

EXAMPLE 167

3-Cyclopentyl-2-(4-fluoro-3-trifluoromethyl-phenyl)-N-(5-nitro-pyridin-2-yl)-propionamide

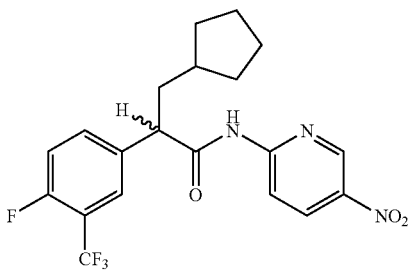

A solution of triphenylphosphine (393 mg, 1.5 mmol) in methylene chloride (10.0 mL) was cooled to 0° C. and then treated with N-bromosuccinimide (303 mg, 1.7 mmol). After stirring at 0° C. for 10 min, the reaction mixture was treated with 3-cyclopentyl-2-(4-fluoro-3-trifluoromethyl-phenyl)-propionic acid (prepared as in Example 87, 304 mg, 1.0 mmol). The reaction mixture was stirred at 0° C. for 20 min and at 25° C. for 30 min. At this time, the reaction mixture was treated with 2-amino-5-nitropyridine (290 mg, 1.5 mmol) and pyridine (0.14 mL, 1.8 mmol). The resulting reaction mixture was stirred at 25° C. for 20 h. The reaction mixture was then concentrated in vacuo. Flash chromatography (Merck Silica gel 60, 200–400 mesh, 90/10 hexanes/ethyl acetate) afforded 3-cyclopentyl-2-(4-fluoro-3-trifluoromethyl-phenyl)-N-(5-nitro-pyridin-2-yl)-propionamide (425 mg, 60%) as a white solid: mp 121–122° C.; EI-HRMS m/e calcd for $C_{20}H_{19}F_4N_3O_3$ ($M^+$) 425.1363, found 425.1363.

In an analogous manner, there was obtained:
a) From 2-amino-5-cyanopyridine and 3-cyclopentyl-2-(4-fluoro-3-trifluoromethyl-phenyl)-propionic acid: N-(5-Cyano-pyridin-2-yl)-3-cyclopentyl-2-(4-fluoro-3-trifluoromethyl-phenyl)-propionamide as a pale-yellow oil: EI-HRMS m/e calcd for $C_{21}H_{19}F_4N_3O$ ($M^+$) 405.1464, found 445.1477.

EXAMPLE 168

6-[3-Cyclopentyl-2-(4-fluoro-3-trifluoromethyl-phenyl)-propionylamino]-nicotinic Acid Methyl Ester

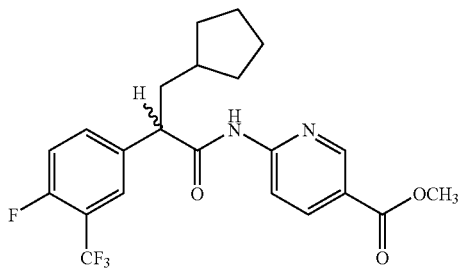

A solution of 3-cyclopentyl-2-(4-fluoro-3-trifluoromethyl-phenyl)-propionic acid (prepared as in Example 87, 202 mg, 0.66 mmol), benzotriazol-1-yloxy-tris(dimethylamino)phosphonium hexafluorophosphate (294 mg, 0.66 mmol), and 6-amino-nicotinic acid methyl ester (111 mg, 0.73 mmol) in N,N-dimethylformamide (3.32 mL) at 25° C. was treated with N,N-diisopropylethylamine (0.24 mL, 1.39 mmol). The reaction mixture was stirred at 25° C. for 12 h. At this time, the reaction was poured into water (50 mL) and extracted into ethyl acetate (3×35 mL). The combined organic layers were dried over sodium sulfate, filtered, and concentrated in vacuo. Flash chromatography (Merck Silica gel 60, 230–400 mesh, 80/20 hexanes/ethyl acetate) afforded 6-[3-cyclopentyl-2-(4-fluoro-3-trifluoromethyl-phenyl)-propionylamino]-nicotinic acid methyl ester (36.7 mg, 12.6%) as a white foam: EI-HRMS m/e calcd for $C_{22}H_{22}F_4N_2O_3$ ($M^+$) 438.1566, found 438.1568.

In an analogous coupling procedure, there were obtained:
a) From 2-amino-5-bromopyridine and 3-cyclopentyl-2-(4-fluoro-3-trifluoromethyl-phenyl)-propionic acid: N-(5-Bromo-pyridin-2-yl)-3-cyclopentyl-2-(4-fluoro-3-trifluoromethyl-phenyl)-propionamide as a pale-yellow oil: EI-HRMS m/e calcd for $C_{20}H_{19}BrF_4N_2O$ ($M^+$) 458.0617, found 458.0612.
b) From 2-aminoimidazole sulfate and 3-cyclopentyl-2-(4-methanesulfonyl-3-trifluoromethyl-phenyl)-propionic acid (prepared as in Example 155A): 3-Cyclopentyl-N-(1H-imidazol-2-yl)-2-(4-methanesulfonyl-3-trifluoromethyl-phenyl)-propionamide as a white solid: mp 270–275° C.; EI-HRMS m/e calcd for $C_{19}H_{22}F_3N_3O_3S$ ($M^+$) 429.1334, found 429.1331.

BIOLOGICAL ACTIVITY EXAMPLES

EXAMPLE A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2).

Recombinant

Scheme 2

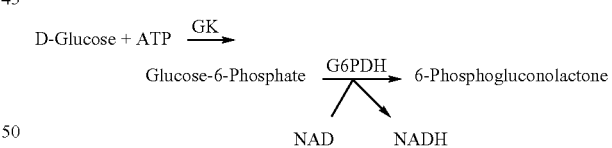

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μl. The incubation mixture contained: 25 mM Hepes buffer (pH, 7.1), 25 mM KCl, 5 mM D-glucose, 1 mM ATP, 1.8 mM NAD, 2 mM MgCl$_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 µM.

REFERENCES FOR EXAMPLE A

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167–173, 1995.

Neet, K., Keenan, R. P., and Tippett, P. S. Observation of a kinetic slow transition in monomeric glucokinase. *Biochemistry* 29; 770–777, 1990.

EXAMPLE B

In Vivo Activity

Glucokinase Activator in vivo Screen Protocol: C57BL/6J mice are orally dosed via gavage with Glucokinase (GK) activator at 50 mg/kg body weight following a two hour fasting period. Blood glucose determinations are made five times during the six hour post-dose study period.

Mice (n=6) are weighed and fasted for a two hour period prior to oral treatment. GK activators are formulated at 6.76 mg/ml in Gelucire vehicle (Ethanol:Gelucire 44/14: PEG400q.s. 4:66:30 v/w/v. Mice are dosed orally with 7.5 µl formulation per gram of body weight to equal a 50 mg/kg dose. Immediately prior to dosing, a pre dose (time zero) blood glucose reading is acquired by snipping off a small portion of the animals tail (~1 mm) and collecting 15 µl blood into a heparinized capillary tube for analysis. Following GK activator administration, additional blood glucose readings are taken at 1, 2, 4 and 6 hours post dose from the same tail wound. Results are interpreted by comparing the mean blood glucose values of six vehicle treated mice with six GK activator treated mice over the six hour study duration. Compounds are considered active when they exhibit a statistically significant ($p \leq 0.05$) decrease in blood glucose compared to vehicle for two consecutive assay time points.

What is claimed is:
1. A compound selected from the group consisting of
3-cyclopentyl-2-(3-fluoro-4-methanesulfonyl-phenyl)-N-pyridin-2-yl-propionamide,
3-cyclopentyl-2-(R)-(3,4-dichlorophenyl)-N-pyridin-2-yl-propionamide,
3-cyclopentyl-2-(4-fluoro-3-trifluoromethyl-phenyl)-N-pyrid in-2-yl-propionamide,
2(R)-(3-chloro-4-methanesulfonyl-phenyl)-3-cyclopentyl-N-pyridin-2-yl-propionamide,
N-(5-cyano-pyridin-2-yl)-3-cyclopentyl-2-(4-methylsulfanyl-3-trifluoromethyl-phenyl)-propionamide,
N-(5-cyano-pyridin-2-yl)-3-cyclopentyl-2-(4-fluoro-3-trifluoromethyl-phenyl)-propionamide,
N-(5-cyano-pyridin-2-yl)-3-cyclopentyl-2-(3,4-dichlorophenyl)-propionamide,
6-[3-cyclopentyl-2-(3,4-dichlorophenyl)-propionylamino]-nicotinic acid,
6-[3-cyclopentyl-2-2(R)-(3,4-dichlorophenyl)-propionylamino]-nicotinic acid,
6-[2-(4-chloro-phenyl)-3-cyclopentyl-propionylamino]-nicotinic acid,
6-[2-(3-chloro-phenyl)-3-cyclopentyl-propionylamino]-nicotinic acid methyl ester and
6-[2-(4-chloro-phenyl)-3-cyclopentyl-propionylamino]-nicotinic acid methyl ester.
2. A compound selected from the group consisting of
6-[3-cyclopentyl-2-(4-nitro-phenyl)-propionylamino]-nicotinic acid methyl ester,
6-[2-(4-amino-phenyl)-3-cyclopentyl-propionylamino]-nicotinic acid methyl ester,
6-[2-(3-chloro-phenyl)-3-cyclopentyl-propionylamino]-nicotinic acid,
6-[2-(4-cyano-phenyl)-3-cyclopentyl-propionylamino]-nicotinic acid methyl ester,
6-[3-cyclopentyl-2-(4-trifluoromethyl-phenyl)-propionylamino]-nicotinic acid methyl ester,
6-[3-cyclopentyl-2-(4-fluoro-3-trifluoromethyl-phenyl)-propionylamino]-nicotinic acid methyl ester, 3-cyclopentyl-2-(3,4-dichlorophenyl)-N-(5-hydroxy-pyridin-2-yl)-propionamide,
N-(5-bromo-pyridin-2-yl)-3-cyclopentyl-2-(4-fluoro-3-trifluoromethyl-phenyl)-propionamide,
N-(5-bromo-pyridin-2-yl)-3-cyclopentyl-2-(4-methanesulfonyl-3-trifluoromethyl-phenyl)-propionamide,
N-(5-bromo-pyridin-2-yl)-2-(4-chloro-3-nitro-phenyl)-3-cyclopentyl-propionamide,
N-(5-bromo-pyridin-2-yl)-3-cyclopentyl-2-(4-methylsulfanyl-3-trifluoromethyl-phenyl)-propionamide and
N-(5-chloro-pyridin-2-yl)-3-cyclopentyl-2(R)-(3,4-dichlorophenyl)-propionamide.
3. A compound selected from the group consisting of
N-(5-bromo-pyridin-2-yl) 2(R)-(3-chloro-4-methanesulfonyl-phenyl)-3-cyclopentyl-propionamide,
3-cyclopentyl-2-(4-methylsulfonyl-3-trifluoromethyl-phenyl)-N-(5-nitro-pyrid in-2-yl)-propionamide,
3-cyclopentyl-2-(4-fluoro-3-trifluoromethyl-phenyl)-N-(5-nitro-pyridin-2-yl)-propionamide,
2(R)-(3-chloro-4-methanesulfonyl-phenyl)-3-cyclopentyl-N-(5-methyl-pyridin-2-yl)-propionamide,
3-cyclopentyl-2-(3,4-dichloro-phenyl)-N-(5-methylpyridin)-2-yl-propionamide,
3-cyclopentyl-2-(3,4-dichloro-phenyl)-N-(4-methylpyridin)-2-yl-propionamide,

3-cyclopentyl-2-(3,4-dichloro-phenyl)-N-(6-methylpyridin)-2-yl-propionamide,
3-cyclopentyl-N-(5-methyl-pyridin-2-yl)-2-(4-trifluoromethanesulfonyl-phenyl)-propionamide,
3-cyclopentyl-2-(4-fluoro-3-trifluoromethyl-phenyl)-N-(5-methyl-pyridin-2-yl)-propionamide,
3-cyclopentyl-2-(4-methanesulfonyl-phenyl)-N-(5-methyl-pyridin-2-yl)-propionamide and
6-[3-cyclopentyl-2-(3,4-dichloro-phenyl)-propionylamino]-N-methyl-nicotinamide.

* * * * *